US007101969B1

(12) United States Patent
Pelletier et al.

(10) Patent No.: US 7,101,969 B1
(45) Date of Patent: Sep. 5, 2006

(54) **COMPOSITIONS AND METHODS INVOLVING AN ESSENTIAL *STAPHYLOCOCCUS AUREUS* GENE AND ITS ENCODED PROTEIN**

(75) Inventors: Jerry Pelletier, Baie-D'Urfe (CA); Philippe Gros, St. Lambert (CA); Mike DuBow, Montreal (CA)

(73) Assignee: Targanta Therapeutics, Quebec (CA)

( * ) Notice: Subject to any disclaimer, the term of this patent is extended or adjusted under 35 U.S.C. 154(b) by 737 days.

(21) Appl. No.: 09/689,952

(22) Filed: Oct. 12, 2000

Related U.S. Application Data

(63) Continuation-in-part of application No. 09/470,512, filed on Dec. 22, 1999, now Pat. No. 6,376,652, which is a continuation-in-part of application No. 09/407,804, filed on Sep. 28, 1999.

(60) Provisional application No. 60/110,992, filed on Dec. 3, 1998.

(51) Int. Cl.
*C07K 14/00* (2006.01)
*G01N 33/53* (2006.01)

(52) U.S. Cl. ............ 530/350; 530/300; 435/7.1; 435/243; 435/252.3; 514/2; 514/12; 536/23.7; 424/9.1

(58) Field of Classification Search ............ 514/12, 514/2; 530/359, 300; 536/23.7; 435/252.3, 435/243, 7.1; 424/9.1
See application file for complete search history.

(56) References Cited

U.S. PATENT DOCUMENTS

| 4,946,778 | A | 8/1990 | Ladner et al. ............ 435/69.6 |
| 6,037,123 | A | 3/2000 | Benton et al. |
| 6,187,541 | B1 | 2/2001 | Benton et al. |
| 6,228,588 | B1 | 5/2001 | Benton et al. |

FOREIGN PATENT DOCUMENTS

| EP | 00786519 A2 | 7/1997 |
| WO | WO 00/32825 | 6/2000 |

OTHER PUBLICATIONS

Myers, et al., Detection of Single Base Substitutions by Ribonuclease Cleavage at Mismatches in RNA:DNA Duplexes, (1985), Science 230, 1242.
Wolff, et al., Long-term persistence of plasmid DNA and foreign gene expression in mouse muscle, (1992), Hum. Mol. Genet., vol. 1 No. 6, 363-369.
Frimodt-Møller, Epidemiology of *Staphylococcus aureus* bacteremia in Denmark from 1957 to 1990, (1997), Clin. Microbiol. Infect. 3:297-305.
Benvenisty and Reshef, Direct introduction of genes into rats and expression of the genes, (1986) PNAS USA 89:95551.
Seeger, et al., The cloned genome of ground squirrel hepatitis virus is infectious in the animal, (1984), PNAS USA 81:5849.
Cotton, et al., Reactivity of cytosine and thymine in single-base-pair mismatches with hydroxylamine and osmium tetroxide and its application to the study of mutations, (1985), Proc. Natl. Acad. Sci., USA 85, 4397-4401.
Chee, et al., Accessing Genetic Information with High-Density DNA Arrays, (1996), Science 274, 610.
Kaneda, et al., Increased Expression of DNA Cointroduced with Nuclear Protein in Adult Rat Liver, (1989), 243:375.
Tang, et al., Genetic immunization is a simple method for eliciting an immune response, (1992), Nature 356:152.
de Haard, et al., A Large Non-immunized Human Fab Fragment Phage Library That Permits Rapid Isolation and Kinetic Analysis of High Affinity Antibodies, (1999), J. Biol. Chem. 274: 18218-18230.
Wu, et al., Targeting Genes: Delivery and Persistent Expression of a Foreign Gene Driven by Mammalian Regulatory Elements in Vivo, (1989), J. Biol. Chem. 264: 16985.
Bruand, C. and Ehrlich, S.D., The *Bacillus subtilis* dnaI gene is part of the dnaB operon, (1995), Microbiology 141, 1199-1200.
Kimmerly, et al.; "*Staphylococcus epidermis* strain SR1 clone step. 1049g03 genomic sequence"; (2000); Database accession No. AF270108; XP002267915.
Qian, et al.; "*Staphylococcus aureus* clone sabac-135, complete sequence"; (2000); Database accession No. AC078832; XP002267916.
Takami, et al.; "*Bacillus halodurans* DnaI"; (2000); Database accession No. Q9K863; XP002267917.
Kunsch, et al.; "*Staphylococcus aureus* contig SEQ ID #106"; (1999); Database accession No. AAV74417; XP002267918.
Ogasawara, et al.; "*Bacillus subtilis* dnaB gene for initiation of chromosomal replication"; (1987); Database accession No. X04963; XP002267919.

(Continued)

*Primary Examiner*—Jon Weber
*Assistant Examiner*—Chih-Min Kam
(74) *Attorney, Agent, or Firm*—Kathleen M. Williams; Palmer & Dodge LLP

(57) ABSTRACT

This invention relates to newly identified polynucleotides and polypeptides, and their production and uses, as well as their variants, agonists and antagonists, and their uses. In particular, the invention relates to polynucleotides and polypeptides of a *Staphylococcus aureus* (*S. aureus*) DnaI related protein, as well as its variants. The invention also relates to a specific interaction between the *S. aureus* DnaI related protein or specific regions thereof, and a growth-inhibitory protein encoded by the *S. aureus* bacteriophage 77 genome. The phage open reading frame (ORF) product interacts with amino acids 150–313 of *S. aureus* DnaI polypeptide, and the invention relates to the use of this interaction target site as the basis of drug screening assays. Accordingly, the invention provides a method for the inhibition of bacterial growth, and the treatment of bacterial infection via the inhibition of DnaI.

10 Claims, 47 Drawing Sheets

OTHER PUBLICATIONS

Kunsch, et al.; "*Enterococcus faecalis* genome contig SEQ ID No.:341"; (1999); Databse accession No. AAX13278; XP002267920.

Ogasawara, et al.; "*Bacillus subtilis* DnaI"; (1988); Database accession No. P06567; XP002267921.

Bruand, et al.; "Primosome Assembly Site in *Bacillus Subtilis*"; (1995); *EMBD Journal*; vol. 14, No. 11, pp. 2642-2650.

Black, et al.; "DNA encoding a *Staphylococcus aureus* protein of unknown function"; (1998); Database accession No. AAT83989; XP002268024.

Supplementary Partial European Search Report dated Jan. 26, 2004.

Franken, M. et al., (1996), "Comparative Analysis Identifies Conserved Tumor Necrosis Factor Receptor-Associated Factor 3 Binding Sites in Human and Simian Epstein-Barr Virus Oncogene LMP1", *Journal of Virology*, 70(11):7819-7826.

Figure 1A

SEQ ID NO:1

```
1      atgggaggag gacagtcaat aatgaagcaa tttaaaagta taattaacac gtcgcaggac
61     tttgaaaaaa gaatagaaaa gataaaaaaa gaagtaatca atgacccaga tgttaagcaa
121    tttttggaag cgcatcgagc tgaattaacg aatgctatga ttgatgaaga cttaaatgtg
181    ttacaagagt ataaagatca acaaaaacat tatgacggtc ataaatttgc tgattgtcca
241    aatttcgtaa aggggcatgt gcctgagtta tatgttgata ataccgaat taaaatacgc
301    tatttacaat gcccatgtaa aatcaagtac gacgaagaac gctttgaagc tgagctaatt
361    acatctcatc atatgcaacg agatacttta aatgccaaat tgaaagatat ttatatgaat
421    catcgagacc gtcttgatgt agctatggca gcagatgata tttgtacagc aataactaat
481    ggggaacaag tgaaaggcct ttacctttat ggtccatttg ggacaggtaa atcttttatt
541    ctaggtgcaa ttgcgaatca gctcaaatct aagaaggtac gttcgacaat tatttattta
601    ccggaattta ttagaacatt aaaaggtggc tttaaagatg gttcttttga aaagaaatta
661    catcgcgtaa gagaagcaaa catttaatg cttgatgata ttggggctga agaagtgact
721    ccatgggtga gagatgaggt aattggacct tgctacatt atcgaatggt tcatgaatta
781    ccaacattct ttagttctaa ttttgactat agtgaattgg aacatcattt agcgatgact
841    cgtgatggtg aagagaagac taaagcagca cgtattattg aacgtgtcaa atctttgtca
901    acaccatact ttttatcagg agaaaatttc agaaacaatt ga
```

Figure 1B

SEQ ID NO:2

```
1      MGGGQSIMKQ FKSIINTSQD FEKRIEKIKK EVINDPDVKQ FLEAHRAELT NAMIDEDLNV
61     LQEYKDQQKH YDGHKFADCP NFVKGHVPEL YVDNNRIKIR YLQCPCKIKY DEERFEAELI
121    TSHHMQRDTL NAKLKDIYMN HRDRLDVAMA ADDICTAITN GEQVKGLYLY GPFGTGKSFI
181    LGAIANQLKS KKVRSTIIYL PEFIRTLKGG FKDGSFEKKL HRVREANILM LDDIGAEEVT
241    PWVRDEVIGP LLHYRMVHEL PTFFSSNFDY SELEHHLAMT RDGEEKTKAA RIIERVKSLS
301    TPYFLSGENF RNN
```

Figure 2A

SEQ ID NO:3 Complete genome sequence of bacteriophage 77

```
1       gatcaaaata cttggggaac ggttagggag taaacttcgc gataatttta aaaattcatg
61      tataaccccc ctcttataac cattttaagg caggtgatga aatggagatt atagtcgatg
121     aaaatttagt gcttaaagaa aaagaaaggc tacaagtatt atataaagac atacctagca
181     ataaattaaa agtagttgat ggtttaatta ttcaagcagc aaggctacgt gtaatgcttg
241     attacatgtg ggaagacata aaagaaaaag gtgattatga tttatttact caatctgaaa
301     aggcgccacc atatgaaagg gaaagaccag tagccaaact atttaatgct agagatgctg
361     catatcaaaa aataatcaaa caattatcgg atttattgcc cgaagagaaa gaagacacag
421     aaacgccatc tgatgattac ctatgattag taataaaatac gttgatgaat atataaattt
481     gtggaaacaa ggaaagataa ttttaaataa agaaagaatt gatctcttta attatctaca
541     aaaacatata tattcacgag atgatgtata ttttgatgaa cagaaaatcg aggattgtat
601     caaatttatt gaaaaatggt attttccaac attaccattt caaggttta tcatagctaa
661     tatatttctt atagataaaa atacagatga agctttcttt acagaatttg ctattttcat
721     gggacgtgga ggcgggaaaa acggtctaat aagtgctatt agtgattttc tttctacgcc
781     cttacacgga gttaaagaat atcacatctc cattgttgct aatagtgaag atcaagcaaa
841     aacatcgttt gatgaaatca gaaccgtttt aatggataac aaacgaaata agacgggtaa
901     aacgccaaaa gctccttatg aagttagtaa agcaaaaata ataaaccgtg caactaaatc
961     ggttattcga tataacacat caaacacaaa aaccaaagac ggtggacgtg aggggtgtgt
1021    tattttgat gaaattcatt atttctttgg tcctgaaatg gtaaacgtca aacgtggtgg
1081    attaggtaaa aagaaaaata gaagaacgtt ttatataagt actgatggtt ttgttagaga
1141    gggttatatc gatgcaatga agcacaaaat tgcaagtgta ttaagtggca aggttaaaaa
1201    tagtagattg tttgcttttt attgtaagtt agacgatcca aaagaagttg atgacagaca
1261    gacgtgggaa aaggcgaacc caatgttaca taaaccgtta tcagaatacg ctaaaacact
1321    gctaagcacg attgaagaag aatataacga tttaccattc aaccgttcaa ataagcccga
1381    attcatgact aagcgaatga atttgcctga agttgacctt gaaaaagtaa tagcaccatg
1441    gaaagaaata ctagcgacta atagagagat accaaattta gataatcaaa tgtgtattgg
1501    tggtttagac tttgcaaaca ttcgagattt tgcaagtgta gggctattat tccgaaaaaa
1561    cgatgattac atttggttag gacattcgtt tgtaagacaa gggttttgg atgatgtcaa
1621    attagaacct cctattaaag aatgggaaaa aatgggatta ttgaccattg tcgatgatga
1681    tgtcattgaa attgaatata tagttgattg gttttttaaag gctagagaaa aatatgggct
1741    tgaaaaagtc atagctgata attatagaac tgatattgta agacgtgcgt ttgaggatgc
1801    tggcataaaa cttgaagtac ttagaaatcc aaaagcaata catggattac ttgcaccacg
1861    tatcgataca atgtttgcga acataacgt aatatatgga gacaatcctt tgatgcgttg
1921    gtttactaat aatgttgctg taaaaatcaa gccggatgga aataaagagt atatcaaaaa
1981    agatgaagtc agacgtaaaa cggatggatt catggctttt gttcacgcat tatatagagc
2041    agacgatata gtagacaaag acatgtctaa agcgcttgat gcattaatga gtatagattt
2101    ctaatagagg aggtgagaca tgagtattct agaaaagata tttaaaacta ggaaagatat
2161    aacatatatg cttgatttag atatgataga agatctatca caacaagcgt atgtgaaacg
2221    tttagcgatt gatagttgta ttgaatttgt tgcgcgagct gtcgctcaaa gtcattttaa
2281    agtattggaa ggtaatagaa ttcaaaagaa tgatgtttac tacaagttaa atataaaacc
2341    aaatactgac ttatcaagcg atagttttg gcaacaagtt atatataaac taatttatga
2401    taacgaggtt ttaatcgtag taagtgacag caaagaatta cttatcgcag atagcttta
2461    cagagaagag tacgctttgt atgatgatat attcaaagat gtaacggtta aagattatac
2521    ttatcaacgt actttcacaa tgcaagaggt catatattta aagtacaaca acaataaagt
2581    gacacacttt gtagaaagtc tattcgaaga ttacgggaaa atattcggaa gaatgatagg
2641    tgcacaatta aaaaactatc aaataagagg gattttgaaa tctgcctcta gcgcatatga
2701    cgaaaagaat atagaaaaat tacaagcgtt cacaaataaa ttattcaata cttttaataa
```

Figure 2B

```
2761    aaatcaacta gcaatcgcgc ctttgataga aggttttgat tatgaggaat tatctaatgg
2821    tggtaagaat agtaacatgc cttttctga attgagtgag ctaatgagag atgcaataaa
2881    aaatgttgcg ttgatgattg gtatacctcc aggtttgatt tacggagaaa cagctgattt
2941    ggaaaaaaac acgcttgtat ttgagaagtt ctgtttaaca cctttattaa aaaagattca
3001    gaacgaatta aacgcgaaac tcataacaca aagcatgtat ttgaaagata caagaataga
3061    aattgtcggt gtgaataaaa aagacccact tcaatatgct gaagcaattg acaaacttgt
3121    aagttctggt tcatttacaa ggaatgaggt gcggattatg ttaggtgaag aaccatcaga
3181    caatcctgaa ttagacgaat acctgattac taaaaactac gaaaagcta acagtggtga
3241    aaatgatgaa aaagaaaaag atgaaaacac tttgaaaggt ggtgatgaag atgaaagcgg
3301    agattaaagg cgtcatcgtt tccaacgaag ataaatgggt ttacgaaatg cttggtatgg
3361    attcgacttg tcctaaagat gttttaacac aactagaatt tagtgatgaa gatgttgata
3421    ttataattaa ctcaaatggt ggtaacctag tagctggtag tgaaatatat acacatttaa
3481    gagctcataa aggcaaagtg aatgttcgta tcacagcaat agcagcaagt gcggcatcgc
3541    ttatcgcaat ggctggtgac cacatcgaaa tgagtccggt tgctagaatg atgattcaca
3601    atccttcaag tattgcgcaa ggagaagtga aagatctaaa tcatgctgca gaaacattag
3661    aacatgttgg tcaaataatg gctgaggcat atgcggttag agctggtaaa aacaaacaag
3721    aacttataga aatgatggct aaggaaacgt ggctaaatgc tgatgaagcc attgaacaag
3781    gttttgcgga tagtaaaatg tttgaaaacg acaatatgca aattgtagca agcgatacac
3841    aagtgttatc gaaagatgta ttaaatcgtg taacagcttt ggtaagtaaa acgccagagg
3901    ttaacattga tattgacgca atagcaaata aagtaattga aaaataaat atgaaagaaa
3961    aggaatcaga aatcgatgtt gcagatagta aattatcagc aaatggattt tcaagattcc
4021    tttttttaata caaaaatagg aggtcataaa atgactataa atttatcgga aacattcgca
4081    aatgcgaaaa acgaatttat taatgcagta aacaacgtg aaccgcaaga aagacaaaat
4141    gaattgtacg gtgacatgat taaccaacta tttgaagaaa ctaaattaca agcaaaagca
4201    gaagctgaaa gagtttctag tttacctaaa tcagcacaaa ctttgagtgc aaaccaaaga
4261    aatttcttta tggatatcaa taagagtgtt ggatataaag aagaaaaact tttaccagaa
4321    gaaacaattg atagaatctt cgaagattta acaacgaatc atccattatt agctgactta
4381    ggtattaaaa atgctggttt gcgtttgaag ttcttaaaat ccgaaacttc tggcgtggct
4441    gtttggggta aaatctatgg tgaaattaaa ggtcaattag atgctgcgtt cagtgaagaa
4501    acagcaattc aaaataaatt gacagcgttt gttgttttac caaaagattt aaatgatttt
4561    ggtcctgcgt ggattgaaag atttgttcgt gttcaaatcg aagaagcatt tgcagtggcg
4621    cttgaaactg cgttcttaaa aggtactggt aaagaccaac cgattggctt aaaccgtcaa
4681    gtacaaaaag gtgtatcggt aactgatggt gcttatccag agaaagaaga acaaggtacg
4741    cttacatttg ctaatccgcg cgctacggtt aatgaattga cgcaagtgtt taaataccac
4801    tcaactaacg agaaaggtaa atcagtagcg gttaaaggta atgtaacaat ggttgttaat
4861    ccgtccgatg cttttgaggt tcaagcacag tatacacatt taaatgcaaa tggcgtatat
4921    gttactgctt taccatttaa tttgaatgtt attgagtcta cagttcaaga agcaggtaag
4981    gttttaacgt acgttaaagg tctatatgat ggttatttag ctggtggtat taatgttcag
5041    aaatttaaag aaacacttgc gttagatgat atggatttat acactgcaaa acaatttgct
5101    tacggcaaag cgaaagataa taaagttgct gctgtttgga aattagattt aaaaggacat
5161    aaaccagctt tagaagatac cgaagaaaca ctataaaatt ttatgaggtg ataaaatggt
5221    gaaatttaaa gttgttagag aatttaaaga catagagcac aatcaacaca agtacaaagt
5281    aggggagttg tatccagctg aagggtataa caatcctcgt gttgaattgt tgacaaatca
5341    aatcaaaaat aagtacgaca aagtttatat cgtaccttta gataagctga caaaacaaga
5401    attattagaa ctatgcgaat cattacaaaa aaaagcgtct agttcaatgg ttaaaagtga
5461    aatcatcgac ttattgaatg gtgaagacaa tgacgattga tgatttgctt gtcaaattta
5521    aatcacttga aagattgac cataattcag aggatgagta cttaaagcag ttgttaaaaa
5581    tgtcgtacga gcgtataaaa aatcagtgcg gagttttga attagagaat ttaataggtc
5641    aagaattgat acttatacgc gctagatatg cttatcaaga tttattagaa cacttcaacg
5701    acaattacag acctgaaata atagattttt cgttatctct aatggaggta tcagaagatg
```

Figure 2C

```
5761       aagaaagtgt ttaagaaacc tagaattaca actaaacgtt taaatacgcg tgttcatttt
5821       tataagtata ctgaaaataa tggtccagaa gctggagaaa aagaagaaaa attattatat
5881       agctgttggg cgagtattga tggtgtctgg ttacgtgaat tagaacaagc tatctcaaac
5941       ggaacgcaaa atgacattaa attgtatatt cgtgatccgc aaggtgatta tttacccagt
6001       gaagaacatt atcttgaaat tgaatcaaga tatttcaaaa atcgtttgaa tataaagcaa
6061       gtatcaccag atttggataa taaagacttt attatgattc gcggaggata tagttcatga
6121       gtgtgaaagt gacaggtgat aaagcattag aaagagaatt agaaaaacat tttggcataa
6181       aagagatggt aaaagttcaa gataaggcgt taatagctgg tgctaaggta attgttgaag
6241       aaataaaaaa acaactcaaa ccttcagaag actcaggagc actgattagt gagattggtc
6301       gtactgaacc tgaatggata aaggggaaac gtactgttac aattaggtgg cgtgggcctt
6361       ttgaacgatt tagaatagta catttaattg aaaatggtca tgttgagaaa aagtcaggaa
6421       aatttgtaaa acctaaagct atgggtggga ttaatagagc aataagacaa gggcaaaata
6481       agtattttga gacgctaaaa agggagttga aaaaattgtg attgatattt tgtacaaagt
6541       tcatgaagtg attagtcaag acagaattat tagagagcac gtaaatatca ataatattaa
6601       gttcaataaa taccctaatg taaaagatac tgatgtacct tttattgtta ttgacgatat
6661       cgacgaccca atacctacaa cttatactga cggagatgag tgtgcatata gttatattgt
6721       ccaaatagat gtttttgtta agtacaatga tgaatataat gcgagaatca taagaaataa
6781       gatatctaat cgcattcaaa agttattatg gtctgaacta aaaatgggaa atgtttcaaa
6841       tggaaaaccg gaatatatag aagaatttaa aacatataga agctctcgcg tttacgaggg
6901       catttttat aaggaggaaa attaaatggc agtaaaacat gcaagtgcgc caaaggcgta
6961       tattaacatt actggtttag gtttcgctaa attaacgaaa gaaggcgcgg aattaaaata
7021       tagtgatatt acaaaaacaa gaggattaca aaaaattggt gttgaaactg gtggagaact
7081       aaaaacagct tatgctgatg gcggtccaat tgaatcaggg aatacagacg gagaaggtaa
7141       aatctcatta caaatgcatg cgttccctaa agagattcgc aaaattgttt ttaatgaaga
7201       ttatgatgaa gatggcgttt acgaagagaa acaaggtaaa caaaacaatt acgtagctgt
7261       atggttcaga caagagcgta agacggtac atttagaaca gttttattac ctaaagttat
7321       gtttacaaat cctaaaatcg atggagaaac ggctgagaaa gattgggatt tctcaagtga
7381       agaggttgaa ggtgaggcac ttttcccttt agttgataat aaaaagtcag tacgtaagta
7441       tatctttgat tcagctaaca tgacaaatca tgatggagac ggtgaaaaag gcgaagaggc
7501       tttcttaaag aaaatttag gcgaagaata tactggaaac gtgacagagg gtaacgaaga
7561       aactttgtaa caaaaccggc ttcatcggaa actgcggtaa agtcggttaa tataccagat
7621       agcattaaaa cacttaaagt tggcgacaca tacgatttaa atgttgtagt agagccatct
7681       aatcaaagta agttattgaa atacacaaca gatcaaacga atattgtatc aatcaatagt
7741       gatggtcaag ttactgcgga agcacaaggc attgctacgg ttaaagcaac agttggtaat
7801       atgagtgaca ctataacaat aaatgtagaa gcataagagg gggcaacccc tctatttat
7861       ttgaaaataa ggagagtatt ataaaatggc aaaattaaaa cgtaacatta ttcaattagt
7921       agaagatcca aaagcaaatg aaattaaatt acaaacgtac ttaacaccac acttcatttc
7981       atttgaaatt gtatacgaag caatggattt aatcgatgat attgaggacg aaaatagcac
8041       gatgaagcca agagaaatcg ctgacagatt gatggatatg gttgtaaaaa tttacgataa
8101       ccaattcaca gttaaagacc taaagaacg tatgcatgca cctgatggaa tgaatgcact
8161       tcgtgaacaa gtgattttca ttactcaagg tcaacaaact gaggaaacta gaaattttat
8221       ccagaacatg aaataaagcc tgaagattta acatataaag caatgttgaa aaatatggat
8281       actctcatga tggacttaat tgaaaatggt aaagacgcta acgaagtttt aaaaatgcca
8341       tttcattatg tgctttccat atatcaaaat aaaaataatg acatttctga agaaaaagca
8401       gaggctttaa ttgatgcatt ttaaccttaa ccgtttggtt agggttattt ttttgaactt
8461       ttttagaaag gaggtaaaaa atgggagaaa gaataaaagg tttatctata ggtttggatt
8521       tagatgcagc aaatttaaat agatcatttg cagaaatcaa acgaaacttt aaaactttaa
8581       attctgactt aaaattaaca ggcaacaact tcaaatatac cgaaaaatca actgatagtt
8641       acaaacaaag gattaaagaa cttgatggaa ctatcacagg ttataagaaa aacgttgatg
8701       atttagccaa gcaatatgac aaggtatctc aagaacaggg cgaaaacagt gcagaagctc
```

Figure 2D

```
8761    aaaagttacg acaagaatat aacaaacaag caaatgagct gaattattta gaaagagaat
8821    tacaaaaaac atcagccgaa tttgaagagt tcaaaaaagc tcaagttgaa gctcaaagaa
8881    tggcagaaag tggctgggga aaaaccagta aagtttttga aagtatggga cctaaattaa
8941    caaaaatggg tgatggttta aaatccattg gtaaaggttt gatgattggt gtaactgcac
9001    ctgttttagg tattgcagca gcatcaggaa aagcttttgc agaagttgat aaaggtttag
9061    atactgttac tcaagcaaca ggcgcaacag gcagtgaatt aaaaaaattg cagaactcat
9121    ttaaagatgt ttatggcaat tttccagcag atgctgaaac tgttggtgga gttttaggag
9181    aagttaatac aaggttaggt tttacaggta agaacttga aatgccaca gagtcattct
9241    tgaaattcag tcatataaca ggttctgacg gtgtgcaagc cgtacagtta attaccgtg
9301    caatgggcga tgcaggtatc gaagcaagtg aatatcaaag tgtttggat atggtagcaa
9361    aagcggcgca agctagtggg ataagtgttg atacattagc tgatagtatt actaaatacg
9421    gcgctccaat gagagctatg ggctttgaga tgaaagaatc aattgcttta ttctctcaat
9481    gggaaaagtc aggcgttaat actgaaatag cattcagtgg tttgaaaaaa gctatatcaa
9541    attggggtaa agctggtaaa aacccaagag aagaatttaa gaagacatta gcagaaattg
9601    aaaagacgcc ggatatagct agcgcaacaa gtttagcgat tgaagcattt ggtgcaaagg
9661    caggtcctga tttagcagac gctattaaag gtggtcgctt tagttatcaa gaattttaa
9721    aaactattga agattcccaa ggcacagtaa accaaacatt taaagattct gaaagtggct
9781    ccgaaagatt taaagtagca atgaataaat taaaattagt aggtgctgat gtatgggctt
9841    ctattgaaag tgcgtttgct cccgtaatgg aagaattaat caaaaagcta tctatagcgg
9901    ttgattggtt ttccaattta agtgatggtt ctaaagatc aattgttatt ttcagtggta
9961    ttgctgctgc aattggtcct gtagttttg ggttaggtgc atttataagt acaattggca
10021   atgcagtaac tgtattagct ccattgttag ctagtattgc aaaggctggt ggattgatta
10081   gttttttatc gactaaagta cctatattag gaactgtctt cacagcttta actggtccaa
10141   ttggcattgt attaggtgta ttggctggtt tagcagtcgc atttacaatt gcttataaga
10201   aatctgaaac atttagaaat tttgttaatg gtgcaattga aagtgttaaa caaacattta
10261   gtaattttat tcaatttatt caacctttcg ttgattctgt taaaacatc tttaaacaag
10321   cgatatcagc aatagttgat ttcgcaaaag atatttggag tcaaatcaat ggattcttta
10381   atgaaaacgg aatttccatt gttcaagcac ttcaaaatat atgcaacttt attaaagcga
10441   tatttgaatt tattttaaat tttgtaatta accaattat gttcgcgatt tggcaagtga
10501   tgcaatttat ttggccggcg gttaaagcct tgattgtcag tacttgggag aacataaaag
10561   gtgtaataca aggtgcttta aatatcatac ttggcttgat taagttcttc tcaagtttat
10621   tcgttggtga ttggcgagga gtttgggacg ccgttgtgat gattcttaaa ggagcagttc
10681   aattaatttg gaatttagtt caattatggt ttgtaggtaa aatacttggt gttgttaggt
10741   actttggcgg gttgctaaaa ggattgatag caggaatttg ggacgtaata agaagtatat
10801   tcagtaaatc tttatcagca atttggaatg caacaaaaag tatttttgga tttttattta
10861   atagcgtaaa atcaattttc acaaatatga aaaattggt atctaatact tggagcagta
10921   tccgtacgaa tacaatagga aaagcgcagt cattatttag tggcgtcaaa tcaaaattta
10981   ctaatttatg gaatgcgacg aaagaaattt ttagtaattt aagaaattgg atgtcaaata
11041   tttggaattc cattaaagat aatacggtag gaattgcaag ccgtttatgg agtaaggtac
11101   gtggaatttt cacaaatatg cgcgatggct tgagttccat tatagataag attaaaagtc
11161   atatcggcgg tatggtaagc gctattaaaa aaggacttaa taattaatc gacggtttaa
11221   actgggtcgg tggtaagttg gaatggata aaatacctaa gttacacact ggtacagagc
11281   acacacatac tactacaaga ttagttaaga acggtaagat tgcacgtgac acattcgcta
11341   cagttgggga taagggacgc ggaaatggtc caaatggttt tagaaatgaa atgattgaat
11401   tccctaacgg taaacgtgta atcacaccta atacagatac taccgcttat ttacctaaag
11461   gctcaaaagt atacaacggt gcacaaactt attcaatgtt aaacgaaacg cttccaagat
11521   ttagtttagg tactatgtgg aaagatatta aatctggtgc atcatcggca tttaactgga
11581   caaaagataa aataggtaaa ggtaccaaat ggcttggcga taaagttggc gatgttttag
11641   attttatgga aaatccaggc aaacttttaa attatatact tgaagctttt ggaattgatt
11701   tcaattcttt aactaaaggt atgggaattg caggcgacat aacaaaagct gcatggtcta
```

Figure 2E

```
11761    agattaagaa aagtgctact gattggataa aagaaaattt agaagctatg ggcggtggcg
11821    atttagtcgg cggaatatta gaccctgaca aaattaatta tcattatgga cgtaccgcag
11881    cttataccgc tgcaactgga agaccatttc atgaaggtgt cgattttcca tttgtatatc
11941    aagaagttag aacgccgatg ggtggcagac ttacaagaat gccatttatg tctggtggtt
12001    atggtaatta tgtaaaaatt actagtggcg ttatcgatat gctatttgcg catttgaaaa
12061    actttagcaa atcaccacct agtggcacga tggtaaagcc cggtgatgtt gttggtttaa
12121    ctggtaatac cggatttagt acaggaccac atttacattt tgaaatgagg agaaatggac
12181    gacatttga ccctgaacca tatttaagga atgctaagaa aaaggaaga ttatcaatag
12241    gtggtggcgg tgctacttct ggaagtggcg caacttatgc cagtcgagta atccgacaag
12301    cgcaaagtat tttaggtggt cgttataaag gtaaatggat tcatgaccaa atgatgcgcg
12361    ttgcaaaacg tgaaagtaac taccagtcaa atgcagtgaa taactgggat ataaatgctc
12421    aaagaggaga cccatcaaga ggattattcc aaatcatcgg ctcaactttt agagcaaacg
12481    ctaaacgtgg atatactaac tttaataatc cagtacatca aggtatctca gcaatgcagt
12541    acattgttag acgatatggt tggggtggtt ttaaacgtgc tggtgattac gcatatgcta
12601    caggtggaaa agtttttgat ggttggtata acttaggtga agacggtcat ccagaatgga
12661    ttattccaac agatccagct cgtagaaatg atgcaatgaa gattttgcat tatgcagcag
12721    cagaagtaag agggaaaaaa gcgagtaaaa ataagcgtcc tagccaatta tcagacttaa
12781    acgggtttga tgatcctagc ttattattga aatgattga acaacagcaa caacaaatag
12841    ctttattact gaaaatagca caatctaacg atgtgattgc agataaagat tatcagccga
12901    ttattgacga atacgctttt gataaaaagg tgaacgcgtc tatagaaaag cgagaaaggc
12961    aagaatcaac aaaagtaaag tttagaaaag gaggaattgc tattcaatga tagacactat
13021    taaagtgaac aacaaaacaa ttccttggtt gtatgtcgaa agagggtttg aaatacccctc
13081    ttttaattat gttttaaaaa cagaaaatgt agatggacgt tcgggggtcta tatataaagg
13141    gcgtaggctt gaatcttata gtttttgatat acctttggtg gtacgtaatg actatttatc
13201    tcacaacggc attaaaacac atgatgacgt cttgaatgaa ttagtaaagt tttttaacta
13261    cgaggaacaa gttaaattac aattcaaatc taaagattgg tactggaacg cttatttcga
13321    aggaccaata aagctgcaca aagaatttac aatacctgtt aagttcacta tcaaagtagt
13381    actaacagac ccttacaaat attcagtaac aggaaataaa aatactgcga tttcagacca
13441    agtttcagtt gtaaatagtg ggactgctga cactccttta attgttgaag cccgagcaat
13501    taaaccatct agttacttta tgattactaa aaatgatgaa gattatttta tggttggtga
13561    tgatgaggta accaaagaag ttaaggatta catgcctcct gtttatcata gtgagtttcg
13621    tgatttcaaa ggttggacta agatgattac tgaagatatt ccaagtaatg acttaggtgg
13681    taaggtcggc ggtgactttg tgatatccaa tcttggcgaa ggatataaag caactaattt
13741    tcctgatgca aaaggttggg ttggtgctgg cacgaaacga gggctcccta aagcgatgac
13801    agattttcaa attacctata aatgtattgt tgaacaaaaa ggtaaaggtg ccggaagaac
13861    agcacaacat atttatgata gtgatggtaa gttacttgct tctattggtt atgaaaataa
13921    atatcatgat agaaaaatag gacatattgt tgttacgttg tataaccaaa aaggagaccc
13981    caaaaagata tacgactatc agaataaacc gataatgtat aacttggaca gaatcgttgt
14041    ttatatgcgg ctcagaagag taggtaataa attttctatt aaaacttgga aatttgatca
14101    cattaaagac ccagatagac gtaaacctat tgatatggat gagaaagagt ggatagatgg
14161    cggtaagttt tatcagcgtc cagcttctat catagctgtc tatagtgcga agtataacgg
14221    ttataagtgg atggagatga atgggttagg ttcattcaat acggagattc taccgaaacc
14281    gaaaggcgca agggatgtca ttatacaaaa aggtgattta gtaaaaatag atatgcaagc
14341    aaaaagtgtt gtcatcaatg aggaaccaat gttgagcgag aaatcgtttg gaagtaatta
14401    tttcaatgtt gattctgggt acagtgaatt aatcatacaa cctgaaaacg tctttgatac
14461    gacggttaaa tggcaagata gatatttata gaaggagat gagtgtgaa tacatgttttt
14521    agattttaac gacaagatta tagatttcct ttctactgat gacccttcct tagttagagc
14581    gattcataaa cgtaatgtta atgacaattc agaaatgctt gaactgctca tatcatcaga
14641    aagagctgaa aagttccgtg aacgacatcg tgttattata agggattcaa acaaacaatg
14701    gcgtgaattt attattaact gggttcaaga tacgatggac ggctacacag agatagaatg
```

Figure 2F

```
14761    tatagcgtct tatcttgctg atataacaac agctaaaccg tatgcaccag gcaaatttga
14821    gaaaaagaca acttcagaag cattgaaaga tgtgttgagc gatacaggtt gggaagtttc
14881    tgaacaaacc gaatacgatg gcttacgtac tacgtcatgg acttcttatc aaactagata
14941    tgaagtttta aagcaattat gtacaaccta taaaatggtt ttagattttt atattgagct
15001    tagctctaat accgtcaaag gtagatatgt agtactcaaa aagaaaaaca gcttattcaa
15061    aggtaaagaa attgaatatg gtaaagattt agtcgggtta actaggaaga ttgatatgtc
15121    agaaatcaaa acagcattaa ttgctgtggg acctgaaaat gacaaaggga agcgtttaga
15181    gctagttgtg acagatgacg aagcgcaaag tcaattcaac ctacctatgc gctatatttg
15241    ggggatatat gaaccacaat cagatgatca aaatatgaat gaaacacgat taagttcttt
15301    agccaaaaca gagttaaata aacgtaagtc ggcagttatg tcatatgaga ttacttctac
15361    tgatttggaa gttacgtatc cgcacgagat tatatcaatt ggcgatacag tcagagtaaa
15421    acatagagat tttaacccgc cattgtatgt agaggcagaa gttattgctg aagaatataa
15481    cataatttca gaaaatagca catatacatt cggtcaacct aaagagttca aagaatcaga
15541    attacgagaa gagtttaaca agcgattgaa cataatacat caaaagttaa acgataatat
15601    tagcaatatc aacactatag ttaaagatgt tgtagatggt gaattagaat actttgaacg
15661    caaaatacac aaaagtgata caccgccaga aaatccagtc aatgatatgc tttggtatga
15721    tacaagtaac cctgatgttg ctgtcttgcg tagatattgg aatggtcgat ggattgaagc
15781    aacaccaaat gatgttgaaa aattaggtgg tataacaaga gagaaagcgc tattcagtga
15841    attaaacaat atttttatta atttatctat acaacacgct agtcttttgt cagaagctac
15901    agaattactg aatagcgagt acttagtaga taatgatttg aaagcggact tacaagcaag
15961    tttagacgct gtgattgatg tttataatca aattaaaaat aatttagaat ctatgacacc
16021    cgaaactgca acgattggtc ggttggtaga tacacaagct ttatttcttg agtatagaaa
16081    gaaattacaa gatgtttata cagatgtaga agatgtcaaa atcgccattt cagatagatt
16141    taaattatta cagtcacaat acactgatga aaaatataaa gaagcgttgg aataaatagc
16201    aacaaaattt ggtttaacgg tgaatgaaga tttgcagtta gtcggagaac ctaatgttgt
16261    taaatcagct attgaagcag ctagagaatc cacaaaagaa caattacgtg actatgtaaa
16321    aacatcggac tataaaacag acaaagacgg tattgttgaa cgtttagata ctgctgaagc
16381    tgagagaacg actttaaaag gtgaaatcaa agataaagtt acgttaaacg aatatcgaaa
16441    cggattggaa gaacaaaaac aatatactga tgaccagtta agtgatttgt ccaataatcc
16501    tgagattaaa gcaagtattg aacaagcaaa tcaagaagcg caagaagctt taaaatcata
16561    cattgatgct caagatgatc ttaaagagaa ggaatcgcaa gcgtatgctg atggtaaaat
16621    ttcggaagaa gagcaacgcg ctatacaaga tgctcaagct aaacttgaag aggcaaaaca
16681    aaacgcagaa ctaaaggcta gaaacgctga aaagaaagct aatgcttata cagacaacaa
16741    ggtcaaagaa agcacagatg cacagaggaa aacattgact cgctatggtt ctcaaattat
16801    acaaaatggt aaggaaatca aattaagaac tactaaagaa gagtttaatg caaccaatcg
16861    tacactttca aatatattaa acgagattgt tcaaaatgtt acagatggaa caacaatcag
16921    atatgatgat aacggagtgg ctcaagcttt gaatgtgggg ccacgtggta ttagattaaa
16981    tgctgataaa attgatatta acggtaatag agaaataaac cttcttatcc aaaatatgcg
17041    agataaagta gataaaaccg atattgtcaa cagtcttaat ttatcaagag agggtcttga
17101    tatcaatgtt aatagaattg gaattaaagg cggtgacaat aacagatatg ttcaaataca
17161    gaatgattct attgaactag gtggtattgt gcaacgtact tggagaggga aacgttcaac
17221    agacgatatt tttacgcgac tgaaagacgg tcacctaaga tttagaaata acaccgctgg
17281    cggttcactt tatatgtcac attttggtat ttcgacttat attgatggtg aaggtgaaga
17341    cggtggttca tctggtacga ttcaatggtg ggataaaact tacagtgata gtggcatgaa
17401    tggtataaca atcaattcct atggtggtgt cgttgcacta acgtcagata ataatcgggt
17461    tgttctggag tcttacgctt catcgaatat caaaagcaaa caggcaccgg tgtatttata
17521    tccaaacaca gacaaagtgc ctggattaaa ccgatttgca ttcacgctgt ctaatgcaga
17581    taatgcttat tcgagtgacg gttatattat gtttggttct gatgagaact atgattacgg
17641    tgcgggtatc aggttttcta aagaaagaaa taaggtcttt gttcaaattg ttaatggacg
17701    atatgcaaca ggtggagata caacaatcga agcagggtat ggcaaattta atatgctgaa
```

Figure 2G

```
17761    acgacgtgat ggtaataggt atattcatat acagagtaca gacctactgt ctgtaggttc
17821    agatgatgca ggagatagga tagcttctaa ctcaatttat agacgtactt attcggccgc
17881    agctaatttg catattactt ctgctggcac aattgggcgt tcgacatcag cgcgtaaata
17941    caagttatct atcgaaaatc aatataacga tagagatgaa caactggaac attcaaaagc
18001    tattcttaac ttacctatta gaacgtggtt tgataaagct gagtctgaaa ttttagctag
18061    agagctgaga gaagatagaa aattatcgga agcacacctat aaacttgata gatacgtagg
18121    tttgattgct gaagaggtgg agaatttagg attaaaagag tttgtcacgt atgatgacaa
18181    aggagaaatt gaaggtatag cgtatgatcg tctatggatt catcttatcc ctgttatcaa
18241    agaacaacaa ctaagaatca agaaattgga ggagtcaaag aatgcaggat aacaaacaag
18301    gattacaagc taatcctgaa tatacaattc attatttatc acaggaaatt atgaggttaa
18361    cacaagaaaa cgcgatgtta aaagcgtata tacaagaaaa taaagaaaat caacaatgtg
18421    ctgaggaaga gtaatcctta gcactatttt tatacaaaaa tttaaggagg tcatttaatt
18481    atggcaaaag aaattatcaa caatacagaa aggtttattt tagtacaaat cgacaaagaa
18541    ggtacagaac gtgtagtata tcaagatttc acaggaagtt ttacaacttc tgaaatggtt
18601    aaccatgctc aagattttaa atctgaagaa aacgctaaga aaattgcgga gacgttaaat
18661    ttgttatatc aattaactaa caaaaaacaa cgtgtgaaag tagttaaaga agtagttgaa
18721    agatcagatt tatctccaga ggtaacagtt aacactgaaa cagtatgaaa agctatgagt
18781    tagatactca tagtctttat tcttttagaa agcgggtgta ctgaattggg gtggttcaaa
18841    aaacacgaac atgaatggcg catcagaagg ttagaagaga atgataaaac aatgctcagc
18901    acactcaacg aaattaaatt aggtcaaaaa acccaagagc aagttaacat taaattagat
18961    aaaaccttag atgctattca aaaagaaaga gaaatagatg aaaagaataa gaaagaaaat
19021    gataagaaca tacgtgatat gaaaatgtgg gtgcttggtt tagttgggac aatatttggg
19081    tcgctaatta tagcattatt gcgtatgctt atgggcatat agagaggtg attaccatgt
19141    tcggattaaa ttttggagct tcgctgtgga cgtgtttctg gtttggtaag tgtaagtaat
19201    agttaagagt cagtgcttcg gcactggctt tttatttgg ataaaaggag caaacaaatg
19261    gatgcaaaag taataacaag atacatcgta ttgatcttag cattagtaaa tcaattctta
19321    gcgaacaaag gtattagccc aattccagta gacgatgaaa ctatatcatc aataatactt
19381    actgtagtcg ctttatatac aacgtataaa gacaatccaa catctcaaga aggtaaatgg
19441    gcaaatcaaa aattaaagaa atataaagct gaaaataagt atagaaaagc aacagggcaa
19501    gcgccaatta aagaagtaat gacacctacg aatatgaacg acacaaatga tttagggtag
19561    gtggttgata tatgttaatg acaaaaaatc aagcagaaaa atggtttgac aattcattag
19621    ggaaacaatt caacccagat ggttggtatg gatttcagtg ttatgattac gccaatatgt
19681    tctttatgtt agcgacaggc gaaaggctgc aaggtttata tgcttataat atcccgtttg
19741    ataataaagc aaagattgaa aaatatggtc aaataattaa aaactatgac agcttttac
19801    cgcaaaagtt ggatattgtc gttttcccgt caaagtatgg tggcggagct ggacacgttg
19861    aaattgttga gagcgcaaat ttaaatactt tcacatcatt tggtcaaaac tggaacggta
19921    aaggttggac taatggcgtt gcgcaacctg gttggggtcc tgaaactgtg acaagacatg
19981    ttcattatta tgacaatcca atgtatttta ttaggttaaa cttccctaac aacttaagcg
20041    ttggcaataa agctaaaggt attattaagc aagcgactac aaaaaaagag gcagtaatta
20101    aacctaaaaa aattatgctt gtagccggtc atggttataa cgatcctgga gcagtaggaa
20161    acggaacaaa cgaacgcgat tttatacgta aatatataac gcctaatatc gctaagtatt
20221    taagacatgc aggacatgaa gttgcattat acggtggctc aagtcaatca caagatatgt
20281    atcaagatac tgcatacggt gttaatgtag caataaaaa agattatggc ttatattggg
20341    ttaaatcaca ggggtatgac attgttctag aaatacattt agacgcagca ggagaaagcg
20401    caagtggtgg gcatgttatt atctcaagtc aattcaatgc agatactatt gataaaagta
20461    tacaagatgt tattaaaaat aacttaggac aaataagagg tgtgacacct cgtaatgatt
20521    tactaaatgt taatgtatca gcagaaataa atataaatta tcgtttatct gaattaggtt
20581    ttattactaa taaaaatgat atggattgga ttaagaaaaa ctatgacttg tattctaaat
20641    taatagccgg tgcgattcat ggtaagccta taggtggttt ggtagctggt aatgttaaaa
20701    catcagctaa aaacaaaaaa aatccaccag tgccagcagg ttatacactc gataagaata
```

Figure 2H

```
20761    atgtcccTta taaaaaagaa caaggcaatt acacagtagc taatgttaaa ggtaataatg
20821    taagagacgg ttattcaact aattcaagaa ttacagggGt attacccaac aacacaacaa
20881    ttacgtatga cggtgcatat tgtattaatg gttatagatg gattacttat attgctaata
20941    gtggacaacg tcgttatata gcgacaggag aggtagacaa ggcaggtaat agaataagta
21001    gttttggtaa gtttagcacg atttagtatt tacttagaat aaaaattttg ctacattaat
21061    tatagggaat cttacagtta ttaaataact atttggatgg atgttaatat tcctatacac
21121    tttttaacat ttctctcaag atttaaatgt agataacagg caggtacttc ggtacttgcc
21181    tattttttta tgttatagct agccttcggg ctagtttttt gttatgatgt gttacacatg
21241    catcaactat ttacatctat ccttgttcac ccaagcatgt cactggatgt tttttcttgc
21301    gatagagagc atagtttTca tactactccc cgtagtatat atgactttag cattcccgta
21361    taacagttta cggggtgctt ttatgttata attgctttta tatagtagga gtgaactata
21421    tagccgggca gaggccatgt atctgactgt tggtcccaca ggagacatct tccttgtcat
21481    cactcgatac atatatctta acaacataga aatgttacat tcgctataac cgtatcttaa
21541    tcgatacggt tatatttatt cccctacaac caacaaaacc acagatccta ttaatttagg
21601    attgtggtta ttttttgcgt ttttttgggg caaaaaaagg gcagattatt tgaaaaaggg
21661    caaacgcttg tggaaaagct aaaaggttaa aaatgacaaa aaccttgata caacagtgtt
21721    tttggacgct cgtgtacgtt agagaatgac cggtttacca tcatacaagg gtgggattaa
21781    cttgtgttaa aaagccttta atatcagttg ttacaaagga tttgtagcgt ctttaaaaat
21841    aaaaaagggc agaaaaaggg cagataccTT ttagtacaca agttttTcta attttTgctc
21901    taactctctg tccattttct ctgttacatg tgtatacacc ttTatagTcg tttttTcatc
21961    tgtatgtcct actctttTca taattgcttt taacgatata ttcatttccg ccaataaact
22021    tatgtgtgta tgccttagtg tgtgagtagt aactttttta tttatattta atgattctgc
22081    agctgaggac aatcgtttgt ttatcctact gccttgcata ggatttcctt ggcaagttgt
22141    gaatataaac cctctatcaa catagcttgg ttcccattgt tgcatctttt tatTttctaa
22201    cattattttt ttcaatacat ttgctatcct tgaattgatg gcgatttttc ttcttgaacc
22261    tgcggtctta gtagtatctt tgtgaccaaa tccagcatta catttgattc tgtgaatagt
22321    gccattaata gcgatcgttt tattTttgag gtcaacatct ttaacttgga gagctaataa
22381    ctcacctatg cgcatacctg ttaaagcttg aacttctaca gccccagcaa ctaaaatacg
22441    agctctatac tgcatgttat tatcgttcag tataaaatcg cgtatctgta ttacctgttc
22501    catctctaaa tagttataca ttttcgcttc ttcttttttct atatcttcta tcgtcttact
22561    cttctttggt agtgtgacgc tatttaatat gtgttcgttt ggataattgt aaaatttaac
22621    ggcgtattTa atagcttctt tcatatgtcc aagttgacgc tttacctgat ttgcagaata
22681    tacgtttgat aatttgttaa taaatgtttg catgtacttt gtatcaattt tgtttaaaag
22741    taaattttga gaactgttct ttttgatgtt tttgattctt gttttcaaat tatcaagcgt
22801    cgttacttta aagccagatg tttttTatatg atattcaagc cattcatcta ataacgcgtg
22861    aaaagtcaaa gttttTaatt cgcttgacga cttgttgTtt agttttTctt ttatttTttc
22921    ttctaaacga aacattgcct cttTttgcga ttgctttgta ttcttattca agacaacact
22981    tacacgtttc catttatctg tatacggatc tttgtatttc tcgtagtatc tatacttcgt
23041    ttcattgttc ttatttTtaa attttTcaaa ccacattTta catccctcct caaaattggc
23101    aaaaaataat aagggtaggc gggctaccca tgaaaattgt ataaaaaag acgcctgtat
23161    aaaatacaga cgccacttat aattataaga ttacatggtt aattaccaaa aatggtaacg
23221    aatatatacg tgttTaaag gataaaccTT taatatatTa aaattatatc atcttatatc
23281    agggatctgc aatatatTat tattaattct atttatcagt aacataatat ccgaagaatc
23341    tattactgga tttttaattt tttggggtaa aactttTctt atgcgaaact tactaatcgg
23401    ctggaaagaa tttatgcaag cgtaactatt accttTtaat ttttTtacct tatcaattgc
23461    tgatactatg ttattaatgt ttctgtcaat ttTatttaat ttatttTcaa tttctaaact
23521    atcagatata aattcaataa aataatcttt agtgatgaat tctgtgttgt tttttTggta
23581    tttTtTatcg aaaacttctt ttaatatagc tgaattattT tgcgcgctaa ttaaatttaa
23641    aaacaatctt aaataatact cccattTcaa atcaaaattc atctttaaat acttTtTgtt
23701    ttctttagag gataagggaa taacatTtac tatatcctcc gtattagaat cattTtTatt
```

Figure 2I

```
23761    catcactatt gcaaagtgtg aattagaaaa ttctttatta acgtttatac cgaaatctac
23821    aaaaactatt tctccttgtt taaactttgg ataaaaacct ttatggtttt tttcaccttc
23881    aaatctcttg agtaaatagt gaatatctga atctaacttt ttaaattttg gatttccaga
23941    agttttaat ttattaatgc gttttctat attatgcgtc atcatttctc ctttattctc
24001    gctcacactc tcaccaccat tcaacgtcta cacttgtagg cgttttttga ttagtaaaat
24061    cataatgaat cttctttggt taacttatcg ccatctattt tttgtgaaat aaattccaag
24121    tatttacgcg cattatgtga cgataaatct ttaggtaact cataagtgaa tggttgatta
24181    ccactagtta aaacttcata tactatagtt tcttttttta ttttgcaatt agttattttc
24241    attataaact cctttaaaac actgctgaaa tagacgtctt tttcaaataa gcatgattaa
24301    tactttaatt ctttaatcca catatattta aagtgaggt agtaggtaat aaatataaga
24361    cttaaagtta agattgcttt tttcatgtca atttctcctt tgtttatatt tatattaaag
24421    cgctaaatat acgttattaa tcacaataca actttgccca ttactttaat atcactaaac
24481    gaagcgactt tgatatcatc atacttcgga tttagagata ccaaattaat atagtcttcg
24541    catatatcta cacgcttgat aagacttact ccatctaata caacgagtgc aattgtacca
24601    tctttaatag aatcttcttt cttaataaaa gcgtatgttc cttgttttaa cataggttcc
24661    attgaatcac cattaactaa aatacaaaaa tcagcatttg atggcgtttc gtcttcttta
24721    aaaaatactt cttcatgcaa tatgtcatca tataattctt ctcctatgcc agcaccagtt
24781    gcaccacatg caatatacga tactagttta gactctttat attcatctat agaagtgact
24841    ttattctgtt catctaattg ctcatttgca tagttaagta cgttttcttg gcggggaggt
24901    gtgagttgag aaaatatgtt attgatttt gacattatcg tttcatcttg acgttcttcg
24961    tcaggaactc gataagaatc tacatcatac cccataagcc acgcttcacc gacatttaaa
25021    gttttagata ataagaataa tttatgttgg tctggagaag accttccatt aacatactgg
25081    gataagtgac tttttgacat tttaatatc aattctttt gaaagggttt cgactttct
25141    agaatatcta cttgacgcaa gttcctatct ttcataattt gttttaatct ttcagaagtg
25201    ttttgcattg gtaatgcctc cttgaaattc attatatagg aagggaaata aaaatcaata
25261    caaaagttca acttttttaa cttttgtgt tgacattgtt caaaattggg gttatagtta
25321    ttatagttca aatgtttgaa cttaggaggt gattatttga atactaatac aactttgat
25381    ttttcgttat tgaacggtaa gatagtcgaa gtgtactcga cacaatttaa ctttgctata
25441    gctttaggtg tatcagaaag aactttgtct ttgaagttga acaacaaagt accatggaaa
25501    acaacagaca ttattaaagc ttgtaagtta ttgggaatac ctataaaaga tgttcacaaa
25561    tattttttta aacagaaagt tcaaatgttt gaacttaata agtaaaggag gcataacaca
25621    tgcaagaacg agaaaaggtt aataaaagta acacatcttc aaatgaagca tcaaaaccctt
25681    ttaggacaaa ttgaagctta cgacaaaacg cttaaagaaa taaagtacac tcgagacctt
25741    tacaacaaac acctaagcat gaacaacgaa gacgcattcg ctggtttgga aatggtagag
25801    gatgaaatta ctaaaaagct acgaagtgct atcaaagagt tccaaaaagt agtgaaagcg
25861    ttagacaagc ttaacggtgt tgaaagcgat aacaaagtta ctgatttaac agagtggcgg
25921    aaagtgaatc agtaacattc acttcttaat ataaccacgc ttatcaacat ccacattgag
25981    cagatgtgag cgagagctgg cgatgatatg agccgcgttt aaatacattc gatagtcatt
26041    gcgataaccg tctgctgaat gtgggtgttg aggaaaaagg aggatactca aatgcaagca
26101    ttacaaacat taattttaa agagctacca gtaagaacag tagaaattga aaacgaacct
26161    tatttgtag gaaaagatat tgctgagatt ttaggatatg caagatcaaa caatgccatt
26221    agaaatcatg ttgatagcga ggacaagctg acgcaccaat ttagtgcatc aggtcaaaac
26281    agaaatatga tcattatcaa cgaatcagga ttatacagtc taatcttcga tgcttctaaa
26341    caaagcaaaa acgaaaaaat tagagaaacc gctagaaaat tcaaacgctg ggtaacatca
26401    gatgtcctac cagctattcg caaacacggt atatacgcaa cagacaatgt aattgaacaa
26461    acattaaaag atccagacta catcattaca gtgttgactg agtataagaa agaaaaagag
26521    caaaacttac ttttacaaca gcaagtagaa gttaacaaac caaagtatt attcgctgac
26581    tcggtagctg gtagtgataa ttcaatactt gttggagaac tagcgaaaat acttaaacaa
26641    aacggtgttg atataggaca aaacagattg ttcaaatggt taagaaataa tggatatctc
26701    attaaaaaga gtggagaaag ttataactta ccaactcaaa agagtatgga tctaaaaatc
```

Figure 2J

```
26761    ttggatatca aaaaacgaat aattaataat ccagatggtt caagtaaagt atcacgtaca
26821    ccaaaagtaa caggcaaagg acaacaatac tttgttaata agtttttagg agaaaaacaa
26881    acatcttaaa aggaggaaca caatggaaca aatcacatta accaaagaag agttgaaaga
26941    aattatagca aaagaagtta gagaggctat aaatggcaag aaaccaatca gttcaggttc
27001    aattttcagt aaagtaagaa tcaataatga cgatttagaa gaaatcaata aaaaactcaa
27061    tttcgcaaaa gatttgtcgc taggaagatt gaggaagctc aatcatccga ttccgctaaa
27121    aaagtatcag catggcttcg aatcaattca tcaaaaagct tatgtacaag atgttcatga
27181    ccatattaga aaattaacat tatcaatttt tggagtgaca cttaattcag acttgagtga
27241    aagtgaatac aacctagcag caaaagttta tcgagaaatc aaaaactatt atttatacat
27301    ctatgaaaag agagtttcag aattaactat cgatgatttc gaataaagga ggaacaacaa
27361    atgttacaaa aatttagaat tgcgaaagaa aaaaataaat taaaactcaa attactcaag
27421    catgctagtt actgtttaga aagaaacaac aaccctgaac tgttgcgagc agttgcagag
27481    ttgttgaaaa aggttagcta aattcaacgg taaggatttg ccctgcctcc acacttagag
27541    tttgagatcc aacaaacaca taagttttag tagggtctag aaaaaatgtt tcgatttcct
27601    cttttgtaac agtttcaatt ccttcatatc ctggaaaaac aatttttcttt aaatccgaaa
27661    catgtttttt tgaaccatcc tttaaagtaa ctagaagttt catacttatc acctccttag
27721    gttgataaca acattataca cgaaggagc ataaacaata tgcaagcatt acaaacaaat
27781    tcgaacatcg gagaaatgtt caatattcaa gaaaagaaa atggagaaat cgcaatcagc
27841    ggtcgagaac ttcatcaagc attagaagtt aagacagcat ataagattg gtttccaaga
27901    atgcttaaat acggatttga agaaaataca gattacacag ctatcgctca aaaaagagca
27961    acagctcaag gcaatatgac tcactatatt gaccacgcac tcacactaga cactgcaaaa
28021    gaaatcgcaa tgattcaacg tagtgaacct ggcaaacgtg caagacaata tttcatccaa
28081    gttgaaaaag catggaacag cccagaaatg attatgcaac gtgctttaaa aattgctaac
28141    aacacaatca atcaattaga aacaaagatt gcacgtgaca aaccaaaaat tgtatttgca
28201    gatgcagtag ctactactaa gacatcaatt ttagttggag agttagcaaa gatcattaaa
28261    caaaacggta taaacatcgg gcaacgcaga ttgtttgagt ggttacgtca aaacggattc
28321    cttattaaac gcaagggtgt ggattataac atgcctacac agtattcaat ggaacgtgag
28381    ttattcgaaa ttaaagaaac atcaatcaca cattcggacg tcacacatc aattagtaag
28441    acgccaaaag taacaggtaa aggacaacaa tactttgtta acaagttttt aggagaaaaa
28501    caaacaactt aataggagga attacaaatg aacgcactat acaaaacaac cctcctcatc
28561    acaatggcag ttgtgacgtg aaggtttgg aagattgaga agcacactag aaaacctgtg
28621    attagtagca gggcgttgag tgactatcta acaacaaat ctttaaccat accgaaagat
28681    gctgaaaatt ctactgaatc tgctcgtcgc cttttgaagt tcgccgaaca aactattagc
28741    aaataacaac attatacacg aaggaaaga tagaaatgcc aaaaatcata gtaccaccaa
28801    caccagaaaa cacatataga ggcgaagaaa aatttgtgaa aaagttatac gcaacaccta
28861    cacaaatcca tcaattgttt ggagtatgta gaagtacagt atacaactgg ttgaaatatt
28921    accgcaaaga taatttaggt gtagaaaatt tatacattga ttattcacca acaggcactc
28981    tgattaatat ttctaaattg gaagagtatt tgatcagaaa gcataaaaaa tggtattagg
29041    aggatattaa atgagcaaca tttataaaag ctacctagta gcagtattat gcttcacagt
29101    cttagcgatt gtacttatgc cgtttctata cttcactaca gcatggtcaa ttgcgggatt
29161    cgcaagtatc gcaacattca tgtactacaa agaatgcttt tcaaagaat aaaaaaactg
29221    ctacttgttg gagcaagtaa cagtatcaaa cacttaagaa aaaattcatg ttcaatataa
29281    aacgaaaaac ggaggaagtc aagatgtatt acgaaatagg cgaaatcata cgcaaaaata
29341    ttcatgttaa cggattcgat tttaagctat tcattttaaa aggtcatatg gcatatcaa
29401    tacaagttaa agatatgaac aacgtaccaa ttaaacatgc ttatgtcgta gatgagaatg
29461    acttagatat ggcatcagac ttatttaacc aagcaataga tgaatggatt gaagagaaca
29521    cagacgaaca ggacagacta attaacttag tcatgaaatg gtaggaggtc gctatgaagc
29581    agactgtaac ttatatcatt cgtcataggg atatgccaat ttatataact aacaaaccaa
29641    ctgataacaa ttcagatatt agttactcca caaatagaaa tagagctagg gagtttaacg
29701    gtatggaaga agcgagtatc aatatggatt atcacaaagc aatcaagaaa acagtgacag
```

Figure 2K

```
29761    aaactattga gtacgaggag gtagaacatg actgaggaaa aacaagaacc acaagaaaaa
29821    gtaagcatac tcaaaaaact aaagataaat aatatcgctg agaaaaataa aaggaaattc
29881    tataaatttg cagtatacgg aaaaattggc tcaggaaaaa ccacgtttgc tacaagagat
29941    aaagacgctt tcgtcattga cattaacgaa ggtggaacaa cggttactga cgaaggatca
30001    gacgtagaaa tcgagaacta tcaacacttt gtttatgttg taaattttt  acctcaaatt
30061    ttacaggaga tgagagaaaa cggacaagaa atcaatgttg tagttattga aactattcaa
30121    aaacttagag atatgacatt gaatgatgtg atgaaaaata agtctaaaaa accaacgttt
30181    aatgattggg gagaagttgc tgaacgaatt gtcagtatgt acagattaat aggaaaactt
30241    caagaagaat acaaattcca ctttgttatt acaggtcatg aaggtatcaa caaagataaa
30301    gatgatgaag gtagcactat caaccctact atcactattg aagcgcaaga acaaattaaa
30361    aaagctatta cttctcaaag tgatgtgtta gctagggcaa tgattgaaga atttgatgat
30421    aacggagaaa agaaagctag atatattcta aacgctgaac cttctaatac gtttgaaaca
30481    aagattagac attcaccttc aataacaatt aacaataaga aatttgcaaa tcctagcatt
30541    acggacgtag tagaagcaat tagaaatgga aactaaaaat taattaaaag gacggtattt
30601    aattatgaaa atcacaggac aagcgcaatt tactaaagaa acaaatcaag aaaagtttta
30661    taacggctca gcagggtttc aagctggaga attcacagtg aaagttaaaa atattgaatt
30721    caatgataga gaaaatagat atttcacaat cgtatttgaa aatgatgaag gcaaacaata
30781    taaacataat caatttgtac cgccgtataa atatgatttc caagaaaaac aattgattga
30841    attagttact cgattaggta ttaagttaaa tcttcctagc ttagattttg ataccaatga
30901    tcttattggt aagtttgtc acttggtatt gaaatggaaa ttcaatgaag atgaaggtaa
30961    gtattttacg gattttcat ttattaaacc ttacaaaaag ggcgatgatg ttgttaacaa
31021    acctattccg aagacagata agcaaaaagc tgaagaaaat aacggggcac aacaacaaac
31081    atcaatgtct caacaaagca atccatttga aagcagtggc caatttggat atgacgacca
31141    agatttagcg ttttaaggtg tggtttaaat gcaatacatt acaagatacc agaaagataa
31201    cgacggtact tattccgtcg ttgctactgg tgttgaactt gaacaaagtc acattgactt
31261    actagaaaac ggatatccac taaaagcaga agtagaggtt ccggacaata aaaaactatc
31321    tatagaacaa cgcaaaaaaa tattcgcaat gtgtagagat atagaacttc actggggcga
31381    accagtagaa tcaactagaa aattattaca aacagaattg gaaattatga aaggttatga
31441    agaaatcagt ctgcgcgact gttctatgaa agttgcaagg gagttaatag aactgattat
31501    agcgtttatg tttcatcatc aaatacctat gagtgtagaa acgagtaagt tgttaagcga
31561    agataaagcg ttattatatt gggctacaat caaccgcaac tgtgtaatat gcggaaagcc
31621    tcacgcagac ctggcacatt atgaagcagt cggcagaggc atgaacagaa acaaaatgaa
31681    ccactatgac aaacatgtat tagcgttatg tcgcgaacat cacaacgagc aacatgcgat
31741    tggcgttaag tcgtttgatg ataaatacca cttgcatgac tcgtggataa aagttgatga
31801    gaggctcaat aaaatgttga aaggagagaa aaaggaatga atagactaag aataataaaa
31861    atagcactcc taatcgtcat cttggcggaa gagattagaa atgctatgca tgctgtaaaa
31921    gtggagaaaa ttttaaaatc tccgtttagt taatacagat ttttacaaaga gctttaccat
31981    aggcggacaa actaattgag cctttttga tgtctattac ccaggggctg taatgtaact
32041    ttaatacttc aaattcaatg ccagaaagtt tacttattgt ttctaggttg tgtcctgact
32101    ttaacattct tttaacaaat tctaatcccg aaacaaatct ttgttttct  ataatcttat
32161    taaagtgatt taaaaactga ggagcataaa acttattata aattccttt  tttgttaagt
32221    aagacatgtc aaaagtttca tttaaaaccc ctaaccttac taggttatta attgaaattt
32281    cggttgattc tatatctaac ggagagtctt ttattaacgt gtccgatata ttcataccgt
32341    cattctttgg gtttaaaacc gctctatatt taacggcagg atgtacttcg tgattcttta
32401    aatgttttaa aagaatagca tcatttgggg ataattgttt aattatttca acaaatgaat
32461    ggtgggttaa tgagtttttt ctgtcatcca tagatgatgc tattagtttt gcgaacatat
32521    tacttaaagt tttttcacta atgtaaaact ttgaagcttc tagcagga cctagaagag
32581    aaaattgtgg ttcttgtaaa ttattttag gtacagaaga tatttctttt ttaaattgtt
32641    ctttgaattt ttcaaattct acttctcttt gataaataac tttatccaca taaggtgga
32701    atttcccaaa gacaagttcc caagttttag agaatgtttc tacaggccct tttgatgcgc
```

Figure 2L

```
32761    cttcaataat tttatcaata cctttaccta aaataggatc cataattatt caccccaat
32821    ctaacgcaat agcgataata aaattatacc agaaaggaga atcaacatga ctgaccaacc
32881    aagttactac tcaataatta cagcaaatgt cagatacgat aaccgactta ctgacagcga
32941    aaagttactt tttgcagaaa taacatcttt aagtaacaaa tacggatact gcacagcaag
33001    taatggttac tttgcaactt tatacaacgt tgttaaggaa actatatctc gtagaatttc
33061    gaaccttacc aactttggtt atctaaaaat cgaaattatc aagaaggta atgaagttaa
33121    acaaggaag atgtacccct tgacgcaaac gtcaatacct attgacgcaa aaatcaatac
33181    ccctattgat aattctgtca atacccctat tgacgcaaat gtcaaagaga atattacaag
33241    tattaataat acaagtaata acaatataaa tagaatagat atattgtcgg gcaacccgac
33301    agcatcttct atacccctata aagaaattat cgattactta aacaaaaaag cgggcaagca
33361    ttttaaacac aatacagcta aaacaaaaga ttttattaaa gcaagatgga atcaagattt
33421    taggttggag gattttaaaa aggtgattga tatcaaaaca gctgagtggc taaacacgga
33481    tagcgataaa taccttagac cagaaacact ttttggcagt aaatttgagg ggtacctcaa
33541    tcaaaaaata caaccaactg gcacggatca attggaacgc atgaagtacg acgaaagtta
33601    ttgggattag ggggatatta tgaaccact attcagcgaa aagataaacg aaagcttgaa
33661    aaaatatcaa cctactcatg tcgaaaagg attgaaatgt gagagatgtg gaagtgaata
33721    cgacttatat aagtttgctc ctactaaaaa acacccgaat ggttacgagt ataaagacgg
33781    ttgcaaatgt gaaatctatg aggaatataa gcgaaacaag caacggaaga taaacaacat
33841    attcaatcaa tcaaacgtta atccgtcttt aagagatgca acagtcaaaa actacaagcc
33901    acaaaatgaa aaacaagtac acgctaaaca aacagcaata gagtacgtac aaggcttctc
33961    tacaaaagaa ccaaaatcat taatattgca aggttcatac ggaactggta aaagccacct
34021    agcatacgct atcgcaaaag cagtcaaagc taaagggcat acggttgctt ttatgcacat
34081    accaatgttg atggatcgta tcaaagcgac atacaacaaa aatgcagtag agactacaga
34141    cgagctagtc agattgctaa gtgatattga tttacttgta ctagatgata tgggtgtaga
34201    aaacacagag cacactttaa ataaactttt cagcattgtt gataacagag taggtaaaaa
34261    caacatcttt acaactaact ttagtgataa agaactaaat caaaatatga actggcaacg
34321    tataaattcg agaatgaaaa aagagcaag aaaagtaaga gtaatcggag acgatttcag
34381    ggagcgagat gcatggtaac caaagaattt ttaaaaacta aacttgagtg ttcagatatg
34441    tacgctcaga aactcataga tgaggcacag ggcgatgaaa ataggttgta cgacctattt
34501    atccaaaaac ttgcagaacg tcatacacgc cccgctatcg tcgaatatta aggagtgtta
34561    aaaatgccga aagaaaaata ttacttatac cgagaagatg gcacagaaga tattaaggtc
34621    atcaagtata aagacaacgt aaatgaggtt tattcgctca caggagccca tttcagcgac
34681    gaaaagaaaa ttatgactga tagtgaccta aaacgattca aaggcgctca cgggcttcta
34741    tatgagcaag aattaggttt acaagcaacg atatttgata tttagaggtg gacgatgagt
34801    aaatacaacg ctaagaaagt tgagtacaaa ggaattgtat ttgatagcaa agtagagtgt
34861    gaatattacc aatatttaga aagtaatatg aatggcacta attatgatca tatcgaaata
34921    caaccgaaat tcgaattatt accaaaacta gataaacaac gaaagattga atatattgca
34981    gacttcgcgt tatatctcga tggcaaactg attgaagtta tcgacattaa aggtatgcca
35041    accgaagtag caaaacttaa agctaagatt ttcagacata aatacagaaa cataaaactc
35101    aattggatat gtaaagcgcc taagtataca ggtaaaacat ggattacgta cgaggaatta
35161    attaaagcaa gacgagaacg caaaagagaa atgaagtgat ctaatgcaac aacaagcata
35221    tataaatgca acgattgata taaggatacc tacagaagtt gaatatcagc attttgatga
35281    tgtggataaa gaaaagaag cgctggcaga ttacttatat aacaatcctg acgaaatact
35341    agagtatgac aatttaaaaa ttagaaacgt aaatgtagag gtggaataaa tgggcagtgt
35401    tgtaatcatt aataataaac catataaatt taacaatttt gaaaaagaa ataatggcaa
35461    agcgtgggat aaatgctgga attgttctaa acgtgttag aggttgttgg gagttttcag
35521    aagctttaga cgcgccttat ggcatgcacc taaaagaata tagagaaatg aaacaaatgg
35581    aaaagattaa acaagcgaga ctcgaacgtg aattggaaag agcgaaag aaagaggctg
35641    agctacgtaa gaagaagcca catttgttta atgtacctca aaaacattca cgtgatccgt
35701    actggttcga tgtcacttat aaccaaatgt tcaagaaatg gagtgaagca taatgagcat
```

Figure 2M

```
35761     aatcagtaac agaaaagtag atatgaacaa aacgcaagac aacgttaagc aacctgcgca
35821     ttacacatac ggcgacattg aaattataga ttttattgaa caagttacgg cacagtaccc
35881     accacaatta gcattcgcaa taggtaatgc aattaaatac ttgtctagag caccgttaaa
35941     gaatggtcat gaggatttag caaaggcgaa gttttacgtc gatagagtat ttgacttgtg
36001     ggagtgatga ccatgacaga tagcggacgt aaagaatact taaaacattt tttcggctct
36061     aagagatatc tgtatcagga taacgaacga gtggcacata tccatgtagt aaatggcact
36121     tattactttc acggtcatat cgtgccaggt tggcaaggtg tgaaaagac atttgataca
36181     gcggaagagc ttgaaacata tataaagcaa agtgatttgg aatatgagga acagaagcaa
36241     ctaactttat tttaaaaggg cggaaacaat gaaaatcaaa attgaaaaag aaatgaattt
36301     acctgaactt atccaatggg cttgggataa ccccaagtta tcaggtaata aaagattcta
36361     ttcaaatgat gttgagcgca actgttttgt gacttttcat gttgatagca tcttatgtaa
36421     tgtgactgga tatgtatcaa ttaacgataa atttactgtt caagaggaga tataacaatg
36481     aaaatcaaag ttaaaaaaga aatgagatta gatgaattaa ttaaatgggc gcgagaaaat
36541     ccggatctat cacaaggaaa aatatttttt tcaacaggat ttagtgatgg attcgttcgt
36601     tttcatccaa atacaaataa gtgttcgacg tcaagtttta ttccaattga tatccccttc
36661     atagttgata ttgaaaaaga agtaacggaa gagactaagg ttgataggtt gattgaatta
36721     ttcgagattc aagaaggaga ctataactct acactatatg agaacactag tataaaagaa
36781     tgtttatatg gcagatgtgt gcctaccaaa gcattctaca tcttaaacga tgacctaact
36841     atgacgttaa tctggaaaga tggggagttg ctagtatgat gttgaaattt aaagcttggg
36901     ataaagataa aaaagttatg agtattattg acgaaatcga ttttaatagt gggtacattt
36961     tgatttcaac aggttataaa agtttcaatg aagtaaaact attacaatac acaggattta
37021     aagatgtgca cggtgtggag atttatgaag gggatattgt tcaagattgt tattcgagag
37081     aagtaagttt tatcgagttt aaagaaggag cctttttatat aacttttagc aatgtaactg
37141     aattactaag tgaaaatgac gatattattg aaattgttgg aaatattttt gaaaatgaga
37201     tgctattgga ggttatgaga tgacgttcac cttatcagat gaacaatata aaaatctttg
37261     tactaactct aacaagttat tagataaact tcacaaagca ttaaaagatc gtgaagagta
37321     caagaagcaa cgagatgagc ttattgggga tatagcgaag ttacgagatt gtaacaaaga
37381     tctagagaag aaagcaagcg catgggatag gtattgcaag agcgttgaaa aagatttaat
37441     aaacgaattc ggtaacgatg atgaaagagt taaattcgga atggaattaa acaataaaat
37501     ttttatggag gatgacacaa atgaataatc gcgaaaaaat cgaacagtcc gttattagtg
37561     ctagtgcgta taacggtaat gacacagagg ggttgctaaa agagattgag gacgtgtata
37621     agaaagcgca agcgtttgat gaaatacttg agggaatgac aaatgctatt caacattcag
37681     ttaaagaagg tattgaactt gatgaagcag tagggattat ggcaggtcaa gttgtctata
37741     aatatgagga ggaataggaa aatgactaac acattacaag taaaactatt atcaaaaaat
37801     gctagaatgc ccgaacgaaa tcataagacg gatgcaggtt atgacatatt ctcagctgaa
37861     actgtcgtac tcgaaccaca agaaaaagca gtgatcaaaa cagatgtagc tgtgagtata
37921     ccagagggct atgtcggact attaactagt cgtagtggtg taagtagtaa aacgtattta
37981     gtgattgaaa caggcaagat agacgcggga tatcatggca atttagggat taatatcaag
38041     aatgatgaag aacgtgatgg aataccctt ttatatgatg atatagacgc tgaattagaa
38101     gatggattaa taagcatttt agatataaaa ggtaactatg tacaagatgg aagaggcata
38161     agaagagttt accaaatcaa caaaggcgat aaactagctc aattggttat cgtgcctata
38221     tggacaccgg aactaaagca agtggaggaa ttcgaaagtg tttcagaacg tggagcaaaa
38281     ggcttcggaa gtagcggagt gtaaagacat cttagatcga gttaaggagg ttttggggaa
38341     gtgacgcaat acttagtcac aacattcaaa gattcaacag gacgaccaca tgaacatatt
38401     actgtggcta gagataatca gacgttaca gttattgagg cagagagtaa agaagaagcg
38461     aaagagaagt acgaggcaca agttaaaaga gatgcagtta ttaaagtggg tcagttgtat
38521     gaaaatataa gggagtgtgg gaaatgacgg atgttaaaat taaaactatt tcaggtggag
38581     tttatttgt aaaaacagct gaacctttg aaaaatatgt tgaaagaatg acgagttta
38641     atggttatat ttacgcaagt actataatca agaaaccaac gtatattaaa acagatacga
38701     ttgaatcaat cacacttatt gaggagcatg ggaaatgaat cagctgagaa ttttattaca
```

Figure 2N

```
38761     tgacggtagt agtttgatat tacatgaaga tgaattattt aacgaaatag tatttgtttt
38821     ggacaatttt agaaatgatg atgactattt aacgatagaa aaagattatg gcagagaact
38881     tgtattgaac aaaggttata tagttgggat caatgttgag gaggcagatg atgattaaca
38941     tacctaaaat gaaattcccg aaaaagtaca ctgaaataat caaaaaatat aaaaataaag
39001     cacctgaaga aaaggctaag attgaagatg attttattaa agaaattaaa gataaagaca
39061     gtgaatttta cagtcctacg atggctaata tgaatgaata tgaattaagg gctatgttaa
39121     gaatgatgcc tagtttaatt gatactggag atgacaatga tgattaaaaa acttaaaaat
39181     atggatgggt tcgacatctt tattgttgga atactgtcat tattcggtat attcgcattg
39241     ctacttgtta tcacattgcc tatctataca gtggctagtt accaacacaa agaattacat
39301     caaggaacta ttacagataa atataacaag agacaagata aagaagacaa gttctatatt
39361     gtattagaca acaaacaagt cattgaaaat tccgacttat tattcaaaaa gaaatttgat
39421     agcgcagata tacaagctag gttaaaagta ggcgataagg tagaagttaa aacaatcggt
39481     tatagaatac acttttaaa tttatatccg gtcttatacg aagtaaagaa ggtagataaa
39541     caatgattaa acaaatacta agactattat tcttactagc aatgtatgag ttaggtaagt
39601     atgtaactga gcaagtgtat attatgatga cggctaatga tgatgtagag gcgccgagtg
39661     attacgtctt tcgagcggag gtgagtgaat aatgagaata tttatttatg atttgatcgt
39721     tttgctgttt gctttcttaa tatccatata tattattgat gatggagtga taataaatgc
39781     attaggaatt tttggtatgt ataaaattat agattccttt tcagaaaata ttataaagag
39841     gtagataaaa atgaacgagc aaataatagg aagcatatat actttagcag gaggtgttgt
39901     gctttattca gttaaagaga ttttttaggta ttttacagat tctaacttac aacgtaaaaa
39961     aatcaattta gaacaaatat atccgatata tttagattgt tttaaaaagg ctaaaaagat
40021     gattggagct tatattattc caacagaaca gcatgaattt ttagattttt ttgatattga
40081     agtctttaat aatttagata agcaaagtaa aaaagcgtat gaaatgtta ttggatttag
40141     acaaatgatt aatttatcaa atagagttaa ggcaatggaa gattttaaga tgagtttcaa
40201     caatgaattt agtacaaatc agattttttt taatccttct tttgttatgg aaacaattgc
40261     tattataaat gaatatcaaa aagatatatc ttatttaaaa aatataatta ataaaatgaa
40321     tgaaaataga gcttataatc atattgatag ttttatcact tcagagtacc gacgaaaaat
40381     aaacgattat aatctttatc ttgataaatt tgaagaacag tttagtcaaa agtttaaaat
40441     aaacagaact tcgataaaag aaagaattat tattaattta aacaagagga gatttaaatg
40501     atgtggatta ctatgactat tgtatttgct atattgctat tagtttgtat cagtattaat
40561     agtgatcgtg caagagagat acaagcactt agatatatga atgattatct acttgatgaa
40621     gtagttaaaa ctaaagggta caacgggtta gaagaataca ggattgaatt gaagcgaatg
40681     aataacgata ttaaaaagta atttatatta tcggaggtat tgcattgaat gataaagatt
40741     gagaaacacg atatcaaaaa gcttgaagaa tacattcagc acatcgataa ctatcgaaga
40801     gagttgaaga tgcgagaata tgaattactt gaaagtcatg aaccagataa tgcgggagct
40861     ggcaaaagta atttgccggg taacccgatt gaacgatgtg caataaagaa gtttagtgat
40921     aacaggtaca atacattaag aaatatagtt aacggtgtag atagattgat aggtgaaagt
40981     gatgaggata cgcttgagtt attaaggttt agatattggg attgtcctat tggttgttat
41041     gaatgggaag atatagcaca ttactttggt acaagtaaga caagtatatt acgtagaagg
41101     aatgcactga tcgataagtt agcaaagtat attggttatg tgtagcggac ttttacccta
41161     tgtaagtccg cattaaaaca gtttattatg ttagtatcag attaatattt aaagttatta
41221     aatgctaata cgacgcatga acaagaggcg catcactatg tgatgtgtct ttttatttat
41281     gaggtatgaa catgttcaaa ctaattgtaa atacattact acacatcaag tatagatgga
41341     tcttgatact acttaagtta tataaggtga aacattatga ttgactaaaga cgaacgtata
41401     cgattctata agtctaaaga atggcaaata acaagaaaaa gagtgctaga aagagataat
41461     tatgaatgtc aacaatgtaa gagagacggc aagttaacga catatgacaa aagcaagcgt
41521     aagtcgttgg atgtagatca tatattatcg ctagaacatc atccggagtt tgctcatgac
41581     ttaaacaatt tagaaacact gtgtattaaa tgtcacaaca aaaagaaaa gagatttata
41641     aaaaagaaa ataaatggaa agacgaaaaa tggtaaatac ccccgggtca aaaaaatcaa
41701     aagcgat
```

Phage: Bacteriophage 77. Minimal ORF size: 33 a.a. Orfs "with" RBS. Number of ORFs: 99.

Figure 4

SEQ ID NO:4 (P77ORF104)

```
1      atggtaacca aagaattttt aaaaactaaa cttgagtgtt cagatatgta cgctcagaaa
61     ctcatagatg aggcacaggg cgatgaaaat aggttgtacg acctatttat ccaaaaactt
121    gcagaacgtc atacacgccc cgctatcgtc gaatattaa
```

SEQ ID NO:5 (P77ORF104)

1      MVTKEFLKTK LECSDMYAQK LIDEAQGDEN RLYDLFIQKL AERHTRPAIV EY

Figure 5

Predicted tryptic peptide masses of conceptual ORF in Contig 1383:

```
1     MGGGQSIMKqfkSIINTSQDFEKrIEKikK        30
31    evindpdvkQFLEAHRaeltnamidedlnv        60
61    lqeykDQQKhydghkFADCPNFVKghvpel        90
91    yvdnnrIKirYLQCPCKikYDEERfeaeli       120
121   tshhmqrDTLNAKlkDIYMNHRdrlDVAMA       150
151   ADDICTAITNGEQVKglylygpfgtgkSFI       180
181   LGAIANQLKskKvrSTIIYLPEFIRtlkGG       210
211   FKdgsfekKlhrVReanilmlddigaeevt       240
241   pwvrDEVIGPLLHYRmvhelptffssnfdy       270
271   selehhlamtrDGEEKtkAARiierVKsls       300
301   tpyflsgenfrNN
```

Tryptic peptide fragment:

GHVPELYVDNNR      Predicted peptide mass MH+ = 1413.538

STIIYLPEFIR       Predicted peptide mass MH+ = 1352.6221

SLSTPYFLSGENFR    Predicted peptide mass MH+ = 1618.7923

Figure 6A

Optimal global alignment
Sequence 1 SEQ ID NO: 6    DnaC nucleotide *B. subtilis* (1471 letters)
Sequence 2 SEQ ID NO: 7    DnaC nucleotide *S. aureus* (1513 letters)

```
seq1    1 AT-GACAGACCTTCTGAATGACCGGCTTC---CTCCGCAAAATATAGAAGCCGAACAAGC  56
          || || |||    || |||| |    ||      ||||| ||   ||||||| ||||| |
seq2    1 ATGGATAGA----ATGTATGAGCAAAATCAAATGCCGCATAACAATGAAGCTGAACAGTC  56 seq1   57 CGTGTTAGGCGCTATTTTTTTACAGCC-GTCTGCTTTAACACTGGCTTCAGAAGTATTGA  115
          | | |||||  | ||| ||| |   || || |||    || |  || || ||  || ||
seq2   57 TGTCTTAGGTTCAATTATTATAGATCCAGAATTGATTAATACT-ACTCAGGAAGTTTTGC  115 seq1  116 TTCCAGATGATTTCTATAGAATGTCCCACCAAAAAATCTATAATGCGATGCTGGTGCTCG  175
          ||||  ||  ||||| ||||    ||||  || ||| |  |||| |||||| ||||| |
seq2  116 TTCCTGAGTCGTTTTATAGGGGTGCCCATCAACATATTTTCCGTGCAATGATGCACTTAA  175 seq1  176 GTGACCGAGGTGAACCGGTTGATCTGGTGACA--GTTACATCAGAGCTTGCGAACACAGA  233
          ||      |  | ||||| | || | ||| |    || |||  |  ||| | |  |  |
seq2  176 ATGAAGATAATAAAGAAATTGATGTTGTAACATTGATGGATC--AATTATCGACGGAAGG  233 seq1  234 CCTGCTGGAAGAAGTAGGCGGTATTTCATAT-TTG-ACAGATATCGCAAACTCGGTGCCG  291
           | | | |||  || |   || ||||| |  |||  |||  | ||| ||  ||   |  
seq2  234 TACGTTGAATGAAGCGGGTGGCCCCGCAATATCTTGCAGAGTTATCTACAAAT--GTACCA  291 seq1  292 ACAGCGGCTAACATAGAATATTACGCGAAAATCGTTGAGGAAAAATCGATT-CTTCGCCG  350
          |  || |  |||  |  | | | ||| ||  || ||| ||||   |    |  ||  |
seq2  292 ACGACGCGAAATGTTCAGTATTATACTGATATCGTT-TCTAAGCATGCATTAAAACGTAG  350 seq1  351 ATTAATCAGAACTGCGACAACGATTGCTCAAGACGGGTATACCCGTGAGGATGAGGTCGA  410
          ||| ||  |||| ||  ||||| |  | |  ||  | |    | ||    || |  ||
seq2  351 ATTGATTCAAACTGCAGATAGTATTGCCAATGATGGATATAATGATGAACTTGAACTAGA  410 seq1  411 --GGATTTACTCAGTGAAGCGGAAAAAACGATTATGGAAGTGGCA-CAGCGCAAAAACAC  467
            |||||    | |||||  || |    ||  || ||| |||| ||  ||   |   ||
seq2  411 TGCGATTT--TAAGTGATGCAGAACGTCGAATTTTAGAGCTATCATCTTCTCGTGAAAGC  468 seq1  468 GAGTGCCTTCCAAAATATTAAGGACGTCCTTGTCCAGACCTATGATAATATC-GAACAGC  526
          || ||  |||  ||  | |   ||| ||| || ||  ||    |||| |   |  |||
seq2  469 GA-TGGCTTTAAAGACATTCGAGACGTCTTAGGACAAGTGTATGA-AACAGCTGAAGAGC  526 seq1  527 TTTACAATCGAAAAGGTGAT--ATCA-CGGGAATTCCAACAGGGTTTACGGAGCTTGACC  583
          ||    |   |||| ||||   ||   ||  |||| ||||| || |  |  || ||||
seq2  527 TT---GATCAAAATAGTGGTCAAACACCAGGTATACCTACAGGATATCGAGATTTAGACC  583 seq1  584 GGATGACTGCGGGTTTCCAGCGCAACGACTTGATCATTGTGGCTGCCCGTCCTTCAGTAG  643
           ||||   || |||| |  |||||| | |||| ||| |  |||| |||| |||||||||
seq2  584 AAATGACAGCAGGGTTCAACCGAAATGATTTAATTATCCTTGCAGCGCGTCCATCTGTAG  643 seq1  644 GGAAAACAGCCTTTGCCCTGAACATCGCACAAAACGTGGCGAC----GAAGACCGATG-A  698
          | ||  | ||  | ||  |  |  | ||||||| |||||  |    ||||| | ||| |
seq2  644 GTAAGACTGCGTTCGCACTTAATATTGCACAAAAAGTTGCAACGCATGAAGA--TATGTA  701
```

Figure 6B

```
seq1    699  GAGCGTAGCGATTTTCAGTCTTGAGATGGGTGCCGAGCAGCTCGTTATGCGTATGCTCTG   758
             |  ||  |  ||||||   ||  ||||||||||| || ||| |    |  ||||||  | ||
seq2    702  TACAGTTGGTATTTTCTCGCTAGAGATGGGTGCTGATCAGTTAGCCACACGTATGATTTG   761 seq1    759  TGCCGAGGGAAATATCAATGCCCAGAATC---TCCGTACAGGTAACCTGACCGAAGAGGA   815
             |       |||||| |  ||   ||| |||    |  | ||||||  ||||  || || ||
seq2    762  TAGTTCTGGAAATGT---TGACTCAAACCGCTTAAGAACGGGTACTATGACTGAGGAAGA   818 seq1    816  TTGGGGCAAGCTGACGATGGCAATGGGAAGCCTATCGAACAGCGGGATTTACATCGATGA   875
             ||||    |   ||| |||||  | ||    |||   |  |  ||||| |||  |  ||||
seq2    819  TTGGAGTCGTTTTACTATAGCGGTAGGTAAATTATCACGTACGAAGATTTTTATTGATGA   878 seq1    876  TACACCGGGTATTCGAGTGAGTGAAATCCGTGCCAAGTGCCGCCGCTTGAAGCAGGAAAG   935
             |||||||||||||| |  ||  |  |  ||  || || || |  | ||  || || ||
seq2    879  TACACCGGGTATTCGAATTAATGATTTACGTTCTAAATGTCGTCGATTAAAGCAAGAACA   938 seq1    936  CGGGCTGGGCATGATTTTGATCGATTACCTGCAATTGATTCAGGGAAGCGGT---CGTTC   992
             ||  |  ||||||||||||| ||||  |  ||| ||||| ||||| |   |      |  |
seq2    939  TGGCTTAGACATGATTGTGATTGACTACTTACAGTTGATTCAAGGTAGTGGTTCACGTGC   998 seq1    993  AAAGGACAACCGTCAGCAGGAAGTATCTGAAATTTCCCGTGAACTGAAGTCGATTGCGAG   1052
             || |||  || |||||||||||| |||  ||||| |  |||  |  |||  |  |||  |
seq2    999  GTCCGATAACAGACAACAGGAAGTTTCTGAAATCTCTCGTACATTAAAAGCATTAGCCCG   1058 seq1    1053 GGAGCTGCAAGTCCCTGTTATCGCGCTTTCTCAGCTTTCCAGGGGTGTTGAGCAGCGTCA   1112
             ||  |  ||  ||  |||||||| ||  ||| |  ||| |  | |||||||  |||  ||
seq2    1059 TGAATTAGAATGTCCAGTTATCGCATTAAGTCAGTTATCTCGTGGTGTTGAACAACGACA   1118 seq1    1113 GGATAAACGTCCGATGATGTCTGATATCCGGGAATCAGGAAGTATCGAGCAGGACGCGGA   1172
             ||||||||||||  |||||  |||||| |  |||||| ||||| ||  ||| |||  ||||
seq2    1119 AGATAAACGTCCAATGATGAGTGATATTCGTGAATCTGGTTCGATTGAGCAAGATGCCGA   1178 seq1    1173 TATTGTCGCGTTCCTTTATCGTGATGACTACT----------------------ATGA   1208
             ||| || | ||| || ||||||||||| ||||                         ||||
seq2    1179 TATCGTTGCATTCTTATACCGTGATGATTACTATAACCGTGGCGGCGATGAAGATGATGA   1238 seq1    1209 CAAAGA----------------AACCGA--GAATAAAA--ATATTATCGAAATTATTAT   1247
             |  |||                |  ||  |||  ||  ||  || ||||||||||  ||
seq2    1239 CGATGATGGTGGTTTCGAGCCACAAACGAATGATGAAAACGGTGAAATTGAAATTATCAT   1298 seq1    1248 CGCCAAACAGCGTAACGGCCCGGTAGGAACCGTGTCTCTTGC-GTTCGTAAAAGAATACA   1306
             || || || ||||||||| ||  ||| ||||| |    | |   ||  ||| |||| |
seq2    1299 TGCTAAGCAACGTAACGGTCCAACAGGCACAGT-TAAGTTACATTTTATGAAACAATATA   1357 seq1    1307 ACAAATTCGTCAACCTGGAACGGCGTTTTGATGACGCAGGCGTTCCGCCCGGCGCA     1362
             | |||||    |||   ||   || |||| |  |  ||||| |||         |
seq2    1358 ATAAATT----TACCGATATCG--ATTATGCACATGCAGATATGATG------TAA     1401
```

Figure 6C

SEQ ID NO:6 DnaC nucleotide B. subtilis

```
   1 ATGACAGACC TTCTGAATGA CCGGCTTCCT CCGCAAAATA TAGAAGCCGA
  51 ACAAGCCGTG TTAGGCGCTA TTTTTTTACA GCCGTCTGCT TTAACACTGG
 101 CTTCAGAAGT ATTGATTCCA GATGATTTCT ATAGAATGTC CCACCAAAAA
 151 ATCTATAATG CGATGCTGGT GCTCGGTGAC CGAGGTGAAC CGGTTGATCT
 201 GGTGACAGTT ACATCAGAGC TTGCGAACAC AGACCTGCTG GAAGAAGTAG
 251 GCGGTATTTC ATATTTGACA GATATCGCAA ACTCGGTGCC GACAGCGGCT
 301 AACATAGAAT ATTACGCGAA AATCGTTGAG GAAAAATCGA TTCTTCGCCG
 351 ATTAATCAGA ACTGCGACAA CGATTGCTCA AGACGGGTAT ACCCGTGAGG
 401 ATGAGGTCGA GGATTTACTC AGTGAAGCGG AAAAAACGAT TATGGAAGTG
 451 GCACAGCGCA AAAACACGAG TGCCTTCCAA AATATTAAGG ACGTCCTTGT
 501 CCAGACCTAT GATAATATCG AACAGCTTTA CAATCGAAAA GGTGATATCA
 551 CGGGAATTCC AACAGGGTTT ACGGAGCTTG ACCGGATGAC TGCGGGTTTC
 601 CAGCGCAACG ACTTGATCAT TGTGGCTGCC CGTCCTTCAG TAGGGAAAAC
 651 AGCCTTTGCC CTGAACATCG CACAAAACGT GGCGACGAAG ACCGATGAGA
 701 GCGTAGCGAT TTTCAGTCTT GAGATGGGTG CCGAGCAGCT CGTTATGCGT
 751 ATGCTCTGTG CCGAGGGAAA TATCAATGCC CAGAATCTCC GTACAGGTAA
 801 CCTGACCGAA GAGGATTGGG GCAAGCTGAC GATGGCAATG GGAAGCCTAT
 851 CGAACAGCGG GATTTACATC GATGATACAC CGGGTATTCG AGTGAGTGAA
 901 ATCCGTGCCA AGTGCCGCCG CTTGAAGCAG GAAAGCGGGC TGGGCATGAT
 951 TTTGATCGAT TACCTGCAAT TGATTCAGGG AAGCGGTCGT TCAAAGGACA
1001 ACCGTCAGCA GGAAGTATCT GAAATTTCCC GTGAACTGAA GTCGATTGCG
1051 AGGGAGCTGC AAGTCCCTGT TATCGCGCTT TCTCAGCTTT CCAGGGGTGT
1101 TGAGCAGCGT CAGGATAAAC GTCCGATGAT GTCTGATATC CGGGAATCAG
1151 GAAGTATCGA GCAGGACGCG GATATTGTCG CGTTCCTTTA TCGTGATGAC
1201 TACTATGACA AAGAAACCGA GAATAAAAAT ATTATCGAAA TTATTATCGC
1251 CAAACAGCGT AACGGCCCGG TAGGAACCGT GTCTCTTGCG TTCGTAAAAG
1301 AATACAACAA ATTCGTCAAC CTGGAACGGC GTTTTGATGA CGCAGGCGTT
1351 CCGCCCGGCG CA
```

Figure 6D

SEQ ID NO:7 DnaC nucleotide *S. aureus*

```
   1  ATGGATAGAA TGTATGAGCA AAATCAAATG CCGCATAACA ATGAAGCTGA
  51  ACAGTCTGTC TTAGGTTCAA TTATTATAGA TCCAGAATTG ATTAATACTA
 101  CTCAGGAAGT TTTGCTTCCT GAGTCGTTTT ATAGGGGTGC CCATCAACAT
 151  ATTTTCCGTG CAATGATGCA CTTAAATGAA GATAATAAAG AAATTGATGT
 201  TGTAACATTG ATGGATCAAT TATCGACGGA AGGTACGTTG AATGAAGCGG
 251  GTGGCCCGCA ATATCTTGCA GAGTTATCTA CAAATGTACC AACGACGCGA
 301  AATGTTCAGT ATTATACTGA TATCGTTTCT AAGCATGCAT TAAAACGTAG
 351  ATTGATTCAA ACTGCAGATA GTATTGCCAA TGATGGATAT AATGATGAAC
 401  TTGAACTAGA TGCGATTTTA AGTGATGCAG AACGTCGAAT TTTAGAGCTA
 451  TCATCTTCTC GTGAAAGCGA TGGCTTTAAA GACATTCGAG ACGTCTTAGG
 501  ACAAGTGTAT GAAACAGCTG AAGAGCTTGA TCAAAATAGT GGTCAAACAC
 551  CAGGTATACC TACAGGATAT CGAGATTTAG ACCAAATGAC AGCAGGGTTC
 601  AACCGAAATG ATTTAATTAT CCTTGCAGCG CGTCCATCTG TAGGTAAGAC
 651  TGCGTTCGCA CTTAATATTG CACAAAAAGT TGCAACGCAT GAAGATATGT
 701  ATACAGTTGG TATTTTCTCG CTAGAGATGG GTGCTGATCA GTTAGCCACA
 751  CGTATGATTT GTAGTTCTGG AAATGTTGAC TCAAACCGCT TAAGAACGGG
 801  TACTATGACT GAGGAAGATT GGAGTCGTTT TACTATAGCG GTAGGTAAAT
 851  TATCACGTAC GAAGATTTTT ATTGATGATA CACCGGGTAT TCGAATTAAT
 901  GATTTACGTT CTAAATGTCG TCGATTAAAG CAAGAACATG GCTTAGACAT
 951  GATTGTGATT GACTACTTAC AGTTGATTCA AGGTAGTGGT TCACGTGCGT
1001  CCGATAACAG ACAACAGGAA GTTTCTGAAA TCTCTCGTAC ATTAAAAGCA
1051  TTAGCCCGTG AATTAGAATG TCCAGTTATC GCATTAAGTC AGTTATCTCG
1101  TGGTGTTGAA CAACGACAAG ATAAACGTCC AATGATGAGT GATATTCGTG
1151  AATCTGGTTC GATTGAGCAA GATGCCGATA TCGTTGCATT CTTATACCGT
1201  GATGATTACT ATAACCGTGG CGGCGATGAA GATGATGACG ATGATGGTGG
1251  TTTCGAGCCA CAAACGAATG ATGAAAACGG TGAAATTGAA ATTATCATTG
1301  CTAAGCAACG TAACGGTCCA ACAGGCACAG TTAAGTTACA TTTTATGAAA
1351  CAATATAATA AATTTACCGA TATCGATTAT GCACATGCAG ATATGATGTA
1401  A
```

Figure 6E

Sequence 1 SEQ ID NO: 8      DnaC *B. subtilis* (490 letters)
Sequence 2 SEQ ID NO: 9      DnaC *S. aureus* (503 letters)

```
seq1    1 MTDLLNDRLPPQNIEAEQAVLGAIFLQPSALTLASEVLIPDDFYRMSHQKIYNAMLVLGD   60
          | :       |  ||||:|||:| : |   :    |||:|: ||| :|| |: ||: | :
seq2    1 MDRMYEQNQMPHNNEAEQSVLGSIIIDPELINTTQEVLLPESFYRGAHQHIFRAMMHLNE   60 seq1   61 RGEPVDLVTVTSELANTDLLEEVGGISYLTDIANSVPTAANIEYYAKIVEEKSILRRLIR  120
          : :|:||: :|:   | || || :::  :|||  |::||  ||  : ::  ||||:
seq2   61 DNKEIDVVTLMDQLSTEGTLNEAGGPQYLAELSTNVPTTRNVQYYTDIVSKHALKRRLIQ  120 seq1  121 TATTIAQDGYTREDEVEDLLSEAEKTIMEVAQRKNTSAFQNIKDVLVQTYDNIEQLYNRK  180
          || :|| |||   |  |:: :||:|| :|:|:    : :   |::|:||| | |:  |:|
seq2  121 TADSIANDGYNDELELDAILSDAERRILELSSSRESDGFKDIRDVLGQVYETAEELDQNS  180 seq1  181 GDITGIPTGFTELDRMTAGFQRNDLIIVAARPSVGKTAFALNIAQNVATKTD-ESVAIFS  239
          |    ||||: :||:||||| ||||||||||:|||||||||||||||||| |||  :| |||
seq2  181 GQTPGIPTGYRDLDQMTAGFNRNDLIILAARPSVGKTAFALNIAQKVATHEDMYTVGIFS  240 seq1  240 LEMGAEQLVMRMLCAEGNINAQNLRTGNLTEEDWGKLTMAMGSLSNSGIYIDDTPGIRVS  299
          |||||:|| ||:|: ||:::  |||| :|||||:  | :|:| | | : |:||||||||||!::
seq2  241 LEMGADQLATRMICSSGNVDSNRLRTGTMTEEDWSRFTIAVGKLSRTKIFIDDTPGIRIN  300 seq1  300 EIRAKCRRLKQESGLGMILIDYLQLIQGSG-RSKDNRQQEVSEISRELKSIARELQVPVI  358
          ::  :|||||||:||||::|||||||||||||||| |||||||||||||||||||::|||| |||
seq2  301 DLRSKCRRLKQEHGLDMIVIDYLQLIQGSGSRASDNRQQEVSEISRTLKALARELECPVI  360 seq1  359 ALSQLSRGVEQRQDKRPMMSDIRESGSIEQDADIVAFLYRDDYYDK--------------  404
          |||||||||||||||||||||||||||||||||||||||||||||!::
seq2  361 ALSQLSRGVEQRQDKRPMMSDIRESGSIEQDADIVAFLYRDDYYNRGGDEDDDDDGGFEP  420 seq1  405 ETENKN-IIEIIIAKQRNGPVGTVSLAFVKEYNKFVNLERRFDDAGVPPGA          454
          :|  ::|  ||||||||||||||||||| |||  | |:|:||||   :::      |
seq2  421 QTNDENGEIEIIIAKQRNGPTGTVKLHFMKQYNKFTDIDYAHADM-----M          466
```

Figure 6F

SEQ ID NO:8 DnaC *B. subtilis*

```
  1  MTDLLNDRLP  PQNIEAEQAV  LGAIFLQPSA  LTLASEVLIP  DDFYRMSHQK
 51  IYNAMLVLGD  RGEPVDLVTV  TSELANTDLL  EEVGGISYLT  DIANSVPTAA
101  NIEYYAKIVE  EKSILRRLIR  TATTIAQDGY  TREDEVEDLL  SEAEKTIMEV
151  AQRKNTSAFQ  NIKDVLVQTY  DNIEQLYNRK  GDITGIPTGF  TELDRMTAGF
201  QRNDLIIVAA  RPSVGKTAFA  LNIAQNVATK  TDESVAIFSL  EMGAEQLVMR
251  MLCAEGNINA  QNLRTGNLTE  EDWGKLTMAM  GSLSNSGIYI  DDTPGIRVSE
301  IRAKCRRLKQ  ESGLGMILID  YLQLIQGSGR  SKDNRQQEVS  EISRELKSIA
351  RELQVPVIAL  SQLSRGVEQR  QDKRPMMSDI  RESGSIEQDA  DIVAFLYRDD
401  YYDKETENKN  IIEIIAKQR   NGPVGTVSLA  FVKEYNKFVN  LERRFDDAGV
451  PPGA
```

SEQ ID NO:9 DnaC *S. aureus*

```
  1  MDRMYEQNQM  PHNNEAEQSV  LGSIIIDPEL  INTTQEVLLP  ESFYRGAHQH
 51  IFRAMMHLNE  DNKEIDVVTL  MDQLSTEGTL  NEAGGPQYLA  ELSTNVPTTR
101  NVQYYTDIVS  KHALKRRLIQ  TADSIANDGY  NDELELDAIL  SDAERRILEL
151  SSSRESDGFK  DIRDVLGQVY  ETAEELDQNS  GQTPGIPTGY  RDLDQMTAGF
201  NRNDLIILAA  RPSVGKTAFA  LNIAQKVATH  EDMYTVGIFS  LEMGADQLAT
251  RMICSSGNVD  SNRLRTGTMT  EEDWSRFTIA  VGKLSRTKIF  IDDTPGIRIN
301  DLRSKCRRLK  QEHGLDMIVI  DYLQLIQGSG  SRASDNRQQE  VSEISRTLKA
351  LARELECPVI  ALSQLSRGVE  QRQDKRPMMS  DIRESGSIEQ  DADIVAFLYR
401  DDYYNRGGDE  DDDDDGGFEP  QTNDENGEIE  IIIAKQRNGP  TGTVKLHFMK
451  QYNKFTDIDY  AHADMM
```

Tryptic peptide mass spectrum of interacting protein (1% Triton X-100 elute)

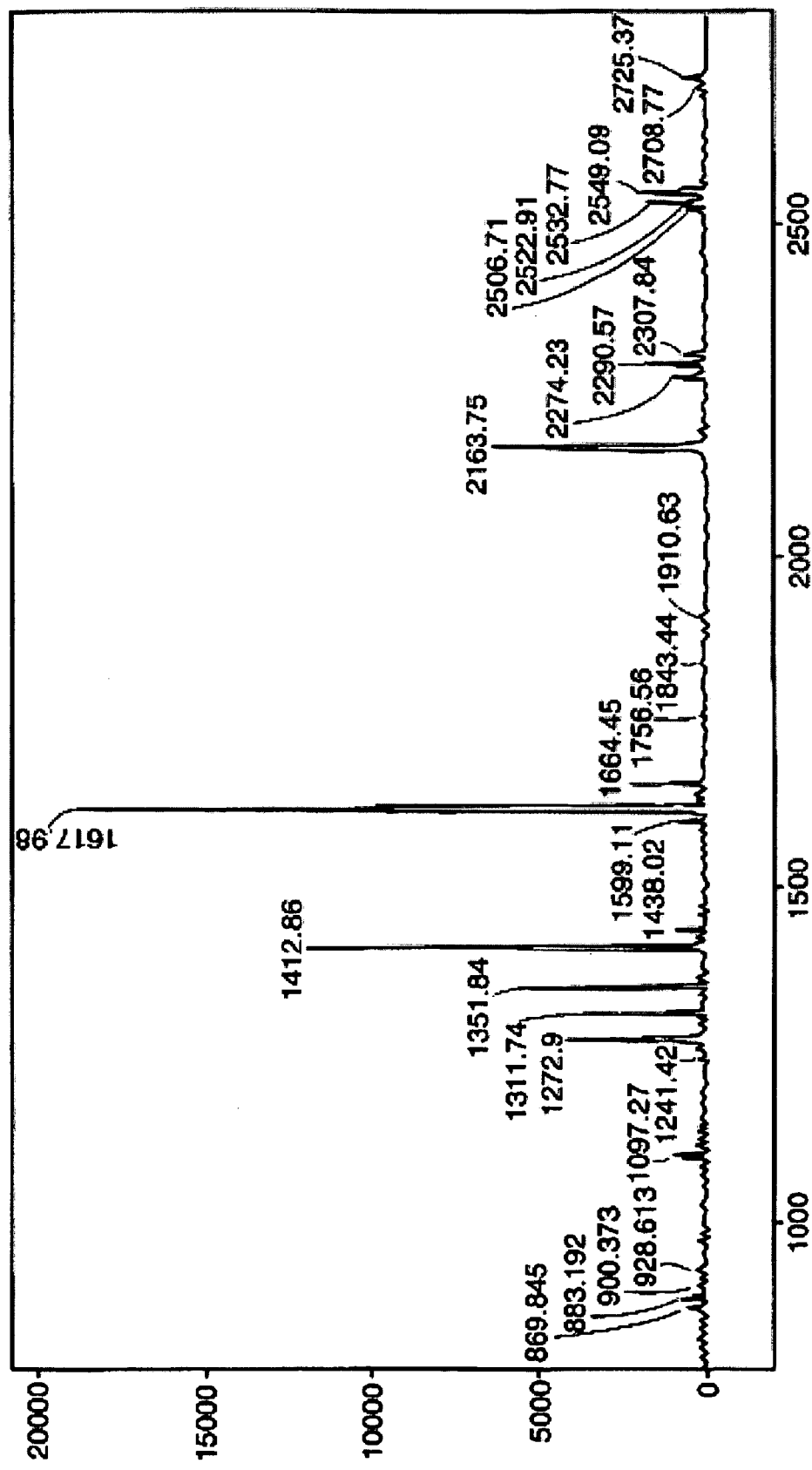
Figure 11B Tryptic peptide mass spectrum of interacting protein (1% SDS eluate)

SD plate without Trp and Leu      SD plate without Trp, Leu, His and Ade

SD: Synthetic medium, Trp: tryptophan, Leu: leucine, His: histidine, Ade: adenine 1) pGBKT7-53 and pGADT7-T
2) pGBKT7-53 and pGAD dnaI
3) pGBK77ORF104 and pGADT7-T
4) pGBKT7-LAM and pCL1
5) pGBK77ORF104 and pGAD dnaI
6) pGBK dnaI and pGAD77ORF104

Figure 14C

Amino acid residues corresponding to interacting partial proteolytic fragments.

| Protease | Proteolytic fragment ID (from Fig. 14A, B) | ID of SEQ ID NO:2 fragment interacting with 77ORF104 | |
|---|---|---|---|
| | | From amino | to carboxyl |
| Endoproteinase Glu-C | V24 | 117 | 313 |
| | V24 | 119 | 313 |
| | | | |
| Chymotrypsin | C38 | 12 | 313 |
| | C25 | 83 | 313 |
| | C24 | 77 | 305 |
| | C23 | 77 | 304 |
| | C22 | 116 | 313 |
| | C21 | 131 | 313 |
| | | | |
| SEQ ID NO:2 | complete | 1 | 313 |

Figure 15

SEQ ID NO: 16
>S. aureus DnaI: amino acid 150-313
AADDICTAITNGEQVKGLYLYGPFGTGKSFILGAIANQLKSKKVRSTIIYLPEFIRTLKG
GFKDGSFEKKLHRVREANILMLDDIGAEEVTPWVRDEVIGPLLHYRMVHELPTFFSSNFD
YSELEHHLAMTRDGEEKTKAARIIERVKSLSTPYFLSGENFRNN SEQ ID NO: 17
>S. aureus dnaI: nucleotide 448-942
gcagcagatgatatttgtacagcaataactaatggggaacaagtgaaaggccctttacctt
tatggtccatttgggacaggtaaatctttattctaggtgcaattgcgaatcagctcaaa
tctaagaaggtacgttcgacaattatttatttaccggaatttattagaacattaaaaggt
ggctttaaagatggttcttttgaaaagaaattacatcgcgtaagagaagcaaacatttta
atgcttgatgatattggggctgaagaagtgactccatgggtgagagatgaggtaattgga
cctttgctacactatcgaatggttcatgaattaccaacattctttagttctaattttgac
tatagtgaattggaacatcatttagcgatgactcgtgatggtgaagagaagactaaagca
gcacgtattattgaacgtgtcaaatctttgtcaacaccatacttttatcaggagaaaat
ttcagaaacaattga SEQ ID NO: 18
>S. aureus DnaI: amino acid 64-313
YKDQQKHYDGHKFADCPNFVKGHVPELYVDNNRIKIRYLQCPCKIKYDEERFEAELITSH
HMQRDTLNAKLKDIYMNHRDRLDVAMAADDICTAITNGEQVKGLYLYGPFGTGKSFILGA
IANQLKSKKVRSTIIYLPEFIRTLKGGFKDGSFEKKLHRVREANILMLDDIGAEEVTPWV
RDEVIGPLLHYRMVHELPTFFSSNFDYSELEHHLAMTRDGEEKTKAARIIERVKSLSTPY
FLSGENFRNN TL minus SD medium         THAL minus SD medium 1. pGADDnaI(150-313) and pGBKORF104
2. pGADDnaI(150-313) and pGBKLam
3. pGADDnaI(64-313) and pGBKORF104
4. pGADDnaI(64-313) and pGBKLam
5. pGADDnaI and pGBKORF104
6. 77pGADORF12 and pGBKORF104

US 7,101,969 B1

COMPOSITIONS AND METHODS INVOLVING AN ESSENTIAL *STAPHYLOCOCCUS AUREUS* GENE AND ITS ENCODED PROTEIN

This application is a continuation-in-part of U.S. patent application Ser. No. 09/470,512, filed Dec. 22, 1999, now U.S. Pat. No. 6,376,652, which is a CIP of U.S. patent application Ser. No. 09/407,804, filed Sep. 28, 1999, and claims the benefit of U.S. Provisional Application No. 60/110,992, filed Dec. 3, 1998.

FIELD OF THE INVENTION

The invention relates to bacterial and bacteriophage genes.

BACKGROUND OF THE INVENTION

The Staphylococci make up a medically important genera of microbes known to cause several types of diseases in humans. *S. aureus* is a Gram positive organism which can be found on the skin of healthy human hosts. It is responsible for a large number of bacteremias, where its portal of entry can be the skin, lungs, urinary tract or infected intravascular devices (Steinberg et al., (1996)) Clin. Infect. Dis. 23: 255–259; Røder et al., (1999) Arch. Intern. Med. 159: 462–469). It can cause fatal endocarditis or damage to the heart and, due to its exotoxin, can cause death via "Toxic Shock" (Frimodt-Møller et al., (1997) Clin. Microbiol. Infect. 3: 297–305; Sanabria et al., (1990) Arch. Intern. Med. 150: 1305–1309).

Only *S. aureus* and *Staphylococcus epidermidis*, of the nineteen species of *Staphylococcus* described in Bergey's Manual (1992), have significant interactions with humans. They are among the normal flora of humans, and are found on nasal passages, skin and mucous membranes. *S. aureus*, when pathogenic in humans, can cause a number of suppurative (pus-forming) infections, as well as food poisoning, endocarditis, and toxic shock syndrome.

*S. aureus* causes superficial skin lesions, such as boils, styes and furunculosis; more serious infections include pneumonia, mastitis, phlebitis, meningitis, and urinary tract infections, in addition to osteomyelitis and endocarditis. *S. aureus* is also a major cause of hospital acquired (nosocomial) infection of surgical wounds and infections associated with inserted and implanted medical devices. Lastly, *S. aureus* causes food poisoning through the release of enterotoxins into food, and toxic shock syndrome through the release of superantigens into the blood stream. *S. aureus* also secretes two types of toxin with superantigen activity: 1) enterotoxins, of which there are six antigenic types (named SE-A, B, C, D, E and G) and 2) toxic shock syndrome toxin (TSST-1).

*S. aureus* has been successfully treated with the penicillin derivative Methicillin in the past, but is now becoming increasingly resistant (MRSA—Methicillin Resistant *S. aureus*) to this antibiotic (Harbath et al., (1998) Arch. Intern. Med. 158: 182–189.). For example, *S. aureus* endocarditis mortality can range from 26–45%, and combined β-lactam/aminoglycoside therapy is proving increasingly ineffective in disease eradication (Røder et al., (1999) Arch. Intern. Med. 159: 462–469). However, MRSA infections continue to be sensitive to treatment with vancomycin, which is the drug of last resort. Infections caused by MRSA have been increasing in children and adults; isolates have been found in 97% of all large, university-based teaching hospitals in the United States. Since 1996, three cases of vancomycin resistant *S. aureus* have been reported. This new strain represents a particularly dangerous development of an aggressive bacterial pathogen which does not respond to any known antibiotic. The emergence of resistance to vancomycin has the potential to result in untreatable (and thus fatal) *S. aureus* infections.

It is no longer uncommon to isolate *S. aureus* strains which are resistant to most of the standard antibiotics, and thus there is an unmet medical need and demand for new anti-microbial agents, vaccines, drug screening methods, and diagnostic tests for this organism.

SUMMARY OF THE INVENTION

The present invention relates to DnaI and DnaI-related proteins, in particular *S. aureus* DnaI polypeptides and dnaI polynucleotides, recombinant materials and methods for their production. The invention also relates to a pair of interacting proteins, a growth-inhibitory (or inhibitor) bacteriophage 77 ORF 104 gene product that interacts with the *S. aureus* DnaI polypeptide, the interacting regions of the *S. aureus* DnaI related protein and the protein encoded by the *S. aureus* bacteriophage 77 ORF 104, forming the basis for screening assays. It also relates to polynucleotides and polypeptides of a multiprotein complex believed to be involved in initiation of DNA replication containing DnaI as a subunit, and also may include DnaC and related proteins, as well as variants of them. In another aspect, the invention relates to methods for using such polypeptides and polynucleotides, including treatment of microbial diseases, amongst others. In a further aspect, the invention relates to methods for identifying agonists and antagonists using the materials provided by the invention, and for treating microbial infections and conditions associated with such infections with the identified agonist or antagonist compounds. In a still further aspect, the invention relates to diagnostic assays for detecting diseases associated with microbial infections and conditions associated with such infections, such as assays for detecting DnaI expression or activity.

The invention encompasses a method of identifying a compound that is active on a polypeptide comprising the amino acid sequence of SEQ ID NO: 16. The method comprises contacting a candidate compound with the polypeptide, and detecting binding of the candidate compound to the polypeptide, wherein detection of binding is indicative that the compound is active on the polypeptide.

In one embodiment, the step of detecting comprises the step of measuring the binding of a candidate compound, wherein the compound is directly or indirectly detectably labeled, to the polypeptide.

In another embodiment, the step of detecting comprises measurement by phage display.

In another embodiment, the step of detecting comprises measurement by surface plasmon resonance.

In another embodiment, the step of detecting comprises measurement by FRET.

In another embodiment, the step of detecting comprises measurement of fluorescence polarization changes.

In another embodiment, the step of detecting comprises a scintillation proximity assay.

In another embodiment, the step of detecting comprises a biosensor assay.

In another embodiment, the active compound is selected from the group consisting of a small molecule, a peptidomimetic compound, and a fragment or derivative of a bacteriophage inhibitor protein.

In another embodiment, the active compound is a peptide synthesized by a recombinant expression system and purified, or artificially synthesized.

The invention also encompasses a method of identifying a compound that is active on a polypeptide comprising the amino acid sequence of SEQ ID NO: 16, the method comprising the steps of contacting a first and a second polypeptide in the presence and absence of a candidate compound, wherein the first polypeptide comprises the amino acid sequence of SEQ ID NO: 16 or a fragment or variant thereof that specifically binds phage 77ORF104 and the second polypeptide comprises phage 77 ORF 104 or a domain thereof that specifically binds a polypeptide of SEQ ID NO: 16, and detecting the binding of the first and second polypeptides to each other, wherein a decrease in the binding of the first and the second polypeptides in the presence of the candidate compound relative to the binding in the absence of the candidate compound identifies the candidate compound as a compound that is active on a polypeptide comprising the amino acid sequence of SEQ ID NO: 16.

In one embodiment, the first or the second polypeptide is directly or indirectly detectably labeled.

In another embodiment, the step of detecting comprises measurement by phage display.

In another embodiment, the step of detecting comprises measurement by surface plasmon resonance.

In another embodiment, the step of detecting comprises measurement by FRET.

In another embodiment, the step of detecting comprises measurement of fluorescence polarization changes.

In another embodiment, the step of detecting comprises a scintillation proximity assay.

In another embodiment, the step of detecting comprises a biosensor assay.

The invention further encompasses an agonist or an antagonist of the activity of a DnaI polypeptide or a gene encoding the polypeptide.

The invention further encompasses a method of identifying a compound that is active on a DnaI polypeptide, comprising the steps of contacting a candidate compound with cells expressing a polypeptide comprising SEQ ID NO: 16 and detecting DnaI activity in the cells, wherein a decrease in activity relative to DnaI activity in cells not contacted with a candidate compound is indicative of inhibition of DnaI activity.

The invention further encompasses a method of making an antibacterial compound, comprising the steps of: a) determining whether a candidate compound is active on a polypeptide comprising the amino acid sequence of SEQ ID NO: 16 or a gene encoding the polypeptide; and b) synthesizing or purifying the candidate compound in an amount sufficient to provide a therapeutic effect when administered to an organism infected by a bacterium naturally producing a polypeptide comprising the amino acid sequence of SEQ ID NO: 16.

In one embodiment, the candidate compound is selected from the group consisting of a small molecule, a peptidomimetic compound, and a fragment or derivative of a bacteriophage inhibitor protein.

In one embodiment, the candidate compound is a peptide synthesized by a recombinant expression system and purified, or artificially synthesized.

The invention further encompasses a method for inhibiting a bacterium, comprising contacting the bacterium with a compound active on a polypeptide comprising the amino acid sequence of SEQ ID NO: 16 or a gene encoding the polypeptide.

In one embodiment, the step of contacting is performed in vitro.

In another embodiment, the step of contacting is performed in vivo in an animal.

In another embodiment, the compound is selected from the group consisting of a small molecule, a peptidomimetic compound, and a fragment or derivative of a bacteriophage inhibitor protein.

In another embodiment, the compound is a peptide synthesized by a recombinant expression system and purified, or is artificially synthesized.

The invention further encompasses a method for treating a bacterial infection in an animal suffering from an infection, comprising administering to the animal a therapeutically effective amount of a compound active on a polypeptide comprising the amino acid sequence of SEQ ID NO: 16 or a gene encoding the polypeptide. The animal is preferably, but not necessarily a mammal, more preferably a human.

In one embodiment, the compound is selected from the group consisting of a small molecule, a peptidomimetic compound, and a bacteriophage inhibitor protein.

The invention further encompasses a method of prophylactic treatment to prevent bacterial infection comprising contacting an indwelling device with a compound active on a polypeptide comprising the amino acid sequence of SEQ ID NO: 16 before its implantation into a mammal, such contacting being sufficient to prevent *S. aureus* infection at the site of implantation.

The invention further encompasses a method of prophylactic treatment to prevent infection of an animal by a bacterium comprising administering to the animal a compound that is active on a polypeptide comprising the amino acid sequence of SEQ ID NO: 16 or a gene encoding the polypeptide in an amount sufficient to reduce adhesion of the bacterium to a tissue surface of the mammal.

The invention further encompasses a method of diagnosing in an individual an infection with *Staphylococcus aureus*, comprising: determining the presence in the individual of a polypeptide comprising the amino acid sequence of SEQ ID NO: 16.

In one embodiment, the determining step comprises contacting a biological sample of the individual with an antibody specific for an epitope present on a polypeptide comprising the amino acid sequence of SEQ ID NO: 16.

The invention further encompasses a method of diagnosing in an individual an infection with *Staphylococcus aureus*, comprising determining the presence in the individual of a nucleic acid sequence encoding a polypeptide comprising the amino acid sequence of SEQ ID NO: 16.

In one embodiment, the determining step comprises contacting a nucleic acid sample of said individual with an isolated, purified or enriched nucleic acid probe of at least 15 nucleotides in length that hybridizes under stringent hybridization conditions with the sequence of SEQ ID NO: 1, or the complement of such probe.

The invention further encompasses an isolated, purified or enriched polynucleotide comprising a nucleotide sequence that has at least 55% identity to the sequence of SEQ ID NO: 1, or the complement of said nucleotide sequence.

The invention further encompasses an isolated, purified or enriched polynucleotide consisting of nucleotides 448–942 of SEQ ID NO: 1, herein referred to as SEQ ID NO: 17, comprising a nucleotide sequence encoding the polypeptide of SEQ ID NO: 16 or the complement of such nucleotide sequence.

The invention further encompasses an isolated, purified or enriched polynucleotide consisting of the sequence of SEQ ID NO: 17.

The invention further encompasses an isolated, purified or enriched polypeptide having at least 55% identity to the amino acid sequence of SEQ ID NO: 16.

The invention further encompasses an isolated, purified or enriched polypeptide of at least 50 amino acids in length having at least 50% identity to the amino acid sequence of SEQ ID NO: 16.

The invention further encompasses an isolated, purified or enriched polypeptide having at least 70% similarity to the amino acid sequence of SEQ ID NO: 16.

The invention further encompasses an isolated, purified or enriched polypeptide of at least 20 amino acids in length having at least 60% similarity to the amino acid sequence of SEQ ID NO: 16.

The invention further encompasses an isolated polypeptide comprising the amino acid sequence of SEQ ID NO: 16.

The invention further encompasses an isolated polypeptide consisting of the amino acid sequence of SEQ ID NO: 16.

The invention further encompasses an isolated, purified or enriched antibody specific for a polypeptide comprising SEQ ID NO: 16.

The invention further encompasses a composition comprising two polypeptides, a bacteriophage 77 ORF 104 polypeptide and a polypeptide comprising the amino acid sequence of SEQ ID NO: 16 or a variant thereof that specifically binds phage 77 ORF 104 polypeptide.

The invention further encompasses a composition comprising a nucleic acid encoding bacteriophage 77 ORF 104 and a nucleic acid comprising SEQ ID NO: 17 or a variant thereof that encodes a polypeptide that specifically binds bacteriophage 77 ORF 104 polypeptide.

Further features and advantages of the invention will become more fully apparent in the following description of the embodiments and drawings thereof, and from the claims.

BRIEF DESCRIPTION OF THE DRAWINGS

FIG. 1 shows the nucleotide (A; SEQ ID NO: 1) and amino acid (B; SEQ ID NO: 2) sequences of S. aureus DnaI.

FIGS. 2A–2N shows the complete nucleotide sequence of the S. aureus bacteriophage 77 genome (SEQ ID NO: 3).

FIG. 4 shows the nucleotide (A; SEQ ID NO: 4) and the amino acid (B; SEQ ID NO: 5) sequences of S. aureus bacteriophage 77 ORF 104.

FIG. 5 shows the predicted tryptic peptide masses of the ORF (SEQ ID NOs: 10–13) (identified in the University of Oklahoma S aureus genomic database that closely matches the tryptic peptide profile of the polypeptide bound by 77ORF104

FIGS. 6A–E shows sequences and alignments of B. subtilis DnaC sequences with the homologous sequences from S. aureus. 6C) shows an alignment of B. subtilis dnaC polynucleotide sequence (SEQ ID NO: 6) with the homologous S. aureus dnaC polynucleotide sequence (SEQ ID NO: 7) identified by BLAST searching the S. aureus database at The Institute of Genomic Research (TIGR) web site with the B. subtilis dnaC sequence. 6E) shows an alignment of B. subtilis DnaC amino acid sequence (SEQ. ID NO: 8) with the predicted amino acid sequence of the polypeptide (SEQ ID NO: 9) encoded by the S. aureus dnaC polynucleotide sequence shown in FIG. 6B.

FIGS. 11A–11B show results of a tryptic peptide mass spectrum analysis showing relatedness between the interacting protein eluted with Triton X-100 (indicated by arrow in FIG. 8C) and the interacting protein eluted with 1% SDS (indicated by arrow in FIG. 8D). Of note are the tryptic peptides having monoisotopic MH+ masses of 1351.8, 1412.7, and 1617.8 Da.

FIGS. 14A–14C show the interaction between partial proteolysis fragments of DnaI and ORF 104 from *S. aureus* bacteriophage 77. Partial proteolytic fragments generated by A) endoproteinase GluC or B) chymotrypsin were subjected to affinity chromatography using columns containing either 0 or 2.0 mg/ml of 77ORF104 protein. Partial proteolytic fragments interacting with the 77ORF104 and not the control column were excised for peptide mapping. Lanes are indicated as Mr, molecular weight markers; L, load; FT, flowthrough; 1, 1 M NaCl elution; 2, 1% SDS elution; ACB, affinity chromatography buffer. The interacting bands excised for peptide mapping are indicated according to the apparent Mr by SDS-PAGE, bands not interacting are indicated with (–). C) List of identified DnaI proteolytic fragments interacting with 77 ORF 104. Partial proteolytic fragments interacting with 77ORF104 were purified by reverse phase, analyzed with MALDI-TOF, and the observed high molecular weight fragments mapped to the corresponding amino acid sequence of SEQ ID NO: 2. The minimal domain of DnaI interacting with 77 ORF 104 as determined by partial proteolysis with chymotrypsin is amino acids 131 to 313 and with endoproteinase Glu-C is amino acids 119 to 313 of SEQ ID NO: 2.

FIG. 15 shows the amino acid sequence of the DnaI fragments tested in yeast two-hybrid system for interaction with 77ORF104. SEQ ID NO: 16 contains the amino acids 150 to 313 of SEQ ID NO: 2 and SEQ ID NO: 17 contains the corresponding nucleotides 448 to 942 of SEQ ID NO: 1. SEQ ID NO: 18 contains the amino acids 64 to 313 of SEQ ID NO: 2.

DESCRIPTION OF THE INVENTION

Figure 3:
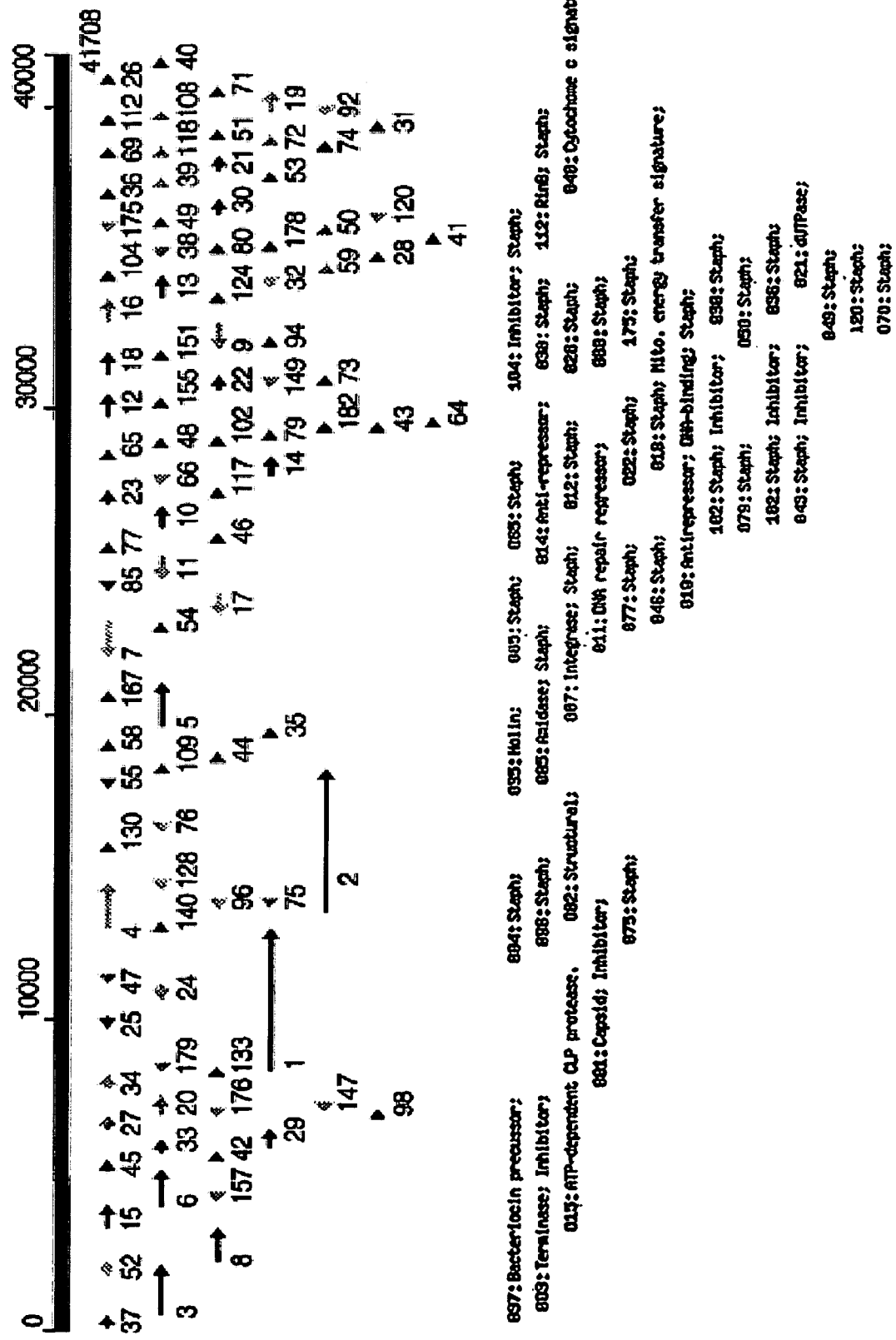
FIG. 3 shows an ORF map of the S. aureus bacteriophage 77 genome.

The invention is based on the discovery of an essential gene and its encoded polypeptide in *S. aureus* and portions thereof useful in screening, diagnostics, and therapeutics. The invention also relates to *S. aureus* DnaI polypeptides and polynucleotides as described in greater detail below, and to a pair of polynucleotides encoding a pair of interacting polypeptides, and the pair of polypeptides themselves, or interacting domains thereof, where the pair includes a *S. aureus* DnaI polypeptide and a 77 ORF 104 polypeptide. Also, the invention relates to polynucleotides and polypeptides of a protein complex, thought to be involved in initiation of DNA replication, containing DnaI and DnaC related proteins, as well as their variants. In particular, the invention relates to polypeptides and polynucleotides of a DnaI of *S. aureus*, which is related by amino acid sequence homology to *B. subtilis* DnaI polypeptide. The invention relates especially to DnaI having the nucleotide and amino acid sequences disclosed as SEQ ID NO: 1 and SEQ ID NO: 2, respectively. The sequences presented as SEQ ID NOs: 1 and 2 represent an exemplification of the invention, since those of ordinary skill will recognize that such sequences can be usefully employed in polynucleotides in general, including ribopolynucleotides.

We have used the methodology of two previous inventions (U.S. patent application Ser. No. 09/407,804, filed Sep. 28, 1999, and U.S. Provisional Patent Application 60/110, 992 filed Dec. 3, 1998) to identify and characterize an essential polynucleotide and polypeptide sequence from *S. aureus*. Thus, the present invention provides polynucleotide and polypeptide sequences isolated from *S. aureus* that can be used in a drug screening assay to identify compounds with anti-microbial activity. The polynucleotide and polypeptide sequences can be isolated using a method similar to those described herein, or using another method. In addition, such polynucleotide and polypeptide sequences can be chemically synthesized.

Definitions

The phrase "active on", with reference to a particular cellular target, such as the product of a particular gene, means that the target is an important part of a cellular pathway which includes that target and that an agent or compound acts on that pathway. Thus, in some cases the agent or compound may act on a component upstream or downstream of the stated target, including a regulator of that pathway or a component of that pathway. In general, an antibacterial agent is active on an essential cellular function, often on a product of an essential gene.

As used herein, the terms "inhibit", "inhibition", "inhibitory", and "inhibitor" all refer to a function of reducing a biological activity or function. Such reduction in activity or function can, for example, be in connection with a cellular component (e.g., an enzyme), or in connection with a cellular process (e.g., synthesis of a particular protein), or in connection with an overall process of a cell (e.g., cell growth). In reference to cell growth, the inhibitory effects may be bacteriocidal (killing of bacterial cells) or bacteriostatic (i.e.—stopping or at least slowing bacterial cell growth). The latter slows or prevents cell growth such that fewer cells of the strain are produced relative to uninhibited cells over a given time period. From a molecular standpoint, such inhibition may equate with a reduction in the level of, or elimination of, the transcription and/or translation of a specific bacterial target(s), or reduction or elimination of activity of a particular target biomolecule.

As used herein, the term "DnaI polypeptide" refers to a polypeptide encompassing *S. aureus* DnaI (SEQ ID NO: 2) or an active domain of *S. aureus* DnaI. As used herein, the term "active domain of *S. aureus* DnaI" is a polypeptide fragment or portion of *S. aureus* DnaI that retains an activity of *S. aureus* DnaI. The term "DnaI polypeptide" is meant to encompass *S. aureus* DnaI or an active domain of *S. aureus* DnaI that is fused to another, non-DnaI polypeptide sequence.

"DnaI activity" is defined as one or more of the following:

A) The activity of a polypeptide having the *S. aureus* DnaI sequence provided herein, a fragment or analog thereof or a protein comprising a *S. aureus* DnaI polypeptide that directly interacts with bacteriophage 77 ORF 104 protein or a DnaI-binding fragment thereof in a manner that results in at least a 10-fold reduction of $^3$H-thymidine incorporation in a bacterial DNA replication assay relative to $^3$H-thymidine incorporation in an assay lacking bacteriophage 77 ORF 104 or a DnaI-binding fragment thereof.

To assay for DnaI activity by $^3$H-thymidine incorporation, the level of radiolabeled thymidine incorporation into DNA is measured in *S. aureus* cells expressing an arsenite-inducible 77 ORF104 construct in the presence or absence of 5 µM sodium arsenite. Samples (0.5 ml) are withdrawn from cultures at appropriate time intervals and mixed with 4.5 µl of labeling solution (0.2 µCi/ml of $^3$H-thymidine (73 Ci/mmol, NEN Life Science Products, Inc.) and 70 pmol of unlabeled thymidine). After 15 minutes of reaction, incorporation is stopped by adding 5 µl of 0.2% NaN$_3$ and 5 µl of 30 µg/ml unlabeled thymidine. Samples are precipitated with 10% (w/v) trichloroacetic acid and filtered through glass fiber filters (GF-C, Whatman). The results are expressed as $^3$H-thymidine counts incorporated, normalized to the OD of the culture.

B) The activity of a polypeptide having the *S. aureus* DNA sequence provided herein, or a fragment or analog thereof, or a protein comprising a *S. aureus* DnaI polypeptide that is necessary for at least a 10% inhibition of plasmid replication by bacteriophage 77 ORF 104 protein in the plasmid DNA replication assay. This assay is as follows, the plasmid pC194 replicates in *S. aureus* by a rolling circle mechanism. The single-stranded origin, sso, of pC194 is involved in the synthesis of the lagging strand of DNA. The plasmid pADG6406 is a derivative of pC194 lacking sso. The absence of sso leads to the accumulation of single-stranded plasmid DNA. The single stranded initiation site, ssiA, is located on the lagging strand of pAM 1, and is a site for replicative primosome assembly. SsiA was inserted into plasmid pADG6406. *S. aureus* cells carrying plasmids are grown to mid-log phase and their total DNA is extracted and analyzed by Southern hybridization using $^{32}$P-labeled plasmid DNA as probe. The presence of pADG6406 with ssiA is associated with a decrease in the ratio of single-stranded to double-stranded plasmid DNA compared to the ratio in cells bearing the same plasmid lacking the ssiA insert. This system is used to measure the effect of 77 ORF 104 expression on single-stranded DNA synthesis. A plasmid containing 77 ORF 104 under an arsenite-inducible promoter is transformed into *S. aureus* harboring pADG6406. The ratio of single-stranded to double-stranded DNA of pADG6406 is measured in the presence and absence of sodium arsenite. An increase in the ratio of single-stranded to double-stranded DNA of 10% or more in the presence of 77 ORF 104 indicates an effect on DnaI activity.

C) The activity of a polypeptide having the *S. aureus* sequence provided herein, a fragment or analog thereof, or a protein comprising a *S. aureus* DnaI polypeptide in the loading of *S. aureus* DnaC helicase onto replicative primosomes. The following helicase assay can be adapted from an in vitro assay with SPP1 phage G38P (DnaA), G39P (DnaI) and G40P (DnaC) polypeptides (Ayora et al., 1999, J. Mol. Biol. 288: 71–85) Helicases are capable of unwinding DNA with a 5' to 3' unwinding polarity. To determine the role of *S. aureus* DnaI on the helicase unwinding activity, an annealed substrate with a 3 single-stranded (ss) DNA tail (preformed fork) is incubated with a constant quantity of purified DnaC helicase and increasing amounts of either purified DnaI, DnaA or preformed DnaA-DnaI complex. The reaction mixture is subjected to conditions that support helicase activity. The reaction contains 50 mM NaCl, 1 mM ATP, 50 µg/ml BSA and 0.24 nM $^{32}$P-labeled oligomer annealed to M13 ssDNA offered as substrate. The DNA molecule in the reaction mixture is analyzed for whether it is converted to single-stranded (ss) DNA. The reaction is stopped by the addition of 5 µl of stopping solution (100 mM EDTA, 2% (w/v) SDS in DNA loading buffer (Sambrook 1989)) and subsequently loaded onto a 10% non-denaturing PAGE gel. The gel is run and dried prior to autoradiography. The ratio of the oligo released from the M1 3 ssDNA is evaluated.

D) The binding or interaction of a polypeptide comprising the amino acid sequence of SEQ ID NO: 16, provided herein, to bacteriophage 77 ORF 104 protein or a portion thereof capable of binding a polypeptide comprising the amino acid sequence of SEQ ID NO. 16. The interaction or binding of a polypeptide comprising the amino acid sequence of SEQ ID NO. 16 and a binding portion of bacteriophage 77 ORF 104 may be between isolated polypeptides consisting essentially of the sequence necessary for binding, or, alternatively, the respective polypeptide sequence may be comprised within a larger polypeptide. A number of methods, useful in the invention, to measure the binding of bacteriophage 77 ORF 104 to a polypeptide comprising the amino acid sequence of SEQ ID NO: 16 are described below. For example, Phage display is a powerful quantitative assay to measure protein:protein interaction using calorimetric ELISA (enzyme-linked immunosorbent assay). Surface plasmon resonance assays can be used as a quantitative method to measure binding between two molecules by the change in mass near an immobilized sensor caused by the binding of one protein from the aqueous phase to a second immobilized on the sensor. An additional useful binding assay is Fluorescence Resonance Energy Transfer (FRET), in which the close proximity of two fluorophores, each bound to a separate molecule, causes the excitation spectrum of one fluorophore to overlap with the excitation spectrum of the second, and thus dual fluorescence following excitation of only one fluorophore is indicative of binding. An additional assay useful in the present invention is fluorescence polarization, in which the quantifiable polarization value for a given fluorescently-tagged molecule is altered upon binding to a second molecule. A scintillation proximity assay can also be used to measure binding of a polypeptide comprising the amino acid sequence of SEQ ID NO: 16 and bacteriophage 77ORF104, in which the emmitance of radioactive particles is altered upon binding. Additionally, binding can be evaluated by a Bio Sensor assay, which is based on the ability of the sensor to register changes in admittance induced by ion-channel modulation following binding. A further assay which can be used to measure the binding of a polypeptide comprising the amino acid sequence of SEQ ID NO: 16 and bacteriophage 77 ORF 104 is the yeast two hybrid assay, in which the binding of the two polypeptides within the context of two fusion proteins expressed in yeast cells, permits the expression of reporter molecules which, in turn produces a measurable, or detectable signal.

The activity of the dnaI gene is defined as the expression of an RNA encoding a S. aureus DnaI polypeptide according to the invention.

As used herein, the term "polynucleotide encoding a polypeptide" or equivalent language encompasses polynucleotides that include a sequence encoding a polypeptide of the invention, particularly a bacterial polypeptide and more particularly a polypeptide of S. aureus DnaI protein having an amino acid sequence set out in FIG. 1, SEQ ID NO: 2. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions that also may contain coding and/or non-coding sequences.

As used herein, the term "dnaI gene" is meant to encompass a polynucleotide encoding a S. aureus DnaI polypeptide. Any additional nucleotide sequences necessary to direct transcription of RNA encoding a S. aureus DnaI polypeptide, either in a cell or in vitro, will be termed "regulatory sequences", which include but are not limited to transcriptional promoters and enhancers, and transcription terminators.

As used herein, the term "ORF 104" or "phage 77 ORF 104" or "77ORF104" encompasses a polynucleotide having the sequence provided in FIG. 4 (SEQ ID No: 4), which encodes a gene product known as the 77 ORF 104 gene product.

As used herein, the term "polynucleotide(s)" generally refers to any polyribonucleotide or poly-deoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation, selenoylation, sulfation and transfer-RNA mediated addition of amino acids to proteins, such as arginylation, and ubiquitination. See, for instance: PROTEINS—STRUCTURE AND MOLECULAR PROPERTIES, 2nd Ed., T. E. Creighton, W. H. Freeman and Company, New York (1993); Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990); and Rattan et al., Protein Synthesis: Posttranslational Modifications and Aging, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

As used herein, the term "variant(s)" refers to a polynucleotide or polypeptide that differs from a reference polynucleotide or polypeptide, respectively, but retains one or more of the biological activities of DnaI as described herein. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, and truncations in the polypeptide encoded by the reference sequence, or in the formation of fusion proteins, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes variants of each of the polypeptides of the invention, that is polypeptides that vary from the referents by conservative amino acid substitutions whereby a residue is substituted by another with like characteristics. Typically, such substitutions are among Val, Leu and Ile; among Ser and Thr; among the acidic residues Asp and Glu; and among the basic residues Lys and Arg; or aromatic residues Phe and Tyr. Particularly preferred are variants in which 1–10, 1–5, 1–3, 2–3, or 1 amino acid or amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

As uses herein, the term "fragment", when used in reference to a polypeptide, is a variant polypeptide having an amino acid sequence that is entirely the same as part but not all of the amino acid sequence of DnaI polypeptide according to the invention. As with S. aureus DnaI polypeptides, fragments may be "free-standing" ("consisting of"), or comprised within a larger polypeptide of which they form a part or region, most preferably as a single continuous region in a single larger polypeptide.

The term "isolated", when used in reference to a nucleic acid means that a naturally occurring sequence has been removed from its normal cellular (e.g., chromosomal) environment or is synthesized in a non-natural environment (e.g., artificially synthesized). Thus, the sequence may be in a cell-free solution or placed in a different cellular environment. The term does not imply that the sequence is the only nucleotide chain present, but that it is essentially free (about 90–95% pure at least) of non-nucleotide material naturally associated with it, and thus is distinguished from isolated chromosomes.

The term "enriched", when used in reference to a polynucleotide means that the specific DNA or RNA sequence constitutes a significantly higher fraction (2–5 fold) of the total DNA or RNA present in the cells or solution of interest than in normal or diseased cells or in cells from which the sequence was originally taken. This could be caused by a person by preferential reduction in the amount of other DNA or RNA present, or by a preferential increase in the amount of the specific DNA or RNA sequence, or by a combination of the two. However, it should be noted that enriched does not imply that there are no other DNA or RNA sequences present, just that the relative amount of the sequence of interest has been significantly increased.

As used herein, the term "significantly higher fraction" indicates that the level of enrichment is useful to the person making such an enrichment and indicates an increase enrichment relative to other nucleic acids of at least about 2-fold, or 5- to 10-fold or even more. The term also does not imply that there is no DNA or RNA from other sources. The other source DNA may, for example, comprise DNA from a yeast or bacterial genome, or a cloning vector such as pUC19. This term distinguishes from naturally occurring events, such as viral infection, or tumor type growths, in which the level of one mRNA may be naturally increased relative to other species of mRNA. That is, the term is meant to cover only those situations in which a person has intervened to elevate the proportion of the desired nucleic acid.

As used herein, the term "purified" in reference to nucleic acid does not require absolute purity (such as a homogeneous preparation). Instead, it represents an indication that the sequence is relatively more pure than in the natural environment (compared to the natural level, this level should be at least 2–5 fold greater, e.g., in terms of mg/mL). Individual clones isolated from a genomic or cDNA library may be purified to electrophoretic homogeneity. The claimed DNA molecules obtained from these clones could be obtained directly from total DNA or from total RNA. cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message over its proportion in naturally occurring cells. Thus, purification of at least one order of magnitude, preferably two or three orders, and more preferably four or five orders of magnitude is expressly contemplated. A genomic library can be used in the same way and yields the same approximate levels of purification.

The terms "isolated", "enriched", and "purified" used with respect to nucleic acids, above, may similarly be used to denote the relative purity and abundance of polypeptides. These, too, may be stored in, grown in, screened in, and selected from libraries using biochemical techniques familiar in the art. Such polypeptides may be natural, synthetic or chimeric and may be extracted using any of a variety of methods, such as antibody immunoprecipitation, other "tagging" techniques, conventional chromatography and/or electrophoretic methods. Some of the above utilize the corresponding nucleic acid sequence.

As used herein, the term "complement" when used in reference to a given polynucleotide sequence refers to a sequence of nucleotides which can form a double-stranded heteroduplex in which every nucleotide in the sequence of nucleotides is base-paired by hydrogen bonding to a nucleotide opposite it in the heteroduplex with the given polynucleotide sequence. The term may refer to a DNA or an RNA sequence that is the complement of another RNA or DNA sequence. As used herein, the term "hybridizes" refers to the formation of a hydrogen-bonded heteroduplex between two nucleic acid molecules. Generally, a given nucleic acid molecule will hybridize with its complement, or with a molecule that is sufficiently complementary to the given molecule to permit formation of a hydrogen-bonded heteroduplex between the two molecules.

As used herein, the term "probe" refers to a polynucleotide of at least 15 nucleotides (nt), 20 nt, 30 nt, 40 nt, 50 nt, 75 nt, 100 nt, 200 nt, 500 nt, 1000 nt, and even up to 5000 to 10,000 nt in length.

"Identity" and "similarity," as used herein and as known in the art, are relationships between two or more polypeptide sequences or two or more polynucleotide sequences, as the case may be, as determined by comparing the sequences.

Amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J.

Mol. Biol. 48:443–453). "Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the blosum62 substitution matrix (Hentikoff and Hentikoff, 1992, Proc. Natl. Acad. Sci. USA 89: 10915–10919). By the statement "sequence A is n % similar to sequence B" is meant that n % of the positions of an optimal global alignment between sequences A and B consists of conservative substitutions. By the statement "sequence A is n % identical to sequence B" is meant that n % of the positions of an optimal global alignment between sequences A and B consists of identical residues or nucleotides. Optimal global alignments in this disclosure used the following parameters in the Needleman-Wunsch alignment algorithm:

For polypeptides:
Substitution matrix: blosum62.
Gap scoring function: -A -B*LG, where A=11 (the gap penalty), B=1 (the gap length penalty) and LG is the length of the gap.
For nucleotide sequences:
Substitution matrix: 10 for matches, 0 for mismatches.
Gap scoring function: -A -B*LG where A=50 (the gap penalty), B=3 (the gap length penalty) and LG is the length of the gap.

Typical conservative substitutions are among Met, Val, Leu and lie; among Ser and Thr; among the residues Asp, Glu and Asn; among the residues Gln, Lys and Arg; or aromatic residues Phe and Tyr. In calculating the degree (most often as a percentage) of similarity between two polypeptide sequences, one considers the number of positions at which identity or similarity is observed between corresponding amino acid residues in the two polypeptide sequences in relation to the entire lengths of the two molecules being compared.

As used herein, the term "antibody" is meant to encompass constructions using the binding (variable) region of such an antibody, and other antibody modifications. Thus, an antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or F(ab')$_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate. Neutralizing antibodies are especially useful according to the invention for diagnostics, therapeutics and methods of drug screening and drug design.

As used herein, the term "specific for an epitope present on a S. aureus DnaI polypeptide", when used in reference to an antibody, means that the antibody recognizes and binds an antigenic determinant present on a S. aureus DnaI polypeptide according to the invention.

As used herein, the term "antigenically equivalent derivative(s)" encompasses a polypeptide, polynucleotide, or the equivalent of either which will be specifically recognized by certain antibodies which, when raised to the protein, polypeptide or polynucleotide according to the invention, interferes with the immediate physical interaction between pathogen and mammalian host.

As used herein, the term "essential", when used in connection with a gene or gene product, means that the host cannot survive without, or is significantly growth compromised, in the absence or depletion of functional product. An "essential gene" is thus one that encodes a product that is beneficial, or preferably necessary, for cellular growth in vitro in a medium appropriate for growth of a strain having a wild-type allele corresponding to the particular gene in question. Therefore, if an essential gene is inactivated or inhibited, that cell will grow significantly more slowly than a wild-type strain or even not at all. Preferably, growth of a strain in which such a gene has been inactivated will be less than 20%, more preferably less than 10%, most preferably less than 5% of the growth rate of the wild-type, or the rate will be zero, in the growth medium. Preferably, in the absence of activity provided by a product of the gene, the cell will not grow at all or will be non-viable, at least under culture conditions similar to normal in vivo growth conditions. For example, absence of the biological activity of certain enzymes involved in bacterial cell wall synthesis can result in the lysis of cells under normal osmotic conditions, even though protoplasts can be maintained under controlled osmotic conditions. Preferably, but not necessarily, if such a gene is inhibited, e.g., with an antibacterial agent or a phage product, the growth rate of the inhibited bacteria will be less than 50%, more preferably less than 30%, still more preferably less than 20%, and most preferably less than 10% of the growth rate of the uninhibited bacteria. As recognized by those skilled in the art, the degree of growth inhibition will generally depend upon the concentration of the inhibitory agent. In the context of the invention, essential genes are generally the preferred targets of antimicrobial agents. Essential genes can encode "target" molecules directly or can encode a product involved in the production, modification, or maintenance of a target molecule.

As used herein, "target" refers to a biomolecule or complex of biomolecules that can be acted on by an exogenous agent or compound, thereby modulating, preferably inhibiting, growth or viability of a bacterial cell. A target may be a nucleic acid sequence or molecule, or a polypeptide or a region of a polypeptide.

As used herein, the term "signal that is generated by activation or inhibition of a S. aureus DnaI polypeptide" refers to the measurable indicator of DnaI activity in an assay of DnaI activity. For example, $^3$H-thymidine DNA incorporation, plasmid replication, helicase loading, or simply signal resulting for binding of 77ORF104 to a DnaI polypeptide.

As used herein, the term "standard", used in reference to polypeptide activity, means the amount of activity observed or detected (directly or indirectly) in a given assay performed in the absence of a candidate compound. A "standard" serves as a reference to determine the effect, positive or negative, of a candidate compound on polypeptide activity.

A "candidate compound" as used herein, is any compound with a potential to modulate the expression or activity of a S. aureus DnaI polypeptide.

As used herein, the term "increase in activity" refers to an enhanced level of measurable activity of a polypeptide in a given assay in the presence of a candidate compound relative to the measurable level of activity in the absence of a candidate compound. Activity is considered increased according to the invention if it is at least 10% greater, 20% greater, 50% greater, 75% greater, 100% greater or more, up to 2-fold, 5-fold, 10-fold, 20-fold, 50-fold, 100-fold or more than in the absence of a candidate compound.

As used herein, the term "decrease in activity" refers to a reduced level of measurable activity of a polypeptide in a given assay in the presence of a candidate compound relative to the measurable level of activity in the absence of a candidate compound. Activity is considered decreased according to the invention if it is at least 10% less, preferably 15% less, 20% less, 50% less, 75% less, or even 100% less (i.e., no activity) than that observed in the absence of a candidate compound.

As used herein, the term "conditions that permit their interaction", when used in reference to a S. aureus DnaI polypeptide and a candidate compound means that the two entities are placed together, whether both in solution or with one immobilized or restricted in some way and the other in solution, wherein the parameters (e.g., salt, detergent, protein or candidate compound concentration, temperature, and redox potential, among others) of the solution are such that the S. aureus DnaI polypeptide and the candidate compound may physically associate. Conditions that permit protein: candidate interaction include, for example, the conditions described herein for Phage display, Surface Plasmon Resonance and FRET assays.

As used herein, the term "detectable change in a measurable parameter of DnaI" refers to an alteration in a quantifiable characteristic of a S. aureus DnaI polypeptide.

As used herein, the term "agonist" refers to an agent or compound that enhances or increases the activity of a S. aureus DnaI polypeptide or polynucleotide. An agonist may be directly active on a S. aureus DnaI polypeptide or polynucleotide, or it may be active on one or more constituents in a pathway that leads to enhanced or increased activity of a S. aureus DnaI polypeptide or polynucleotide.

As used herein, the term "antagonist" refers to an agent or compound that reduces or decreases the activity of a S. aureus DnaI polypeptide or polynucleotide. An antagonist may be directly active on a S. aureus DnaI polypeptide or polynucleotide, or it may be active on one or more constituents in a pathway that leads to reduced or decreased activity of a S. aureus DnaI polypeptide or polynucleotide.

As used herein, the term "antibacterial agent" or "antibacterial compound" refers to an agent or compound that has a bacteriocidal or bacteriostatic effect on one or more bacterial strains, preferably such an agent or compound is bacteriocidal or bacteriostatic on at least S. aureus.

As used herein, the term "synthesizing" refers to a process of chemically synthesizing a compound.

As used in the context of treating a bacterial infection a "therapeutically effective amount", "pharmaceutically effective amount" or "amount sufficient to provide a therapeutic effect" indicates an amount of an antibacterial agent which has a therapeutic effect. This generally refers to the inhibition, to some extent, of the normal cellular functioning of bacterial cells required for continued bacterial infection. Further, as used herein, a therapeutically effective amount means an amount of an antibacterial agent that produces the desired therapeutic effect as judged by clinical trial results and/or animal models. This amount can be routinely determined by one skilled in the art and will vary depending on several factors, such as the particular bacterial strain involved and the particular antibacterial agent used. In the same context, an "amount sufficient to reduce adhesion" of a bacterium to a tissue or tissue surface indicates an amount of an antibacterial agent that is effective for prophylactically preventing or reducing the extent of bacterial infection of the given tissue or tissue surface.

As used herein, a "tissue" refers to an aggregation of cells of one or more cell types which together perform one or more specific functions in an organism. As used herein, a "tissue surface" refers to that portion of a tissue that forms a boundary between a given tissue and other tissues or the surroundings of the tissue. A tissue surface may refer to an external surface of an animal, for example the skin or cornea, or, alternatively, the term may refer to a surface that is either internal, for example, the lining of the gut, or to a surface that is exposed to the outside surroundings of the animal only as the result of an injury or a surgical procedure.

As used herein, the term "measuring the binding of a candidate compound" refers to the use of an assay permitting the quantitation of the amount of a candidate compound physically associated with a S. aureus DnaI polypeptide.

As used herein, the term "directly or indirectly detectably labeled" refers to the attachment of a moiety to a candidate compound that renders the candidate compound either directly detectable (e.g., an isotope or a fluorophore) or indirectly detectable (e.g., an enzyme activity, allowing detection in the presence of an appropriate substrate, or a specific antigen or other marker allowing detection by addition of an antibody or other specific indicator).

As used herein, the term "small molecule" refers to compounds having molecular mass of less than 3000 Daltons, preferably less than 2000 or 1500, still more preferably less than 1000, and most preferably less than 600 Daltons. Preferably but not necessarily, a small molecule is not an oligopeptide.

As used herein, the term "mimetic" refers to a compound that can be natural, synthetic, or chimeric and is structurally and functionally related to a reference compound. In terms of the present invention, a "peptidomimetic," for example, is a non-peptide compound that mimics the activity-related aspects of the 3-dimensional structure of a peptide or polypeptide, for example a compound that mimics the structure of a peptide or active portion of a phage- or bacterial ORF-encoded polypeptide.

As used herein, the term "bacteriophage inhibitor protein" refers to a protein encoded by a bacteriophage nucleic acid sequence, which inhibits bacterial function in a host bacterium. Thus, it is a bacteria-inhibiting phage product. The term "bacteriophage inhibitor protein" encompasses a fragment, derivative, or active portion of a bacteriophage inhibitor protein.

As used herein, the term "active portion" refers to an epitope, a catalytic or regulatory domain, or a fragment of a bacteriophage inhibitor protein that is responsible for, or a significant factor in, bacterial target inhibition. The active portion preferably may be removed from its contiguous sequences and, in isolation, still effect inhibition.

As used herein, the term "treating a bacterial infection" refers to a process whereby the growth and/or metabolic activity of a bacterium or bacterial population in a host, preferably a mammal, more preferably a human, is inhibited or ablated.

As used herein, the term "bacterium" refers to a single bacterial strain and includes a single cell and a plurality or population of cells of that strain unless clearly indicated to the contrary. In reference to bacteria or bacteriophage, the term "strain" refers to bacteria or phage having a particular genetic content. The genetic content includes genomic content as well as recombinant vectors. Thus, for example, two otherwise identical bacterial cells would represent different strains if each contained a vector, e.g., a plasmid, with different inserts.

As used herein, the term "diagnosing" refers to the identification of an organism or strain of an organism responsible for a bacterial infection.

As used herein, the term "infection with *Staphylococcus aureus*" refers to the presence, growth or proliferation of cells of a *S. aureus* strain within, or on a surface of, an animal, such as a mammal, preferably a human.

As used herein, the term "bacteriophage 77 ORF 104-encoded polypeptide" refers to a polypeptide encoded by SEQ ID NO: 4 or to a fragment or derivative thereof encompassing an active portion of a bacteriophage 77 ORF 104-encoded polypeptide of sequence disclosed in SEQ ID NO: 5.

As used herein, the term "DnaC" refers to a polypeptide of SEQ ID NO: 9, including that encoded by a polynucleotide of SEQ ID NO: 7 or to a fragment or derivative of such polypeptide encompassing an active portion of *S. aureus* DnaC. In this context, an active portion of *S. aureus* DnaC refers to that fragment or portion of *S. aureus* DnaC that interacts with or is part of a complex including *S. aureus* DnaI or a fragment or derivative of *S. aureus* DnaI.

As used herein, the term "polypeptide complex" refers to a combination of two or more polypeptides in a physical association with each other. It is preferred that such a physical association be required for some aspect of the activity of one or more of the polypeptides in such a polypeptide complex.

As used herein, the term "physical association" refers to an interaction between two moieties involving contact between the two moieties.

As used herein, the term "bodily material(s)" means any material derived from an individual or from an organism infecting, infesting or inhabiting an individual, including but not limited to, cells, tissues and waste, such as, bone, blood, serum, cerebrospinal fluid, semen, saliva, muscle, cartilage, organ tissue, skin, urine, stool or autopsy materials.

As used herein, the term "disease(s)" means any disease caused by or related to infection by a bacterium, including, for example, otitis media, conjunctivitis, pneumonia, bacteremia, meningitis, sinusitis, pleural empyema and endocarditis, and most particularly meningitis, such as for example infection of cerebrospinal fluid.

As used herein, the term "fusion protein(s)" refers to a protein encoded by a gene comprising amino acid coding sequences from two or more separate proteins fused in frame such that the protein comprises fused amino acid sequences from the separate proteins.

As used herein, the term "host cell(s)" is a cell which has been transformed or transfected, or is capable of transformation or transfection by an exogenous polynucleotide sequence.

As used herein, the term "immunologically equivalent derivative(s)" encompasses a polypeptide, polynucleotide, or the equivalent of either which when used in a suitable formulation to raise antibodies in a vertebrate, results in antibodies that act to interfere with the immediate physical interaction between pathogen and mammalian host.

As used herein, the term "immunospecific" means that characteristic of an antibody whereby it possesses substantially greater affinity for the polypeptides of the invention or the polynucleotides of the invention than its affinity for other related polypeptides or polynucleotides respectively, particularly those polypeptides and polynucleotides in the prior art.

As used herein, the term "individual(s)" means a multicellular eukaryote, including, but not limited to a metazoan, a mammal, an ovid, a bovid, a simian, a primate, and a human.

As used herein, the term "Organism(s)" means a (i) prokaryote, including but not limited to, a member of the genus *Streptococcus, Staphylococcus, Bordetella, Corynebacterium, Mycobacterium, Neisseria, Haemophilus, Actinomycetes, Streptomyces, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia* and *Mycoplasma*, and further including, but not limited to, a member of the species or group, Group A *Streptococcus*, Group B *Streptococcus*, Group C *Streptococcus*, Group D *Streptococcus*, Group G *Streptococcus, Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfingens, Clostridium tetani, Clostridium botulinum, Treponema pallidum, Rickettsia rickettsii* and *Chlamydia trachomitis*, (ii) an archaeon, including but not limited to *Archaebacter*, and (iii) a unicellular or filamenous eukaryote, including but not limited to, a protozoan, a fungus, a member of the genus *Saccharomyces, Kluveromyces*, or *Candida*, and a member of the species *Saccharomyces ceriviseae, Kluveromyces lactis*, or *Candida albicans*.

As used herein, the term "recombinant expression system(s)" refers to a system in which vectors comprising sequences encoding polypeptides of the invention or portions thereof, or polynucleotides of the invention are introduced or transformed into a host cell or host cell lysate for the production of the polynucleotides and polypeptides of the invention.

As used herein, the term "artificially synthesized" when used in reference to a peptide, polypeptide or polynucleotide means that the amino acid or nucleotide subunits were chemically joined in vitro without the use of cells or polymerizing enzymes. The chemistry of polynucleotide and peptide synthesis is well known in the art.

In addition to the standard single and triple letter representations for amino acids, the term "X" or "Xaa" may also be used in describing certain polypeptides of the invention. "X" and "Xaa" mean that any of the twenty naturally occurring amino acids may appear at such a designated position in the polypeptide sequence.

As used herein, the term "specifically binding" in the context of the interaction of two polypeptides means that the two polypeptides physically interact via discrete regions or domains on the polypeptides, wherein the interaction is dependent upon the amino acid sequences of the interacting domains. Generally, the equilibrium binding concentration of a polypeptide that specifically binds another is in the range of about 1 µM or lower, preferably 100 nM or lower, 10 nM or lower, 1 nM or lower, 100 pM or lower, and even 10 pM or lower.

As used herein, the term "decrease in the binding" refers to a drop in the signal that is generated by the physical association between two polypeptides under one set of conditions relative to the signal under another set of reference conditions. The signal is decreased if it is at least 10% lower than the level under reference conditions, and preferably 20%, 40%, 50%, 75%, 90%, 95% or even as much as 100% lower (i.e., no detectable interaction).

As used herein, the term "detectable marker", when used in the context of a yeast two-hybrid assay, refers to a polypeptide that confers a trait upon a cell expressing that polypeptide that signals the presence or amount of that polypeptide expressed. Detectable markers are encoded on plasmids that may exist episomally or may be integrated into the genome of a host cell. Detectable markers include, but are not limited to, polypeptides encoding enzymes allowing colorimetric or fluorescent detection (e.g., *E. coli* LacZ, which catalyzes the conversion of the substrate analog X-gal to generate a blue color), polypeptides encoding enzymes conferring antibiotic resistance, and polypeptides encoding enzymes conferring the ability of a yeast strain to grow on medium lacking a given component (i.e., critical for the relief of auxotrophy).

As used herein, the term "results in the expression of a detectable marker" means that the interaction of factors necessary to permit the expression of a detectable marker (e.g., two-hybrid transactivation domain and DNA binding domain fusion proteins) causes the transactivation and translation of detectable levels of a detectable marker. A "detectable level" is that level of expression that can be differentiated from background expression occurring in the substantial absence of one or more factors or conditions necessary for marker expression. Detectable levels will vary depending upon the nature of the detectable marker, but will generally consist of levels at least about 10% or more greater than the background level of a given marker.

As used herein, the term "decrease in the expression" refers to a drop in the expression of a detectable marker under one set of conditions relative to the expression under another set of reference conditions. The expression of a detectable marker is decreased if it is at least 10% lower than the level under reference conditions, and preferably 20%, 40%, 50%, 75%, 90%, 95% or even as much as 100% lower (i.e., not expressed).

How to Identify a *S. aureus* dnaI Sequence:

Using methodology described in detail in Example 1, a *S. aureus* polypeptide that specifically bound the P77 phage ORF 104 protein was isolated. The sequence of a tryptic peptide of the *S. aureus* polypeptide, GHVPENVTDNDR (SEQ ID NO: 19), was used to BLAST search the *S. aureus* nucleotide sequence in the University of Oklahoma *S. aureus* genomic database at http://www.genome.ou.edu/staph.html.

The University of Oklahoma's Advanced Center for Genome Technology web site. One sequence contig of 4850 nucleotides in length (Contig 981), when converted from amino acid sequence, contained within it the similar amino acid sequence GHVPELYVDNNR (SEQ ID NO: 11; FIG. 5). This tentative identification of the candidate protein was then confirmed upon in silico tryptic digestion of the open reading frame found in the contig (FIG. 5). The obtained PSD/CID spectra for tryptic peptides with monoisotopic MH+ masses of 1351.8, 1412.7, and 1617.8 Da were similar to the predicted PSD/CID fragmentation patterns of the tryptic peptides with monoisotopic MH+ masses of 1351.8 and 1617.8 Da found in the contig's +3 open reading frame (FIG. 5).

Comparison of the ORF of the *S. aureus* contig that encodes a tryptic peptide similar to that identified in the *S. aureus* phage 77 ORF 104 binding studies with all other sequences in the public domain databases revealed that the ORF is related to the DnaI protein from *Bacillus subtilis* (Table 1, SEQ ID NOs: 14–15) a protein implicated in chromosome replication. No other significant similarity was found with any other protein in publicly accessible databases. The degree of relatedness of the identified ORF to the *B. subtilis* DnaI protein shows 41% identity and 63% similarity (Table 1, SEQ ID NOs: 14–15).

Many genes of *B. subtilis* involved in DNA replication have been identified through the isolation of thermosensitive mutants. One of these, dnaI2, affected an unknown step of chromosome replication at the restrictive temperature (Karamata, D. and Gross, J. D. (1970) Mol. Gene. Genet. 108, 277–287). The gene was mapped around 250° on the *B subtilis* chromosome and resides immediately downstream of the dnaB gene on the *B. subtilis* chromosome (Bruand, C. and Ehrlich, S. D. (1995) Microbiology 141, 1199–1200). The dnaI2 mutation has been characterized and resides within the dnaI gene and consists of a G to A substitution at nucleotide position 922 (FIG. 1; SEQ ID NO: 1) resulting in a glycine to glutamate change at position 307 (FIG. 1; SEQ ID NO: 2) (Bruand, C. and Ehrlich, S. D. (1995) Microbiology 141, 1199–1200).

DnaC has been genetically identified to be the major component DNA helicase of chromosome replication (Sakamoto, Y., Nakai, S., Moriya, S., Yoshikawa, H., and Ogasawara, N. (1995) Microbiology 141, 641–644) and is thought to unwind duplex DNA progressively and allow for binding of the DNA polymerase III holoenzyme necessary for priming and DNA synthesis. One possible function of DnaI is as a helicase loader, being responsible for transferring DnaC helicase to the oriC. The product of the dnaC and dnaI genes are required for chromosome replication and are all essential for DNA replication in *B. subtilis* (Ceglowski, P., Lurz, R., Alonso, J. C. J. (1993) Mol. Biol. 236, 1324–1340).

Databases were searched for *S. aureus* genes which may be related to the *B. subtilis* dnaC gene. Utilizing the *B. subtilis* amino acid sequence for DnaC (Accession Number P37469), a BLAST search was performed of the *Staphylococcus* database at The Institute of Genomic Research (TIGR) web site and revealed the presence of an ORF within the *S. aureus* genome encoding a related protein. The nucleotide sequence and corresponding protein sequence are presented in FIG. 6B (SEQ ID NO: 7) and FIG. 6D (SEQ ID NO: 9), respectively.

Identification of the Surface of Interaction on DnaI

This invention relates, in part, to a specific interaction between a growth-inhibitory protein encoded by the *Staphylococcus aureus* bacteriophage 77 genome and an essential *S. aureus* protein. This interaction forms the basis for drug screening assays. More specifically, the invention relates to the interacting regions of the protein encoded by the *S. aureus* bacteriophage 77 and the *S. aureus* DnaI proteins, forming the basis for screening assays. The invention provides a method for the identification of DnaI polypeptide fragments that are involved in said interaction between DnaI and ORF 104 from bacteriophage 77. Several approaches and techniques known to those skilled in the art can be used to identify and to characterize fragments of the DnaI interacting with 77 ORF 104. These fragments may include, for example, truncation polypeptides having a portion of an amino acid sequence of the proteins, or variants thereof, such as a continuous series of residues that includes an amino- and/or carboxyl-terminal amino acid sequence for DnaI.

A) Affinity Chromatography

Partial proteolysis of proteins in solution is one method to delineate the domain boundaries in multi-domain proteins. By subjecting proteins to limited digestion, the most accessible cleavage sites are preferentially hydrolyzed. These cleavage sites preferentially reside in less structured regions which include loops and highly mobile areas typical of the joining amino acids between highly structured domains. For this analysis, a purified recombinant DnaI polypeptide (including a fragment of DnaI either purified from a previous protease digestion or expressed from a recombinant nucleic acid vector as a fragment) can be subjected to partial proteolysis. The proteolysis can be performed with low concentrations of proteases, including, but not limited to trypsin, chymotrypsin, endoproteinase Glu-C, and Asp-N with a DnaI polypetide in solution, resulting in the generation of defined proteolytic products as observed by SDS-PAGE. An acceptable concentration and reaction time is defined by the near complete conversion of the full-length protein to stable proteolytic products. The partial proteolytic fragments are then subjected to affinity chromatography with immobilized 77 ORF 104 to determine the region of the DnaI polypeptide containing the 77 ORF 104 binding site. Interacting domains are identified by mass spectrometry to determine the masses of both the intact fragment and the series of fragments from a tryptic digest to identify the amino acid residues contained within the partial proteolytic fragment. Using both sets of data, the amino acid sequence of the partial proteolytic fragment can be precisely determined.

B) Yeast Two-Hybrid analysis

The interaction between 77 ORF 104 and portions of the DnaI polypeptide can also be assessed in vivo using the yeast two hybrid system. To do this, bacteriophage 77 ORF 104 is fused to the DNA binding domain of the yeast transcriptional transactivator Gal4, and different portions of the DnaI polypeptide are fused to the carboxyl terminus of the Gal4 activation domain. The two plasmids bearing such constructs can be introduced sequentially, or in combination, into a yeast cell line, for example AH109 (Clontech Laboratories), previously engineered to contain chromosomally-integrated copies of E. coli lacZ and the selectable HIS3 and ADE2 genes. The lacZ, HIS, and ADE2 reporter genes, each driven by a promoter containing Gal4 binding sites, are used for measuring protein—protein interactions. If the two recombinant proteins interact within the yeast cell, the resulting protein:protein complex activates transcription from promoters containing Gal4 binding sites. Expression of HIS3, and ADE2 genes is manifested by relief of histidine and adenine auxotrophy. As described in the examples below, full length DnaI, as well as DnaI fragments, was found to interact with bacteriophage 77 ORF 104 fusion polypeptides using this system.

Further elucidation of the bacteriophage 77 ORF 104 interacting domain of DnaI can be carried out by first subjecting the full length DnaI polypeptide to deletional mutagenesis, the methods of which are known to those of skill in the art. The mutated DnaI polypeptides can then be subjected to yeast two hybrid analysis as described above, to further narrow those amino acid sequences or polypeptide fragments, for example, those within SEQ ID NO: 16, that are required for the binding of DnaI to bacteriophage 77 ORF 104.

S. aureus DnaI Polypeptides

In one aspect of the invention there are provided polypeptides of S. aureus referred to herein as "DnaI" and "DnaI polypeptides" as well as biologically, diagnostically, prophylactically, clinically or therapeutically useful variants thereof, and compositions comprising the same.

Among the particularly preferred embodiments of the invention are variants of S. aureus DnaI polypeptides encoded by naturally occurring alleles of the dnaI gene. The present invention provides for an isolated polypeptide which comprises or consists of: (a) an amino acid sequence which has at least 50% identity, preferably at least 80% identity, more preferably at least 90%, yet more preferably at least 95%, most preferably at least 97–99% or exact identity, to that of SEQ ID NO:2 over the entire length of SEQ ID NO: 2 or b) an amino acid sequence that has at least 70% similarity, at least 80% similarity, at least 90% similarity, at least 95% similarity, at least 97–99% similarity or even 100% similarity over the entire length of SEQ ID NO: 2.

The polypeptides of the invention include a polypeptide of FIG. 1 (SEQ ID NO: 2) (in particular the mature polypeptide) as well as polypeptides and fragments, particularly those which have the biological activity of DnaI, and also those which have at least 50% identity over 20, 40, 50 or more amino acids to a polypeptide of SEQ ID NO: 2 or the relevant portion, preferably at least 60%, 70%, or 80% identity, more preferably at least 90% identity to a polypeptide of SEQ ID NO: 2 and more preferably at least 90% identity to a polypeptide of SEQ ID NO: 2 and still more preferably at least 95% identity to a polypeptide of SEQ ID NO: 2 and yet still more preferably at least 99% identity to a polypeptide of SEQ ID NO: 2.

The polypeptides of the invention also include a polypeptide or protein fragment that has at least 60%, 70%, 80% or 90% similarity, 95% similarity or even 97–99% similarity over 10, 20, 25, 30 or more amino acids to a polypeptide of SEQ ID NO: 2. It is preferred that a polypeptide of the invention has at least 60% similarity to a polypeptide of SEQ ID NO: 2 over at least 20 amino acids.

It is most preferred that a polypeptide of the invention is derived from S. aureus, however, it may be obtained from other organisms of the same taxonomic genus. A polypeptide of the invention may also be obtained, for example, from organisms of the same taxonomic family or order.

Fragments of DnaI also are included in the invention. These fragments may include, for example, truncation polypeptides having a portion of an amino acid sequence of FIG. 1 (SEQ ID NO: 2), or variants thereof, such as a continuous series of residues that includes an amino- and/or carboxyl-terminal amino acid sequence. Degradation forms of the polypeptides of the invention produced by or in a host cell, particularly S. aureus, are also preferred. Further preferred are fragments characterized by structural or functional attributes such as fragments that comprise alpha-helix and alpha-helix-forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Fragments of DnaI may be expressed as fusion proteins with other proteins or protein fragments.

Preferred fragments also include an isolated polypeptide comprising an amino acid sequence having at least 20, 30, 40, 50, or 100 contiguous amino acids from the amino acid sequence of SEQ ID NO: 2.

Also preferred are biologically "active" fragments which are those fragments that mediate activities of S. aureus DnaI, including those with a similar activity or an improved activity, or with a decreased undesirable activity. Also included are those fragments that are antigenic or immunogenic in an animal, especially in a human. Particularly preferred are fragments comprising domains that confer a function essential for viability of S. aureus.

Fragments of the polypeptides of the invention may be employed for producing the corresponding full-length polypeptide by peptide synthesis; therefore, these variants may be employed as intermediates for producing the full-length polypeptides of the invention.

S. aureus Polynucleotides

It is an object of the invention to provide polynucleotides that encode DnaI polypeptides, particularly polynucleotides that encode the polypeptide herein designated S. aureus DnaI.

In one aspect of the invention a polynucleotide is provided that comprises a region encoding a S. aureus DnaI polypeptide, the polynucleotide comprising a sequence set out in SEQ ID NO: 1. Such a polynucleotide encodes a full length DnaI gene, or a variant thereof. It is contemplated that this full-length gene is essential to the growth and/or survival of an organism which possesses it, such as S. aureus.

As a further aspect of the invention there are provided isolated nucleic acid molecules encoding and/or expressing a fragment of a full-length DnaI polypeptide, particularly a S. aureus DnaI polypeptide or a variant thereof. Further embodiments of the invention include biologically, diagnostically, prophylactically, clinically or therapeutically useful polynucleotides and polypeptides, and variants thereof, and compositions comprising the same.

A polynucleotide of the invention is obtained using S. aureus cells as starting material, the nucleotide sequence information disclosed in SEQ ID NO: 1, and standard cloning and screening methods, such as those for cloning and sequencing chromosomal DNA fragments from bacteria. For example, to obtain a polynucleotide sequence of the invention, such as the polynucleotide sequence disclosed as in SEQ ID NO: 1, a library of clones of chromosomal DNA of S. aureus in E. coli or another suitable host is probed with a radiolabeled oligonucleotide, preferably a 17-mer or longer, derived from a partial sequence. Clones carrying DNA identical to that of the probe can be distinguished using stringent hybridization conditions. As herein used, the terms "stringent conditions" and "stringent hybridization conditions" mean hybridization occurring only if there is at least 95% and preferably at least 97% identity between the sequences. A specific example of stringent hybridization conditions is of a overnight incubation of a hybridization support (e.g., a nylon or nitrocellulose membrane at 42° C. in a solution comprising: $1 \times 10^6$ cpm/ml labeled probe, 50% formamide, 5×SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1×SSC at about 65° C.

Hybridization and wash conditions are well known to those skilled in the art and are exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention. By sequencing the individual clones thus identified by hybridization, it is possible to confirm the identity of the clone.

Alternatively, an amplification process can be utilized to isolate the polynucleotide. In this approach, the sequence disclosed as SEQ ID NO: 1 is targeted by two oligonucleotides, one identical to a sequence on the coding DNA strand at or upstream of the ATG initiation codon and the other which anneals to the opposite strand at or downstream of the stop codon. Priming from these oligonucleotides in a polymerase chain reaction yields a full length gene coding sequence. Such suitable techniques are described by Maniatis, T., Fritsch, E. F. and Sambrook, MOLECULAR CLONING: A LABORATORY MANUAL, $2^{nd}$ Edition, Cold Spring Harbor Laboratory Press, Cold Spring Harbor, N.Y. (1989).

In a further aspect, the present invention provides for an isolated polynucleotide comprising or consisting of: (a) a polynucleotide sequence which has at least 60% identity, preferably at least 70% identity, more preferably at least 80% identity, more preferably at least 90% identity, yet more preferably at least 95%, most preferably at least 97–99% or exact identity, to that of SEQ ID NO: 1 over the entire length of SEQ ID NO: 1; (b) a polynucleotide sequence encoding a polypeptide which has at least 50% identity, preferably at least 60% identity, more preferably at least 70% identity, more preferably at least 80% identity, more preferably at least 90%, yet more preferably at least 95%, most preferably at least 97–99% or exact identity to SEQ ID NO:2 over the entire length of SEQ ID NO:2; or the complement of a sequence of (a) or (b) above.

The invention provides a polynucleotide sequence identical over its entire length to the coding sequence of SEQ ID NO: 1. Also provided by the invention is a coding sequence for a mature polypeptide or a fragment thereof (Including, for example, a fragment encoding a polypeptide of SEQ ID NO: 16), by itself as well as a coding sequence for a mature polypeptide or a fragment in reading frame with another coding sequence, such as a sequence encoding a leader or secretory sequence, a pre-, or pro-, or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize or destabilize mRNAs, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., Proc. Natl. Acad. Sci. 86: 821–824 (1989), or an HA peptide tag (Wilson et al., Cell 37: 767 (1984), both of which may be useful in purifying polypeptide sequences fused to them. Polynucleotides of the invention also include, but are not limited to, polynucleotides comprising a structural gene and its naturally associated sequences that control gene expression.

It is most preferred that a polynucleotide of the invention is derived from *Staphylococcus aureus*, however, it may also be obtained from other organisms of the same taxonomic genus. A polynucleotide of the invention may also be obtained, for example, from organisms of the same taxonomic family or order.

Further preferred embodiments are polynucleotides encoding *S. aureus* dnaI variants that have the amino acid sequence of *S. aureus* DnaI polypeptide of SEQ ID NO: 2 in which several, a few, 5 to 10, 1 to 5, 1 to 3, 2, 1 or no amino acid residues are substituted, modified, deleted and/or added, in any combination. Especially preferred among these polynucleotides are those encoding silent nucleotide alterations that do not alter the coding sequence or activities of *S. aureus* DnaI polypeptides they encode.

Preferred embodiments are polynucleotides encoding polypeptides that retain substantially the same biological function or activity as the mature polypeptide encoded by a DNA of SEQ ID NO: 1.

In accordance with certain preferred embodiments of this invention there are provided polynucleotides that hybridize, particularly under stringent conditions, to *S. aureus* dnaI polynucleotide sequences, such as those polynucleotides in FIG. 1.

The polynucleotides of the invention are useful as hybridization probes for RNA, cDNA and genomic DNA to isolate full-length cDNAs and genomic clones encoding genes that have a high degree of sequence identity to the dnaI gene. Such probes generally will comprise at least 15 to about 100 residues or base pairs, although such probes will preferably have about 20 to 50 nucleotide residues or base pairs. Particularly preferred probes are about 20 to about 30 nucleotide residues or base pairs in length.

A coding region of a related dnaI gene from a bacterial species other than *S. aureus* may be isolated by screening a library using a DNA sequence provided in SEQ ID NO: 1 to synthesize an oligonucleotide probe. A labeled oligonucleotide having a sequence complementary to that of a gene of the invention is then used to screen a library of cDNA, genomic DNA or mRNA to determine to which member(s) of the library the probe hybridizes.

There are several methods available and well known to those skilled in the art to obtain full-length DNAs, or extend short DNAs, for example those based on the method of Rapid Amplification of cDNA ends (RACE) (see, for example, Frohman, et al., PNAS USA 85: 8998–9002, 1988). Recent modifications of the technique, exemplified by the MARATHON™ technology (Clontech Laboratories Inc.) for example, have significantly simplified the search for longer cDNAs. In the MARATHON™ technology, cDNAs are prepared from mRNA extracted from a chosen cell and an 'adaptor' sequence is ligated onto each end. Nucleic acid amplification by PCR is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor-specific primer that anneals further 3' in the adaptor sequence and a gene-specific primer that anneals further 5' in the selected gene sequence). The products of this reaction can then be analyzed by DNA sequencing and a full-length DNA constructed either by joining the product directly to the existing DNA to give a complete sequence, or by carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of SEQ ID NO: 1 are useful for the design of PCR primers in reactions to determine whether or not the polynucleotides identified herein in whole or in part are transcribed in bacteria in infected tissue. That is, the polynucleotides of the invention are useful for diagnosis of infection with a bacterial strain carrying those sequences. It is recognized that such sequences also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide. Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

A polynucleotide of the invention thus may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleotide that when taken in combination with adjacent nucleotide positions, read in the correct reading frame, would have the effect of generating a premature termination codon in such reading frame.

For each and every polynucleotide of the invention there is also provided a polynucleotide complementary to it.

Vectors, Host Cells, and Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention Recombinant DnaI polypeptides of the present invention may be prepared by processes well known to those skilled in the art from genetically engineered host cells comprising expression systems. Accordingly, in a further aspect, the present invention relates to expression systems that comprise a dnaI polynucleotide or polynucleotides of the present invention, to host cells which are genetically engineered with such expression systems, and to the production of polypeptides of the invention by recombinant techniques.

For recombinant production of DnaI polypeptides of the invention, host cells can be genetically engineered to incorporate expression systems or portions thereof or polynucleotides of the invention. Representative examples of appropriate hosts include bacterial cells (Gram positive and Gram negative), fungal cells, insect cells, animal cells and plant cells. Polynucleotides are introduced to bacteria by standard chemical treatment protocols, such as the induction of competence to take up DNA by treatment with calcium chloride (Sambrook et al., supra). Introduction of polynucleotides into fungal (e.g., yeast) host cells is effected, if desired, by standard chemical methods, such as lithium acetate-mediated transformation.

A great variety of expression systems are useful to produce DnaI polypeptides of the invention. Such vectors include among others, chromosomal-, episomal- and virus-derived vectors. For example, vectors derived from bacterial plasmids, from bacteriophages, from transposons, from yeast episomes, from insertion elements, from yeast chromosomal elements, from viruses, and from vectors derived from combinations thereof, are useful in the invention.

DnaI polypeptides of the invention are recovered and purified from recombinant cell cultures by well-known methods including ammonium sulfate or ethanol precipitation, acid or urea extraction, anion or cation exchange chromatography, phosphocellulose chromatography, hydrophobic interaction chromatography, affinity chromatography, hydroxylapatite chromatography, and lectin chromatography. Well known techniques for refolding may be employed to regenerate an active conformation when the DnaI polypeptide is denatured during isolation and/or purification.

Diagnostic, Prognostic, Serotyping, and Mutation Assays

This invention is also related to the use of dnaI polynucleotides and polypeptides of the invention for use as diagnostic reagents. Detection of *S. aureus* dnaI polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the *S. aureus* dnaI gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled dnaI polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al, (1985) Science 230, 1242. Sequence changes at specific locations also may be revealed by nuclease protection assays, such as RNase, V1 and S1 protection assay or a chemical cleavage method. See, for example, Cotton et al., (1985) Proc. Natl. Acad. Sci., USA 85, 4397–4401.

In another embodiment, an array of oligonucleotide probes comprising dnaI nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., (1996) Science 274, 610).

Thus in another aspect, the present invention relates to a diagnostic kit which comprises:

(a) a polynucleotide of the present invention, preferably the nucleotide sequence of SEQ ID NO: 1, or a fragment thereof; (b) a nucleotide sequence complementary to that of (a); (c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a disease, among others.

This invention also relates to the use of dnaI polynucleotides of the present invention as diagnostic reagents. Detection of a mutated form of a polynucleotide of the invention, preferably, SEQ ID NO: 1, which is associated with a disease or pathogenicity will provide a diagnostic tool that can add to, or define, a diagnosis of a disease, a prognosis of a course of disease, a determination of a stage of disease, or a susceptibility to a disease, which results from underexpression, over-expression or altered expression of the polynucleotide. Organisms, particularly infectious organisms, carrying mutations in such polynucleotide may be detected at the polynucleotide level by a variety of techniques, such as those described elsewhere herein.

The dnaI nucleotide sequences of the present invention are also valuable for organism chromosome identification. The sequence is specifically targeted to, and can hybridize with, a particular location on an organism's chromosome, particularly to a *S. aureus* chromosome. The mapping of relevant sequences to chromosomes according to the present invention may be an important step in correlating those sequences with pathogenic potential and/or an ecological niche of an organism and/or drug resistance of an organism, as well as the essentiality of the gene to the organism. Once a sequence has been mapped to a precise chromosomal location, the physical position of the sequence on the chromosome can be correlated with genetic map data. Such data may be found on-line in a sequence database. The relationship between genes and diseases that have been mapped to the same chromosomal region are then identified through known genetic methods, for example, through linkage analysis (coinheritance of physically adjacent genes) or mating studies, such as by conjugation.

The differences in a polynucleotide and/or polypeptide sequence between organisms possessing a first phenotype and organisms possessing a different, second different phenotype can also be determined. If a mutation is observed in some or all organisms possessing the first phenotype but not in any organisms possessing the second phenotype, then the mutation is likely to be the causative agent of the first phenotype.

Polypeptides and polynucleotides for prognosis, diagnosis or other analysis may be obtained from a putatively infected and/or infected individual's bodily materials. Particularly DNA or polynucleotides, from any of these sources may be used directly for detection or may be amplified enzymatically using PCR or other amplification technique with oligonucleotide amplification primers derived from the polynucleotide sequence of S. aureus dna 1. RNA, particularly mRNA, or RNA reverse transcribed to cDNA, is also useful for diagnostics. Following amplification of a S aureus dnaI-related polynucleotide from a sample, characterization of the species and strain of infecting or resident organism is made by an analysis of the amplified polynucleotide relative to one or more reference polynucleotides or sequences relative to a standard from a related organism (i.e. a known strain of S. aureus).

Point mutations can be identified by hybridizing amplified DNA to known dnaI polynucleotide sequences and by detecting differences in melting temperatures or renaturation kinetics. Perfectly or significantly matched sequences can be distinguished from imperfectly or more significantly mismatched duplexes by RNase protection or S1 nuclease mapping. (See, for example, Cotton et al., (1988) Proc. Natl. Acad. Sci. USA 85:4397–4401). Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al, (1985) Science 230, 1242. Sequence changes at specific locations also may be revealed by nuclease protection assays, such as RNase, V1 and S1 protection assay or a chemical cleavage method. (Cotton et al., 1988 Supra).

In another embodiment, an array of oligonucleotide probes comprising dnaI nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., (1996) Science 274, 610).

In another aspect, the present invention relates to a diagnostic kit which comprises: (a) a polynucleotide of the present invention, preferably the nucleotide sequence of SEQ ID NO: 1, or a fragment thereof; (b) a nucleotide sequence complementary to that of (a); (c) a polypeptide of the present invention, preferably the polypeptide of SEQ ID NO:2 or a fragment thereof; or (d) an antibody to a polypeptide of the present invention, preferably to the polypeptide of SEQ ID NO:2. Such a kit will be of use in diagnosing a disease or susceptibility to a disease, among other uses.

The invention further provides a process for diagnosing bacterial infections such as those caused by S. aureus, the process comprising determining from a sample derived from an individual, such as a bodily material, an increased level of expression of a polynucleotide having a sequence disclosed in SEQ ID NO: 1 relative to a sample taken from a non-diseased individual. Increased or decreased expression of a dnaI polynucleotide can be measured using any one of the methods well known in the art for the quantitation of polynucleotides, such as, for example, PCR, RT-PCR, RNase protection, Northern blotting and other hybridization methods, and spectrometry.

In addition, a diagnostic assay in accordance with the invention for detecting over-expression of DnaI polypeptide compared to normal control tissue samples may be used to detect the presence of an infection, for example. Assay techniques that can be used to determine levels of a S. aureus DnaI polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

Gridding and Polynucleotide Subtraction of S. aureus Genomic Sequences

The dnaI polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as hybridization or nucleic acid amplification, using a probe obtained or derived from a bodily sample, to determine the presence a particular polynucleotide sequence or related sequence in an individual.

Antibodies Specific for S. aureus Peptides or Polypeptides

The DnaI polypeptides and polynucleotides of the invention or variants thereof, or cells expressing them are useful as immunogens to produce antibodies immunospecific for such polypeptides or polynucleotides, respectively.

In certain preferred embodiments of the invention there are provided antibodies against S. aureus DnaI polypeptides or polynucleotides encoding them. Antibodies against DnaI-polypeptide or dnaI-polynucleotide are useful for treatment of infections, particularly bacterial infections.

Antibodies generated against the polypeptides or polynucleotides of the invention are obtained by administering the polypeptides and/or polynucleotides of the invention or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures is useful. Examples include various techniques, such as those in Kohler, G. and Milstein, C., Nature 256: 495–497 (1975); Kozbor et al., Immunology Today 4: 72 (1983); and Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other mammals, are useful to express humanized antibodies immunospecific to the polypeptides or polynucleotides of the invention.

When antibodies are administered therapeutically, the antibody or variant thereof is preferably modified to make it less immunogenic in the individual. For example, if the individual is human the antibody is most preferably "humanized," where the complimentarily determining region or regions of the hybridoma-derived antibody has been transplanted into a human monoclonal antibody, for example as described in Jones et al. (1986), Nature 321, 522–525 or Tempest et al., (1991) Biotechnology 9, 266–273.

Alternatively, phage display technology is useful to select antibody genes with binding activities towards a DnaI polypeptide of the invention. In one approach, antibody fragments specific for S. aureus DnaI are selected from an immune library of antibody genes expressed as fusions with coat protein of filamentous phage. Alternatively, naive libraries are screened by phage display techniques to identify genes encoding antibodies specific for DnaI or from naive libraries (McCafferty, et al., (1990), Nature 348, 552–554; Marks, et al., (1992) Biotechnology 10, 779–783; a recent reference is de Haard et al. (1999) J Biol Chem 274: 18218–18230). The ability to recover, for various targets, antibodies with subnanomolar affinities obviates the need for immunization. The affinity of these antibodies can also be improved by, for example, chain shuffling (Clackson et al., (1991) Nature 352: 628).

The above-described antibodies may be employed to isolate or to identify clones expressing the polypeptides or polynucleotides of the invention, for example to purify the polypeptides or polynucleotides by immunoaffinity chromatography.

A variant polypeptide or polynucleotide of the invention, such as an antigenically or immunologically equivalent derivative or a fusion protein of the polypeptide is also useful as an antigen to immunize a mouse or other animal such as a rat or chicken. A fused protein provides stability to the polypeptide acting as a carrier, or acts as an adjuvant or both. Alternatively, the antigen is associated, for example by conjugation, with an immunogenic carrier protein, such as bovine serum albumin, keyhole limpet haemocyanin or tetanus toxoid. Alternatively, when antibodies are to be administered therapeutically, alternatively a multiple antigenic polypeptide comprising multiple copies of the polypeptide, or an antigenically or immunologically equivalent polypeptide thereof may be sufficiently antigenic to improve immunogenicity so as to obviate the use of a carrier.

In accordance with an aspect of the invention, there is provided the use of a dnaI polynucleotide of the invention for therapeutic or prophylactic purposes, in particular genetic immunization. The use of a dnaI polynucleotide of the invention in genetic immunization preferably employs a suitable delivery method such as direct injection of plasmid DNA into muscles (Wolff et al., Hum Mol Genet (1992) 1: 363, Manthorpe et al., Hum. Gene Ther. (1983) 4: 419), delivery of DNA complexed with specific protein carriers (Wu et al., J. Biol. Chem. (1989) 264: 16985), coprecipitation of DNA with calcium phosphate (Benvenisty & Reshef, PNAS USA, (1986) 83: 9551), encapsulation of DNA in various forms of liposomes (Kaneda et al., Science (1989) 243: 375), particle bombardment (Tang et al., Nature (1992) 356:152, Eisenbraun et al., DNA Cell Biol (1993) 12: 791) or in vivo infection using cloned retroviral vectors (Seeger et al., PNAS USA (1984) 81: 5849).

Antagonists and Agonists: Assays and Molecules

The invention is based in part on the discovery that DnaI is a target for the bacteria phage 77ORF104 inhibitory factor. Applicants have recognized the utility of the interaction in the development of antibacterial agents. Specifically, the inventors have recognized that 1) DnaI is a critical target for bacterial inhibition; 2) 77ORF104 or derivatives or functional mimetics thereof are useful for inhibiting bacterial growth; and 3) the interaction between dnaI and of S. aureus and 77ORF104 may be used as a target for the screening and rational design of drugs or antibacterial agents. In addition to methods of directly inhibiting DnaI activity, methods of inhibiting DnaI expression are also attractive for antibacterial activity.

In several embodiments of the invention, there are provided methods for identifying compounds which bind to or otherwise interact with and inhibit or activate an activity or expression of a polypeptide and/or polynucleotide of the invention comprising: contacting a polypeptide and/or polynucleotide of the invention with a compound to be screened under conditions to permit binding to or other interaction between the compound and the polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the polypeptide and/or polynucleotide by detecting the presence or absence of a signal generated from the binding or interaction of the compound with the polypeptide and/or polynucleotide.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing dnaI-induced activities, thereby preventing the action or expression of S. aureus DnaI polypeptides and/or polynucleotides by excluding S. aureus DnaI polypeptides and/or polynucleotides from binding.

Potential antagonists also include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, (1991) J. Neurochem. 56, 560; see also OLIGODEOXYNUCLEOTIDES AS ANTISENSE INHIBITORS OF GENE EXPRESSION, CRC Press, Boca Raton, Fla. (1988), for a description of these molecules). Preferred potential antagonists include compounds related to and variants of 77ORF104 and of DnaI. Other examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Compounds may be identified from a variety of sources, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991). Peptide modulators can also be selected by screening large random libraries of all possible peptides of a certain length.

Compounds could also be derived from the polypeptide sequence of 77ORF104 itself. Peptide fragments representing small overlapping fragments or peptides spanning the entire amino acid sequence of the protein can be used to perform extensive screens. Fragments of 77ORF104 can be produced by proteolytic digestion of the full-length protein as described above. Alternatively, suitable 77ORF104-derived peptide or polypeptide fragments representative of the complete sequence of the protein can be chemically synthesized. For instance, in the multi-pin approach, peptides are simultaneously synthesized by the assembly of small quantities of peptides on plastic pins derivatized with an ester linker based on glycolate and 4-(hydroxymethyl) benzoate (Maeji et al. (1991) Pept Res, 4:142–6).

Certain of the polypeptides of the invention are biomimetics, functional mimetics of the natural *S. aureus* DnaI polypeptide. These functional mimetics are useful for, among other things, antagonizing the activity of *S. aureus* DnaI polypeptide or as an antigen or immunogen in a manner described above. Functional mimetics of the polypeptides of the invention include but are not limited to truncated polypeptides. For example, preferred functional mimetics include a polypeptide comprising the polypeptide sequence set forth in SEQ ID NO: 2 lacking 20, 30, 40, 50, 60, 70 or 80 amino- or carboxy-terminal amino acid residues, including fusion proteins comprising one or more of these truncated sequences. Polynucleotides encoding each of these functional mimetics may be used as expression cassettes to express each mimetic polypeptide. It is preferred that these cassettes comprise 5' and 3' restriction sites to allow for a convenient means to ligate the cassettes together when desired. It is further preferred that these cassettes comprise gene expression signals known in the art or described elsewhere herein.

Screening Assays According to the Invention

It is desirable to devise screening methods to identify compounds which stimulate or which inhibit the function of the DnaI polypeptide or polynucleotide of the invention. Accordingly, the present invention provides for a method of screening compounds to identify those that modulate the function of a polypeptide or polynucleotide of the invention. In general, antagonists may be employed for therapeutic and prophylactic purposes. It is contemplated that an agonist of DnaI may be useful, for example, to enhance the growth rate of bacteria in a sample being cultured for diagnostic or other purposes.

Screening methods generally fall into two broad categories: those that assay binding of candidate compounds; and those that assay a functional aspect of the target.

a) Binding Assays

There are a number of methods of examining binding of a candidate compound to a protein target such as DnaI. Screening methods that measure the binding of a candidate compound to the DnaI polypeptide or polynucleotide, or to cells or supports bearing the polypeptide or a fusion protein comprising the polypeptide, by means of a label directly or indirectly associated with the candidate compound, are useful in the invention.

The screening method may involve competition for binding of a labeled competitor such as 77ORF104 or a fragment that is competent to bind DnaI.

i) Phage Display

Phage display is a powerful assay to measure protein: protein interaction. In this scheme, proteins or peptides are expressed as fusions with coat proteins or tail proteins of filamentous bacteriophage. A comprehensive monograph on this subject is *Phage Display of Peptides and Proteins. A Laboratory Manual* edited by Kay et al. (1996) Academic Press. For phages in the Ff family that include M13 and fd, gene III protein and gene VIII protein are the most commonly-used partners for fusion with foreign protein or peptides. Phagemids are vectors containing origins of replication both for plasmids and for bacteriophage. Phagemids encoding fusions to the gene III or gene VIII can be rescued from their bacterial hosts with helper phage, resulting in the display of the foreign sequences on the coat or at the tip of the recombinant phage.

In the simplest assay, purified recombinant DnaI protein, or a fragment of DnaI, for example comprising the amino acid sequence of SEQ ID NO: 16, could be immobilized in the wells of a microtitre plate and incubated with phages displaying 77ORF104 in fusion with the gene III protein. Washing steps are performed to remove unbound phages and bound phages are detected with monoclonal antibodies directed against phage coat protein (gene VIII protein). Color development by means of an enzyme-linked secondary antibody allows quantitative detection of bound fusion protein. Screening for inhibitors is performed by the incubation of the compound with the immobilized target before the addition of phages. The presence of an inhibitor will specifically reduce the signal in a dose-dependent manner relative to controls without inhibitor.

ii) Surface Plasmon Resonance

Another powerful assay to screen for inhibitors of a for protein: protein interaction is surface plasmon resonance. Surface plasmon resonance is a quantitative method that measures binding between two (or more) molecules by the change in mass near the sensor surface caused by the binding of one protein or other biomolecule from the aqueous phase to a second protein or biomolecule immobilized on the sensor. This change in mass is measured as resonance units versus time after injection or removal of the second protein or biomolecule and is measured using a Biacore Biosensor (Biacore AB). DnaI could be immobilized on a sensor chip (for example, research grade CM5 chip; Biacore AB) using a covalent linkage method (e.g. amine coupling in 10 mM sodium acetate [pH 4.5]). A blank surface is prepared by activating and inactivating a sensor chip without protein immobilization. The binding of 77ORF104 to DnaI, or a fragment of DnaI, for example comprising the amino acid sequence of SEQ ID NO: 16, is measured by injecting purified 77ORF104 over the chip surface. Measurements are performed at room temperature. Conditions used for the assay (i.e., those permitting binding) are as follows: 25 mM HEPES-KOH (pH 7.6), 150 mM sodium chloride, 15% glycerol, 1 mM dithiothreitol, and 0.001% Tween 20 with a flow rate of 10 ul/min. Preincubation of the sensor chip with candidate inhibitors will predictably decrease the interaction between 77ORF104 and DnaI. A decrease in 77ORF104 binding is indicative of competitive binding by the candidate compound.

iii) Fluorescence Resonance Energy Transfer (FRET)

Another method of measuring inhibition of binding of two proteins uses fluorescence resonance energy transfer (FRET; de Angelis, 1999, Physiological Genomics). FRET is a quantum mechanical phenomenon that occurs between a fluorescence donor (D) and a fluorescence acceptor (A) in close proximity (usually <100 A of separation.) if the emission spectrum of D overlaps with the excitation spectrum of A. Variants of the green fluorescent protein (GFP) from the jellyfish *Aequorea Victoria* are fused to a polypeptide or protein and serve as D-A pairs in a FRET scheme to measure protein—protein interaction. Cyan (CFP: D) and yellow (YFP: A) fluorescence proteins are linked with DnaI polypeptide, or a fragment of DnaI, for example comprising the amino acid sequence of SEQ ID NO: 16, and 77ORF104 protein respectively. Under optimal proximity, interaction between DnaI, or a fragment of DnaI, for example comprising the amino acid sequence of SEQ ID NO: 16 and 77ORF104 causes a decrease in intensity of CFP concomitant with an increase in YFP fluorescence.

The addition of a candidate modulator to the mixture of appropriately labeled DnaI and 77ORF104 protein, will result in an inhibition of energy transfer evidenced by, for example, a decease in YFP fluorescence at a given concentration of 77ORF104 relative to a sample without the candidate inhibitor.

iv) Fluorescence Polarization

In addition to the surface plasmon resonance and FRET methods, fluorescence polarization measurement is useful to quantitate protein—protein binding. The fluorescence polarization value for a fluorescently-tagged molecule depends on the rotational correlation time or tumbling rate. Protein complexes, such as those formed by S. aureus DnaI polypeptide; or a fragment of DnaI, for example comprising the amino acid sequence of SEQ ID NO: 16 associating with a fluorescently labeled polypeptide (e.g., 77ORF104 or a binding fragment thereof), have higher polarization values than a fluorescently labeled monomeric protein. Inclusion of a candidate inhibitor of the DnaI interaction results in a decrease in fluorescence polarization relative to a mixture without the candidate inhibitor if the candidate inhibitor disrupts or inhibits the interaction of DnaI with its polypeptide binding partner. It is preferred that this method be used to characterize small molecules that disrupt the formation of polypeptide or protein complexes.

v) Scintillation Proximity Assay

A scintillation proximity assay may be used to characterize the interaction between a S. aureus DnaI polypeptide, or a fragment of DnaI polypeptide, for example comprising the amino acid sequence of SEQ ID NO: 16 and another polypeptide. For the assay, S. aureus DnaI polypeptide can be covalently coupled to beads. Addition of radio-labeled 77ORF104 results in binding where the radioactive source molecule is in close proximity to the scintillation fluid. Thus, signal is emitted upon 77ORF104 polypeptide binding, and compounds that prevent association between S. aureus DnaI polypeptide and 77ORF104 diminish the scintillation signal.

vi) Bio Sensor Assay

ICS biosensors have been described by AMBRI (Australian Membrane Biotechnology Research Institute; http//www.ambri.com.au/). In this technology, the self-association of macromolecules such as DnaI, or a fragment of DnaI, for example comprising the amino acid sequence of SEQ ID NO: 16, and bacteriophage 77 ORF 104, is coupled to the closing of gramacidin-facilitated ion channels in suspended membrane bilayers and hence to a measurable change in the admittance (similar to impedance) of the biosensor. This approach is linear over six order of magnitude of admittance change and is ideally suited for large scale, high through-put screening of small molecule combinatorial libraries.

It is important to note that in assays of protein—protein interaction, it is possible that a modulator of the interaction need not necessarily interact directly with the domain(s) of the proteins that physically interact. It is also possible that a modulator will interact at a location removed from the site of protein—protein interaction and cause, for example, a conformational change in the DnaI polypeptide. Modulators (inhibitors or agonists) that act in this manner are of interest since the change they induce may modify the activity of the DnaI polypeptide.

b. Assays of DnaI Functional Activity.

i) Assay for DNA Replication, $^3$H-thymidine Incorporation

To measure the effect of 77ORF104 expression on S. aureus DNA replication, the level of radiolabeled thymidine incorporation into DNA is measured in the presence or in the absence of sodium arsenite (5 uM). Samples (0.5 ml) are withdrawn from the cultures at appropriate time intervals and mixed to 4.5 ul of labeling solution (0.2 uCi/ml of $^3$H-thymidine (73 Ci/mmol, NEN Life Science Products, Inc) and 70 pmol of cold thymidine). After 15 min of reaction, incorporation is stopped by adding solution containing 0.2% NaN$_3$ and 1 mM cold thymidine. Samples are precipitated with 10% w/v trichloroacetic acid and filtered through glass fiber filters (GF-C, Whatman). The results are expressed as $^3$H-thymidine counts incorporated normalized to OD culture.

The assay is performed in the presence of varying concentrations of candidate inhibitors in place of 77 ORF104 to screen for inhibitors. At least a 10-fold reduction in 3H-thymidine incorporation in the presence of 77 ORF104 or other inhibitor indicates a reduction in DnaI activity.

ii) Plasmid Replication

The plasmid pC194 replicates in S. aureus by rolling circle mechanism. The single stranded origin, sso of the pC194 is involved in the synthesis of the lagging DNA strand. The plasmid pADG6406 is a derivative of pC194 lacking sso. The absence of sso leads the accumulation of plasmid single-stranded DNA. The single-stranded (ss) initiation site, ssiA, is located on the lagging strand of pAM 1 and is a site for primosome assembly. SsiA was inserted into plasmid pADG6404. S aureus harboring plasmids are grown to mid-log phase and their total DNA is extracted and analyzed by Southern hybridization, using $^{32}$P-labeled plasmid DNA as probe. The presence of pADG6406 with ssiA is associated to a decrease in the ratio of ss to double stranded (ds) DNA compared to that of the plasmid without ssiA. This system is used to measure the effect of 77ORF104 or a candidate inhibitor polypeptideexpression on ss DNA synthesis. In an assay, a plasmid containing 77ORF104 or a candidate inhibitor polypeptide coding sequence under an arsenite inducible promotor is introduced into a S aureus strain harboring pADG6406. The ratio of ss to ds DNA of pADG6406 is measured in the presence or in the absence of sodium arsenite (5 uM). An increase in the ratio of ss to ds DNA (10% or more) indicates an effect of the candidate modulator. In another aspect, the present invention relates to a screening kit for identifying agonists, antagonists, ligands, receptors, substrates, enzymes, etc. for a polypeptide and/or polynucleotide of the present invention; or compounds which decrease or enhance the production of such polypeptides and/or polynucleotides, which comprises: (a) a polypeptide and/or a polynucleotide of the present invention; (b) a recombinant cell expressing a polypeptide and/or polynucleotide of the present invention; (c) a cell membrane expressing a polypeptide and/or polynucleotide of the present invention; or (d) antibody to a polypeptide and/or polynucleotide of the present invention; which polypeptide is preferably that of SEQ ID NO: 2, and which polynucleotide is preferably that of SEQ ID NO: 1.

It will be appreciated that in any such kit, (a), (b), (c) or (d) may comprise a substantial component.

It will be readily appreciated by the skilled artisan that a polypeptide and/or polynucleotide of the present invention may also be used in a method for the structure-based design of an agonist, antagonist or inhibitor of the polypeptide and/or polynucleotide, by: (a) determining in the first instance the three-dimensional structure of the polypeptide and/or polynucleotide, or complexes thereof; (b) deducing the three-dimensional structure for the likely reactive site(s), binding site(s) or motif(s) of an agonist, antagonist or inhibitor; (c) synthesizing candidate compounds that are predicted to bind to or react with the deduced binding site(s), reactive site(s), and/or motif(s); and (d) testing whether the candidate compounds are indeed agonists, antagonists or inhibitors. It will be further appreciated that this will normally be an iterative process, and this iterative process may be performed using automated and computer-controlled steps.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host that is responsible for sequelae of infection. In particular, the molecules of the invention may be used: in the prevention of adhesion of bacteria, in particular Gram positive and/or Gram negative bacteria, to eukaryotic, preferably mammalian, extracellular matrix proteins on in-dwelling devices or to extracellular matrix proteins in wounds; to block bacterial adhesion between eukaryotic, preferably mammalian, extracellular matrix proteins and bacterial DnaI proteins that mediate tissue damage and/or; to block the normal progression of pathogenesis in infections initiated other than by the implantation of in-dwelling devices or by other surgical techniques.

In accordance with yet another aspect of the invention, there are provided dnaI antagonists, preferably bacteriostatic or bacteriocidal antagonists.

The antagonists of the invention may be employed, for instance, to prevent, inhibit and/or treat diseases.

Compositions, Kits and Administration

In a further aspect of the invention there are provided compositions comprising a dnaI polynucleotide and/or a *S. aureus* DnaI polypeptide for administration to a cell or to a multicellular organism.

The present invention provides for pharmaceutical compositions comprising a therapeutically effective amount of a polypeptide and/or polynucleotide, such as the soluble form of a polypeptide and/or polynucleotide of the present invention, antagonist peptide or small molecule compound, in combination with a pharmaceutically acceptable carrier or excipient. Such carriers include, but are not limited to, saline, buffered saline, dextrose, water, glycerol, ethanol, and combinations thereof. The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

As used herein, the term "in-dwelling device" refers to surgical implants, prosthetic devices and catheters, i.e., devices that are introduced to the body of an individual and remain in position for an extended time. Such devices include, but are not limited to, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *S. aureus* wound infections.

Many orthopedic surgeons consider that humans with prosthetic joints should be considered for antibiotic prophylaxis before dental treatment that could produce a bacteremia. Deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 mg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as GCC.

The polynucleotide and polypeptide sequences of the invention are particularly useful as components in databases useful for search analyses as well as in sequence analysis algorithms. As used in this section entitled "Sequence Databases, Sequences in a Tangible Medium, and Algorithms," and in claims related to this section, the terms "polynucleotide of the invention" and "polynucleotide sequence of the invention" mean any detectable chemical or physical characteristic of a polynucleotide of the invention that is or may be reduced to or stored in a tangible medium, preferably a computer readable form. For example, chromatographic scan data or peak data, photographic data or scan data therefrom, called bases, and mass spectrographic data. As used in this section entitled Databases and Algorithms and in claims related thereto, the terms "polypeptide of the invention" and "polypeptide sequence of the invention" mean any detectable chemical or physical characteristic of a polypeptide of the invention that is or may be reduced to or stored in a tangible medium, preferably a computer readable form. For example, chromatographic scan data or peak data, photographic data or scan data therefrom, and mass spectrographic data.

The invention provides a computer readable medium having stored thereon polypeptide sequences of the invention and/or polynucleotide sequences of the invention. The computer readable medium can be any composition of matter used to store information or data, including, for example, commercially available floppy disks, tapes, chips, hard drives, compact disks, and video disks.

In a preferred embodiment of the invention there is provided a computer readable medium having stored thereon a member selected from the group consisting of: a polynucleotide comprising the sequence of SEQ ID NO: 1 or SEQ ID NO: 17; a polypeptide comprising the sequence of SEQ ID NO: 2 or SEQ ID NO: 16; a set of polynucleotide sequences wherein at least one of said sequences comprises the sequence of SEQ ID NO: 1 or SEQ ID NO: 17: a set of polypeptide sequences wherein at least one of said sequences comprises the sequence of SEQ ID NO: 2 or SEQ ID NO: 16; a data set representing a polynucleotide sequence comprising the sequence of SEQ ID NO: 1 or SEQ ID NO: 17; a data set representing a polynucleotide sequence encoding a polypeptide sequence comprising the sequence of SEQ ID NO: 2 or SEQ ID NO: 16; a polynucleotide comprising the sequence of SEQ ID NO: 1 or SEQ ID NO: 17; a polypeptide comprising the sequence of SEQ ID NO: 2 or SEQ ID NO: 16; a set of polynucleotide sequences wherein at least one of said sequences comprises the sequence of SEQ ID NO: 1 or SEQ ID NO: 17; a set of polypeptide sequences wherein at least one of said sequences comprises the sequence of SEQ ID NO: 2 or SEQ ID NO: 16; a data set representing a polynucleotide sequence comprising the sequence of SEQ ID NO: 1 or SEQ ID NO: 17; a data set representing a polynucleotide sequence encoding a polypeptide sequence comprising the sequence of SEQ ID NO: 2 or SEQ ID NO: 16.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

EXAMPLES

Example 1

Identification of the Inhibitory ORF 104 from *Staphylococcus aureus* Bacteriophage 77

The *S. aureus* propagating strain 77 (PS 77) was used as a host to propagate its respective phage 77 (ACTT #27699-B 1). The phage was propagated using the agar layer method described by Swanstörm and Adams (Swanström et al. (1951) Proc. Soc. Exptl. Biol. & Med. 78: 372–375). Phage DNA was prepared from the purified phages as described in Sambrook et al. (1989) *Molecular Cloning: A Laboratory Manual*, 2$^{nd}$ Edition, Cold Spring Harbor Laboratory Press, Cold Spring Harbor, N.Y. Blunt-ended sonicated phage DNA fragments were cloned into the pKSII vector (Stratagene). Recombinant clones were sequenced on an ABI 377-36 automated sequencer. To ensure co-linearity of the sequence data and the genome, all regions of the phage genome were sequenced at least once from both directions on two separate clones. Sequence contigs were assembled using Sequencher 3.1 software (GeneCodes) (FIG. 2). An implementation of the publicly available program SEQUIN, available for download at The United States National Library of Medicine's web site, was used on phage genome sequence to identify all putative ORFs larger than 33 codons (FIG. 3).

Figure 7A:
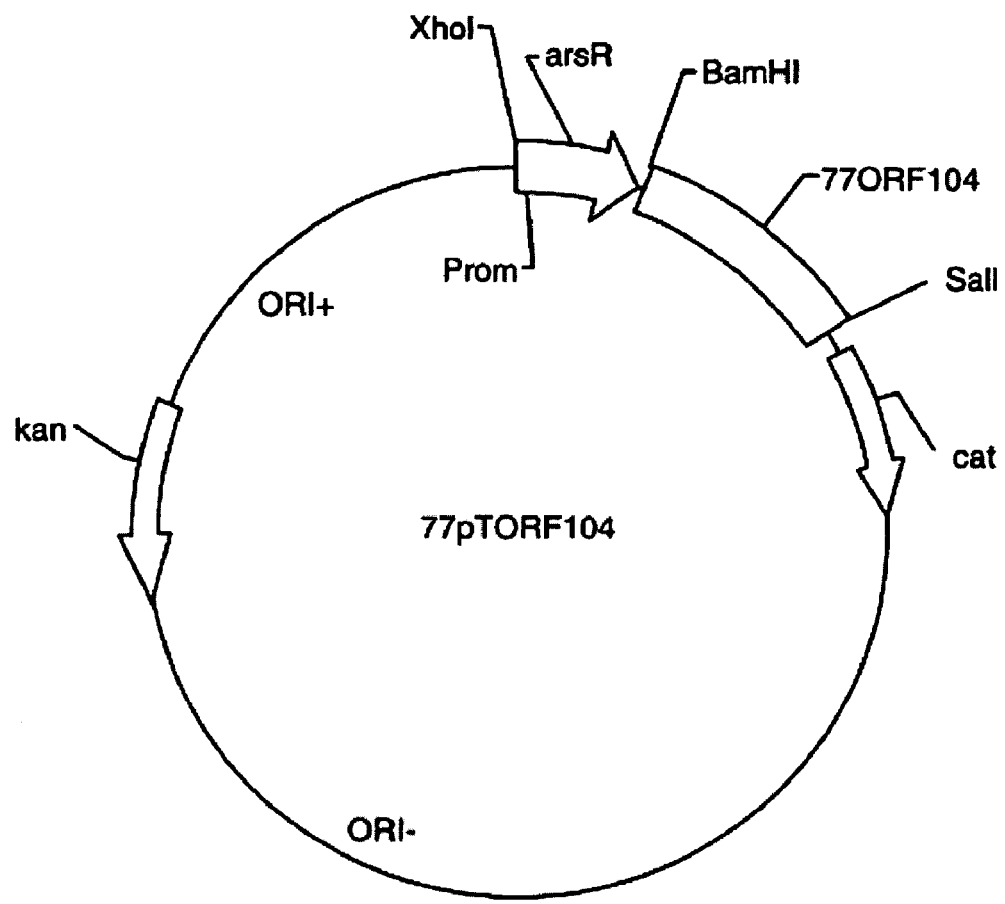
FIGS. 7A–7C show the killing potential of bacteriophage 77 ORF 104 and the expression vector used to induce its expression in S. aureus: A) Schematic diagram of expression vector pT/ORF used to induce expression of 77ORF104 in S. aureus cells; B) Results of a screen to assess the killing potential of 77ORF104 when expressed in S. aureus grown on semi-solid support media; and C) Results showing the inhibitory potential of 77ORF104 when expressed in S. aureus in liquid media.

The 77ORF104 (SEQ ID NO: 4) was amplified by polymerase chain reaction (PCR) from phage genomic DNA (FIG. 4). For PCR amplification, the sense strand primer starts at the initiation codon and is preceded by a BamHI restriction site; the antisense strand starts at the last codon (excluding the stop codon) and is preceded by a SalI restriction site. The PCR product was gel purified and digested with BamHI and SalI. The digested PCR product was then ligated into BamHI- and SalI-digested pT vector (FIG. 7A), and used to transform *S. aureus* strain RN4220 (Kreiswirth et al (1983) Nature 305: 709–712). Selection of recombinant clones was performed on Luria-Bertani (LB) agar plates containing 30 μg/ml of kanamycin.

Figure 7B:
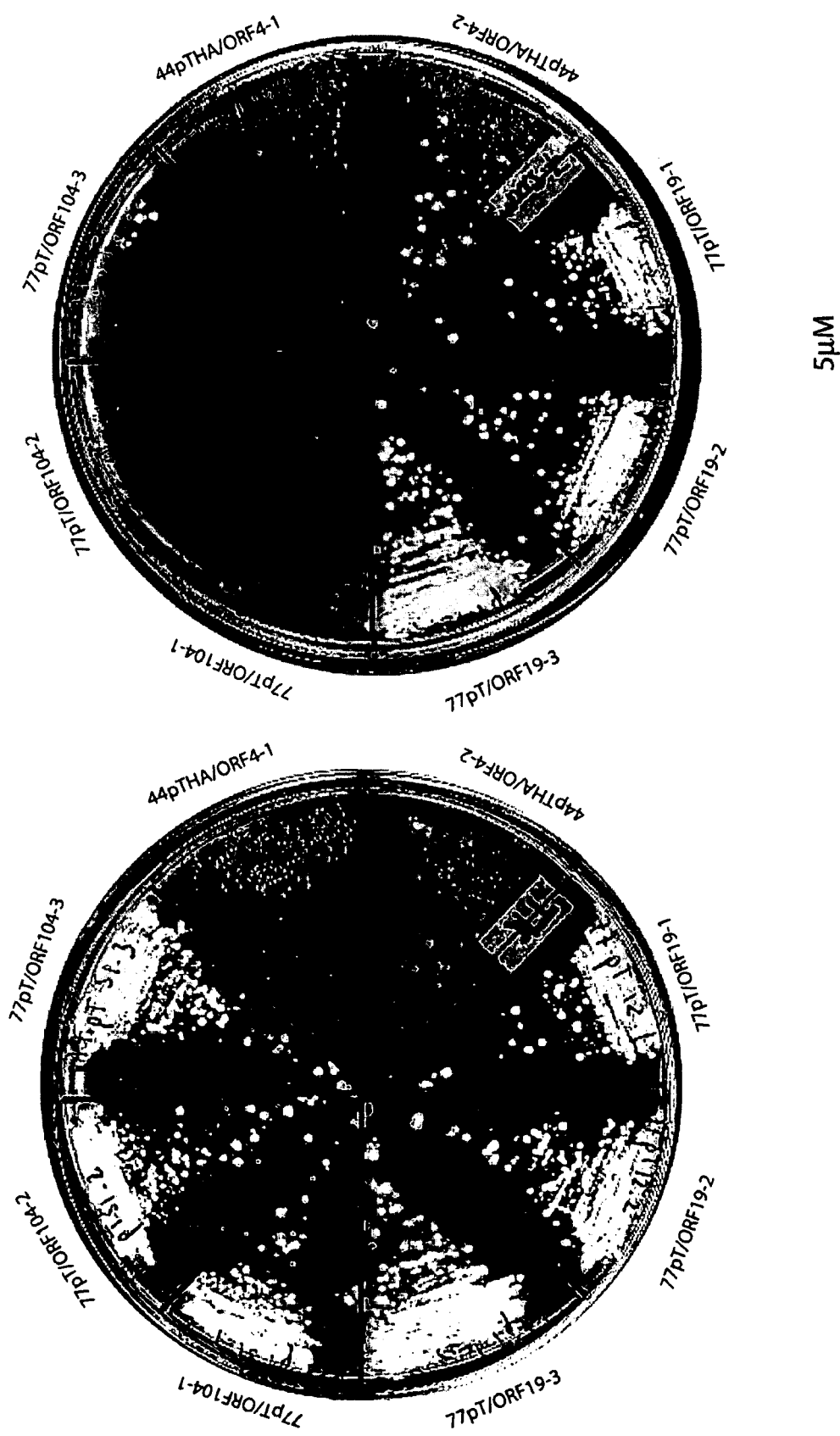
Figure 7C:
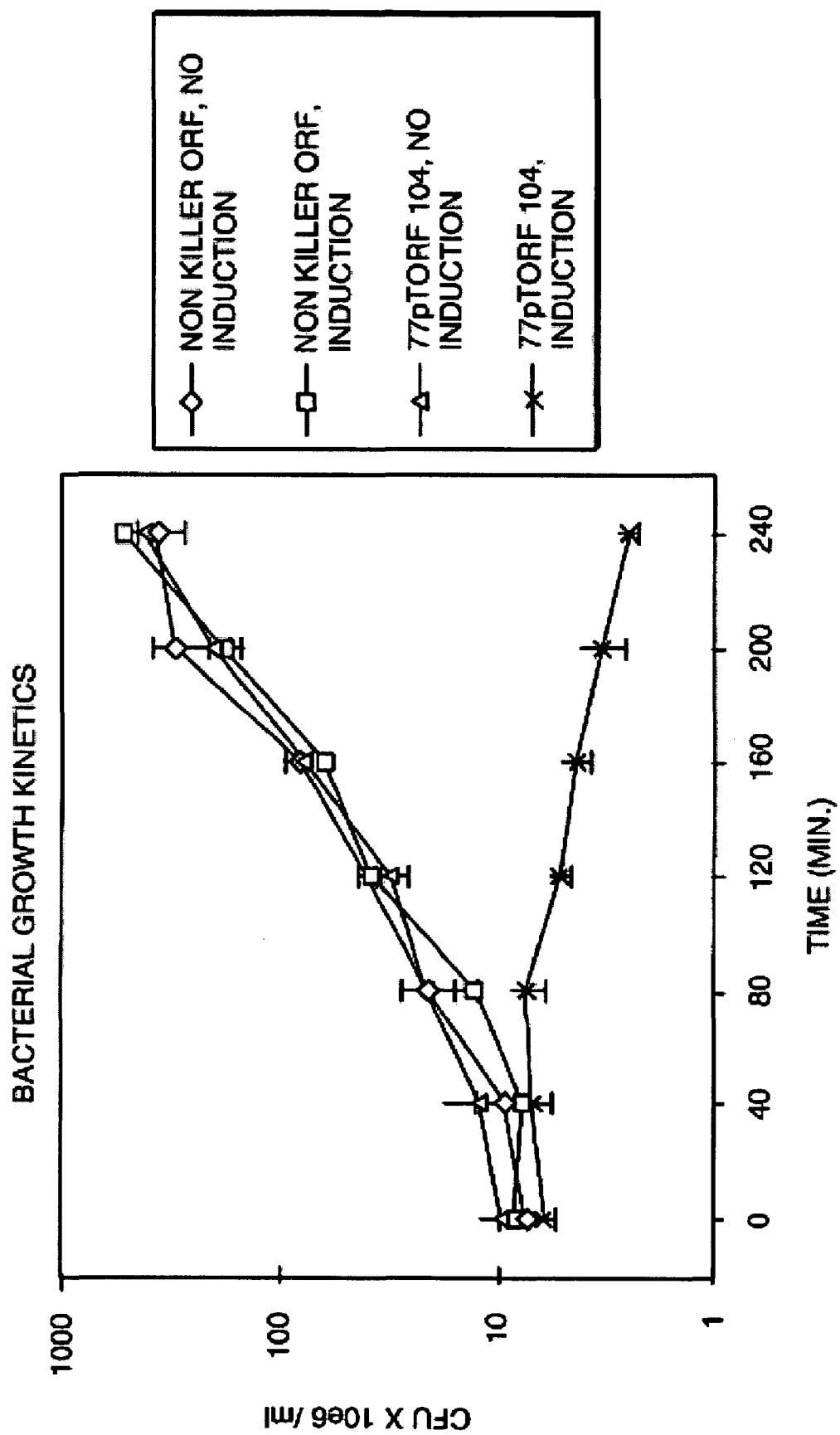
Figure 8A:
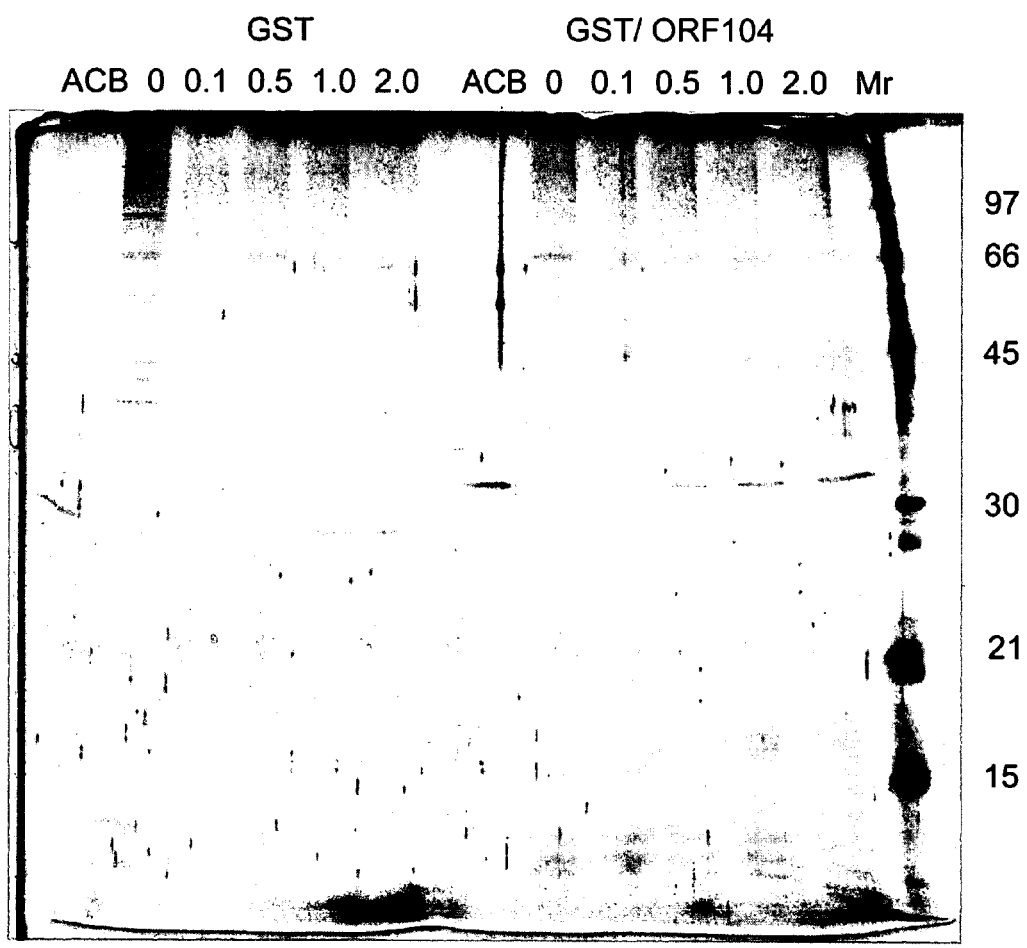
FIGS. 8A–8D show affinity chromatography using GST and GST/ORF104 as ligands with the S. aureus extract prepared by French pressure cell lysis and sonication. Eluates from affinity columns containing the GST and GST/ORF104 ligands at 0, 0.1, 0.5, 1.0, and 2.0 mg/ml resin were resolved by 12.5% SDS-PAGE. Proteins were visualized by silver staining. Micro-columns were eluted with: A) ACB containing 1 M NaCl; B) 250 mM NaCl; C) 1% Triton X-100; and D) 1% SDS. Each molecular weight marker (Mr) is approximately 100 ng. The lanes labeled ACB indicate eluates from a 2.0 mg/ml ligand column loaded only with ACB buffer containing 75 mM NaCl. The arrows indicate bands specifically interacting with GST/ORF104.
Figure 8B:
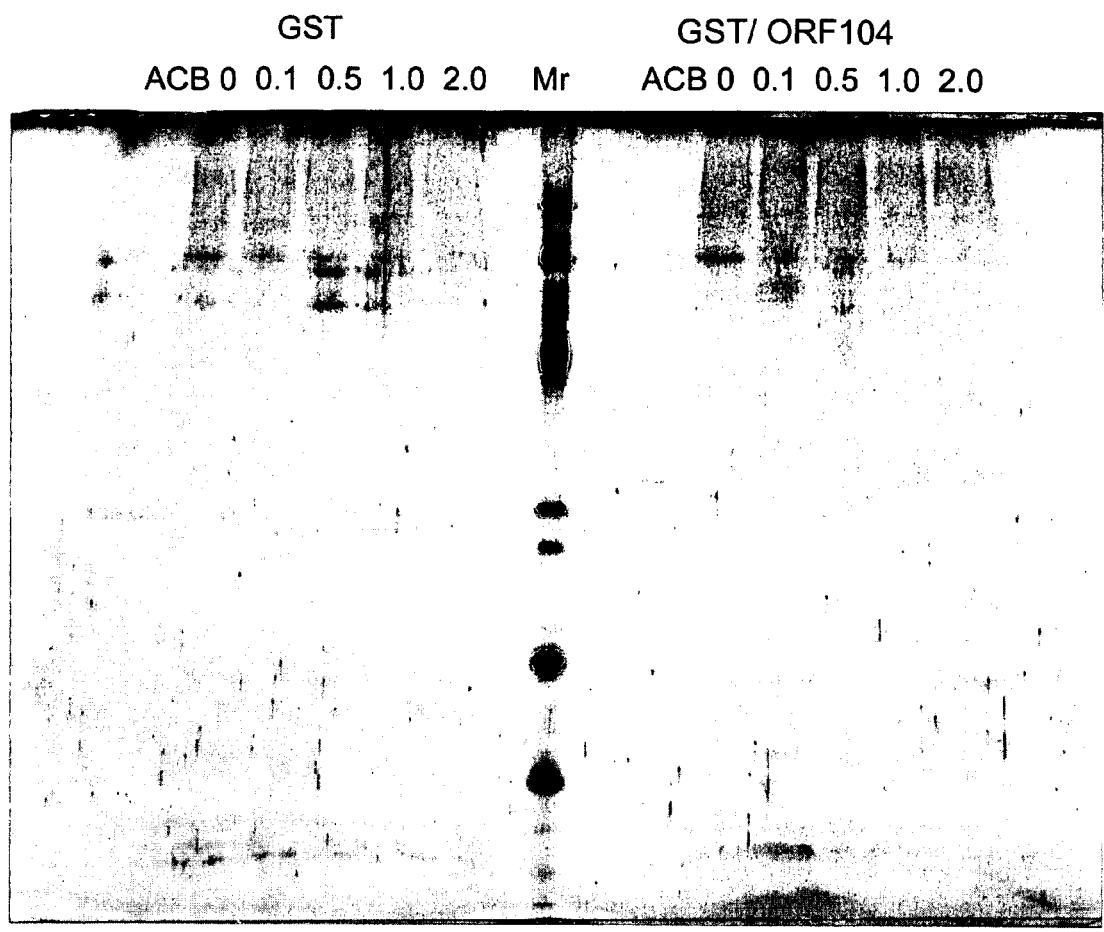
Figure 8C:
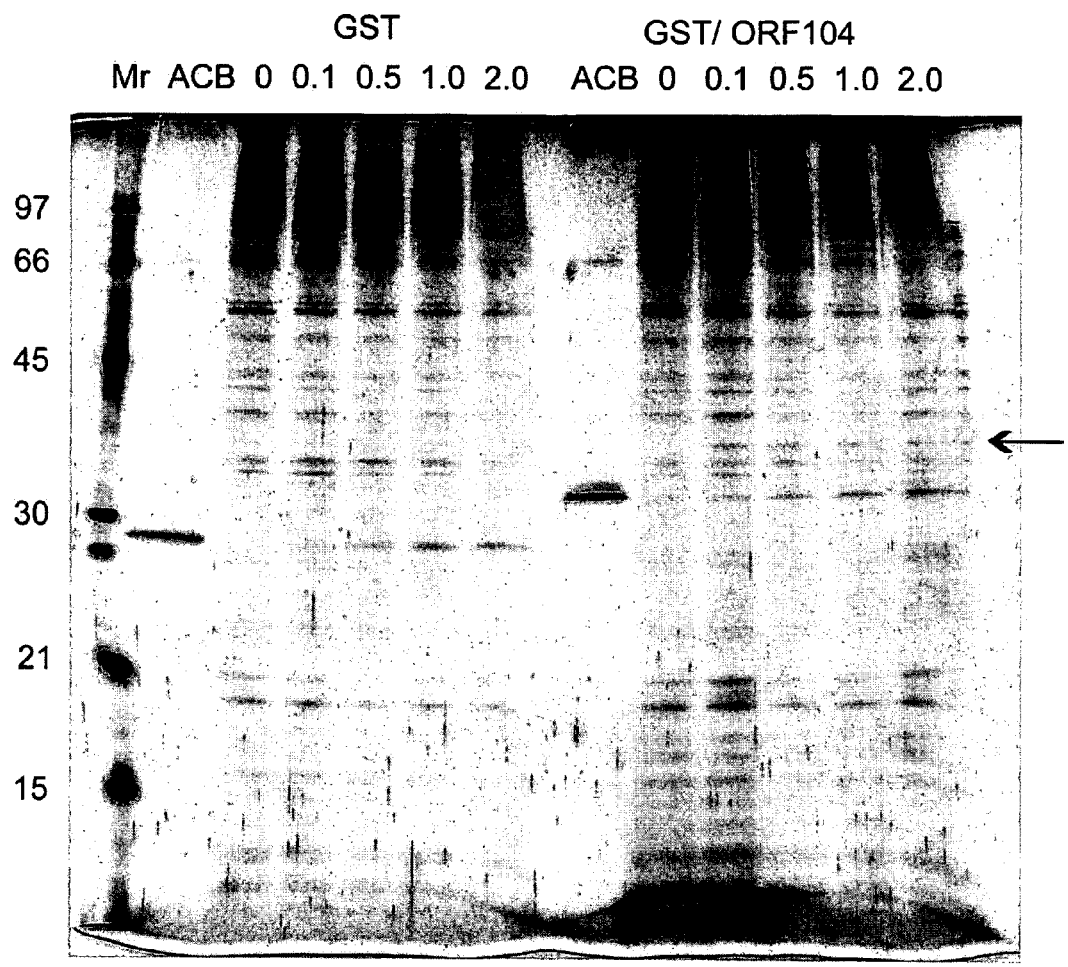
Figure 8D:
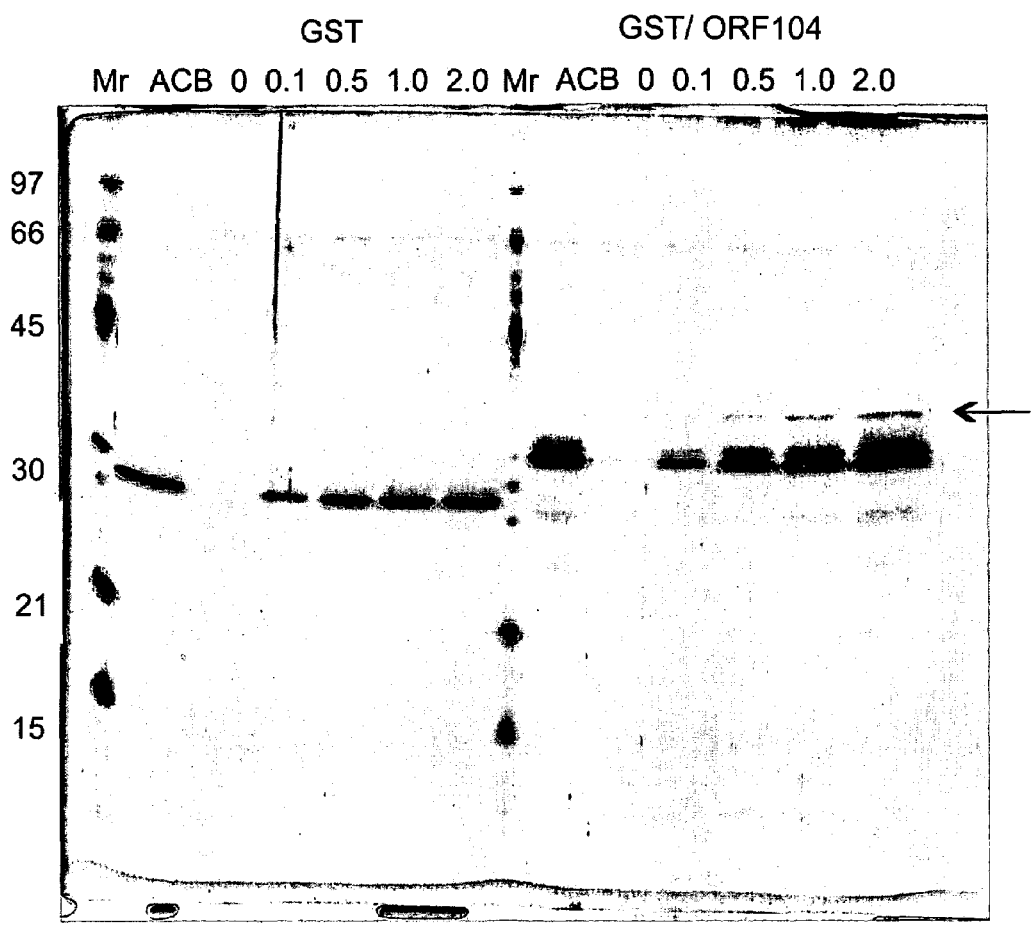

Sodium arsenite (NaAsO$_2$) was used to induce gene expression from the ars promoter/operator. The effect of expression of phage 77 ORFs on bacterial cell growth was then evaluated in functional assays on solid medium and in liquid medium. As shown in FIG. 7B, the induction of expression of phage 77ORF104 by plating transformants on semi-solid medium containing 5 µM sodium arsenite results in the inhibition of bacterial growth on solid medium compared to plating in the absence of inducer or plating of control non-inhibitory ORF (phage 77 ORF 19) transformants. As shown in FIG. 7C, the density of the culture, as assessed by colony forming units (CFU), for S. aureus clones harboring the 77ORF104 increased over time under non-induced conditions. Similar growth rates were also observed with transformants harboring a non-inhibitory ORF (labeled as 'non killer' on the graphs) under both induced and non-induced conditions. At 4 h following induction, the expression of 77ORF104 is cytocidal resulting in a 0.5 log reduction in the number of CFU compared to the number of CFU initially present in the same culture.

Example 2

Identification of a S. aureus Protein Targeted by Bacteriophage 77 ORF 104.

To identify S. aureus proteins that interact with the bacterial growth inhibitory Staphylococcus bacteriophage 77 ORF 104, a GST-fusion of ORF 104 was generated and the recombinant protein purified and utilized to make a GST/ORF104 affinity column. Cellular extracts prepared from S. aureus cells were incubated with the affinity matrix, washed with increasing salt concentrations and different detergents, and the protein elution profile of the washes assessed by SDS-polyacrylamide gel electrophoresis. A protein of molecular mass ~40 kDa was specifically eluted from the affinity matrix. Eluted proteins were further characterized to determine the identity of the interacting protein and to validate the interaction of the protein with 77ORF104 as described in detail below.

A. Generation of GST/ORF 104 Recombinant Protein.

Bacteriophage 77ORF104 was sub-cloned into pGEX 4T-1 (Pharmacia), an expression vector containing the GST moiety. The gene encoding ORF104 was obtained by digestion of pT/ORF104 (FIG. 7A) with BamHI and SalI. The DNA fragment containing ORF104 was gel purified by QiaQuick spin column (Qiagen) and ligated into pGEX 4T-1 (which had been previously digested with BamHI and SalI) to generate pGEX 4T/ORF104. Recombinant expression vectors were identified by restriction enzyme analysis of plasmid minipreps, large-scale DNA preparations were performed with Qiagen columns, and the resulting plasmid was sequenced. Test expressions in E. coli DH5 cells containing the expression plasmids were performed to identify optimal protein expression conditions. E. coli DH5 cells containing the pGEX 4T/ORF104 were grown in Luria-Bertani Broth at 37° C. to an $OD_{600}$ of 0.4 to 0.6 and induced with 1 mM IPTG at 30° C. for 4 hrs.

B. Fusion Protein Purification.

Cells containing GST/ORF104 fusion protein were suspended in 20 ml lysis buffer/liter of cell culture with GST lysis buffer (20 mM Hepes pH 7.2, 500 mM NaCl, 10% glycerol, 1 mM DTT, 1 mM EDTA, 1 mM benzamidine, and 1 PMSF) and lysed by French Pressure cell followed by three bursts of twenty seconds with an ultra-sonicator at 4° C. Triton X-100 was added to the lysate to a final concentration of 0.1% and mixed for 30 minutes at 4° C. The lysate was centrifuged at 4° C. for 30 minutes at 10 000 rpm in a Sorval SS34 rotor. The supernatant was applied to a 4 ml glutathione sepharose column pre-equilibrated with lysis buffer and allowed to flow by gravity. The column was washed with 10 column volumes of lysis buffer and eluted in 1.5 ml fractions with GST elution buffer (20 mM Hepes pH 8.0, 500 mM NaCl, 10% glycerol, 1 mM DTT, 0.1 mM EDTA, and 25 mM reduced glutathione). The fractions were analyzed by 12.5% SDS-PAGE (Laemmli) and visualized by staining with Coomassie Brilliant Blue R250 stain to assess the amount of eluted GST/ORF104 protein.

GST/ORF104 (12 mg) was dialyzed overnight against 20 mM Hepes pH 7.5, 150 mM NaCl, 10% glycerol, 1 mM DTT, 0.1 mM EDTA, made up to 2.5 mM $CaCl_2$ and digested with bovine thrombin at a mass ratio of 1:10 (thrombin: GST ORF104) for 2.5 hrs at 28° C. to cleave the GST domain from the ORF104 domain. The digestion was stopped by the addition of 1 mM PMSF, 1 mM benzamidine and NaCl to a 1 M final concentration. The digested protein was applied to a one ml glutathione sepharose column and flow-through fractions of 1 ml were collected. The fractions were analyzed by 12% SDS-PAGE (Tricine) and visualized by staining with Coomassie Brilliant Blue R250 stain to determine which fractions contain bacterially expressed ORF104 lacking the GST tag.

C. Affinity Column Preparation.

GST and GST/ORF104 fusion protein were dialyzed overnight against Affinity Chromatography Buffer (ACB; 20 mM Hepes pH 7.5, 10% glycerol, 1 mM DTT, and 1 mM EDTA) containing 1 M NaCl. ORF104 protein obtained from thrombin digestion of GST/ORF104 was used without dialysis. Protein concentrations were determined by Bio-Rad Protein Assay and crosslinked to Affigel 10 resin (Bio-Rad) at protein/resin concentrations of 0, 0.1, 0.5, 1.0, and 2.0 mg/ml. The crosslinked resin was sequentially incubated in the presence of ethanolamine, and bovine serum albumin (BSA) prior to column packing and equilibration with ACB containing 75 mM NaCl.

D. S. aureus Extract Preparation.

Two extracts were prepared from S. aureus cell pellets. One lysate was prepared by French Pressure cell followed by sonication and the other by a lysostaphin digestion followed by sonication. The French Pressure cell prepared lysate was prepared by suspending 3 g of frozen S. aureus cells in ACB containing 500 mM NaCl, 1 mM PMSF, and 1 mM benzamidine. The suspended cells were subjected to three passes through the French Pressure cell followed by 3 sonication bursts of 20 seconds each, made up to 0.1% Triton X-100, stirred for 30 minutes, and centrifuged at 50 000 rpm for 3 hrs in a Ti70 fixed angle Beckman rotor. The efficiency of cell lysis was low and the resulting lysate (7 ml) contained 2.4 mg/ml protein. The cell pellet after the French Pressure cell lysis was subjected to cryogenic grinding in liquid nitrogen in the same buffer with a mortar and pestle. The lysate was made up to 0.1% Triton X-100, stirred for 30 minutes, and centrifuged at 50 000 rpm for 3 hrs in a Ti70 fixed angle Beckman rotor yielding a lysate (10 ml) containing 2.0 mg/ml protein. The cell lysates were found to be similar by SDS PAGE and were pooled, concentrated to 8 ml, and dialyzed overnight in a 3000 Mr dialysis membrane against affinity chromatography containing 1 mM PMSF, 1 mM benzamidine, and 75 mM NaCl. The dialyzed protein extract was removed from the dialysis tubing, centrifuged at 10 000 rpm in a Sorval SS34 rotor for 1 hr, and assayed for protein content (Bio-Rad Protein Assay) and salt concentration (conductivity meter).

The second lysate was prepared by lysostaphin digestion followed by sonication. A S. aureus cell pellet (2.9 g) was suspended in 8 ml of 20 mM Hepes pH 7.5, 150 mM NaCl, 10% glycerol, 1 mM DTT, 1 mM PMSF, 1 mM benzamidine, and 1000 units of lysostaphin. The cell suspension was incubated at 37° C. for 30 minutes, cooled to 4° C., and made up to a final concentration of 1 mM EDTA and 500 mM NaCl. The lysate was sonicated on ice using three bursts of 20 seconds each. The lysate was made up to 0.1% Triton X-100, stirred for 30 minutes, and centrifuged at 50 000 rpm for 3 hrs in a Ti70 fixed angle Beckman rotor. The supernatant was removed and dialyzed overnight in a 3000 Mr dialysis membrane against ACB containing 75 mM NaCl, 1 mM benzamidine, and 1 mM PMSF. The dialyzed protein extract was removed from the dialysis tubing, centrifuged at 10 000 rpm in a Sorval SS34 rotor for 1 hr, and assayed for protein content (utilizing the Bio-Rad Protein Assay) and salt concentration (utilizing a conductivity meter). Aliquots of the extracts were frozen at −70° C.

E. Affinity Chromatography.

S. aureus extract (400 μl) was applied to 40 μl columns containing 0, 0.1. 0.5. 1.0, and 2.0 mg/ml ligand and ACB containing 75 mM NaCl (400 μl) was applied to an additional column containing 2.0 mg/ml ligand. The columns were washed with ACB containing 75 mM NaCl (400 μl) and sequentially eluted with ACB containing 1% Triton X-100 and 75 mM NaCl (160 μl), ACB containing 250 mM NaCl (160 μl), ACB containing 1M NaCl (160 μl), and 1% SDS (160 μl). 40 μl of each eluate was resolved by 16 cm 12.5% SDS-PAGE (Laemmli) and the eluted proteins were visualized by silver stain.

F. Identification of S. aureus DnaI Homolog as an ORF104 Interacting Protein

Figure 9:
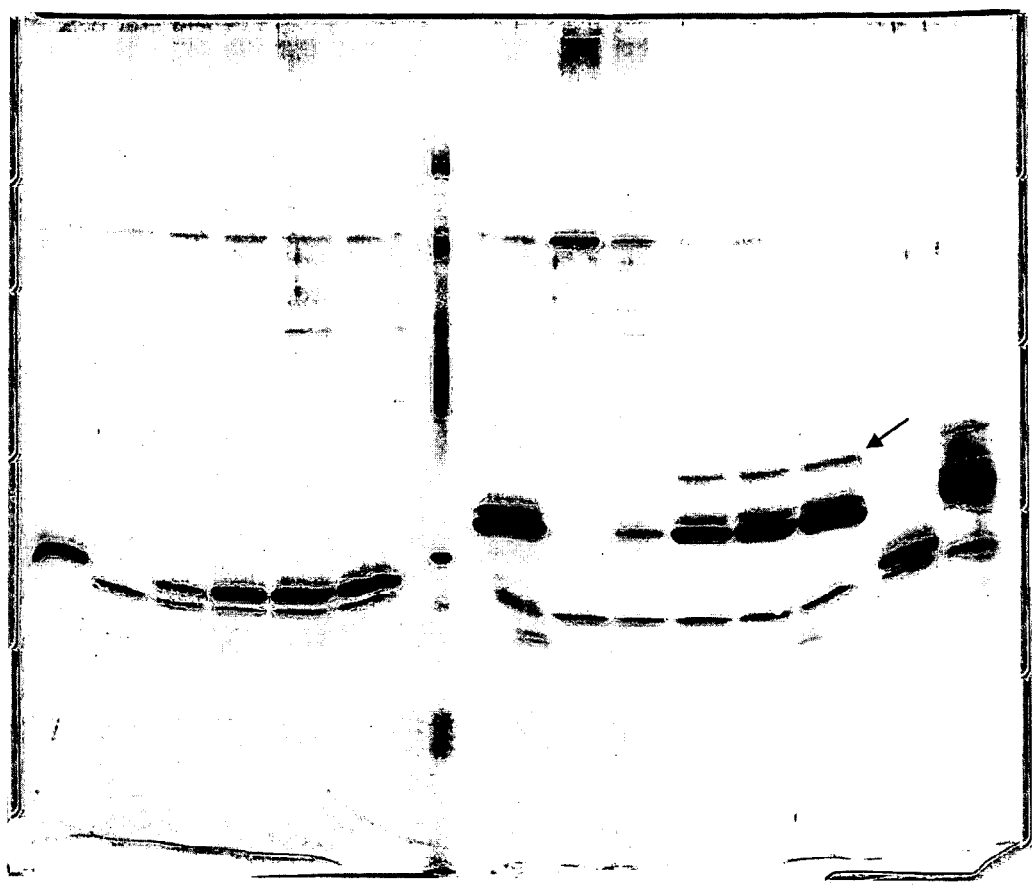
FIG. 9 shows affinity chromatography with GST and GST/ORF104 as ligands with the S. aureus extract prepared by lysis with lysostaphin digestion and sonication. Eluates from affinity columns containing the GST and GST ORF104 ligands at 0, 0.1, 0.5, 1.0, and 2.0 mg/ml resin were resolved by 12.5% SDS-PAGE. Micro-columns were sequentially eluted with 75 mM ACB containing 1% Triton X-100, 250 mM NaCl, 1 M NaCl ACB, and 1% SDS. The elution profile obtained with 1% SDS is shown. Each molecular weight marker (Mr) is approximately 100 ng. The lanes labeled ACB indicate eluates from a 2.0 mg/ml ligand column loaded only with ACB buffer containing 75 mM NaCl. Lanes labeled C and L are corresponding elutions from columns containing GST and GST/ORF104 at 2.0 mg/ml from FIG. 8. The arrow indicates a polypeptide specifically interacting with GST/ORF104.
Figure 10:
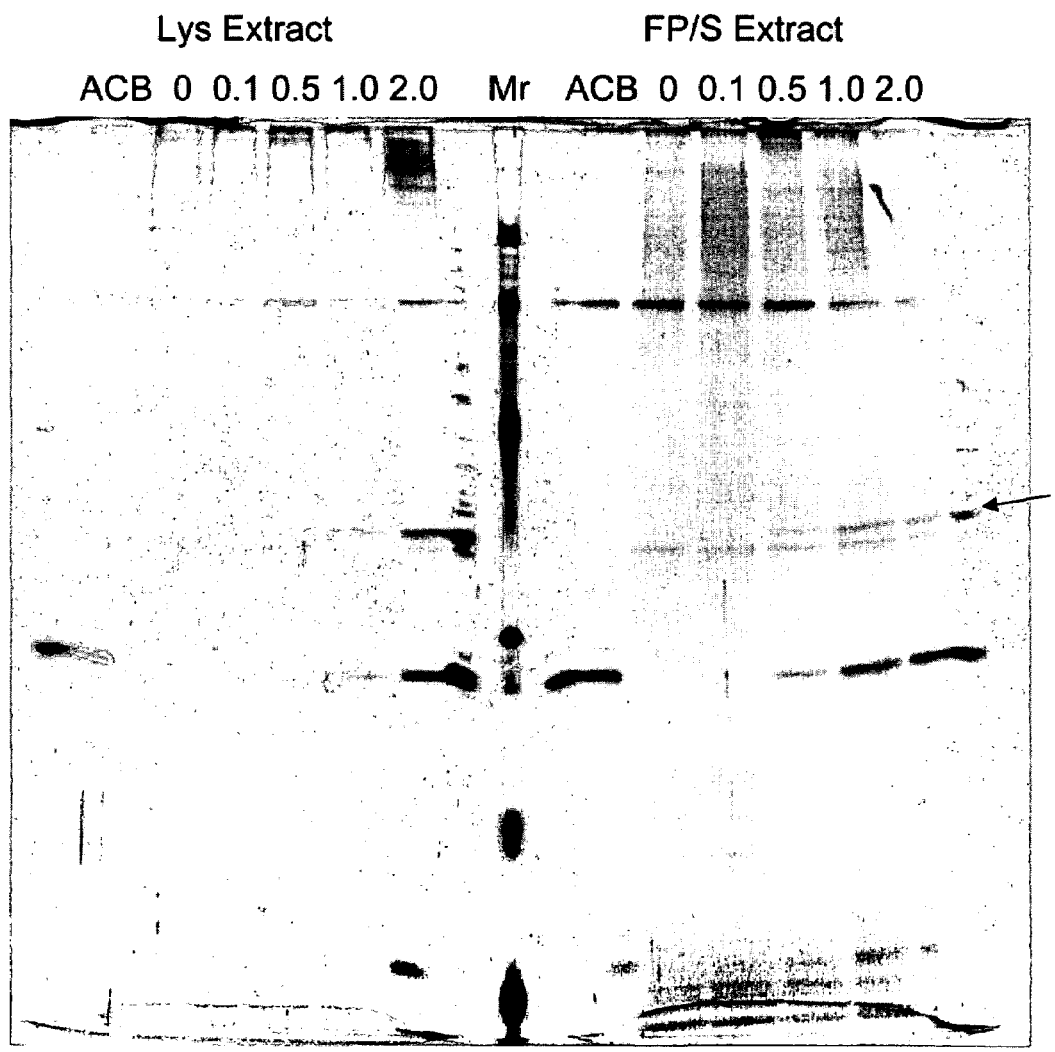
FIG. 10 shows affinity chromatography with ORF104 (GST removed) as ligand with the S. aureus extract prepared by lysis with lysostaphin digestion and sonication (Lys extract) and French pressure cell and sonication (FP/S extract). Eluates from affinity columns containing the ORF104 ligand at 0, 0.1, 0.5, 1.0, and 2.0 mg/ml resin were resolved by 12.5% SDS-PAGE and the gel was stained with silver nitrate. Micro-columns were sequentially eluted with: ACB containing 1% Triton X-100; 250 mM NaCl; 1M NaCl; and 1% SDS. The elution profile obtained with 1% SDS is shown. Each molecular weight marker (Mr) is approximately 100 ng. The lanes labeled ACB indicate eluates from a 2.0 mg/ml ligand column loaded only with ACB buffer containing 75 mM NaCl. The arrow indicates a polypeptide specifically interacting with GST/ORF104.
Figure 11A:
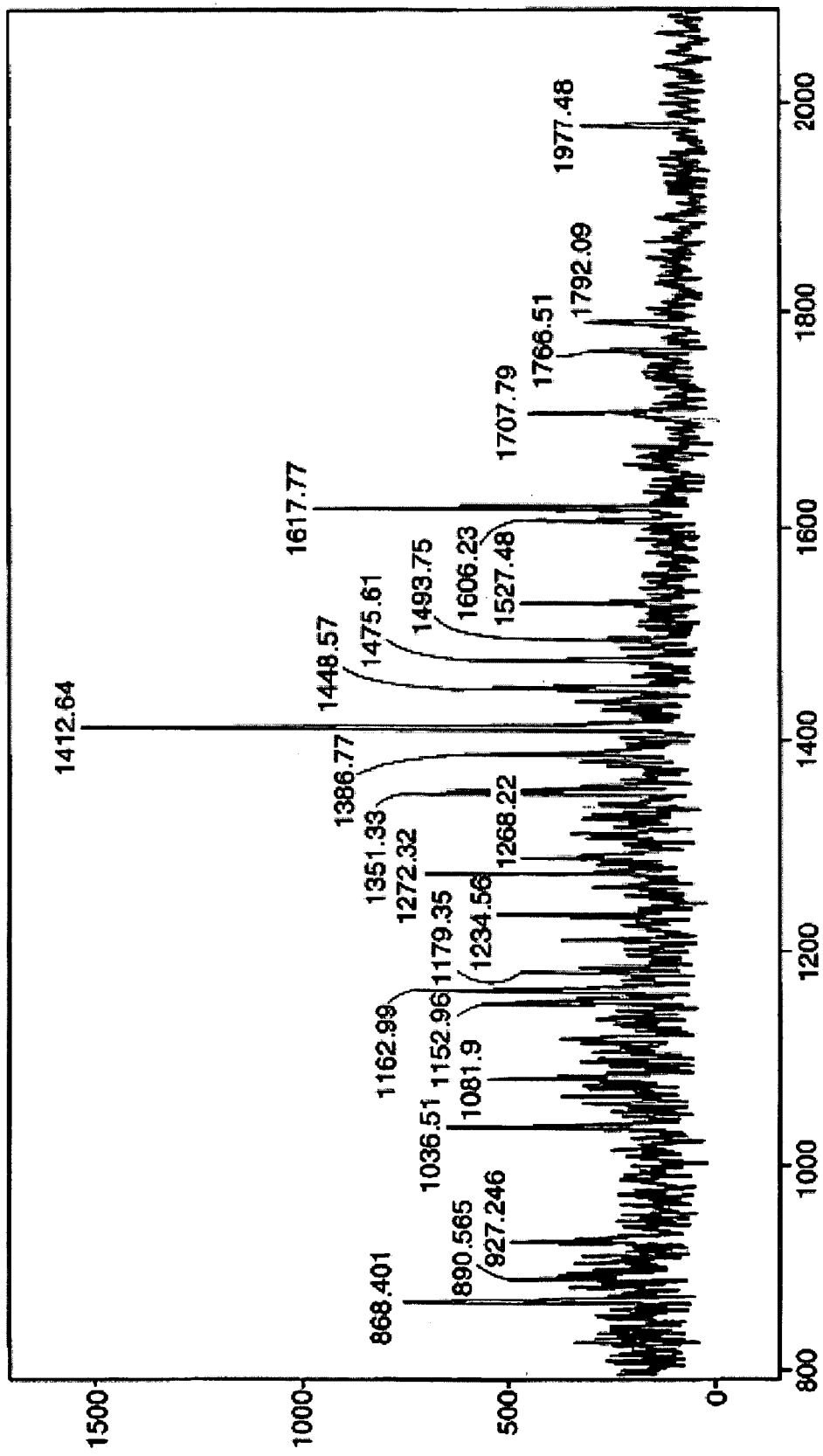

Proteins at approximately 38 kDa were observed specifically in the eluants from the GST/ORF104 and ORF104 (GST removed) columns obtained from ACB containing 75 mM NaCl and 1% Triton X-100, and 1% SDS (FIGS. 8–10; eluting protein indicated by an arrow). These bands were excised from the SDS-PAGE gels and prepared for tryptic peptide mass determination by MALDI-ToF mass spectrometry (Qin, J., et al. (1997) Anal. Chem. 69, 3995–4001). High quality mass spectra were obtained (FIG. 11). The candidate proteins observed in the two eluants were identical as determined by the masses of the tryptic peptides (FIG. 11). Post-Source Decay (PSD) coupled with Collision-Induced Decay (CID) was used to obtain fragmentation spectra of tryptic peptides having monoisotopic MH+ masses of 1351.8, 1412.7, and 1617.8 Da. The fragment masses were used to search all public domain databases resulting in no identification. The PSD/CID spectra obtained for the peptide having a monoisotopic MH+ mass of 1412.7 were then interpreted to obtain a peptide sequence GHVPENVTDNDR (SEQ ID NO: 10), which was used to BLAST search the S. aureus nucleotide sequence database at www.genome.ou.edu/staph.html. One nucleotide sequence, Contig 981, in reading frame +3 encoded the similar amino acid sequence GHVPELYVDNNR (SEQ ID NO: 11). This tentative identification of the candidate protein was then confirmed upon conceptual translation and in silico tryptic digestion of the open reading frame found in Contig 981. Furthermore, the obtained PSD/CID spectra for tryptic peptides with monoisotopic MH+ masses of 1351.8 and 1617.8 Da were similar to the predicted PSD/CID fragmentation patterns of the tryptic peptides with monoisotopic MH+ masses of 1351.8 and 1617.8 Da found in the Contig 981 open reading frame. Comparison of the Contig 981 open reading frame with all other sequences in the public domain databases revealed that Contig 981 is a homologue of Bacillus subtilis DnaI, a protein involved in origin-dependent DNA replication (42% identity and 62% similarity) (Table 1).

G. Yeast Two-Hybrid Confirmation of DnaI and ORF 104 Interaction.

Figure 12A:
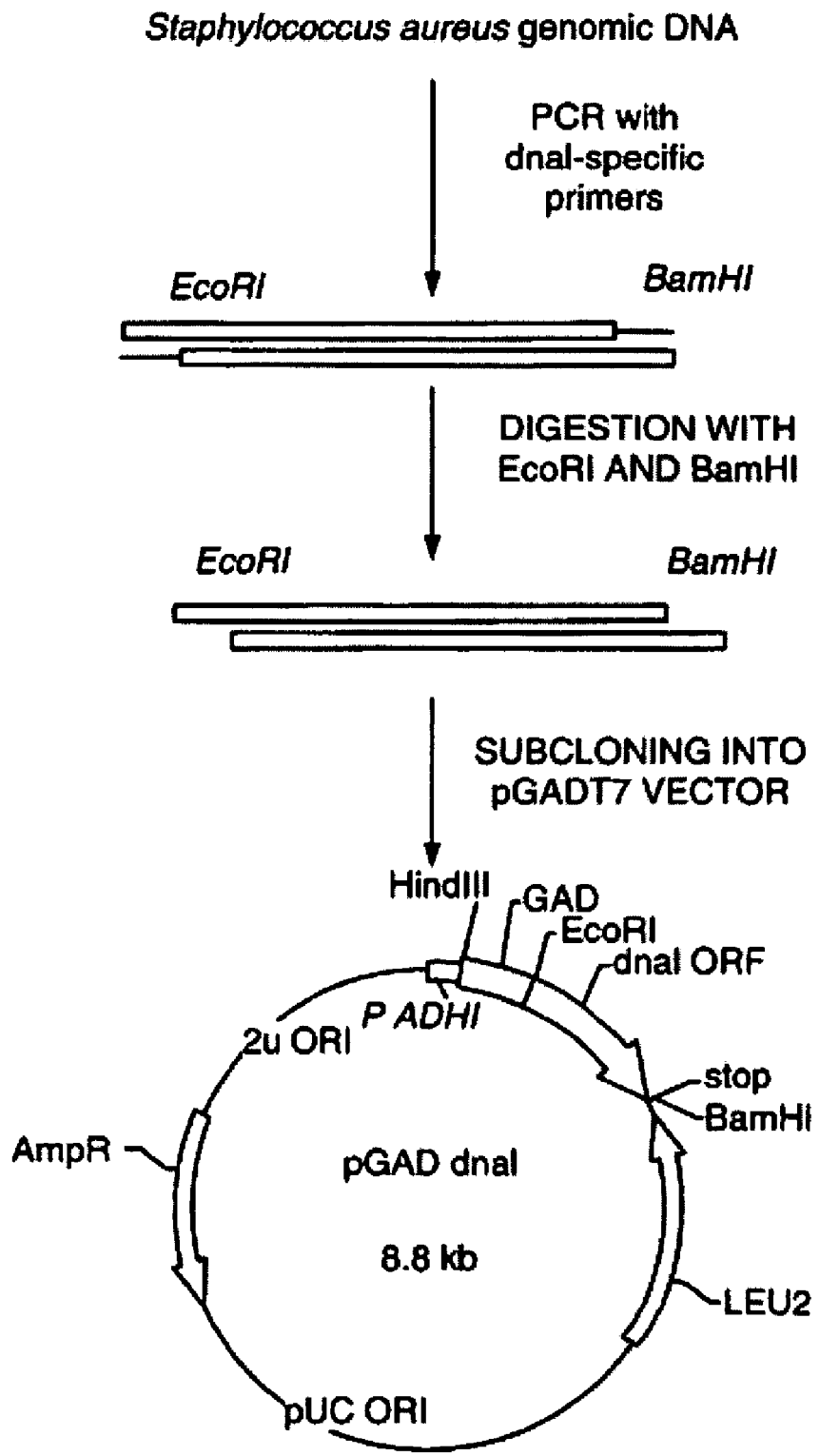
FIGS. 12A–12E show the results of yeast two hybrid analyses designed to test the interaction of S. aureus DnaI and 77 ORF 104. A) Construction of the yeast pGADT7 vector expressing the polypeptide Gal4 activation domain (GAD) fused to the S. aureus DnaI. B) Construction of the yeast pGBKT7 vector expressing the polypeptide Gal4 DNA binding domain (GBK) fused to phage 77 ORF104. 77 ORF 104 and DnaI were also cloned into pGADT7 and pGBKT7, respectively (not shown). C) Yeast two-hybrid assay. D) Yeasts were co-transformed, as indicated (No 1 to 6), in the presence or in the absence of control vectors. pGADT7-T and pGBKT7-53 (NO 1) are positive control for protein: protein interaction and pCL1 (NO 4) is an active Gal4 transcription factor. Co-transformants were plated in parallel on yeast synthetic medium (SD) supplemented with amino acid drop-out lacking tryptophan and leucine (TL minus) and on SD supplemented with amino acid drop-out lacking tryptophan, histidine, adenine and leucine (THAL minus). Co-transformants harboring 77 ORF104 polypeptide only grew on selective THAL minus media in the presence of DnaI (NO 5 and 6). E) Results of the luminescent β-galactosidase enzymatic assays with protein extracts from the same co-transformants (NO 1 to 6).
Figure 12B:
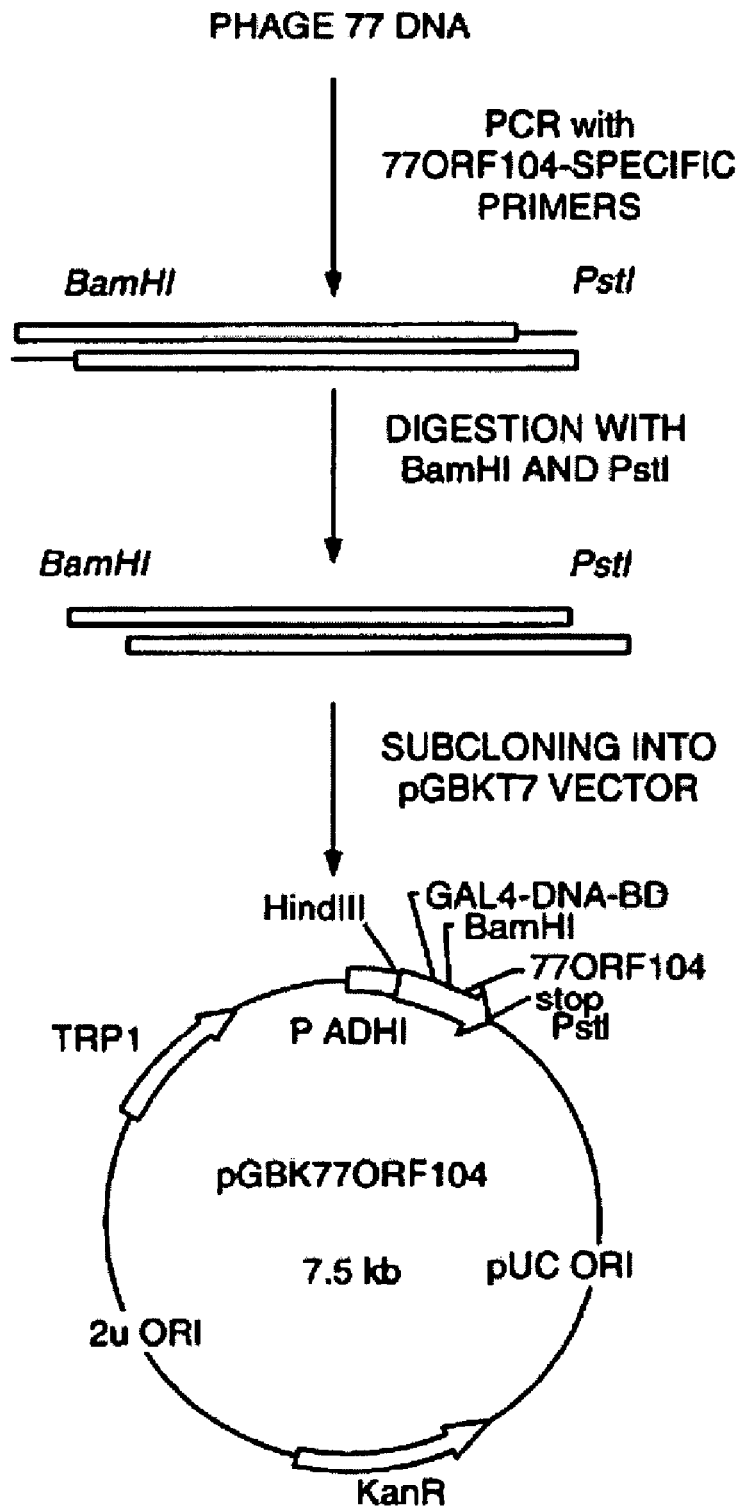
Figure 12C:
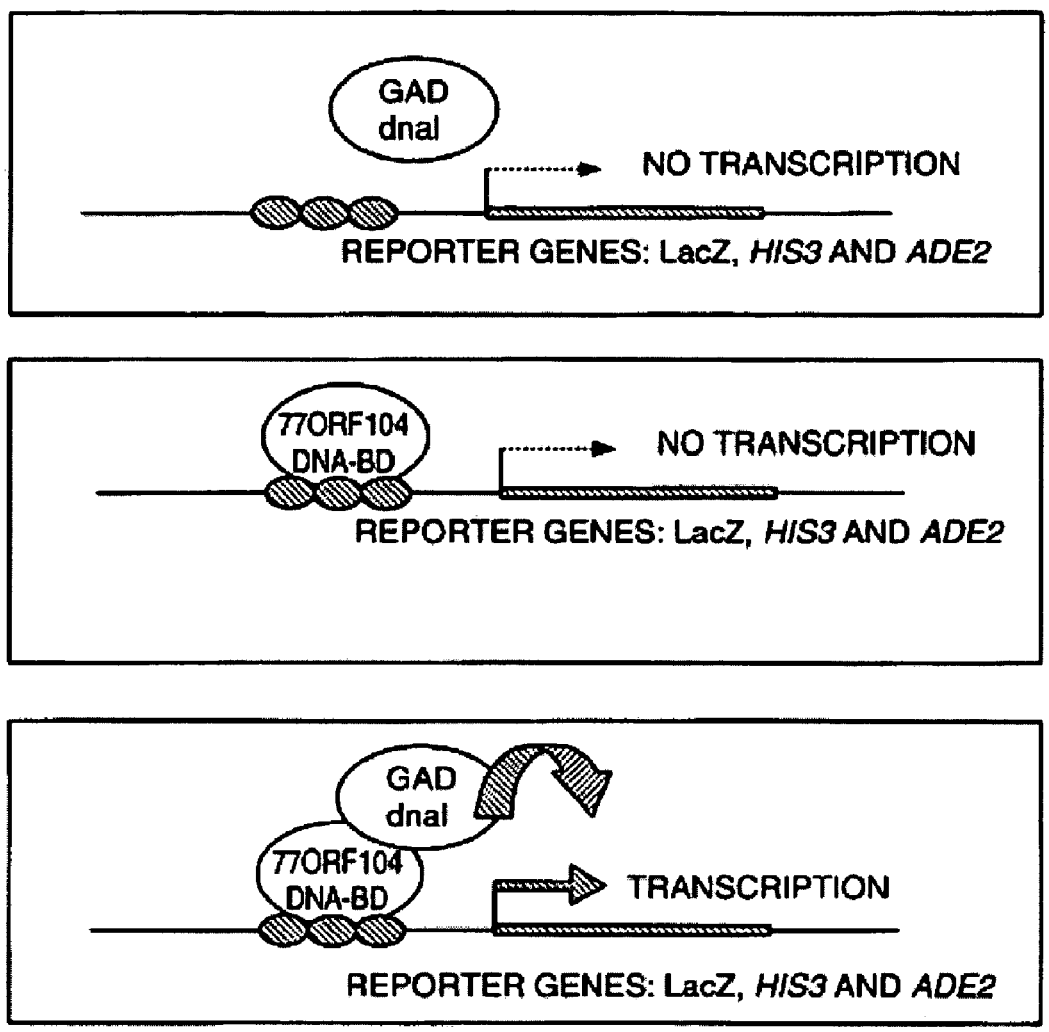

To validate the identification of the S. aureus dnaI homolog as an interacting partner of bacteriophage 77 ORF 104, the interaction was assessed in vivo in the yeast two-hybrid system. As shown in FIG. 12B, bacteriophage 77ORF104 was fused either to the carboxyl terminus of the yeast Gal4 DNA binding (pGBKT7, Clontech Laboratories) or activation (pGADT7, Clontech Laboratories) domains (pGBK77ORF104 and pGAD77ORF104, respectively). The polynucleotide sequence of the DnaI homologue was obtained from the S. aureus genomic DNA by PCR utilizing oligonucleotide primers that targeted the translation initiation and termination codons of the dnaI gene (SEQ ID NO: 1). As shown in FIG. 12A, the sense strand primer targets the initiation codon and is preceded by an EcoRI restriction site (5'-gaattc-3'); the antisense oligonucleotide targets the stop codon and is preceded by a BamHI restriction site (5'-ggatcc-3'). The PCR product was purified using the Qiagen PCR purification kit and digested with EcoRI and BamHI. The digested PCR product was ligated to EcoRI- and BamHI-digested pGADT7 vector (pGAD dnaI). A similar strategy was used for the cloning of DnaI into pGBKT7 vector (pGBK dnaI).

Figure 12D:
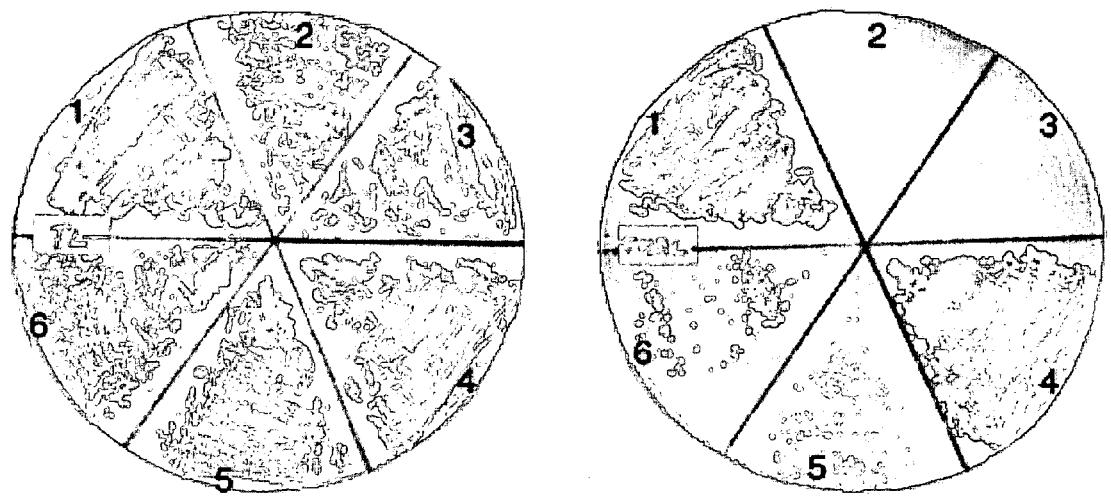
Figure 12E:
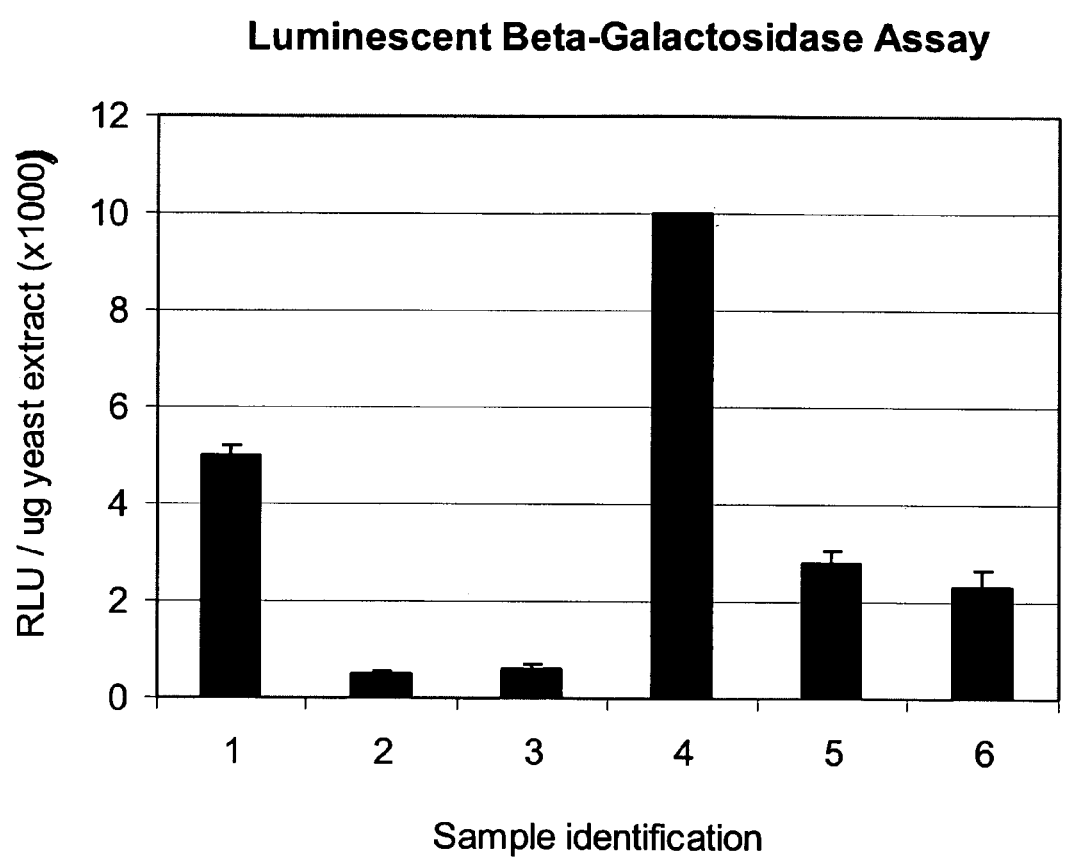
Figure 13:
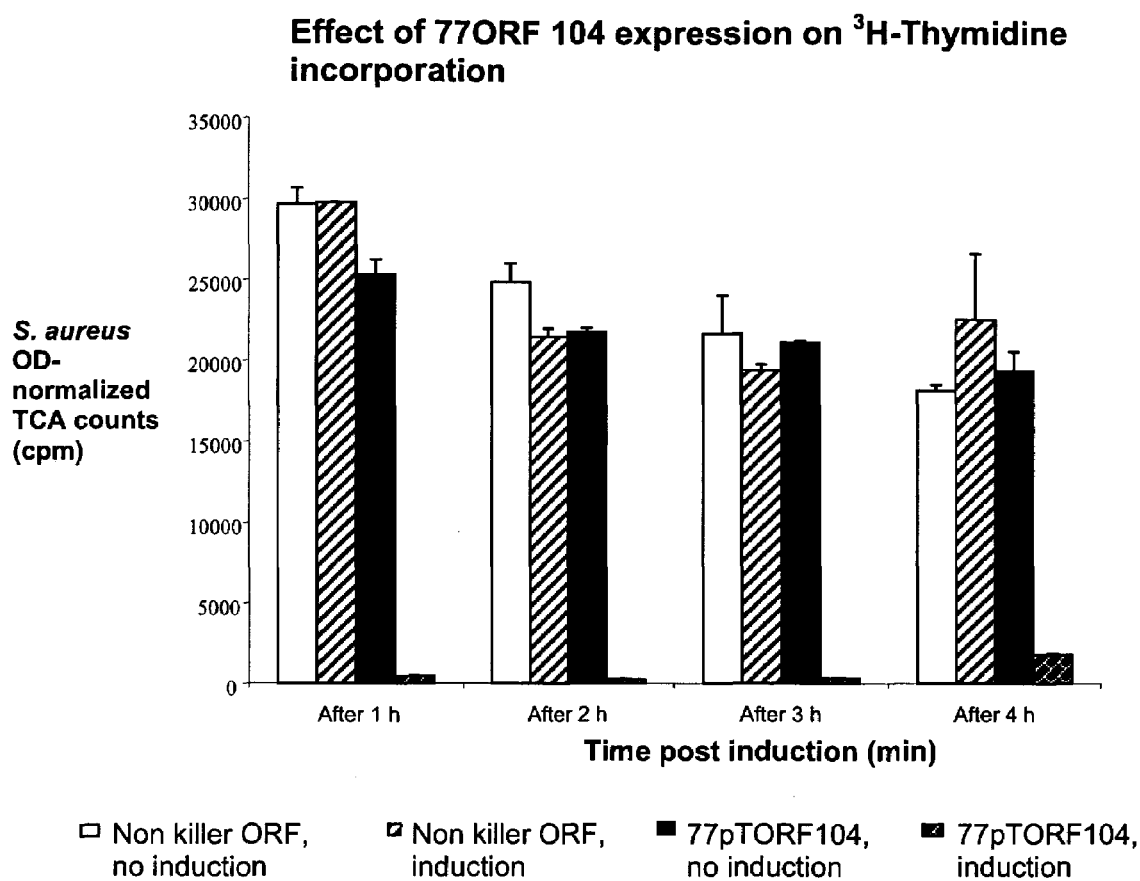
FIG. 13 shows inhibition of *S. aureus* DNA synthesis by bacteriophage 77 ORF 104 protein.

As shown in FIG. 12D, the pGAD and pGBK plasmids bearing different combination of constructs (as indicated in NO 1 to 6) were introduced into a yeast strain (AH109, Clontech Laboratories), previously engineered to contain chromosomally-integrated copies of E. coli lacZ and the selectable HIS3 and ADE2 genes. Co-transformants were plated in parallel on yeast synthetic medium (SD) supplemented with amino acid drop-out lacking tryptophan and leucine (TL minus) and on SD supplemented with amino acid drop-out lacking tryptophan, histidine, adenine and leucine (THAL minus). Co-transformants harboring the 77 ORF104 polypeptide only grew on selective THAL minus media in the presence of DnaI (right Petri, NO 5 and 6). Induction of the reporter HIS3 and ADE2 genes is dependent upon the interaction of dnaI with 77ORF104 proteins since when either plasmid is introduced into yeast host cells with the control plasmid (pGBKT7-53 orpGADT7-T), no reporter expression is observed (NO 2 and 3). pGADT7-T and pGBKT7-53 are positive control for protein:protein interaction (NO 1) and pCL1 is an active Gal4 transcription factor (NO 4). Interaction of DnaI and 77ORF104 is also demonstrated by the presence of luminescent β-galactosidase activity in 77ORF104-DnaI co-transformants (FIG. 12E: NO 5 and 6). These results are consistent with the interpretation that the S. aureus DnaI homologue identified herein is the host target of bacteriophage 77ORF104.

Example 3

Identification of the Surface of Interaction on S. aureus DnaI.

To identify the specific domain of S. aureus DnaI which participates in the interaction with bacteriophage 77ORF104, recombinant DnaI protein was subjected to partial proteolytic digestion and applied to an affinity column containing 77ORF104. Partial proteolytic fragments of DnaI interacting with the 77ORF104 were then analyzed by SDS-PAGE and mass spectrometry, and subsequently characterized by yeast two-hybrid assay to validate the interaction of the DnaI sub-fragment with 77 ORF 104 as described in detail below.

A. Sub-Cloning of DnaI into a Bacterial Inducible Expression System

Full-length DnaI, was amplified from *S. aureus* genomic DNA using the polymerase chain reaction (PCR). For PCR amplification of DnaI, the sense strand primer targets the initiation codon and is preceded by a BamHI restriction site (5'-ggatcc-3'); the antisense oligonucleotide targets the stop codon and is preceded by a SalI restriction site (5'-gtcgac-3') (SEQ ID NO: 1). The digested PCR product was purified using the Qiagen PCR purification kit, ligated into BamHI and SalI digested pGEX-6P-1 vector (# 27-4597, Amersham Pharmacia Biotech), and used to transform *E. coli* strain BL21. The sequence integrity of DnaI polypeptides fused to GST was verified directly by DNA sequencing.

Expression of the GST-DnaI recombinant protein from the plasmid pGEX-6P-1-DnaI was induced by the addition of 0.5 mM IPTG to a 6 liter culture at $OD_{600}$ ~0.5. The protein was expressed at 30° C. for 3 h, the cells were harvested by centrifugation and stored as a cell pellet at −70° C. The frozen cell pellet was thawed, resuspended in Buffer 1 (20 mM HEPES pH 7.3, 500 mM NaCl, 10% glycerol, 1 mM DTT, and 1 mM EDTA) containing 1 mM PMSF and 1 mM benzamidine, and lysed in a French pressure cell followed by three sonication bursts of 20 seconds each at 4° C. The cell lysate was centrifuged at 4° C. for 30 minutes at 10 000 rpm. The supernatant was applied to a 6 ml glutathione sepharose column equilibrated with Buffer 1, washed with 60 ml of Buffer 1 containing 1 mM PMSF and 1 mM benzamidine, and eluted in 6 ml fractions with Buffer 1 containing 50 mM reduced glutathione. Fractions were analyzed by 12% SDS-PAGE and visualized by Coommassie Brilliant Blue R-250 staining.

B. Cleavage and Removal of GST Fusion and Partial Proteolysis of DnaI

Elution fraction 5 containing 7.0 mg GST-DnaI was dialyzed against Buffer 2 (20 mM HEPES pH 7.5, 150 mM NaCl, 10% glycerol, and 1 mM DTT) and subjected to digestion with 40 Units precision protease (Amersham Pharmacia Biotech) at 25° C. for 4 hrs. The digested GST-DnaI was applied to a 1 ml glutathione sepharose column equilibrated with Buffer 2, the flow-through collected, and eluted with Buffer 1 containing 25 mM reduced glutathione. Fractions were analyzed by 12% SDS-PAGE and visualized by Coommassie Brilliant Blue R-250 staining.

The flow-through fraction, containing DnaI, was dialyzed against buffer 2 and subjected to proteolytic digestion in reactions containing the protease/DnaI mass ratio of 1:500 (w/w) of chymotrypsin or 1:50 (w/w) of endoproteinase Glu-C for 2 h at room temperature. The partial proteolysis products obtained from chymotrypsin and endoproteinase Glu-C digestion were used for affinity chromatography. The proteolytic digestion was stopped by the addition of 1 mM PMSF and 1 mM benzamidine and analyzed by SDS-PAGE (one tenth of reaction used for analysis).

C. Affinity Chromatography Between Immobilized 77 ORF 104 and DnaI Proteolytic Fragments 77ORF104 protein was cross-linked to Affigel 10 (Bio-Rad) followed by blocking of the remaining active sites with ethanolamine and the non-specific sites with BSA. The columns were equilibrated with ACB containing 1 M NaCl, and ACB containing 100 mM NaCl. The partial proteolytic digests were diluted to a final volume of 120 μl with ACB containing 100 mM and purified BSA was added to a final concentration of 0.1 mg/ml. The partial proteolytic reaction was split into three fractions, of which 50 ul was applied to a column containing 77ORF104 crosslinked at 2.0 mg/ml, 50 ul was applied to a column containing no ligand, and 10 ul was retained for SDS-PAGE. The columns were washed with 10 column volumes of ACB containing 100 mM NaCl, 4 column volumes of ACB containing 100 mM NaCl and 1% Triton X-100, and eluted sequentially with 4 column volumes ACB containing 1 M NaCl and 1% SDS.

Figure 14A:
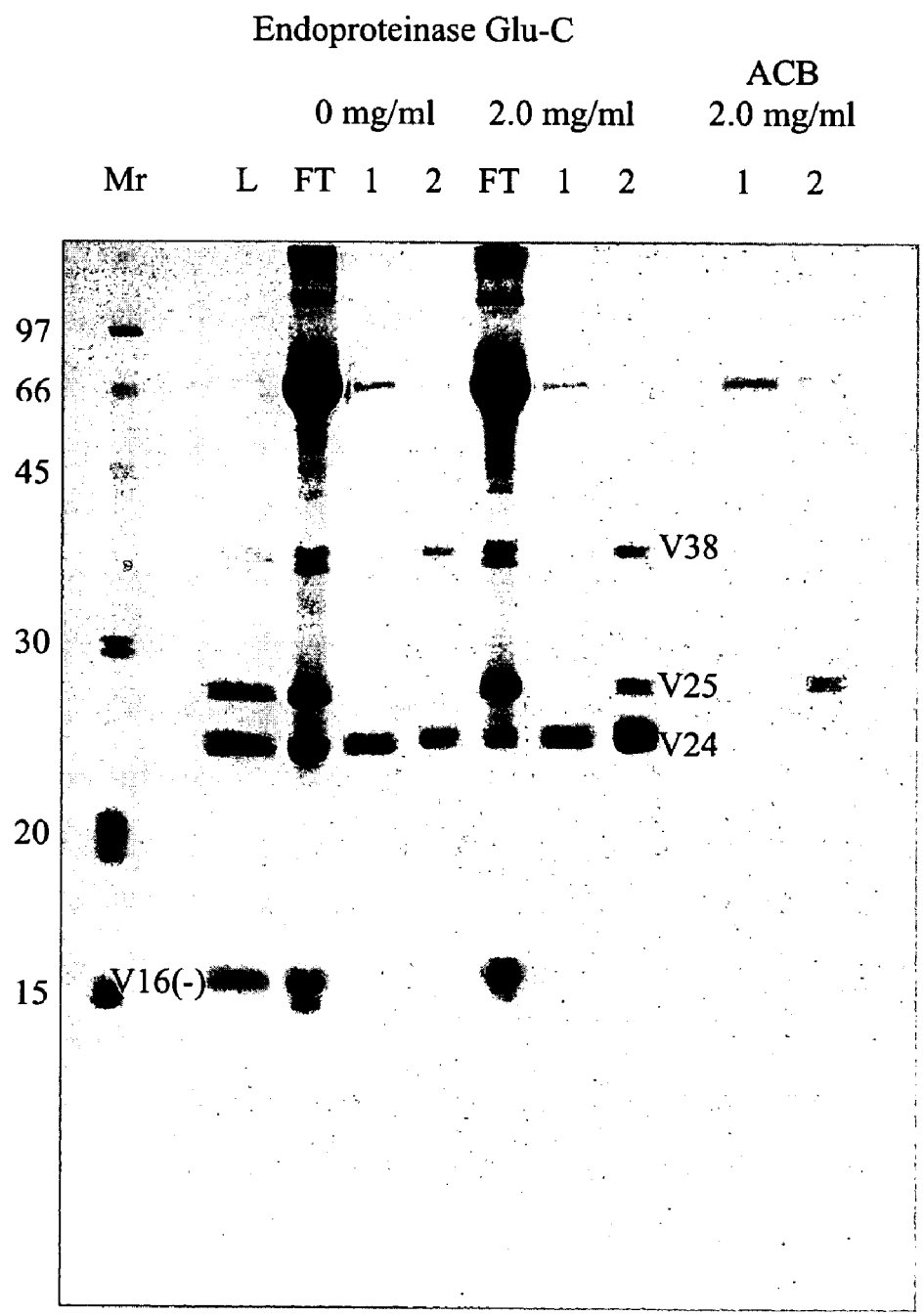
Figure 14B:
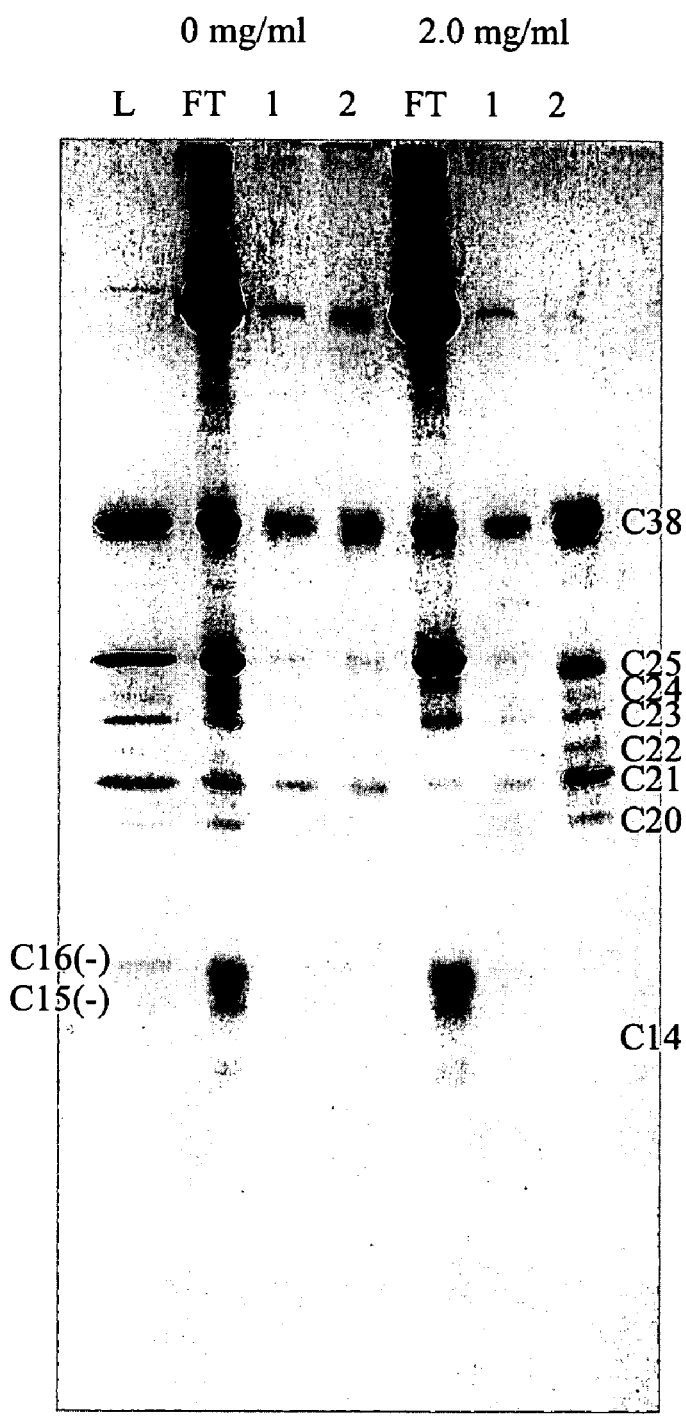

The flow-through and eluates were precipitated with trichloroacetic acid (TCA) and washed with an equal volume of cold (−70° C.) acetone. The TCA-precipitated samples were subjected to 15% SDS-PAGE, and the protein visualized by silver staining (FIGS. 14 A and B).

D. Identification of DnaI Partial Proteolytic Fragments Interacting with 77 ORF 104

The interacting proteolytic fragments were excised, digested by trypsin, and analyzed by mass spectrometry. The peptides contained within each of the interacting proteolytic fragments were analyzed by MALDI-ToF mass spectrometry resulting in the determination of the general region of DnaI for each partial proteolytic peptide. The amino and carboxy terminal ends of the partial proteolytic fragments were determined for several fragments by the acquisition of mass spectrometry data of the unfractionated proteolytic digest followed by mapping the observed mass onto the full length DnaI sequence. Partial proteolytic DnaI fragments interacting with the 77 ORF 104 are presented in FIG. 14C.

E. Sub-Cloning of DnaI Fragments into Yeast Inducible Expression System

The interaction between 77ORF104 and portions of the DnaI polypeptide was also assessed in vivo in the yeast two-hybrid system. Two portions of the polynucleotide sequence of DnaI were amplified by PCR from *S. aureus* genomic DNA by utilizing appropriate pairs of oligonucleotides (FIG. 15). The portion extending from amino acid residues 64 to 313 was obtained with the two following oligonucleotides: the sense strand (with an EcoRI cloning site) 5'-ccggaattcTATAAAGATCAACAAAAAC-3', SEQ ID NO: 12 and the antisense strand (with a BamHI cloning site) 5'-cgcggatccTCAATTGTTTCTGAAATT-3', SEQ ID NO: 13. The polynucleotide sequence encoding amino acids 150–313 of SEQ ID NO: 2 corresponds to nucleotides 448 to 942 of SEQ ID NO: 1 and is herein designated SEQ ID NO: 17. The portion extending from amino acid residues 150 to 313 was obtained with the two following oligonucleotides: the sense strand (with an EcoRI cloning site) 5'-ccggaattcGCAGCAGATGATATTTGT-3', SEQ ID NO: 14 and the antisense strand (with a BamHI cloning site) 5'-cgcggatccTCAATTGTTTCTGAAATT-3', SEQ ID NO: 15. The digested PCR products were gel purified, ligated into EcoRI- and BamHI-digested pGADT7 prey vector, and used to transform *E. coli* strain DH 10β. The sequence integrity of the cloned products was verified directly by DNA sequencing.

Figure 16A:
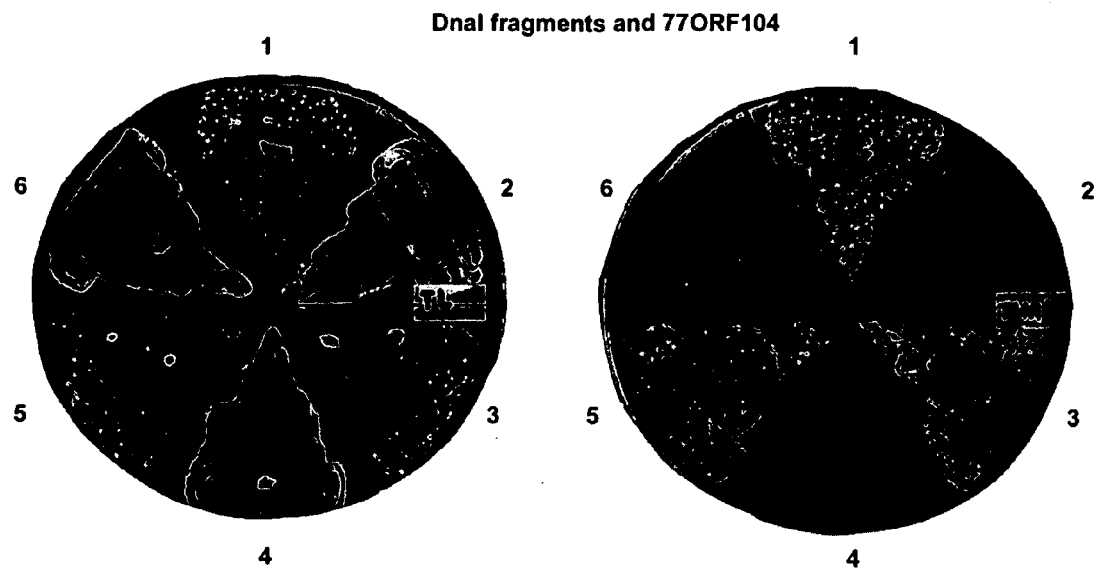
FIGS. 16A–16B show the results of the yeast two-hybrid analysis that were designed to test the interaction between fragments of DnaI and 77 ORF 104. Fragments of *S. aureus* DnaI were cloned into pGADT7 vector. Yeasts were co-transformed with the plasmids indicated from No 1 to 6. pGBKLam and 77pGADORF13 are control vectors driving the expression of non-interacting proteins. Co-transformants were plated in parallel on THAL minus SD medium and on TL minus SD medium. Co-transformants bearing 77ORF104 only grew on selective THAL minus media in the presence of DnaI or DnaI fragments (No 1, 3 and 5). D) Representation of fragments of DnaI interacting with 77ORF104. The minimal domain of DnaI interacting with 77 ORF 104 as determined by yeast two-hybrid analysis is amino acids 150 to 313.
Figure 16B:
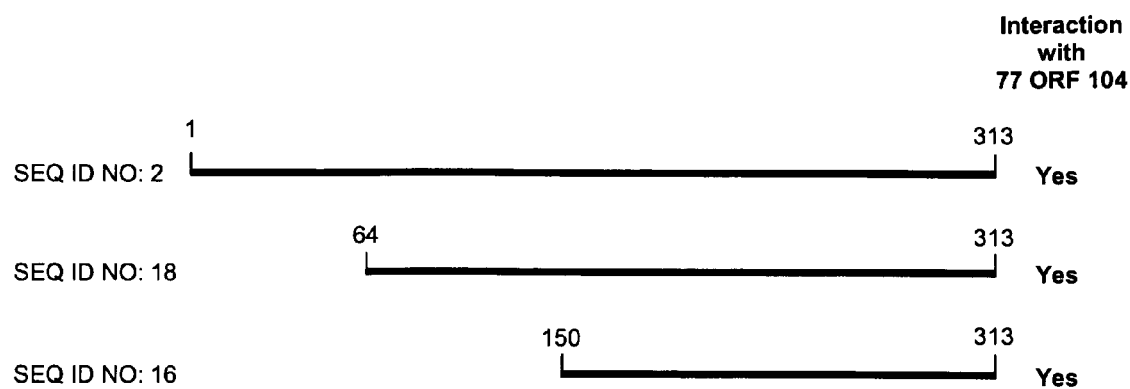

As shown in FIG. 16 different combinaison of bait and prey vectors (as indicated in NO 1 to 6) was introduced into AH109 yeast cells. Portions of DnaI extending from amino acids residues 64 to 313 (herein referred to as SEQ ID NO: 18) as well as from 150 to 313 (herein referred to as SEQ ID NO: 16) were both found to interact with bacteriophage 77ORF104 since the introduction of appropriate plasmids into host yeast cells resulted in their growth on THAL minus SD medium (NO 1 and 3). Induction of these reporter genes is dependent upon the interaction between DnaI-related polypeptides and 77 ORF 104 since the introduction of control plasmids expressing non-interacting protein partners (pGBKLam: NO 2 and 4 or 77pGADORF13: NO 6) did not result in reporter gene expression (FIG. 16A).

Other Embodiments

Other embodiments are within the following claims.

TABLE 1

Similarities in sequence between the DnaI homolog and
sequences deposited in public database.

```
                                                             Score      E
Sequences producing significant alignments:                  (bits)   Value gi|140025|sp|P06567|DNAI_BACSU PRIMOSOMAL PROTEIN DNAI >gi|2797 . . .   231    5e-60
gi|468268 (M15183) ORFY [Bacillus subtilis]                             125    5e-28
gi|2072367|emb|CAA70453| (Y09255) primosomal protein DnaI [Baci . . .    84    1e-15
gi|530419|emb|CAA83732| (Z33058)GTP bind. CD48/PAS1/ SEC18 fam . . .     67    2e-10
gi|2983431 (AE000713) DNA replication protein DnaC [Aquifex aeo . . .    52    4e-06
gi|1176732|sp|P45910|YQAM_BACSU HYPOTHETICAL 36.1 KD PROTEIN IN . . .    50    2e-05
gi|2127076|pir||I40411 hypothetical protein 5 (xre region) - Ba . . .    48    1e-04
gi|1722861|sp|P39782|XKDC_BACSU PHAGE-LIKE ELEMENT PBSX PROTEIN . . .    48    1e-04
gi|1353529 (U38906) ORF12 [Bacteriophage rlt]                            46    4e-04
gi|2983000 (AE000683) chromosome replication initiator protein . . .    45    8e-04
>gi|140025|sp|P06567|DNAI_BACSU PRIMOSOMAL PROTEIN DNAI
            >gi|279708|pir||QBS44 dnaA protein homolog, 44K -
            Bacillus subtilis >gi|39881|emb|CAA28633| (X04963) ORF
            311 (AA 1-311) [Bacillus subtilis]
             >gi|1769996|emb|CAA99605| (Z75208) replication protein
            [Bacillus subtilis]>gi|2293281 (AF008220) DnaI
            [Bacillus subtilis]>gi|2635363|emb|CAB14858| (Z99118)
            helicase loader [Bacillus subtilis]
            Length = 311
 Score =  231 bits (583), Expect = 5e-60
 Identities = 120/280 (42%), Positives = 177/280 (62%), Gaps = 2/280 (0%)

Query:  35  DPDVKQFLEAHRAELTNAMIDEDLNVLQEYKDQQKHYDG-HKFADCPNFVKGHVPELYVD  93
            D DV+ FL+ +   +   MI++ LN L EY +Q K+    +C N ++G+ P+L V+
Sbjct:  31  DQDVQAFLKENEEVIDQKMIEKSLNKLYEYIEQSKNCSYCSEDENCNNLLEGYHPKLVVN  90

Query:  94  NNRIKIRYLQCPCKIKYDEERFEAELITSHHMQRDTLNAKLKDIYMNHRDRLDVAMAADD  153
              I I Y +CP K K D+++ +  L+ S ++Q+D L A  + ++   RL +     D
Sbjct:  91  GRSIDIEYYECPVKRKLDQQKKQQSLMKSMYIQQDLLGATFQQVDISDPSRLAMFQHVTD  150

Query: 154  ICTAITNGEQVKGLYLYGPFGTGKSFILGAIANQLKSKKVRSTIIYLPEFIRTLKGGFKD  213
                +   + KGLYLYG FG GK+F+L AIAN+L    K+  S I+Y+PEF+R LK   +D
Sbjct: 151  FLKSYNETGKGKGLYLYGKFGVGKTFMLAAIANELAEKEYSSMIVYVPEFVRELKNSLQD  210

Query: 214  GSFEKKLHRVREANILMLDDIGAEEVTPWVRDEVIGPLLHYRMVHELPTFFSSNFDYSEL  273
              + E+KL+ V+    +LMLDDIGAE +T WVRDEVIG +L +RM  +LPTFFSSNF  EL
Sbjct: 211  QTLEEKLNMVKTTPVLMLDDIGAESMTSWVRDEVIGTVLQHRMSQQLPTFFSSNFSPDEL  270

Query: 274  EHHLAMTRDGE-EKTKAARIIERVKSLSTPYFLSGENFRN  312
            +HH   ++ GE E+ KAAR++ER+  L+ P  L GEN R+
Sbjct: 271  KHHFTYSQRGEKEEVKAARLMERILYLAAPIRLDGENRRH  310

>gi|468268 (M15183) ORFY [Bacillus subtilis]
            Length = 207
 Score =  125 bits (310), Expect = 5e-28
 Identities = 67/190 (35%), Positives = 105/190 (55%), Gaps = 1/190 (0%)

Query:  20  DFXXXXXXXXXXXXXNDPDVKQFLEAHRAELTNAMIDEDLNVLQEYKDQQKHYDG-HKFAD  78
            DF             D DV+ FL+ +   +   MI++ LN L EY +Q K+     +
Sbjct:  16  DFQNRLEQTKEKVMKDQDVQAFLKENEEVIDQKMIEKSLNKLYEYIEQSKNCSYCSEDEN  75

Query:  79  CPNFVKGHVPELYVDNNRIKIRYLQCPCKIKYDEERFEAELITSHHMQRDTLNAKLKDIY  138
            C N ++G+ P+L V+   I I Y +CP K K D+++ +  L+ S ++Q+D L A  +
Sbjct:  76  CNNLLEGYHPKLVVNGRSIDIEYYECPVKRKLDQQKKQQSLMKSMYIQQDLLGATFQQVD  135

Query: 139  MNHRDRLDVAMAADDICTAITNGEQVKGLYLYGPFGTGKSFILGAIANQLKSKKVRSTII  198
             ++   RL +     D  +    + KGLYLYG FG GK+F+L AIAN+L    K+  S I+
Sbjct: 136  ISDPSRLAMFQHVTDFLKSYNETGKGKGLYLYGKFGVGKTFMLAAIANELAEKEYSSMIV  195

Query: 199  YLPEFIRTLK  208
            Y+PEF+R LK
Sbjct: 196  YVPEFVRELK  205--
```

What is claimed is:

1. A method for inhibiting bacterial growth, comprising contacting bacteria in vitro with an amount of an inhibitor effective to reduce a DnaI activity of a polypeptide comprising the amino acid sequence of SEQ ID NO: 16, wherein said inhibitor inhibits bacterial growth.

2. The method of claim 1 wherein said inhibitor is selected from the group consisting of a small molecule, a peptidomimetic compound, and a bacterial growth inhibitory bacteriophage polypeptide.

3. The method of claim 1 wherein said inhibitor is a peptide synthesized by a recombinant expression system and purified, or artificially synthesized.

4. A method for inhibiting bacterial growth, comprising contacting bacteria in vitro with an effective amount of an inhibitor that decreases a DnaI activity of a polypeptide selected from the group consisting of:
   a polypeptide comprising the amino acid sequence of SEQ ID NO: 2;
   a polypeptide comprising the amino acid sequence of SEQ ID NO: 16; and
   a polypeptide comprising the amino acid sequence of SEQ ID NO: 18,
   wherein said inhibitor inhibits bacterial growth.

5. The method of claim 4, wherein said inhibitor is selected from the group consisting of a small molecule, a peptidomimetic compound, and a bacterial growth inhibitory bacteriophage polypeptide.

6. The method of claim 4, wherein said an inhibitor is a peptide synthesized by a recombinant expression system and purified, or artificially synthesized.

7. A method for inhibiting bacterial growth, comprising contacting a bacteria in vitro with an amount of an inhibitor effective to decrease the activity of a polypeptide selected from the group consisting of
   a DnaI polypeptide comprising at least 50% identity to the amino acid sequence of SEQ IID NO: 2;
   a DnaI polypeptide comprising fragments of the amino acid of SEQ ID NO: 2;
wherein said polypeptide has an activity selected from the group consisting of:
   a) directly interacting with bacteriophage 77 ORF 104 protein or a DnaI-binding fragment thereof in a manner that results in at least 10 fold reduction of $^3$H-thymidine incorporation in a bacterial DNA replication assay relative to $^3$H-thymidine incorporation in an assay lacking bacteriophage 77 ORF 104 protein or a DnaI-binding fragment thereof;
   b) directly interacting with bacteriophage 77 ORF 104 protein or a DnaI-binding fragment thereof in a manner that results in at least 10% inhibition of plasmid replication by bacteriophage 77 ORF 104 protein or a DnaI-binding fragment in a plasmid replication assay; and
   c) aiding in the loading of S. aureus DnaC helicase onto replicative primosomes, wherein said inhibitor inhibits bacterial growth.

8. The method of claim 7, wherein said inhibitor is selected from the group consisting of a small molecule, a peptidomimetic compound, and a bacterial growth inhibitory bacteriophage polypeptide.

9. The method of claim 7, wherein said inhibitor is a peptide synthesized by a recombinant expression system and purified, or artificially synthesized.

10. A method for inhibiting bacterial DNA synthesis, comprising contacting a bacterium in vitro with an effective amount of an inhibitor which decreases the activity of a polypeptide selected from the group consisting of:
   a DnaI polypeptide comprising at least 50% identity to the amino acid sequence of SEQ IID NO: 2;
   a DnaI polypeptide comprising fragments of the amino acid of SEQ ID NO: 2;
wherein said polypeptide has an activity selected from the group consisting of:
   a) directly interacting with bacteriophage 77 ORF 104 protein or a DnaI-binding fragment thereof in a manner that results in at least 10 fold reduction of $^3$H-thymidine incorporation in a bacterial DNA replication assay relative to $^3$H-thymidine incorporation in an assay lacking bacteriophage 77 ORF 104 protein or a DnaI-binding fragment thereof;
   b) directly interacting with bacteriophage 77 ORF 104 protein or a DnaI-binding fragment thereof in a manner that results in at least 10% inhibition of plasmid replication by bacteriophage 77 ORF 104 protein or a DnaI-binding fragment in a plasmid replication assay; and
   c) aiding in the loading of S. aureus DnaC helicase onto replicative primosomes, wherein said inhibitor inhibits bacterial DNA synthesis.

* * * * *

SEQUENCE LISTING

<160> NUMBER OF SEQ ID NOS: 19

<210> SEQ ID NO 1
<211> LENGTH: 942
<212> TYPE: DNA
<213> ORGANISM: Staphylococcus aureus

<400> SEQUENCE: 1

| atgggaggag gacagtcaat aatgaagcaa tttaaaagta taattaacac gtcgcaggac | 60 |
| tttgaaaaaa gaatagaaaa gataaaaaaa gaagtaatca atgacccaga tgttaagcaa | 120 |
| tttttggaag cgcatcgagc tgaattaacg aatgctatga ttgatgaaga cttaaatgtg | 180 |
| ttacaagagt ataaagatca acaaaaacat tatgacggtc ataaatttgc tgattgtcca | 240 |
| aatttcgtaa aggggcatgt gcctgagtta tatgttgata taaccgaat taaaatacgc | 300 |
| tatttacaat gcccatgtaa aatcaagtac gacgaagaac gctttgaagc tgagctaatt | 360 |
| acatctcatc atatgcaacg agatacttta aatgccaaat tgaaagatat ttatatgaat | 420 |
| catcgagacc gtcttgatgt agctatggca gcagatgata tttgtacagc aataactaat | 480 |
| ggggaacaag tgaaaggcct ttacctttat ggtccatttg ggacaggtaa atcttttatt | 540 |
| ctaggtgcaa ttgcgaatca gctcaaatct aagaaggtac gttcgacaat tatttattta | 600 |
| ccggaattta ttagaacatt aaaaggtggc tttaaagatg gttcttttga aaagaaatta | 660 |
| catcgcgtaa gagaagcaaa catttttaatg cttgatgata ttggggctga agaagtgact | 720 |
| ccatgggtga gagatgaggt aattggacct ttgctacatt atcgaatggt tcatgaatta | 780 |
| ccaacattct ttagttctaa ttttgactat agtgaattgg aacatcattt agcgatgact | 840 |
| cgtgatggtg aagagaagac taaagcagca cgtattattg aacgtgtcaa atctttgtca | 900 |
| acaccatact ttttatcagg agaaaatttc agaaacaatt ga | 942 |

<210> SEQ ID NO 2
<211> LENGTH: 313
<212> TYPE: PRT
<213> ORGANISM: Staphylococcus aureus

<400> SEQUENCE: 2

Met Gly Gly Gly Gln Ser Ile Met Lys Gln Phe Lys Ser Ile Ile Asn
1               5                   10                  15

Thr Ser Gln Asp Phe Glu Lys Arg Ile Glu Lys Ile Lys Lys Glu Val
            20                  25                  30

Ile Asn Asp Pro Asp Val Lys Gln Phe Leu Glu Ala His Arg Ala Glu
        35                  40                  45

Leu Thr Asn Ala Met Ile Asp Glu Asp Leu Asn Val Leu Gln Glu Tyr
    50                  55                  60

Lys Asp Gln Gln Lys His Tyr Asp Gly His Lys Phe Ala Asp Cys Pro
65                  70                  75                  80

Asn Phe Val Lys Gly His Val Pro Glu Leu Tyr Val Asp Asn Asn Arg
                85                  90                  95

Ile Lys Ile Arg Tyr Leu Gln Cys Pro Cys Lys Ile Lys Tyr Asp Glu
            100                 105                 110

Glu Arg Phe Glu Ala Glu Leu Ile Thr Ser His His Met Gln Arg Asp
        115                 120                 125

Thr Leu Asn Ala Lys Leu Lys Asp Ile Tyr Met Asn His Arg Asp Arg
    130                 135                 140

-continued

```
Leu Asp Val Ala Met Ala Ala Asp Asp Ile Cys Thr Ala Ile Thr Asn
145                 150                 155                 160
Gly Glu Gln Val Lys Gly Leu Tyr Leu Tyr Gly Pro Phe Gly Thr Gly
                165                 170                 175
Lys Ser Phe Ile Leu Gly Ala Ile Ala Asn Gln Leu Lys Ser Lys Lys
            180                 185                 190
Val Arg Ser Thr Ile Ile Tyr Leu Pro Glu Phe Ile Arg Thr Leu Lys
        195                 200                 205
Gly Gly Phe Lys Asp Gly Ser Phe Glu Lys Lys Leu His Arg Val Arg
    210                 215                 220
Glu Ala Asn Ile Leu Met Leu Asp Asp Ile Gly Ala Glu Glu Val Thr
225                 230                 235                 240
Pro Trp Val Arg Asp Glu Val Ile Gly Pro Leu Leu His Tyr Arg Met
                245                 250                 255
Val His Glu Leu Pro Thr Phe Phe Ser Ser Asn Phe Asp Tyr Ser Glu
            260                 265                 270
Leu Glu His His Leu Ala Met Thr Arg Asp Gly Glu Glu Lys Thr Lys
        275                 280                 285
Ala Ala Arg Ile Ile Glu Arg Val Lys Ser Leu Ser Thr Pro Tyr Phe
    290                 295                 300
Leu Ser Gly Glu Asn Phe Arg Asn Asn
305                 310
```

<210> SEQ ID NO 3
<211> LENGTH: 41708
<212> TYPE: DNA
<213> ORGANISM: Staphylococcus aureus

<400> SEQUENCE: 3

```
gatcaaaata cttggggaac ggttagggag taaacttcgc gataatttta aaaattcatg    60
tataaccccc ctcttataac cattttaagg caggtgatga atggagatt atagtcgatg    120
aaaatttagt gcttaaagaa aagaaaggc tacaagtatt atataaagac atacctagca    180
ataaattaaa agtagttgat ggtttaatta ttcaagcagc aaggctacgt gtaatgcttg    240
attacatgtg ggaagacata aagaaaaag gtgattatga tttatttact caatctgaaa    300
aggcgccacc atatgaaagg gaagaccag tagccaaact attttaatgct agagatgctg    360
catatcaaaa aataatcaaa caattatcgg atttattgcc cgaagagaaa aagacacag    420
aaacgccatc tgatgattac ctatgattag taataaatac gttgatgaat atataaattt    480
gtggaaacaa ggaaagataa ttttaaataa agaaagaatt gatctcttta attatctaca    540
aaaacatata tattcacgag atgatgtata ttttgatgaa cagaaaatcg aggattgtat    600
caaatttatt gaaaaatggt attttccaac attaccattt caaaggttta tcatagctaa    660
tatatttctt atagataaaa atacagatga agctttcttt acagaatttg ctattttcat    720
gggacgtgga ggcgggaaaa acggtctaat aagtgctatt agtgattttc tttctacgcc    780
cttacacgga gttaaagaat atcacatctc cattgttgct aatagtgaag atcaagcaaa    840
aacatcgttt gatgaaatca gaaccgtttt aatggataac aaacgaaata agacgggtaa    900
aacgccaaaa gctccttatg aagttagtaa agcaaaaata ataaccgtg caactaaatc    960
ggttattcga tataacacat caaacacaaa aaccaaagac ggtggacgtg aggggtgtgt   1020
tattttttgat gaaattcatt atttctttgg tcctgaaatg gtaaacgtca acgtggtgg   1080
attaggtaaa agaaaaaata gaagaacgtt ttatataagt actgatggtt ttgttagaga   1140
```

```
gggttatatc gatgcaatga agcacaaaat tgcaagtgta ttaagtggca aggttaaaaa    1200
tagtagattg tttgcttttt attgtaagtt agacgatcca aaagaagttg atgacagaca    1260
gacgtgggaa aaggcgaacc caatgttaca taaaccgtta tcagaatacg ctaaaacact    1320
gctaagcacg attgaagaag aatataacga tttaccattc aaccgttcaa ataagcccga    1380
attcatgact aagcgaatga atttgcctga agttgacctt gaaaaagtaa tagcaccatg    1440
gaaagaaata ctagcgacta atagagagat accaaattta gataatcaaa tgtgtattgg    1500
tggtttagac tttgcaaaca ttcgagattt tgcaagtgta gggctattat tccgaaaaaa    1560
cgatgattac atttggttag acattcgtt tgtaagacaa gggttttttgg atgatgtcaa    1620 attagaacct cctattaaag aatgggaaaa aatgggatta ttgaccattg tcgatgatga    1680
tgtcattgaa attgaatata tagttgattg gttttttaaag gctagagaaa atatgggct    1740 tgaaaaagtc atagctgata attatagaac tgatattgta agacgtgcgt ttgaggatgc    1800
tggcataaaa cttgaagtac ttagaaatcc aaaagcaata catggattac ttgcaccacg    1860
tatcgataca atgtttgcga acataacgt aatatatgga gacaatcctt tgatgcgttg    1920
gtttactaat aatgttgctg taaaaatcaa gccggatgga aataaagagt atatcaaaaa    1980
agatgaagtc agacgtaaaa cggatggatt catggctttt gttcacgcat tatatagagc    2040
agacgatata gtagacaaag acatgtctaa agcgcttgat gcattaatga gtatagattt    2100
ctaatagagg aggtgagaca tgagtattct agaaaagata tttaaaacta ggaaagatat    2160
aacatatatg cttgatttag atatgataga agatctatca caacaagcgt atgtgaaacg    2220
tttagcgatt gatagttgta ttgaatttgt tgcgcgagct gtcgctcaaa gtcattttaa    2280
agtattggaa ggtaatagaa ttcaaaagaa tgatgtttac tacaagttaa atataaaacc    2340
aaatactgac ttatcaagcg atagttttg gcaacaagtt atatataaac taatttatga    2400
taacgaggtt ttaatcgtag taagtgacag caaagaatta cttatcgcag atagcttta    2460 cagagaagag tacgctttgt atgatgatat attcaaagat gtaacggtta aagattatac    2520
ttatcaacgt actttcacaa tgcaagaggt catatattta aagtacaaca acaataaagt    2580
gacacacttt gtagaaagtc tattcgaaga ttacgggaaa atattcggaa gaatgatagg    2640
tgcacaatta aaaaactatc aaataagagg gattttgaaa tctgcctcta gcgcatatga    2700
cgaaaagaat atagaaaaat tacaagcgtt cacaaataaa ttattcaata ctttttaataa    2760 aaatcaacta gcaatcgcgc ctttgataga aggttttgat tatgaggaat tatctaatgg    2820
tggtaagaat agtaacatgc cttttttctga attgagtgag ctaatgagag atgcaataaa    2880
aaatgttgcg ttgatgattg gtataacctcc aggtttgatt tacggagaaa cagctgattt    2940
ggaaaaaaac acgcttgtat ttgagaagtt ctgtttaaca cctttattaa aaaagattca    3000
gaacgaatta aacgcgaaac tcataacaca aagcatgtat ttgaaagata caagaataga    3060
aattgtcggt gtgaataaaa aagacccact tcaatatgct gaagcaattg acaaacttgt    3120
aagttctggt tcatttacaa ggaatgaggt gcggattatg ttaggtgaag aaccatcaga    3180
caatcctgaa ttagacgaat acctgattac taaaaactac gaaaaagcta acagtggtga    3240
aaatgatgaa aaagaaaaag atgaaaacac tttgaaaggt ggtgatgaag atgaaagcgg    3300
agattaaagg cgtcatcgtt tccaacgaag ataaatgggg ttacgaaatg cttggtatgg    3360
attcgacttg tcctaaagat gttttaacac aactagaatt tagtgatgaa gatgttgata    3420
ttataattaa ctcaaatggt ggtaacctag tagctggtag tgaaatatat acacatttaa    3480
gagctcataa aggcaaagtg aatgttcgta tcacagcaat agcagcaagt gcggcatcgc    3540
```

-continued

```
ttatcgcaat ggctggtgac cacatcgaaa tgagtccggt tgctagaatg atgattcaca    3600
atccttcaag tattgcgcaa ggagaagtga agatctaaaa tcatgctgca gaaacattag    3660
aacatgttgg tcaaataatg gctgaggcat atgcggttag agctggtaaa aacaaacaag    3720
aacttataga aatgatggct aaggaaacgt ggctaaatgc tgatgaagcc attgaacaag    3780
gttttgcgga tagtaaaatg tttgaaaacg acaatatgca aattgtagca agcgatacac    3840
aagtgttatc gaaagatgta ttaaatcgtg taacagcttt ggtaagtaaa acgccagagg    3900
ttaacattga tattgacgca atagcaaata agtaattga aaaaataaat atgaaagaaa    3960
aggaatcaga aatcgatgtt gcagatagta aattatcagc aaatggattt tcaagattcc    4020
ttttttaata caaaaatagg aggtcataaa atgactataa atttatcgga acattcgca    4080 aatgcgaaaa acgaatttat taatgcagta acaacggtg aaccgcaaga aagacaaaat    4140
gaattgtacg gtgacatgat taaccaacta tttgaagaaa ctaaattaca agcaaaagca    4200
gaagctgaaa gagtttctag tttacctaaa tcagcacaaa ctttgagtgc aaaccaaaga    4260
aatttcttta tggatatcaa taagagtgtt ggatataaag aagaaaaact tttaccagaa    4320
gaaacaattg atagaatctt cgaagattta acaacgaatc atccattatt agctgactta    4380
ggtattaaaa atgctggttt gcgtttgaag ttcttaaaat ccgaaacttc tggcgtggct    4440
gtttggggta aaatctatgg tgaaattaaa ggtcaattag atgctgcgtt cagtgaagaa    4500
acagcaattc aaaataaatt gacagcgttt gttgttttac caaaagattt aaatgatttt    4560
ggtcctgcgt ggattgaaag atttgttcgt gttcaaatcg aagaagcatt tgcagtggcg    4620
cttgaaactg cgttcttaaa aggtactggt aaagaccaac cgattggctt aaaccgtcaa    4680
gtacaaaaag gtgtatcggt aactgatggt gcttatccag agaaagaaga acaaggtacg    4740
cttacatttg ctaatccgcg cgctacggtt aatgaattga cgcaagtgtt taaataccac    4800
tcaactaacg agaaaggtaa atcagtagcg gttaaaggta atgtaacaat ggttgttaat    4860
ccgtccgatg cttttgaggt tcaagcacag tatacacatt taaatgcaaa tggcgtatat    4920
gttactgctt taccatttaa tttgaatgtt attgagtcta cagttcaaga agcaggtaag    4980
gttttaacgt acgttaaagg tctatatgat ggttatttag ctggtggtat taatgttcag    5040
aaatttaaag aaacacttgc gttagatgat atggatttat acactgcaaa acaatttgct    5100
tacggcaaag cgaaagataa taaagttgct gctgtttgga aattagattt aaaaggacat    5160
aaaccagctt tagaagatac cgaagaaaca ctataaaatt ttatgaggtg ataaaatggt    5220
gaaatttaaa gttgttagag aatttaaaga catagagcac aatcaacaca gtacaaagt    5280 agggagttg tatccagctg aagggtataa caatcctcgt gttgaattgt tgacaaatca    5340
aatcaaaaat aagtacgaca aagtttatat cgtaccttta gataagctga caaaacaaga    5400
attattagaa ctatgcgaat cattacaaaa aaaagcgtct agttcaatgg ttaaaagtga    5460
aatcatcgac ttattgaatg gtgaagacaa tgacgattga tgatttgctt gtcaaattta    5520
aatcacttga aaagattgac cataattcag aggatgagta cttaaagcag ttgttaaaaa    5580
tgtcgtacga gcgtataaaa aatcagtgcg gagtttttga attagagaat ttaataggtc    5640
aagaattgat acttatacgc gctagatatg cttatcaaga tttattagaa cacttcaacg    5700
acaattacag acctgaaata atagatttt cgttatctct aatggaggta tcagaagatg    5760 aagaagtgt ttaagaaacc tagaattaca actaaacgtt taaatacgcg tgttcatttt    5820
tataagtata ctgaaaataa tggtccagaa gctggagaaa aagaagaaa attattatat    5880
```

-continued

```
agctgttggg cgagtattga tggtgtctgg ttacgtgaat tagaacaagc tatctcaaac   5940
ggaacgcaaa atgacattaa attgtatatt cgtgatccgc aaggtgatta tttacccagt   6000
gaagaacatt atcttgaaat tgaatcaaga tatttcaaaa atcgtttgaa tataaagcaa   6060
gtatcaccag atttggataa taaagacttt attatgattc gcggaggata tagttcatga   6120
gtgtgaaagt gacaggtgat aaagcattag aaagagaatt agaaaaacat tttggcataa   6180
aagagatggt aaaagttcaa gataaggcgt taatagctgg tgctaaggta attgttgaag   6240
aaataaaaaa acaactcaaa ccttcagaag actcaggagc actgattagt gagattggtc   6300
gtactgaacc tgaatggata aaggggaaac gtactgttac aattaggtgg cgtgggcctt   6360
ttgaacgatt tagaatagta catttaattg aaaatggtca tgttgagaaa aagtcaggaa   6420
aatttgtaaa acctaaagct atgggtggga ttaatagagc aataagacaa gggcaaaata   6480
agtattttga gacgctaaaa agggagttga aaaaattgtg attgatattt tgtacaaagt   6540
tcatgaagtg attagtcaag acagaattat tagagagcac gtaaatatca ataatattaa   6600
gttcaataaa taccctaatg taaaagatac tgatgtacct tttattgtta ttgacgatat   6660
cgacgaccca atacctacaa cttatactga cggagatgag tgtgcatata gttatattgt   6720
ccaaatagat gttttttgtta agtacaatga tgaatataat gcgagaatca taagaaataa   6780
gatatctaat cgcattccaa agttattatg gtctgaacta aaaatgggaa atgtttcaaa   6840
tggaaaaccg gaatatatag aagaatttaa acatataga agctctcgcg tttacgaggg   6900
catttttttat aaggaggaaa attaaatggc agtaaaacat gcaagtgcgc caaaggcgta   6960
tattaacatt actggtttag gtttcgctaa attaacgaaa gaaggcgcgg aattaaaata   7020
tagtgatatt acaaaaacaa gaggattaca aaaaattggt gttgaaactg gtggagaact   7080
aaaaacagct tatgctgatg gcggtccaat tgaatcaggg aatacagacg gagaaggtaa   7140
aatctcatta caaatgcatg cgttccctaa agagattcgc aaaattgttt ttaatgaaga   7200
ttatgatgaa gatggcgttt acgaagagaa acaaggtaaa caaaacaatt acgtagctgt   7260
atggttcaga caagagcgta aagacggtac atttagaaca gttttattac ctaaagttat   7320
gtttacaaat cctaaaatcg atggagaaac ggctgagaaa gattgggatt tctcaagtga   7380
agaggttgaa ggtgaggcac ttttcccttt agttgataat aaaaagtcag tacgtaagta   7440
tatctttgat tcagctaaca tgacaaatca tgatggagac ggtgaaaaag gcgaagaggc   7500
tttcttaaag aaaatttttag gcgaagaata tactggaaac gtgacagagg taacgaaga   7560
aactttgtaa caaaaccggc ttcatcggaa actgcggtaa agtcggttaa taccagat   7620
agcattaaaa cacttaaagt tggcgacaca tacgatttaa atgttgtagt agagccatct   7680
aatcaaagta agttattgaa atacacaaca gatcaaacga atattgtatc aatcaatagt   7740
gatggtcaag ttactgcgga agcacaaggc attgctacgg ttaaagcaac agttggtaat   7800
atgagtgaca ctataacaat aaatgtgaaa gcataagagg gggcaacccc tctatttttat   7860
ttgaaaataa ggagagtatt ataaaatggc aaaattaaaa cgtaacatta ttcaattagt   7920
agaagatcca aaagcaaatg aaattaaatt acaaacgtac ttaacaccac acttcatttc   7980
atttgaaatt gtatacgaag caatggattt aatcgatgat attgaggacg aaaatagcac   8040
gatgaagcca agagaaatcg ctgacagatt gatggatatg gttgtaaaaa tttacgataa   8100
ccaattcaca gttaaagacc taaagaacg tatgcatgca cctgatggaa tgaatgcact   8160
tcgtgaacaa gtgattttca ttactcaagg tcaacaaact gaggaaacta gaaatttat   8220
ccagaacatg aaataaagcc tgaagattta acatataaag caatgttgaa aaatatggat   8280
```

```
actctcatga tggacttaat tgaaaatggt aaagacgcta acgaagtttt aaaaatgcca    8340
tttcattatg tgctttccat atatcaaaat aaaaataatg acatttctga agaaaaagca    8400
gaggctttaa ttgatgcatt ttaaccttaa ccgtttggtt agggttattt ttttgaactt    8460
ttttagaaag gaggtaaaaa atgggagaaa gaataaaagg tttatctata ggtttggatt    8520
tagatgcagc aaatttaaat agatcatttg cagaaatcaa acgaaacttt aaaactttaa    8580
attctgactt aaaattaaca ggcaacaact tcaaatatac cgaaaaatca actgatagtt    8640
acaaacaaag gattaaagaa cttgatggaa ctatcacagg ttataagaaa aacgttgatg    8700
atttagccaa gcaatatgac aaggtatctc aagaacaggg cgaaaacagt gcagaagctc    8760
aaaagttacg acaagaatat aacaaacaag caaatgagct gaattattta gaaagagaat    8820
tacaaaaaac atcagccgaa tttgaagagt tcaaaaaagc tcaagttgaa gctcaaagaa    8880
tggcagaaag tggctgggga aaaaccagta agttttttga agtatggga cctaaaattaa    8940 caaaaatggg tgatggtttta aaatccattg gtaaaggttt gatgattggt gtaactgcac    9000
ctgttttagg tattgcagca gcatcaggaa aagcttttgc agaagttgat aaaggtttag    9060
atactgttac tcaagcaaca ggcgcaacag gcagtgaatt aaaaaaattg cagaactcat    9120
ttaaagatgt ttatgcaat tttccagcag atgctgaaac tgttggtgga gttttaggag    9180
aagttaatac aaggttaggt tttacaggta agaacttga aaatgccaca gagtcattct    9240
tgaaattcag tcatataaca ggttctgacg gtgtgcaagc cgtacagtta attacccgtg    9300
caatgggcga tgcaggtatc gaagcaagtg aatatcaaag tgttttggat atggtagcaa    9360
aagcggcgca agctagtggg ataagtgttg atacattagc tgatagtatt actaaatacg    9420
gcgctccaat gagagctatg ggctttgaga tgaaagaatc aattgcttta ttctctcaat    9480
gggaaaagtc aggcgttaat actgaaatag cattcagtgg tttgaaaaaa gctatatcaa    9540
attggggtaa agctggtaaa aacccaagag aagaatttaa gaagacatta gcagaaattg    9600
aaaagacgcc ggatatagct agcgcaacaa gtttagcgat tgaagcattt ggtgcaaagg    9660
caggtcctga tttagcagac gctattaaag gtggtcgctt tagttatcaa gaattttaa    9720 aaactattga agattcccaa ggcacagtaa accaaacatt taaagattct gaaagtggct    9780
ccgaaagatt taaagtagca atgaataaat taaaattagt aggtgctgat gtatgggctt    9840
ctattgaaag tgcgtttgct cccgtaatgg aagaattaat caaaaagcta tctatagcgg    9900
ttgattggtt ttccaattta agtgatggtt ctaaagatc aattgttatt ttcagtggta    9960
ttgctgctgc aattggtcct gtagtttttg ggttaggtgc atttataagt acaattggca   10020
atgcagtaac tgtattagct ccattgttag ctagtattgc aaaggctggt ggattgatta   10080 gtttttatc gactaaagta cctatattag gaactgtctt cacagcttta actggtccaa   10140
ttggcattgt attaggtgta ttggctggtt tagcagtcgc atttacaatt gcttataaga   10200
aatctgaaac atttagaaat tttgttaatg gtgcaattga agtgttaaa caaacattta   10260 gtaattttat tcaatttatt caaccttcg ttgattctgt taaaaacatc tttaaacaag   10320
cgatatcagc aatagttgat ttcgcaaaag atatttggag tcaaatcaat ggattcttta   10380
atgaaaacgg aatttccatt gttcaagcac ttcaaaatat atgcaacttt attaaagcga   10440
tatttgaatt tattttaaat tttgtaatta accaattat gttcgcgatt tggcaagtga   10500 tgcaattat ttggccggcg gttaaagcct tgattgtcag tacttgggag aacataaaag   10560
gtgtaataca aggtgcttta aatatcatac ttggcttgat taagttcttc tcaagtttat   10620
```

```
tcgttggtga ttggcgagga gtttgggacg ccgttgtgat gattcttaaa ggagcagttc   10680
aattaatttg gaatttagtt caattatggt ttgtaggtaa aatacttggt gttgttaggt   10740
actttggcgg gttgctaaaa ggattgatag caggaatttg ggacgtaata agaagtatat   10800
tcagtaaatc tttatcagca atttggaatg caacaaaaag tatttttgga tttttattta   10860
atagcgtaaa atcaattttc acaaatatga aaaattggtt atctaatact tggagcagta   10920
tccgtacgaa tacaatagga aaagcgcagt cattatttag tggcgtcaaa tcaaaattta   10980
ctaatttatg gaatgcgacg aaagaaattt ttagtaattt aagaaattgg atgtcaaata   11040
tttggaattc cattaaagat aatacggtag gaattgcaag ccgtttatgg agtaaggtac   11100
gtggaatttt cacaaatatg cgcgatggct tgagttccat tatagataag attaaaagtc   11160
atatcggcgg tatggtaagc gctattaaaa aaggacttaa taaattaatc gacggtttaa   11220
actgggtcgg tggtaagttg ggaatggata aaatacctaa gttacacact ggtacagagc   11280
acacacatac tactacaaga ttagttaaga acggtaagat tgcacgtgac acattcgcta   11340
cagttgggga taagggacgc ggaaatggtc caaatggttt tagaaatgaa atgattgaat   11400
tccctaacgg taaacgtgta atcacaccta atacagatac taccgcttat ttacctaaag   11460
gctcaaaagt atacaacggt gcacaaactt attcaatgtt aaacggaacg cttccaagat   11520
ttagtttagg tactatgtgg aaagatatta aatctggtgc atcatcggca tttaactgga   11580
caaaagataa aataggtaaa ggtaccaaat ggcttggcga taaagttggc gatgttttag   11640
attttatgga aaatccaggc aaactttaa attatatact tgaagctttt ggaattgatt   11700
tcaattcttt aactaaaggt atgggaattg caggcgacat aacaaaagct gcatggtcta   11760
agattaagaa aagtgctact gattggataa aagaaaattt agaagctatg ggcggtggcg   11820
atttagtcgg cggaatatta gaccctgaca aaattaatta tcattatgga cgtaccgcag   11880
cttataccgc tgcaactgga agaccatttc atgaaggtgt cgattttcca tttgtatatc   11940
aagaagttag aacgccgatg ggtggcagac ttacaagaat gccatttatg tctggtggtt   12000
atggtaatta tgtaaaaatt actagtggcg ttatcgatat gctatttgcg catttgaaaa   12060
actttagcaa atcaccacct agtggcacga tggtaaagcc cggtgatgtt gttggtttaa   12120
ctggtaatac cggatttagt acaggaccac atttacattt tgaaatgagg agaaatggac   12180
gacattttga ccctgaacca tatttaagga atgctaagaa aaaaggaaga ttatcaatag   12240
gtggtggcgg tgctacttct ggaagtggcg caacttatgc cagtcgagta atccgacaag   12300
cgcaaagtat tttaggtggt cgttataaag gtaaatggat tcatgaccaa atgatgcgcg   12360
ttgcaaaacg tgaaagtaac taccagtcaa atgcagtgaa taactgggat ataaatgctc   12420
aaagaggaga cccatcaaga ggattattcc aaatcatcgg ctcaactttt agagcaaacg   12480
ctaaacgtgg atatactaac tttaataatc cagtacatca aggtatctca gcaatgcagt   12540
acattgttag acgatatggt tggggtggtt taaacgtgc tggtgattac gcatatgcta   12600
caggtggaaa agttttgat ggttggtata acttaggtga agacggtcat ccagaatgga   12660
ttattccaac agatccagct cgtagaaatg atgcaatgaa gattttgcat tatgcagcag   12720
cagaagtaag agggaaaaaa gcgagtaaaa ataagcgtcc tagccaatta tcagacttaa   12780
acgggtttga tgatcctagc ttattattga aaatgattga acaacagcaa caacaaatag   12840
ctttattact gaaaatagca caatctaacg atgtgattgc agataaagat tatcagccga   12900
ttattgacga atacgctttt gataaaaagg tgaacgcgtc tatagaaaag cgagaaaggc   12960
aagaatcaac aaaagtaaag tttagaaaag gaggaattgc tattcaatga tagacactat   13020
```

```
taaagtgaac aacaaaacaa ttccttggtt gtatgtcgaa agagggtttg aaataccctc    13080 tttaattat gttttaaaaa cagaaaatgt agatggacgt tcggggtcta tatataaagg    13140
gcgtaggctt gaatcttata gttttgatat acctttggtg gtacgtaatg actatttatc    13200
tcacaacggc attaaaacac atgatgacgt cttgaatgaa ttagtaaagt tttttaacta    13260
cgaggaacaa gttaaattac aattcaaatc taaagattgg tactggaacg cttatttcga    13320
aggaccaata aagctgcaca aagaatttac atacctgtt aagttcacta tcaaagtagt    13380
actaacagac ccttacaaat attcagtaac aggaaataaa aatactgcga tttcagacca    13440
agtttcagtt gtaaatagtg ggactgctga cactcctta attgttgaag cccgagcaat    13500
taaaccatct agttacttta tgattactaa aaatgatgaa gattatttta tggttggtga    13560
tgatgaggta accaaagaag ttaaggatta catgcctcct gtttatcata gtgagtttcg    13620
tgatttcaaa ggttggacta agatgattac tgaagatatt ccaagtaatg acttaggtgg    13680
taaggtcggc ggtgactttg tgatatccaa tcttggcgaa ggatataaag caactaattt    13740
tcctgatgca aaaggttggg ttggtgctgg cacgaaacga gggctcccta aagcgatgac    13800
agattttcaa attacctata aatgtattgt tgaacaaaaa ggtaaaggtg ccggaagaac    13860
agcacaacat atttatgata gtgatggtaa gttacttgct tctattggtt atgaaaataa    13920
atatcatgat agaaaaatag acatattgt tgttacgttg tataaccaaa aaggagaccc    13980
caaaaagata tacgactatc agaataaacc gataatgtat aacttggaca gaatcgttgt    14040
ttatatgcgg ctcagaagag taggtaataa attttctatt aaaacttgga aatttgatca    14100
cattaaagac ccagatagac gtaaacctat tgatatggat gagaaagagt ggatagatgg    14160
cggtaagttt tatcagcgtc cagcttctat catagctgtc tatagtgcga agtataacgg    14220
ttataagtgg atggagatga atgggttagg ttcattcaat acggagattc taccgaaacc    14280
gaaaggcgca agggatgtca ttatacaaaa aggtgattta gtaaaaatag atatgcaagc    14340
aaaaagtgtt gtcatcaatg aggaaccaat gttgagcgag aaatcgtttg gaagtaatta    14400 ttcaatgtt gattctgggt acagtgaatt aatcatacaa cctgaaaacg tctttgatac    14460
gacggttaaa tggcaagata gatatttata gaaaggagat gagagtgtga tacatgtttt    14520
agattttaac gacaagatta tagatttcct ttctactgat gaccccttcct tagttagagc    14580 gattcataaa cgtaatgtta atgacaattc agaaatgctt gaactgctca tatcatcaga    14640
aagagctgaa aagttccgtg aacgacatcg tgttattata agggattcaa acaaacaatg    14700
gcgtgaattt attattaact gggttcaaga tacgatggac ggctacacag agatagaatg    14760
tatagcgtct tatcttgctg atataacaac agctaaaccg tatgcaccag gcaaatttga    14820
gaaaaagaca acttcagaag cattgaaaga tgtgttgagc gatacaggtt gggaagtttc    14880 tgaacaaaacc gaatacgatg gcttacgtac tacgtcatgg acttcttatc aaactagata    14940
tgaagtttta aagcaattat gtacaaccta taaaatggtt ttagattttt atattgagct    15000
tagctctaat accgtcaaag gtagatatgt agtactcaaa aagaaaaaca gcttattcaa    15060
aggtaaagaa attgaatatg gtaaagattt agtcgggtta actaggaaga ttgatatgtc    15120
agaaatcaaa acagcattaa ttgctgtggg acctgaaaat gacaaaggga agcgtttaga    15180
gctagttgtg acagatgacg aagcgcaaag tcaattcaac ctacctatgc gctatatttg    15240
ggggatatat gaaccacaat cagatgatca aaatatgaat gaaacacgat taagttcttt    15300
agccaaaaca gagttaaata aacgtaagtc ggcagttatg tcatatgaga ttacttctac    15360
```

-continued

```
tgatttggaa gttacgtatc cgcacgagat tatatcaatt ggcgatacag tcagagtaaa   15420
acatagagat tttaacccgc cattgtatgt agaggcagaa gttattgctg aagaatataa   15480
cataatttca gaaatagca catatacatt cggtcaacct aaagagttca aagaatcaga    15540
attacgagaa gagtttaaca agcgattgaa cataatacat caaaagttaa acgataatat   15600
tagcaatatc aacactatag ttaaagatgt tgtagatggt gaattagaat actttgaacg   15660
caaaatacac aaaagtgata caccgccaga aaatccagtc aatgatatgc tttggtatga   15720
tacaagtaac cctgatgttg ctgtcttgcg tagatattgg aatggtcgat ggattgaagc   15780
aacaccaaat gatgttgaaa attaggtgg tataacaaga gagaaagcgc tattcagtga    15840
attaaacaat atttttatta atttatctat acaacacgct agtcttttgt cagaagctac   15900
agaattactg aatagcgagt acttagtaga taatgatttg aaagcggact acaagcaag    15960 tttagacgct gtgattgatg tttataatca aattaaaaat aatttagaat ctatgacacc   16020
cgaaactgca acgattggtc ggttggtaga tacacaagct ttatttcttg agtatagaaa   16080
gaaattacaa gatgtttata cagatgtaga agatgtcaaa atcgccattt cagatagatt   16140
taaattatta cagtcacaat acactgatga aaaatataaa gaagcgttgg aaataatagc   16200
aacaaaattt ggtttaacgg tgaatgaaga tttgcagtta gtcggagaac ctaatgttgt   16260
taaatcagct attgaagcag ctagagaatc cacaaaagaa caattacgtg actatgtaaa   16320
aacatcggac tataaaacag acaaagacgg tattgttgaa cgtttagata ctgctgaagc   16380
tgagagaacg actttaaaag gtgaaatcaa agataaagtt acgttaaacg aatatcgaaa   16440
cggattggaa gaacaaaaac aatatactga tgaccagtta agtgatttgt ccaataatcc   16500
tgagattaaa gcaagtattg aacaagcaaa tcaagaagcg caagaagctt aaaaatcata   16560
cattgatgct caagatgatc ttaaagagaa ggaatcgcaa gcgtatgctg atggtaaaat   16620
ttcggaagaa gagcaacgcg ctatacaaga tgctcaagct aaacttgaag aggcaaaaca   16680
aaacgcagaa ctaaaggcta gaaacgctga aaagaaagct aatgcttata cagacaacaa   16740
ggtcaaagaa agcacagatg cacagaggaa acattgact cgctatggtt ctcaaattat     16800
acaaaatggt aaggaaatca aattaagaac tactaaagaa gagtttaatg caaccaatcg   16860
tacactttca aatatattaa acgagattgt tcaaaatgtt acagatggaa caacaatcag   16920
atatgatgat aacggagtgg ctcaagcttt gaatgtgggg ccacgtggta ttagattaaa   16980
tgctgataaa attgatatta acggtaatag agaaataaac cttcttatcc aaaatatgcg   17040
agataaagta gataaaaccg atattgtcaa cagtcttaat ttatcaagag agggtcttga   17100
tatcaatgtt aatagaattg gaattaaagg cggtgacaat aacagatatg ttcaaataca   17160
gaatgattct attgaactag gtggtattgt gcaacgtact tggagaggga aacgttcaac   17220
agacgatatt tttacgcgac tgaaagacgg tcacctaaga tttagaaata caccgctgg    17280 cggttcactt tatatgtcac attttggtat ttcgacttat attgatggtg aagtgaaga   17340 cggtggttca tctggtacga ttcaatggtg ggataaaact tacagtgata gtggcatgaa   17400
tggtataaca atcaattcct atggtggtgt cgttgcacta acgtcagata taatcgggt    17460 tgttctggag tcttacgctt catcgaatat caaaagcaaa caggcaccgg tgtatttata   17520
tccaaacaca gacaaagtgc ctggattaaa ccgatttgca ttcacgctgt ctaatgcaga   17580
taatgcttat tcgagtgacg gttatattat gtttggttct gatgagaact atgattacgg   17640
tgcgggtatc aggttttcta aagaaagaaa taaaggtctt gttcaaattg ttaatggacg   17700
atatgcaaca ggtggagata caacaatcga agcagggtat ggcaaattta atatgctgaa   17760
```

-continued

```
acgacgtgat ggtaataggt atattcatat acagagtaca gacctactgt ctgtaggttc     17820
agatgatgca ggagatagga tagcttctaa ctcaatttat agacgtactt attcggccgc     17880
agctaatttg catattactt ctgctggcac aattgggcgt tcgacatcag cgcgtaaata     17940
caagttatct atcgaaaatc aatataacga tagagatgaa caactggaac attcaaaagc     18000
tattcttaac ttacctatta gaacgtggtt tgataaagct gagtctgaaa ttttagctag     18060
agagctgaga gaagatagaa aattatcgga agacacctat aaacttgata gatacgtagg     18120
tttgattgct gaagaggtgg agaatttagg attaaaagag tttgtcacgt atgatgacaa     18180
aggagaaatt gaaggtatag cgtatgatcg tctatggatt catcttatcc ctgttatcaa     18240
agaacaacaa ctaagaatca agaaattgga ggagtcaaag aatgcaggat aacaaacaag     18300
gattacaagc taatcctgaa tatacaattc attatttatc acaggaaatt atgaggttaa     18360
cacaagaaaa cgcgatgtta aaagcgtata tacaagaaaa taagaaaat caacaatgtg      18420 ctgaggaaga gtaatcctta gcactatttt tatacaaaaa tttaaggagg tcatttaatt     18480
atggcaaaag aaattatcaa caatacagaa aggtttattt tagtacaaat cgacaaagaa     18540
ggtacagaac gtgtagtata tcaagatttc acaggaagtt ttacaacttc tgaaatggtt     18600
aaccatgctc aagattttaa atctgaagaa acgctaaga aaattgcgga acgttaaat      18660 ttgttatatc aattaactaa caaaaaacaa cgtgtgaaag tagttaaaga agtagttgaa     18720
agatcagatt tatctccaga ggtaacagtt aacactgaaa cagtatgaaa agctatgagt     18780
tagatactca tagtctttat tcttttagaa agcgggtgta ctgaattggg gtggttcaaa     18840
aaacacgaac atgaatggcg catcagaagg ttagaagaga atgataaaac aatgctcagc     18900
acactcaacg aaattaaatt aggtcaaaaa acccaagagc aagttaacat taaattagat     18960
aaaaccttag atgctattca aaagaaaga gaaatagatg aaaagaataa gaaagaaaat     19020
gataagaaca tacgtgatat gaaaatgtgg gtgcttggtt tagttgggac aatatttggg     19080
tcgctaatta tagcattatt gcgtatgctt atgggcatat aagagaggtg attaccatgt     19140
tcggattaaa ttttggagct tcgctgtgga cgtgtttctg gtttggtaag tgtaagtaat     19200
agttaagagt cagtgcttcg gcactggctt tttatttttgg ataaaggag caaacaaatg     19260 gatgcaaaag taataacaag atacatcgta ttgatcttag cattagtaaa tcaattctta     19320
gcgaacaaag gtattagccc aattccagta gacgatgaaa ctatatcatc aataatactt     19380
actgtagtcg ctttatatac aacgtataaa gacaatccaa catctcaaga aggtaaatgg     19440
gcaaatcaaa aattaaagaa atataaagct gaaaataagt atagaaaagc aacagggcaa     19500
gcgccaatta aagaagtaat gacacctacg aatatgaacg acacaaatga tttagggtag     19560
gtggttgata tatgttaatg acaaaaaatc aagcagaaaa atggtttgac aattcattag     19620
ggaaacaatt caacccagat ggttggtatg gatttcagtg ttatgattac gccaatatgt     19680
tctttatgtt agcgacaggc gaaaggctgc aaggtttata tgcttataat atcccgtttg     19740
ataataaagc aaagattgaa aaatatggtc aaataattaa aaactatgac agcttttttac     19800 cgcaaaagtt ggatattgtc gttttcccgt caaagtatgg tggcggagct ggacacgttg     19860
aaattgttga gagcgcaaat ttaaatactt tcacatcatt tggtcaaaac tggaacggta     19920
aaggttggac taatggcgtt gcgcaacctg gttgggtcc tgaaactgtg acaagacatg      19980
ttcattatta tgcaatcca atgtatttta ttaggttaaa cttccctaac aacttaagcg     20040
ttggcaataa agctaaaggt attattaagc aagcgactac aaaaaaagag gcagtaatta     20100
```

```
aacctaaaaa aattatgctt gtagccggtc atggttataa cgatcctgga gcagtaggaa   20160
acggaacaaa cgaacgcgat tttatacgta aatatataac gcctaatatc gctaagtatt   20220
taagacatgc aggacatgaa gttgcattat acggtggctc aagtcaatca caagatatgt   20280
atcaagatac tgcatacggt gttaatgtag gcaataaaaa agattatggc ttatattggg   20340
ttaaatcaca ggggtatgac attgttctag aaatacattt agacgcagca ggagaaagcg   20400
caagtggtgg gcatgttatt atctcaagtc aattcaatgc agatactatt gataaaagta   20460
tacaagatgt tattaaaaat aacttaggac aaataagagg tgtgacacct cgtaatgatt   20520
tactaaatgt taatgtatca gcagaaataa atataaatta tcgtttatct gaattaggtt   20580
ttattactaa taaaaatgat atggattgga ttaagaaaaa ctatgacttg tattctaaat   20640
taatagccgg tgcgattcat ggtaagccta taggtggttt ggtagctggt aatgttaaaa   20700
catcagctaa aaacaaaaaa atccaccag tgccagcagg ttatacactc gataagaata   20760 atgtcccttta taaaaagaa caaggcaatt acacagtagc taatgttaaa ggtaataatg   20820
taagagacgg ttattcaact aattcaagaa ttacaggggt attacccaac aacacaacaa   20880
ttacgtatga cggtgcatat tgtattaatg gttatagatg gattacttat attgctaata   20940
gtggacaacg tcgttatata gcgacaggag aggtagacaa ggcaggtaat agaataagta   21000
gttttggtaa gttagcacg atttagtatt tacttagaat aaaaattttg ctacattaat   21060
tatagggaat cttacagtta ttaaataact atttggatgg atgttaatat tcctatacac   21120
tttttaacat ttctctcaag atttaaatgt agataacagg caggtacttc ggtacttgcc   21180
tattttttta tgttatagct agccttcggg ctagttttttt gttatgatgt gttacacatg   21240
catcaactat ttcatctcat ccttgttcac ccaagcatgt cactggatgt ttttctttgc   21300
gatagagagc atagttttca tactactccc cgtagtatat atgactttag cattcccgta   21360
taacagttta cggggtgctt ttatgttata attgctttta tatagtagga gtgaactata   21420
tagccgggca gaggccatgt atctgactgt tggtcccaca ggagacatct tccttgtcat   21480
cactcgatac atatatctta acaacataga aatgttacat tcgctataac cgtatcttaa   21540
tcgatacggt tatatttatt cccctacaac caacaaaacc acagatccta ttaatttagg   21600
attgtggtta ttttttgcgt ttttttgggg caaaaaaagg gcagattatt tgaaaagggg   21660
caaacgcttg tggaaaagct aaaaggttaa aaatgacaaa aaccttgata caacagtgtt   21720 tttgacgct cgtgtacgtt agagaatgac cggtttacca tcatacaagg gtgggattaa   21780
cttgtgttaa aaagccttta atatcagttg ttacaaagga tttgtagcgt ctttaaaaat   21840
aaaaaagggc agaaaagggg cagataccctt ttagtacaca agttttctta atttttgctc   21900
taactctctg tccatttctt ctgttacatg tgtatacacc tttatagtcg ttttttcatc   21960
tgtatgtcct actcttttca taattgcttt taacgatata ttcatttccg ccaataaact   22020
tatgtgtgta tgccttagtg tgtgagtagt aacttttttta tttatattta atgattctgc   22080
agctgaggac aatcgtttgt ttatcctact gccttgcata ggatttcctt ggcaagttgt   22140
gaatataaac cctctatcaa catagcttgg ttcccattgt tgcatctttt tattttctaa   22200
cattattttt ttcaatacat ttgctatcct tgaattgatg gcgattttttc ttcttgaacc   22260 tgcggtctta gtagtatctt tgtgaccaaa tccagcatta catttgattc tgtgaatagt   22320
gccattaata gcgatcgttt tattttttgag gtcaacatct ttaacttgga gagctaataa   22380
ctcacctatg cgcatacctg ttaaagcttg aacttctaca gccccagcaa ctaaaatacg   22440
agctctatac tgcatgttat tatcgttcag tataaaatcg cgtatctgta ttacctgttc   22500
```

```
catctctaaa tagttataca ttttcgcttc ttcttttttct atatcttcta tcgtcttact   22560
cttctttggt agtgtgacgc tatttaatat gtgttcgttt ggataattgt aaaatttaac   22620
ggcgtattta atagcttctt tcatatgtcc aagttgacgc tttacctgat ttgcagaata   22680
tacgtttgat aatttgttaa taaatgtttg catgtacttt gtatcaattt tgtttaaaag   22740
taaattttga gaactgttct ttttgatgtt tttgattctt gttttcaaat tatcaagcgt   22800
cgttacttta aagccagatg ttttatatg atattcaagc cattcatcta ataacgcgtg    22860
aaaagtcaaa gttttaatt cgcttgacga cttgttgttt agttttcttt ttatttttc     22920 ttctaaacga aacattgcct cttttttgcga ttgctttgta ttcttattca agacaacact  22980
tacacgtttc catttatctg tatacggatc tttgtatttc tcgtagtatc tatacttcgt   23040
ttcattgttc ttattttaa attttcaaa ccacattta catccctcct caaaattggc      23100
aaaaaataat aagggtaggc gggctaccca tgaaaattgt ataaaaaaag acgcctgtat   23160
aaaatacaga cgccacttat aattataaga ttacatggtt aattaccaaa aatggtaacg   23220
aatatatacg tgttttaaag gataaaccctt taatatatta aaattatatc atcttatatc  23280
agggatctgc aatatattat tattaattct atttatcagt aacataatat ccgaagaatc   23340
tattactgga ttttttaattt tttgggggtaa aacttttctt atgcgaaact tactaatcgg  23400
ctggaaagaa tttatgcaag cgtaactatt accttttaat ttttttaccct tatcaattgc  23460 tgatactatg ttattaatgt ttctgtcaat tttattttaat ttattttcaa tttctaaact  23520
atcagatata aattcaataa aataatcttt agtgatgaat tctgtgttgt tttttttggta 23580 tttttttatcg aaaacttctt ttaatatagc tgaattattt tgcgcgctaa ttaaatttaa  23640
aaacaatctt aaataatact cccatttcaa atcaaaattc atctttaaat acttttttgtt 23700 ttctttagag gataagggaa taacatttac tatatcctcc gtattagaat cattttttatt 23760 catcactatt gcaaagtgtg aattagaaaa ttcttttatta acgtttatac cgaaatctac   23820
aaaaactatt tctccttgtt taaactttgg ataaaaacct ttatggtttt tttcaccttc   23880
aaatctcttg agtaaatagt gaatatctga atctaacttt ttaaattttg gatttccaga   23940
agtttttaat ttattaatgc gttttttctat attatgcgtc atcatttctc ctttattctc  24000
gctcacactc tcaccaccat tcaacgtcta cacttgtagg cgttttttga ttagtaaaat   24060
cataatgaat cttctttggt taacttatcg ccatctattt tttgtgaaat aaattccaag   24120
tatttacgcg cattatgtga cgataaatct ttaggtaact cataagtgaa tggttgatta   24180
ccactagtta aaacttcata tactatagtt tcttttttta ttttgcaatt agttattttc   24240
attataaact ccttttaaac actgctgaaa tagacgtctt tttcaaataa gcatgattaa   24300
tactttaatt ctttaatcca catatattta aaagtgaggt agtaggtaat aaatataaga   24360
cttaaagtta agattgcttt tttcatgtca atttctcctt tgtttatatt tatattaaag   24420
cgctaaatat acgttattaa tcacaataca actttgccca ttactttaat atcactaaac   24480
gaagcgactt tgatatcatc atacttcgga tttagagata ccaaattaat atagtcttcg   24540
catatatcta cacgcttgat aagacttact ccatctaata caacgagtgc aattgtacca   24600
tctttaatag aatcttcttt cttaataaaa gcgtatgttc cttgttttaa cataggttcc   24660
attgaatcac cattaactaa aatacaaaaa tcagcatttg atggcgtttc gtcttctttta  24720 aaaaatactt cttcatgcaa tatgtcatca tataattctt ctcctatgcc agcaccagtt   24780
gcaccacatg caatatacga tactagttta gactctttat attcatctat agaagtgact   24840
```

-continued

```
ttattctgtt catctaattg ctcatttgca tagttaagta cgttttcttg gcggggaggt    24900
gtgagttgag aaaatatgtt attgattttt gacattatcg tttcatcttg acgttcttcg    24960
tcaggaactc gataagaatc tacatcatac cccataagcc acgcttcacc gacatttaaa    25020
gttttagata ataagaataa tttatgttgg tctggagaag accttccatt aacatactgg    25080
gataagtgac ttttttgacat tttaatattc aattctttttt gaaagggttt cgacttttct    25140
agaatatcta cttgacgcaa gttcctatct ttcataattt gttttaatct ttcagaagtg    25200
ttttgcattg gtaatgcctc cttgaaattc attatatagg aagggaaata aaaatcaata    25260
caaaagttca actttttttaa ctttttgtgt tgacattgtt caaaattggg gttatagtta    25320
ttatagttca aatgtttgaa cttaggaggt gattatttga atactaatac aacttttgat    25380
ttttcgttat tgaacggtaa gatagtcgaa gtgtactcga cacaatttaa ctttgctata    25440
gctttaggtg tatcagaaag aactttgtct ttgaagttga acaacaaagt accatggaaa    25500
acaacagaca ttattaaagc ttgtaagtta ttgggaatac ctataaaaga tgttcacaaa    25560 tatttttttta aacagaaagt tcaaatgttt gaacttaata agtaaaggag gcataacaca    25620
tgcaagaacg agaaaaggtt aataaaagta acacatcttc aaatgaagca tcaaaacctt    25680
ttaggacaaa ttgaagctta cgacaaaacg cttaaagaaa taaagtacac tcgagacctt    25740
tacaacaaac acctaagcat gaacaacgaa gacgcattcg ctggtttgga aatggtagag    25800
gatgaaatta ctaaaaagct acgaagtgct atcaaagagt tccaaaaagt agtgaaagcg    25860
ttagacaagc ttaacggtgt tgaaagcgat aacaaagtta ctgatttaac agagtggcgg    25920
aaagtgaatc agtaacattc acttcttaat ataaccacgc ttatcaacat ccacattgag    25980
cagatgtgag cgagagctgg cgatgatatg agccgcgttt aaatacattc gatagtcatt    26040
gcgataaccg tctgctgaat gtgggtgttg aggaaaaagg aggatactca aatgcaagca    26100
ttacaaacat ttaattttaa agagctacca gtaagaacag tagaaattga aaacgaacct    26160 tatttttgtag gaaaagatat tgctgagatt ttaggatatg caagatcaaa caatgccatt    26220
agaaatcatg ttgatagcga ggacaagctg acgcaccaat ttagtgcatc aggtcaaaac    26280
agaaatatga tcattatcaa cgaatcagga ttatacagtc taatcttcga tgcttctaaa    26340
caaagcaaaa acgaaaaaat tagagaaacc gctagaaaat tcaaacgctg ggtaacatca    26400
gatgtcctac cagctattcg caaacacggt atatacgcaa cagacaatgt aattgaacaa    26460
acattaaaag atccagacta catcattaca gtgttgactg agtataagaa agaaaaagag    26520
caaaacttac ttttacaaca gcaagtagaa gttaacaaac caaaagtatt attcgctgac    26580
tcggtagctg gtagtgataa ttcaatactt gttggagaac tagcgaaaat acttaaacaa    26640
aacggtgttg atataggaca aaacagattg ttcaaatggt taagaaataa tggatatctc    26700
attaaaaaga gtggagaaag ttataactta ccaactcaaa agagtatgga tctaaaaatc    26760
ttggatatca aaaaacgaat aattaataat ccagatggtt caagtaaagt atcacgtaca    26820
ccaaaagtaa caggcaaagg acaacaatac tttgttaata agtttttagg agaaaaacaa    26880
acatcttaaa aggaggaaca caatggaaca aatcacatta accaaagaag agttgaaaga    26940
aattatagca aaagaagtta gagaggctat aaatggcaag aaaccaatca gttcaggttc    27000
aattttcagt aaagtaagaa tcaataatga cgatttagaa gaaatcaata aaaaactcaa    27060
tttcgcaaaa gatttgtcgc taggaagatt gaggaagctc aatcatccga ttccgctaaa    27120
aaagtatcag catggcttcg aatcaattca tcaaaaagct tatgtacaag atgttcatga    27180
ccatattaga aaattaacat tatcaatttt tggagtgaca cttaattcag acttgagtga    27240
```

```
aagtgaatac aacctagcag caaaagtttta tcgagaaatc aaaaactatt atttatacat   27300
ctatgaaaag agagtttcag aattaactat cgatgatttc gaataaagga ggaacaacaa   27360
atgttacaaa aatttagaat tgcgaaagaa aaaaataaat taaaactcaa attactcaag   27420
catgctagtt actgtttaga agaaacaac aaccctgaac tgttgcgagc agttgcagag    27480
ttgttgaaaa aggttagcta aattcaacgg taaggatttg ccctgcctcc acacttagag   27540
tttgagatcc aacaaacaca taagttttag tagggtctag aaaaaatgtt tcgatttcct   27600
cttttgtaac agtttcaatt ccttcatatc ctggaaaaac aattttcttt aaatccgaaa   27660 catgttttt tgaaccatcc tttaaagtaa ctagaagttt catacttatc acctccttag    27720
gttgataaca acattataca cgaaaggagc ataaacaata tgcaagcatt acaaacaaat   27780
tcgaacatcg gagaaatgtt caatattcaa gaaaagaaa atggagaaat cgcaatcagc    27840
ggtcgagaac ttcatcaagc attagaagtt aagacagcat ataaagattg gtttccaaga   27900
atgcttaaat acggatttga agaaaataca gattacacag ctatcgctca aaaagagca    27960 acagctcaag gcaatatgac tcactatatt gaccacgcac tcactactaga cactgcaaaa  28020 gaaatcgcaa tgattcaacg tagtgaacct ggcaaacgtg caagacaata tttcatccaa   28080
gttgaaaaag catggaacag cccagaaatg attatgcaac gtgctttaaa aattgctaac   28140
aacacaatca atcaattaga aacaaagatt gcacgtgaca aaccaaaaat tgtatttgca   28200
gatgcagtag ctactactaa gacatcaatt ttagttggag agttagcaaa gatcattaaa   28260
caaaacggta taaacatcgg gcaacgcaga ttgttgagt ggttacgtca aaacggattc    28320
cttattaaac gcaagggtgt ggattataac atgcctacac agtattcaat ggaacgtgag   28380
ttattcgaaa ttaaagaaac atcaatcaca cattcggacg gtcacacatc aattagtaag   28440
acgccaaaag taacaggtaa aggacaacaa tactttgtta acaagttttt aggagaaaaa   28500
caaacaactt aataggagga attacaaatg aacgcactat acaaaacaac cctcctcatc   28560
acaatggcag ttgtgacgtg aaggtttgg aagattgaga agcacactag aaaacctgtg    28620
attagtagca gggcgttgag tgactatcta acaacaaat cttttaaccat accgaaagat   28680 gctgaaaatt ctactgaatc tgctcgtcgc cttttgaagt tcgccgaaca aactattagc   28740
aaataacaac attatacacg aaaggaaaga tagaaatgcc aaaaatcata gtaccaccaa   28800
caccagaaaa cacatataga ggcgaagaaa aatttgtgaa aaagttatac gcaacaccta   28860
cacaaatcca tcaattgttt ggagtatgta gaagtacagt atacaactgg ttgaaatatt   28920
accgcaaaga taatttaggt gtagaaaatt tatacattga ttattcacca acaggcactc   28980
tgattaatat ttctaaattg gaagagtatt tgatcagaaa gcataaaaaa tggtattagg   29040
aggatattaa atgagcaaca tttataaaag ctacctagta gcagtattat gcttcacagt   29100
cttagcgatt gtacttatgc cgtttctata cttcactaca gcatggtcaa ttgcgggatt   29160
cgcaagtatc gcaacattca tgtactacaa agaatgcttt ttcaaagaat aaaaaaactg   29220
ctacttgttg gagcaagtaa cagtatcaaa cacttaagaa aaaattcatg ttcaatataa   29280
aacgaaaaac ggaggaagtc aagatgtatt acgaaatagg cgaaatcata cgcaaaaata   29340
ttcatgttaa cggattcgat tttaagctat tcatttttaaa aggtcatatg gcatatcaa   29400 tacaagttaa agatatgaac aacgtaccaa ttaaacatgc ttatgtcgta gatgagaatg   29460
acttagatat ggcatcagac ttatttaacc aagcaataga tgaatggatt gaagagaaca   29520
cagacgaaca ggacagacta attaacttag tcatgaaatg gtaggaggtc gctatgaagc   29580
```

```
agactgtaac ttatatcatt cgtcataggg atatgccaat ttatataact aacaaaccaa    29640
ctgataacaa ttcagatatt agttactcca caaatagaaa tagagctagg gagtttaacg    29700
gtatggaaga agcgagtatc aatatggatt atcacaaagc aatcaagaaa acagtgacag    29760
aaactattga gtacgaggag gtagaacatg actgaggaaa acaagaacc acaagaaaaa     29820 gtaagcatac tcaaaaaact aaagataaat aatatcgctg agaaaataa aaggaaattc     29880 tataaatttg cagtatacgg aaaaattggc tcaggaaaaa ccacgtttgc tacaagagat    29940
aaagacgctt tcgtcattga cattaacgaa ggtggaacaa cggttactga cgaaggatca    30000
gacgtagaaa tcgagaacta tcaacacttt gtttatgttg taattttttt acctcaaatt    30060
ttacaggaga tgagagaaaa cggacaagaa atcaatgttg tagttattga aactattcaa    30120
aaacttagag atatgacatt gaatgatgtg atgaaaaata agtctaaaaa accaacgttt    30180
aatgattggg gagaagttgc tgaacgaatt gtcagtatgt acagattaat aggaaaactt    30240
caagaagaat acaaattcca ctttgttatt acaggtcatg aaggtatcaa caaagataaa    30300
gatgatgaag gtagcactat caaccctact atcactattg aagcgcaaga acaaattaaa    30360
aaagctatta cttctcaaag tgatgtgtta gctagggcaa tgattgaaga atttgatgat    30420
aacggagaaa agaaagctag atatattcta aacgctgaac cttctaatac gtttgaaaca    30480
aagattagac attcaccttc aataacaatt aacaataaga aatttgcaaa tcctagcatt    30540
acggacgtag tagaagcaat tagaaatgga aactaaaaat taattaaaag gacggtattt    30600
aattatgaaa atcacaggac aagcgcaatt tactaaagaa acaaatcaag aaaagtttta    30660
taacggctca gcagggtttc aagctggaga attcacagtg aaagttaaaa atattgaatt    30720
caatgataga gaaaatagat atttcacaat cgtatttgaa aatgatgaag gcaaacaata    30780
taaacataat caatttgtac cgccgtataa atatgatttc caagaaaaac aattgattga    30840
attagttact cgattaggta ttaagttaaa tcttcctagc ttagattttg ataccaatga    30900
tcttattggt aagttttgtc acttggtatt gaaatggaaa ttcaatgaag atgaaggtaa    30960 gtatttacg gattttttcat ttattaaacc ttacaaaaag ggcgatgatg ttgttaacaa    31020
acctattccg aagacagata agcaaaaagc tgaagaaaat aacggggcac aacaacaaac    31080
atcaatgtct caacaaagca atccatttga aagcagtggc caatttggat atgacgacca    31140
agatttagcg tttttaaggtg tggtttaaat gcaatacatt acaagatacc agaaagataa    31200
cgacggtact tattccgtcg ttgctactgg tgttgaactt gaacaaagtc acattgactt    31260
actagaaaac ggatatccac taaaagcaga agtagaggtt ccggacaata aaaaactatc    31320
tatagaacaa cgcaaaaaaa tattcgcaat gtgtagagat atagaacttc actggggcga    31380
accagtagaa tcaactagaa aattattaca aacagaattg gaaattatga aaggttatga    31440
agaaatcagt ctgcgcgact gttctatgaa agttgcaagg gagttaatag aactgattat    31500
agcgtttatg tttcatcatc aaatacctat gagtgtagaa acgagtaagt tgttaagcga    31560
agataaagcg ttattatatt gggctacaat caaccgcaac tgtgtaatat gcggaaagcc    31620
tcacgcagac ctggcacatt atgaagcagt cggcagaggc atgaacagaa acaaaatgaa    31680
ccactatgac aaacatgtat tagcgttatg tcgcgaacat cacaacgagc aacatgcgat    31740
tggcgttaag tcgtttgatg ataaatacca cttgcatgac tcgtggataa aagttgatga    31800
gaggctcaat aaaatgttga aaggagagaa aaaggaatga atagactaag aataataaaa    31860
atagcactcc taatcgtcat cttggcggaa gagattagaa atgctatgca tgctgtaaaa    31920
gtggagaaaa ttttaaaatc tccgtttagt taatacaggt ttttacaaaa gctttaccat    31980
```

```
aggcggacaa actaattgag ccttttttga tgtctattac ccaggggctg taatgtaact    32040
ttaatacttc aaattcaatg ccagaaagtt tacttattgt ttctaggttg tgtcctgact    32100
ttaacattct tttaacaaat tctaatcccg aaacaaatct ttgttttttct ataatcttat   32160 taaagtgatt taaaaactga ggagcataaa acttattata aattcctttt tttgttaagt   32220
aagacatgtc aaaagtttca tttaaaaccc ctaaccttac taggttatta attgaaattt   32280
cggttgattc tatatctaac ggagagtctt ttattaacgt gtccgatata ttcataccgt   32340
cattctttgg gtttaaaacc gctctatatt taacggcagg atgtacttcg tgattcttta   32400
aatgttttaa aagaatagca tcatttgggg ataattgttt aattatttca acaaatgaat   32460
ggtgggttaa tgagtttttt ctgtcatcca tagatgatgc tattagtttt gcgaacatat   32520
tacttaaagt ttttttcacta atgtaaaact ttgaagcttc tagagcagga cctagaagag   32580
aaaattgtgg ttcttgtaaa ttattttttag gtacagaaga tatttctttt ttaaattgtt   32640
ctttgaattt ttcaaattct acttctcttt gataaataac tttatccaca taaaggtgga   32700
atttcccaaa gacaagttcc caagttttag agaatgtttc tacaggccct tttgatgcgc   32760
cttcaataat tttatcaata cctttaccta aaataggatc cataattatt cacccccaat   32820
ctaacgcaat agcgataata aaattatacc agaaaggaga atcaacatga ctgaccaacc   32880
aagttactac tcaataatta cagcaaatgt cagatacgat aaccgactta ctgacagcga   32940
aaagttactt tttgcagaaa taacatcttt aagtaacaaa tacggatact gcacagcaag   33000
taatggttac tttgcaactt tatacaacgt tgttaaggaa actatatctc gtagaatttc   33060
gaaccttacc aactttggtt atctaaaaat cgaaattatc aaagaaggta atgaagttaa   33120
acaaaggaag atgtaccccct tgacgcaaac gtcaataccct attgacgcaa aaatcaatac   33180
ccctattgat aattctgtca ataccccctat tgacgcaaat gtcaaagaga atattacaag   33240
tattaataat acaagtaata acaatataaa tagaatagat atattgtcgg gcaacccgac   33300
agcatcttct atacccctata aagaaattat cgattactta acaaaaaag cgggcaagca   33360 ttttaaacac aatacagcta aaacaaaaga ttttattaaa gcaagatgga atcaagattt   33420
taggttggag gattttaaaa aggtgattga tatcaaaaca gctgagtggc taaacacgga   33480
tagcgataaa taccttagac cagaaacact ttttggcagt aaatttgagg ggtacctcaa   33540
tcaaaaaata caaccaactg gcacggatca attggaacgc atgaagtacg acgaaagtta   33600
ttgggattag ggggatatta tgaaaccact attcagcgaa aagataaacg aaagcttgaa   33660
aaaatatcaa cctactcatg tcgaaaaagg attgaaatgt gagagatgtg gaagtgaata   33720
cgacttatat aagtttgctc ctactaaaaa acacccgaat ggttacgagt ataaagacgg   33780
ttgcaaatgt gaaatctatg aggaatataa gcgaaacaag caacggaaga taaacaacat   33840
attcaatcaa tcaaacgtta atccgtcttt aagagatgca acagtcaaaa actacaagcc   33900
acaaaatgaa aaacaagtac acgctaaaca aacagcaata gagtacgtac aaggcttctc   33960
tacaaaagaa ccaaaatcat taatattgca aggttcatac ggaactggta aaagccacct   34020
agcatacgct atcgcaaaag cagtcaaagc taaagggcat acggttgctt ttatgcacat   34080
accaatgttg atggatcgta tcaaagcgac atacaacaaa aatgcagtag agactacaga   34140
cgagctagtc agattgctaa gtgatattga tttacttgta ctagatgata tgggtgtaga   34200
aaacacagag cacactttaa ataaacttttt cagcattgtt gataacagag taggtaaaaa   34260 caacatctttt acaactaact ttagtgataa agaactaaat caaaatatga actggcaacg   34320
```

```
tataaattcg agaatgaaaa aaagagcaag aaaagtaaga gtaatcggag acgatttcag      34380
ggagcgagat gcatggtaac caaagaattt ttaaaaacta aacttgagtg ttcagatatg      34440
tacgctcaga aactcataga tgaggcacag ggcgatgaaa ataggttgta cgacctattt      34500
atccaaaaac ttgcagaacg tcatacacgc cccgctatcg tcgaatatta aggagtgtta      34560
aaaatgccga agaaaaata ttacttatac cgagaagatg gcacagaaga tattaaggtc      34620
atcaagtata aagacaacgt aaatgaggtt tattcgctca caggagccca tttcagcgac      34680
gaaaagaaaa ttatgactga tagtgaccta aaacgattca aaggcgctca cgggcttcta      34740
tatgagcaag aattaggttt acaagcaacg atatttgata tttagaggtg gacgatgagt      34800
aaatacaacg ctaagaaagt tgagtacaaa ggaattgtat ttgatagcaa agtagagtgt      34860
gaatattacc aatatttaga aagtaatatg aatggcacta attatgatca tatcgaaata      34920
caaccgaaat tcgaattatt accaaaacta gataaacaac gaaagattga atatattgca      34980
gacttcgcgt tatatctcga tggcaaactg attgaagtta tcgacattaa aggtatgcca      35040
accgaagtag caaaacttaa agctaagatt ttcagacata aatacagaaa cataaaactc      35100
aattggatat gtaaagcgcc taagtataca ggtaaaacat ggattacgta cgaggaatta      35160
attaaagcaa gacgagaacg caaaagagaa atgaagtgat ctaatgcaac aacaagcata      35220
tataaatgca acgattgata taaggatacc tacagaagtt gaatatcagc attttgatga      35280
tgtggataaa gaaaaagaag cgctggcaga ttacttatat aacaatcctg acgaaatact      35340
agagtatgac aatttaaaaa ttagaaacgt aaatgtagag gtggaataaa tgggcagtgt      35400
tgtaatcatt aataataaac catataaatt taacaatttt gaaaaagaa ataatggcaa      35460 agcgtgggat aaatgctgga attgtttcta acgtgttag aggttgttgg gagttttcag      35520
aagctttaga cgcgccttat ggcatgcacc taaaagaata tagagaaatg aaacaaatgg      35580
aaaagattaa acaagcgaga ctcgaacgtg aattggaaag agagcgaaag aaagaggctg      35640
agctacgtaa gaagaagcca catttgttta atgtacctca aaaacattca cgtgatccgt      35700
actggttcga tgtcacttat aaccaaatgt tcaagaaatg gagtgaagca taatgagcat      35760
aatcagtaac agaaaagtag atatgaacaa aacgcaagac aacgttaagc aacctgcgca      35820
ttacacatac ggcgacattg aaattataga tttattgaa caagttacgg cacagtaccc      35880
accacaatta gcattcgcaa taggtaatgc aattaaatac ttgtctagag caccgttaaa      35940
gaatggtcat gaggatttag caaaggcgaa gttttacgtc gatagagtat ttgacttgtg      36000
ggagtgatga ccatgacaga tagcggacgt aaagaatact taaaacattt tttcggctct      36060
aagagatatc tgtatcagga taacgaacga gtggcacata tccatgtagt aaatggcact      36120
tattactttc acggtcatat cgtgccaggt tggcaaggtg tgaaaaagac atttgataca      36180
gcggaagagc ttgaaacata tataaagcaa agtgatttgg aatatgagga acagaagcaa      36240
ctaactttat tttaaaaggg cggaaacaat gaaaatcaaa attgaaaaag aaatgaattt      36300
acctgaactt atccaatggg cttgggataa ccccaagtta tcaggtaata aaagattcta      36360
ttcaaatgat gttgagcgca actgttttgt gacttttcat gttgatagca tcttatgtaa      36420
tgtgactgga tatgtatcaa ttaacgataa atttactgtt caagaggaga tataacaatg      36480
aaaatcaaag ttaaaaaaga aatgagatta gatgaattaa ttaaatgggc gcgagaaaat      36540
ccggatctat cacaaggaaa atatttttt tcaacaggat ttagtgatgg attcgttcgt      36600
tttcatccaa atacaaataa gtgttcgacg tcaagtttta ttccaattga tatccccttc      36660
atagttgata ttgaaaaaga agtaacggaa gagactaagg ttgataggtt gattgaatta      36720
```

```
ttcgagattc aagaaggaga ctataactct acactatatg agaacactag tataaaagaa    36780
tgtttatatg gcagatgtgt gcctaccaaa gcattctaca tcttaaacga tgacctaact    36840
atgacgttaa tctggaaaga tggggagttg ctagtatgat gttgaaattt aaagcttggg    36900
ataaagataa aaaagttatg agtattattg acgaaatcga ttttaatagt gggtacattt    36960
tgatttcaac aggttataaa agtttcaatg aagtaaaact attacaatac acaggattta    37020
aagatgtgca cggtgtggag atttatgaag gggatattgt tcaagattgt tattcgagag    37080
aagtaagttt tatcgagttt aaagaaggag ccttttatat aacttttagc aatgtaactg    37140
aattactaag tgaaaatgac gatattattg aaattgttgg aaatattttt gaaaatgaga    37200
tgctattgga ggttatgaga tgacgttcac cttatcagat gaacaatata aaaatctttg    37260
tactaactct aacaagttat tagataaact tcacaaagca ttaaaagatc gtgaagagta    37320
caagaagcaa cgagatgagc ttattgggga tatagcgaag ttcgagatt gtaacaaaga    37380 tctagagaag aaagcaagcg catgggatag gtattgcaag agcgttgaaa aagatttaat    37440
aaacgaattc ggtaacgatg atgaaagagt taaattcgga atggaattaa acaataaaat    37500 tttatggag gatgacacaa atgaataatc gcgaaaaaat cgaacagtcc gttattagtg    37560
ctagtgcgta taacggtaat gacacagagg ggttgctaaa agagattgag gacgtgtata    37620
agaaagcgca agcgtttgat gaaatacttg agggaatgac aaatgctatt caacattcag    37680
ttaaagaagg tattgaactt gatgaagcag tagggattat ggcaggtcaa gttgtctata    37740
aatatgagga ggaataggaa aatgactaac acattacaag taaaactatt atcaaaaaat    37800
gctagaatgc ccgaacgaaa tcataagacg gatgcaggtt atgacatatt ctcagctgaa    37860
actgtcgtac tcgaaccaca agaaaaagca gtgatcaaaa cagatgtagc tgtgagtata    37920
ccagagggct atgtcggact attaactagt cgtagtggtg taagtagtaa aacgtattta    37980
gtgattgaaa caggcaagat agacgcggga tatcatggca attagggat taatatcaag    38040 aatgatgaag aacgtgatgg aatacccttt ttatatgatg atatagacgc tgaattagaa    38100
gatggattaa taagcatttt agatataaaa ggtaactatg tacaagatgg aagaggcata    38160
agaagagttt accaaatcaa caaaggcgat aaactagctc aattggttat cgtgcctata    38220
tggacaccgg aactaaagca agtggaggaa ttcgaaagtg tttcagaacg tggagcaaaa    38280
ggcttcggaa gtagcggagt gtaaagacat cttagatcga gttaaggagg ttttggggaa    38340
gtgacgcaat acttagtcac aacattcaaa gattcaacag gacgaccaca tgaacatatt    38400
actgtggcta gagataatca gacgtttaca gttattgagg cagagagtaa agaagaagcg    38460
aaagagaagt acgaggcaca agttaaaaga gatgcagtta ttaaagtggg tcagttgtat    38520
gaaaatataa gggagtgtgg gaaatgacgg atgttaaaat taaaactatt tcaggtggag    38580 tttatttgt aaaaacagct gaaccttttg aaaaatatgt tgaaagaatg acgagtttta    38640
atggttatat ttacgcaagt actataatca agaaaccaac gtatattaaa acagatacga    38700
ttgaatcaat cacacttatt gaggagcatg ggaaatgaat cagctgagaa ttttattaca    38760
tgacggtagt agtttgatat tacatgaaga tgaattattt aacgaaatag tatttgtttt    38820
ggacaatttt agaatgatg atgactattt aacgatagaa aaagattatg gcagagaact    38880
tgtattgaac aaaggttata tagttgggat caatgttgag gaggcagatg atgattaaca    38940
tacctaaaat gaaattcccg aaaaagtaca ctgaaataat caaaaaatat aaaaataaag    39000
cacctgaaga aaaggctaag attgaagatg attttattaa agaaattaaa gataaagaca    39060
```

```
gtgaatttta cagtcctacg atggctaata tgaatgaata tgaattaagg gctatgttaa  39120
gaatgatgcc tagtttaatt gatactggag atgacaatga tgattaaaaa acttaaaaat  39180
atggatgggt tcgacatctt tattgttgga atactgtcat tattcggtat attcgcattg  39240
ctacttgtta tcacattgcc tatctataca gtggctagtt accaacacaa agaattacat  39300
caaggaacta ttacagataa atataacaag agacaagata agaagacaa gttctatatt  39360
gtattagaca acaaacaagt cattgaaaat tccgacttat tattcaaaaa gaaatttgat  39420
agcgcagata tacaagctag gttaaaagta ggcgataagg tagaagttaa aacaatcggt  39480
tatagaatac actttttaaa tttatatccg gtcttatacg aagtaaagaa ggtagataaa  39540
caatgattaa acaaatacta agactattat tcttactagc aatgtatgag ttaggtaagt  39600
atgtaactga gcaagtgtat attatgatga cggctaatga tgatgtagag gcgccgagtg  39660
attacgtctt tcgagcggag gtgagtgaat aatgagaata tttatttatg atttgatcgt  39720
tttgctgttt gctttcttaa tatccatata tattattgat gatggagtga taataaatgc  39780
attaggaatt tttggtatgt ataaaattat agattccttt tcagaaaata ttataaagag  39840
gtagataaaa atgaacgagc aaataatagg aagcatatat actttagcag gaggtgttgt  39900
gctttattca gttaaagaga ttttttaggta ttttacagat tctaacttac aacgtaaaaa  39960
aatcaattta gaacaaatat atccgatata tttagattgt tttaaaaagg ctaaaaagat  40020
gattggagct tatattattc caacagaaca gcatgaattt ttagattttt ttgatattga  40080
agtctttaat aatttagata agcaaagtaa aaaagcgtat gaaaatgtta ttggatttag  40140
acaaatgatt aatttatcaa atagagttaa ggcaatggaa gattttaaga tgagtttcaa  40200
caatgaattt agtacaaatc agatttttttt taatccttct tttgttatgg aaacaattgc  40260
tattataaat gaatatcaaa aagatatatc ttatttaaaa aatataatta ataaaatgaa  40320
tgaaaataga gcttataatc atattgatag ttttatcact tcagagtacc gacgaaaaat  40380
aaacgattat aatctttatc ttgataaatt tgaagaacag tttagtcaaa agtttaaaat  40440
aaacagaact tcgataaaag aaagaattat tattaattta aacaagagga gatttaaatg  40500
atgtggatta ctatgactat tgtatttgct atattgctat tagtttgtat cagtattaat  40560
agtgatcgtg caagagagat acaagcactt agatatatga atgattatct acttgatgaa  40620
gtagttaaaa ctaaagggta caacgggtta gaagaataca ggattgaatt gaagcgaatg  40680
aataacgata ttaaaaagta atttatatta tcggaggtat tgcattgaat gataaagatt  40740
gagaaacacg atatcaaaaa gcttgaagaa tacattcagc acatcgataa ctatcgaaga  40800
gagttgaaga tgcgagaata tgaattactt gaaagtcatg aaccagataa tgcgggagct  40860
ggcaaaagta atttgccggg taacccgatt gaacgatgtg caataaagaa gtttagtgat  40920
aacaggtaca atacattaag aaatatagtt aacggtgtag atagattgat aggtgaaagt  40980
gatgaggata cgcttgagtt attaaggttt agatattggg attgtcctat tggttgttat  41040
gaatgggaag atatagcaca ttactttggt acaagtaaga caagtatatt acgtagaagg  41100
aatgcactga tcgataagtt agcaaagtat attggttatg tgtagcggac ttttacccta  41160
tgtaagtccg cattaaaaca gtttattatg ttagtatcag attaatattt aaagttatta  41220
aatgctaata cgacgcatga acaagaggcg catcactatg tgatgtgtct tttatttat  41280
gaggtatgaa catgttcaaa ctaattgtaa atacattact acacatcaag tatagatgag  41340
tcttgatact acttaagtta tataaggtga aacattatga tgactaaaga cgaacgtata  41400
cgattctata agtctaaaga atggcaaata acaagaaaaa gagtgctaga aagagataat  41460
```

```
tatgaatgtc aacaatgtaa gagagacggc aagttaacga catatgacaa aagcaagcgt    41520
aagtcgttgg atgtagatca tatattatcg ctagaacatc atccggagtt tgctcatgac    41580
ttaaacaatt tagaaacact gtgtattaaa tgtcacaaca aaaagaaaa gagatttata     41640 aaaaagaaa ataaatggaa agacgaaaaa tggtaaatac ccccgggtca aaaaatcaa      41700 aagcgatc                                                              41708

<210> SEQ ID NO 4
<211> LENGTH: 159
<212> TYPE: DNA
<213> ORGANISM: Staphylococcus aureus

<400> SEQUENCE: 4
atggtaacca aagaattttt aaaaactaaa cttgagtgtt cagatatgta cgctcagaaa     60
ctcatagatg aggcacaggg cgatgaaaat aggttgtacg acctatttat ccaaaaactt    120
gcagaacgtc atacacgccc cgctatcgtc gaatattaa                           159

<210> SEQ ID NO 5
<211> LENGTH: 52
<212> TYPE: PRT
<213> ORGANISM: Staphylococcus aureus

<400> SEQUENCE: 5

Met Val Thr Lys Glu Phe Leu Lys Thr Lys Leu Glu Cys Ser Asp Met
1               5                   10                  15

Tyr Ala Gln Lys Leu Ile Asp Glu Ala Gln Gly Asp Glu Asn Arg Leu
                20                  25                  30

Tyr Asp Leu Phe Ile Gln Lys Leu Ala Glu Arg His Thr Arg Pro Ala
        35                  40                  45

Ile Val Glu Tyr
    50

<210> SEQ ID NO 6
<211> LENGTH: 1362
<212> TYPE: DNA
<213> ORGANISM: Bacillus subtilis

<400> SEQUENCE: 6
atgacagacc ttctgaatga ccggcttcct ccgcaaaata tagaagccga acaagccgtg     60
ttaggcgcta tttttttaca gccgtctgct ttaacactgg cttcagaagt attgattcca    120
gatgatttct atagaatgtc ccaccaaaaa atctataatg cgatgctggt gctcggtgac    180
cgaggtgaac cggttgatct ggtgacagtt acatcgagc ttgcgaacac agacctgctg     240
gaagaagtag gcggtatttc atatttgaca gatatcgcaa actcggtgcc gacagcggct    300
aacatagaat attacgcgaa atcgttgag gaaaaatcga ttcttcgccg attaatcaga    360
actgcgacaa cgattgctca agacgggtat acccgtgagg atgaggtcga ggatttactc    420
agtgaagcgg aaaaaacgat tatgaagtg cacagcgca aaaacacgag tgccttccaa     480
aatattaagg acgtccttgt ccagacctat gataatatcg aacagcttta caatcgaaaa    540
ggtgatatca cggaattcc aacagggttt acggagcttg accggatgac tgcgggtttc    600
cagcgcaacg acttgatcat tgtggctgcc cgtccttcag tagggaaaac agcctttgcc    660
ctgaacatcg cacaaaacgt ggcgacgaag accgatgaga gcgtagcgat tttcagtctt    720
gagatgggtg ccgagcagct cgttatgcgt atgctctgtg ccgagggaaa tatcaatgcc    780
```

-continued

| | |
|---|---|
| cagaatctcc gtacaggtaa cctgaccgaa gaggattggg gcaagctgac gatggcaatg | 840 |
| ggaagcctat cgaacagcgg gatttacatc gatgatacac cgggtattcg agtgagtgaa | 900 |
| atccgtgcca agtgccgccg cttgaagcag gaaagcgggc tgggcatgat tttgatcgat | 960 |
| tacctgcaat tgattcaggg aagcggtcgt tcaaaggaca accgtcagca ggaagtatct | 1020 |
| gaaatttccc gtgaactgaa gtcgattgcg agggagctgc aagtccctgt tatcgcgctt | 1080 |
| tctcagcttt ccagggggtgt tgagcagcgt caggataaac gtccgatgat gtctgatatc | 1140 |
| cgggaatcag gaagtatcga gcaggacgcg gatattgtcg cgttcctttta tcgtgatgac | 1200 |
| tactatgaca agaaaccga gaataaaaat tattatcgaa ttattatcgc caaacagcgt | 1260 |
| aacggcccgg taggaaccgt gtctcttgcg ttcgtaaaag aatacaacaa attcgtcaac | 1320 |
| ctggaacggc gttttgatga cgcaggcgtt ccgcccggcg ca | 1362 |

<210> SEQ ID NO 7
<211> LENGTH: 1401
<212> TYPE: DNA
<213> ORGANISM: Staphylococcus aureus

<400> SEQUENCE: 7

| | |
|---|---|
| atggatagaa tgtatgagca aaatcaaatg ccgcataaca atgaagctga acagtctgtc | 60 |
| ttaggttcaa ttattataga tccagaattg attaatacta ctcaggaagt tttgcttcct | 120 |
| gagtcgtttt ataggggtgc ccatcaacat atttttccgtg caatgatgca cttaaatgaa | 180 |
| gataataaag aaattgatgt tgtaacattg atggatcaat tatcgacgga aggtacgttg | 240 |
| aatgaagcgg gtggcccgca atatcttgca gagttatcta caaatgtacc aacgacgcga | 300 |
| aatgttcagt attatactga tatcgttttct aagcatgcat taaaacgtag attgattcaa | 360 |
| actgcagata gtattgccaa tgatggatat aatgatgaac ttgaactaga tgcgatttta | 420 |
| agtgatgcag aacgtcgaat tttagagcta tcatcttctc gtgaaagcga tggctttaaa | 480 |
| gacattcgag acgtcttagg acaagtgtat gaaacagctg aagagcttga tcaaaatagt | 540 |
| ggtcaaacac caggtatacc tacaggatat cgagatttag accaaatgac agcagggttc | 600 |
| aaccgaaatg atttaattat ccttgcagcg cgtccatctg taggtaagac tgcgttcgca | 660 |
| cttaatattg cacaaaaagt tgcaacgcat gaagatatgt atacagttgg tattttctcg | 720 |
| ctagagatgg gtgctgatca gttagccaca cgtatgattt gtagttctgg aaatgttgac | 780 |
| tcaaaccgct taagaacggg tactatgact gaggaagatt ggagtcgttt tactatagcg | 840 |
| gtaggtaaat tatcacgtac gaagattttt attgatgata caccgggtat tcgaattaat | 900 |
| gatttacgtt ctaaatgtcg tcgattaaag caagaacatg gcttagacat gattgtgatt | 960 |
| gactacttac agttgattca aggtagtggt tcacgtgcgt ccgataacag acaacaggaa | 1020 |
| gtttctgaaa tctctcgtac attaaaagca ttagcccgtg aattagaatg tccagttatc | 1080 |
| gcattaagtc agttatctcg tggtgttgaa caacgacaag ataaacgtcc aatgatgagt | 1140 |
| gatattcgtg aatctggttc gattgagcaa gatgccgata tcgttgcatt cttataccgt | 1200 |
| gatgattact ataaccgtgg cggcgatgaa gatgatgacg atgatggtgg tttcgagcca | 1260 |
| caaacgaatg atgaaaacgg tgaaattgaa attatcattg ctaagcaacg taacggtcca | 1320 |
| acaggcacag ttaagttaca tttttatgaaa caatataata aatttaccga tatcgattat | 1380 |
| gcacatgcag atatgatgta a | 1401 |

<210> SEQ ID NO 8
<211> LENGTH: 454

<212> TYPE: PRT
<213> ORGANISM: Bacillus subtilis

<400> SEQUENCE: 8

```
Met Thr Asp Leu Leu Asn Asp Arg Leu Pro Gln Asn Ile Glu Ala
 1               5                  10                  15

Glu Gln Ala Val Leu Gly Ala Ile Phe Leu Gln Pro Ser Ala Leu Thr
                20                  25                  30

Leu Ala Ser Glu Val Leu Ile Pro Asp Asp Phe Tyr Arg Met Ser His
                35                  40                  45

Gln Lys Ile Tyr Asn Ala Met Leu Val Leu Gly Asp Arg Gly Glu Pro
 50                  55                  60

Val Asp Leu Val Thr Val Thr Ser Glu Leu Ala Asn Thr Asp Leu Leu
 65                  70                  75                  80

Glu Glu Val Gly Gly Ile Ser Tyr Leu Thr Asp Ile Ala Asn Ser Val
                    85                  90                  95

Pro Thr Ala Ala Asn Ile Glu Tyr Tyr Ala Lys Ile Val Glu Glu Lys
                100                 105                 110

Ser Ile Leu Arg Arg Leu Ile Arg Thr Ala Thr Thr Ile Ala Gln Asp
            115                 120                 125

Gly Tyr Thr Arg Glu Asp Glu Val Glu Asp Leu Leu Ser Glu Ala Glu
        130                 135                 140

Lys Thr Ile Met Glu Val Ala Gln Arg Lys Asn Thr Ser Ala Phe Gln
145                 150                 155                 160

Asn Ile Lys Asp Val Leu Val Gln Thr Tyr Asp Asn Ile Glu Gln Leu
                165                 170                 175

Tyr Asn Arg Lys Gly Asp Ile Thr Gly Ile Pro Thr Gly Phe Thr Glu
            180                 185                 190

Leu Asp Arg Met Thr Ala Gly Phe Gln Arg Asn Asp Leu Ile Ile Val
        195                 200                 205

Ala Ala Arg Pro Ser Val Gly Lys Thr Ala Phe Ala Leu Asn Ile Ala
    210                 215                 220

Gln Asn Val Ala Thr Lys Thr Asp Glu Ser Val Ala Ile Phe Ser Leu
225                 230                 235                 240

Glu Met Gly Ala Glu Gln Leu Val Met Arg Met Leu Cys Ala Glu Gly
                245                 250                 255

Asn Ile Asn Ala Gln Asn Leu Arg Thr Gly Asn Leu Thr Glu Glu Asp
            260                 265                 270

Trp Gly Lys Leu Thr Met Ala Met Gly Ser Leu Ser Asn Ser Gly Ile
        275                 280                 285

Tyr Ile Asp Asp Thr Pro Gly Ile Arg Val Ser Glu Ile Arg Ala Lys
    290                 295                 300

Cys Arg Arg Leu Lys Gln Glu Ser Gly Leu Gly Met Ile Leu Ile Asp
305                 310                 315                 320

Tyr Leu Gln Leu Ile Gln Gly Ser Gly Arg Ser Lys Asp Asn Arg Gln
                325                 330                 335

Gln Glu Val Ser Glu Ile Ser Arg Glu Leu Lys Ser Ile Ala Arg Glu
            340                 345                 350

Leu Gln Val Pro Val Ile Ala Leu Ser Gln Leu Ser Arg Gly Val Glu
        355                 360                 365

Gln Arg Gln Asp Lys Arg Pro Met Met Ser Asp Ile Arg Glu Ser Gly
    370                 375                 380

Ser Ile Glu Gln Asp Ala Asp Ile Val Ala Phe Leu Tyr Arg Asp Asp
385                 390                 395                 400
```

```
Tyr Tyr Asp Lys Glu Thr Glu Asn Lys Asn Ile Ile Glu Ile Ile Ile
                405                 410                 415

Ala Lys Gln Arg Asn Gly Pro Val Gly Thr Val Ser Leu Ala Phe Val
            420                 425                 430

Lys Glu Tyr Asn Lys Phe Val Asn Leu Glu Arg Arg Phe Asp Asp Ala
        435                 440                 445

Gly Val Pro Gly Ala
    450

<210> SEQ ID NO 9
<211> LENGTH: 466
<212> TYPE: PRT
<213> ORGANISM: Staphylococcus aureus

<400> SEQUENCE: 9

Met Asp Arg Met Tyr Glu Gln Asn Gln Met Pro His Asn Asn Glu Ala
1               5                   10                  15

Glu Gln Ser Val Leu Gly Ser Ile Ile Asp Pro Glu Leu Ile Asn
            20                  25                  30

Thr Thr Gln Glu Val Leu Leu Pro Glu Ser Phe Tyr Arg Gly Ala His
        35                  40                  45

Gln His Ile Phe Arg Ala Met Met His Leu Asn Glu Asp Asn Lys Glu
    50                  55                  60

Ile Asp Val Val Thr Leu Met Asp Gln Leu Ser Thr Glu Gly Thr Leu
65                  70                  75                  80

Asn Glu Ala Gly Gly Pro Gln Tyr Leu Ala Glu Leu Ser Thr Asn Val
                85                  90                  95

Pro Thr Thr Arg Asn Val Gln Tyr Tyr Thr Asp Ile Val Ser Lys His
            100                 105                 110

Ala Leu Lys Arg Arg Leu Ile Gln Thr Ala Asp Ser Ile Ala Asn Asp
        115                 120                 125

Gly Tyr Asn Asp Glu Leu Glu Leu Asp Ala Ile Leu Ser Asp Ala Glu
    130                 135                 140

Arg Arg Ile Leu Glu Leu Ser Ser Ser Arg Glu Ser Asp Gly Phe Lys
145                 150                 155                 160

Asp Ile Arg Asp Val Leu Gly Gln Val Tyr Glu Thr Ala Glu Glu Leu
                165                 170                 175

Asp Gln Asn Ser Gly Gln Thr Pro Gly Ile Pro Thr Gly Tyr Arg Asp
            180                 185                 190

Leu Asp Gln Met Thr Ala Gly Phe Asn Arg Asn Asp Leu Ile Ile Leu
        195                 200                 205

Ala Ala Arg Pro Ser Val Gly Lys Thr Ala Phe Ala Leu Asn Ile Ala
    210                 215                 220

Gln Lys Val Ala Thr His Glu Asp Met Tyr Thr Val Gly Ile Phe Ser
225                 230                 235                 240

Leu Glu Met Gly Ala Asp Gln Leu Ala Thr Arg Met Ile Cys Ser Ser
                245                 250                 255

Gly Asn Val Asp Ser Asn Arg Leu Arg Thr Gly Thr Met Thr Glu Glu
            260                 265                 270

Asp Trp Ser Arg Phe Thr Ile Ala Val Gly Lys Leu Ser Arg Thr Lys
        275                 280                 285

Ile Phe Ile Asp Asp Thr Pro Gly Ile Arg Ile Asn Asp Leu Arg Ser
    290                 295                 300

Lys Cys Arg Arg Leu Lys Gln Glu His Gly Leu Asp Met Ile Val Ile
```

-continued

```
                305                 310                 315                 320
Asp Tyr Leu Gln Leu Ile Gln Gly Ser Gly Ser Arg Ala Ser Asp Asn
                    325                 330                 335
Arg Gln Gln Glu Val Ser Glu Ile Ser Arg Thr Leu Lys Ala Leu Ala
                340                 345                 350
Arg Glu Leu Glu Cys Pro Val Ile Ala Leu Ser Gln Leu Ser Arg Gly
            355                 360                 365
Val Glu Gln Arg Gln Asp Lys Arg Pro Met Met Ser Asp Ile Arg Glu
        370                 375                 380
Ser Gly Ser Ile Glu Gln Asp Ala Asp Ile Val Ala Phe Leu Tyr Arg
385                 390                 395                 400
Asp Asp Tyr Tyr Asn Arg Gly Gly Asp Glu Asp Asp Asp Asp Asp Gly
                405                 410                 415
Gly Phe Glu Pro Gln Thr Asn Asp Glu Asn Gly Glu Ile Glu Ile Ile
                420                 425                 430
Ile Ala Lys Gln Arg Asn Gly Pro Thr Gly Thr Val Lys Leu His Phe
                435                 440                 445
Met Lys Gln Tyr Asn Lys Phe Thr Asp Ile Asp Tyr Ala His Ala Asp
            450                 455                 460
Met Met
465

<210> SEQ ID NO 10
<211> LENGTH: 313
<212> TYPE: PRT
<213> ORGANISM: Staphylococcus aureus

<400> SEQUENCE: 10

Met Gly Gly Gly Gln Ser Ile Met Lys Gln Phe Lys Ser Ile Ile Asn
1               5                   10                  15
Thr Ser Gln Asp Phe Glu Lys Arg Ile Glu Lys Ile Lys Lys Glu Val
            20                  25                  30
Ile Asn Asp Pro Asp Val Lys Gln Phe Leu Glu Ala His Arg Ala Glu
        35                  40                  45
Leu Thr Asn Ala Met Ile Asp Glu Asp Leu Asn Val Leu Gln Glu Tyr
    50                  55                  60
Lys Asp Gln Gln Lys His Tyr Asp Gly His Lys Phe Ala Asp Cys Pro
65                  70                  75                  80
Asn Phe Val Lys Gly His Val Pro Glu Leu Tyr Val Asp Asn Asn Arg
                85                  90                  95
Leu Lys Ile Arg Tyr Leu Gln Cys Pro Cys Lys Ile Lys Tyr Asp Glu
            100                 105                 110
Glu Arg Phe Glu Ala Glu Leu Ile Thr Ser His Asn Met Gln Arg Asp
        115                 120                 125
Thr Leu Asn Ala Lys Leu Lys Asp Leu Tyr Met Asn His Arg Asp Arg
    130                 135                 140
Leu Asp Val Ala Met Ala Ala Asp Ile Cys Thr Ala Ile Thr Asn
145                 150                 155                 160
Gly Glu Gln Val Lys Gly Leu Tyr Leu Tyr Gly Pro Phe Gly Thr Gly
                165                 170                 175
Lys Ser Phe Leu Leu Gly Ala Ile Ala Asn Gln Leu Lys Ser Lys Lys
            180                 185                 190
Val Arg Ser Thr Ile Ile Tyr Leu Pro Glu Phe Ile Arg Thr Leu Lys
        195                 200                 205
```

```
Gly Gly Phe Lys Asp Gly Ser Phe Glu Lys Lys Leu His Arg Val Arg
        210                 215                 220
Glu Ala Asn Ile Leu Met Leu Asp Asp Ile Gly Ala Glu Glu Val Thr
225                 230                 235                 240
Pro Trp Val Arg Asp Glu Val Ile Gly Pro Leu Leu His Tyr Arg Met
                245                 250                 255
Val His Glu Leu Pro Thr Phe Phe Ser Ser Asn Phe Asp Tyr Ser Glu
                260                 265                 270
Leu Glu His His Leu Ala Met Thr Arg Asp Gly Glu Glu Lys Thr Lys
                275                 280                 285
Ala Ala Arg Ile Ile Glu Arg Val Lys Ser Leu Ser Thr Pro Tyr Phe
        290                 295                 300
Leu Ser Gly Glu Asn Phe Arg Asn Asn
305                 310
```

<210> SEQ ID NO 11
<211> LENGTH: 12
<212> TYPE: PRT
<213> ORGANISM: Staphylococcus aureus
<220> FEATURE:
<221> NAME/KEY: misc_feature
<223> OTHER INFORMATION: predicted tryptic peptide

<400> SEQUENCE: 11

```
Gly His Val Pro Glu Leu Tyr Val Asp Asn Asn Arg
1               5                   10
```

<210> SEQ ID NO 12
<211> LENGTH: 11
<212> TYPE: PRT
<213> ORGANISM: Staphylococcus aureus
<220> FEATURE:
<221> NAME/KEY: misc_feature
<223> OTHER INFORMATION: predicted tryptic peptide

<400> SEQUENCE: 12

```
Ser Thr Ile Ile Tyr Leu Pro Glu Phe Ile Arg
1               5                   10
```

<210> SEQ ID NO 13
<211> LENGTH: 14
<212> TYPE: PRT
<213> ORGANISM: Staphylococcus aureus
<220> FEATURE:
<221> NAME/KEY: misc_feature
<223> OTHER INFORMATION: predicted tryptic peptide

<400> SEQUENCE: 13

```
Ser Leu Ser Thr Pro Tyr Phe Leu Ser Gly Glu Asn Phe Arg
1               5                   10
```

<210> SEQ ID NO 14
<211> LENGTH: 280
<212> TYPE: PRT
<213> ORGANISM: Bacillus subtilis

<400> SEQUENCE: 14

```
Asp Gln Asp Val Gln Ala Phe Leu Lys Glu Asn Glu Glu Val Ile Asp
1               5                   10                  15
Gln Lys Met Ile Glu Lys Ser Leu Asn Lys Leu Tyr Glu Tyr Ile Glu
                20                  25                  30
Gln Ser Lys Asn Cys Ser Tyr Cys Ser Glu Asp Glu Asn Cys Asn Asn
        35                  40                  45
```

```
Leu Leu Glu Gly Tyr His Pro Lys Leu Val Val Asn Gly Arg Ser Ile
     50                  55                  60

Asp Ile Glu Tyr Tyr Glu Cys Pro Val Lys Arg Lys Leu Asp Gln Gln
 65                  70                  75                  80

Lys Lys Gln Gln Ser Leu Met Lys Ser Met Tyr Ile Gln Gln Asp Leu
                 85                  90                  95

Leu Gly Ala Thr Phe Gln Gln Val Asp Ile Ser Asp Pro Ser Arg Leu
                100                 105                 110

Ala Met Phe Gln His Val Thr Asp Phe Leu Lys Ser Tyr Asn Glu Thr
                115                 120                 125

Gly Lys Gly Lys Gly Leu Tyr Leu Tyr Gly Lys Phe Gly Val Gly Lys
        130                 135                 140

Thr Phe Met Leu Ala Ala Ile Ala Asn Glu Leu Ala Glu Lys Glu Tyr
145                 150                 155                 160

Ser Ser Met Ile Val Tyr Val Pro Glu Phe Val Arg Glu Leu Lys Asn
                165                 170                 175

Ser Leu Gln Asp Gln Thr Leu Glu Glu Lys Leu Asn Met Val Lys Thr
                180                 185                 190

Thr Pro Val Leu Met Leu Asp Asp Ile Gly Ala Glu Ser Met Thr Ser
        195                 200                 205

Trp Val Arg Asp Glu Val Ile Gly Thr Val Leu Gln His Arg Met Ser
        210                 215                 220

Gln Gln Leu Pro Thr Phe Phe Ser Ser Asn Phe Ser Pro Asp Glu Leu
225                 230                 235                 240

Lys His His Phe Thr Tyr Ser Gln Arg Gly Glu Lys Glu Glu Val Lys
                245                 250                 255

Ala Ala Arg Leu Met Glu Arg Ile Leu Tyr Leu Ala Ala Pro Ile Arg
            260                 265                 270

Leu Asp Gly Glu Asn Arg Arg His
            275                 280

<210> SEQ ID NO 15
<211> LENGTH: 278
<212> TYPE: PRT
<213> ORGANISM: Bacillus halodurans

<400> SEQUENCE: 15

Pro His Val Gln Leu Phe Leu Glu Glu His Pro Ser Leu Ser Pro Ile
 1                   5                  10                  15

Thr Leu Glu Gln Gly Leu Ser Lys Leu Tyr Glu Tyr Gln Lys Glu Gln
                 20                  25                  30

Ser His Cys Ala His Cys Pro Gly Leu Gln Lys Cys Pro Asn Leu Met
             35                  40                  45

Lys Gly Tyr Gln Pro Thr Leu Tyr Val Glu Arg Asp Ser Leu Glu Leu
         50                  55                  60

Ser Tyr Ser Pro Cys Pro Leu Lys Glu Glu Glu Arg Glu Lys Lys
 65                  70                  75                  80

Lys Arg Ser Leu Ile Arg Ser Leu Tyr Ile Pro Lys Glu Ile Leu Glu
                 85                  90                  95

Ala Lys Phe Asp Asp Val Glu Ser Glu Pro Gly Arg Ser Ile Ala Ser
                100                 105                 110

His Arg Ala Leu Glu Phe Ala Leu Ser Ala Lys Pro Gly Glu Asp Gly
                115                 120                 125

Met Gly Leu Tyr Leu Tyr Gly Lys Phe Gly Val Gly Lys Thr Phe Leu
```

```
                130                 135                 140
Met Gly Ala Ile Ala Asn Glu Leu Lys Asp Arg Gly Ile Asp Ser Thr
145                 150                 155                 160

Ile Val Tyr Val Pro Asp Phe Phe Arg Glu Leu Lys Gln Ser Ile Gly
                165                 170                 175

Asp Gly Thr Phe Gln Gln Lys Leu Asp Phe Val Lys Asn Ala Gln Val
            180                 185                 190

Leu Ile Phe Asp Asp Ile Gly Ala Glu Thr Met Thr Ser Trp Val Arg
        195                 200                 205

Asp Asp Val Leu Gly Val Ile Leu Gln Tyr Arg Ile Met Glu Lys Leu
210                 215                 220

Pro Thr Leu Phe Thr Ser Asn Tyr Asp Tyr Asp Glu Leu Glu Glu His
225                 230                 235                 240

Leu Ala Tyr Asn Asp Lys Ser Gly Thr Glu Leu Leu Lys Ala Lys Arg
                245                 250                 255

Val Met Glu Arg Ile Arg His Tyr Thr Val Ser Val Met Val Gln Gly
            260                 265                 270

Gln Asn Arg Arg Glu His
        275

<210> SEQ ID NO 16
<211> LENGTH: 164
<212> TYPE: PRT
<213> ORGANISM: Staphylococcus aureus

<400> SEQUENCE: 16

Ala Ala Asp Asp Ile Cys Thr Ala Ile Thr Asn Gly Glu Gln Val Lys
1               5                   10                  15

Gly Leu Tyr Leu Tyr Gly Pro Phe Gly Thr Gly Lys Ser Phe Ile Leu
                20                  25                  30

Gly Ala Ile Ala Asn Gln Leu Lys Ser Lys Val Arg Ser Thr Ile
            35                  40                  45

Ile Tyr Leu Pro Glu Phe Ile Arg Thr Leu Lys Gly Gly Phe Lys Asp
        50                  55                  60

Gly Ser Phe Glu Lys Lys Leu His Arg Val Arg Glu Ala Asn Ile Leu
65                  70                  75                  80

Met Leu Asp Asp Ile Gly Ala Glu Glu Val Thr Pro Trp Val Arg Asp
                85                  90                  95

Glu Val Ile Gly Pro Leu Leu His Tyr Arg Met Val His Glu Leu Pro
                100                 105                 110

Thr Phe Phe Ser Ser Asn Phe Asp Tyr Ser Glu Leu Glu His His Leu
            115                 120                 125

Ala Met Thr Arg Asp Gly Glu Glu Lys Thr Lys Ala Ala Arg Ile Ile
        130                 135                 140

Glu Arg Val Lys Ser Leu Ser Thr Pro Tyr Phe Leu Ser Gly Glu Asn
145                 150                 155                 160

Phe Arg Asn Asn

<210> SEQ ID NO 17
<211> LENGTH: 495
<212> TYPE: DNA
<213> ORGANISM: Staphylococcus aureus

<400> SEQUENCE: 17
gcagcagatg atatttgtac agcaataact aatggggaac aagtgaaagg cctttacctt    60
```

-continued

```
tatggtccat ttgggacagg taaatctttt attctaggtg caattgcgaa tcagctcaaa      120
tctaagaagg tacgttcgac aattatttat ttaccggaat ttattagaac attaaaaggt      180
ggctttaaag atggttcttt tgaaaagaaa ttacatcgcg taagagaagc aaacatttta      240
atgcttgatg atattgggc tgaagaagtg actccatggg tgagagatga ggtaattgga       300
cctttgctac attatcgaat ggttcatgaa ttaccaacat tctttagttc aattttgac       360 tatagtgaat tggaacatca tttagcgatg actcgtgatg gtgaagagaa gactaaagca      420
gcacgtatta ttgaacgtgt caaatctttg tcaacaccat actttttatc aggagaaaat      480
ttcagaaaca attga                                                        495
```

<210> SEQ ID NO 18
<211> LENGTH: 250
<212> TYPE: PRT
<213> ORGANISM: Staphylococcus aureus

<400> SEQUENCE: 18

```
Tyr Lys Asp Gln Gln Lys His Tyr Asp Gly His Lys Phe Ala Asp Cys
1               5                   10                  15

Pro Asn Phe Val Lys Gly His Val Pro Glu Leu Tyr Val Asp Asn Asn
            20                  25                  30

Arg Ile Lys Ile Arg Tyr Leu Gln Cys Pro Cys Lys Ile Lys Tyr Asp
        35                  40                  45

Glu Glu Arg Phe Glu Ala Glu Leu Ile Thr Ser His His Met Gln Arg
    50                  55                  60

Asp Thr Leu Asn Ala Lys Leu Lys Asp Ile Tyr Met Asn His Arg Asp
65                  70                  75                  80

Arg Leu Asp Val Ala Met Ala Ala Asp Asp Ile Cys Thr Ala Ile Thr
                85                  90                  95

Asn Gly Glu Gln Val Lys Gly Leu Tyr Leu Tyr Gly Pro Phe Gly Thr
            100                 105                 110

Gly Lys Ser Phe Ile Leu Gly Ala Ile Ala Asn Gln Leu Lys Ser Lys
        115                 120                 125

Lys Val Arg Ser Thr Ile Ile Tyr Leu Pro Glu Phe Ile Arg Thr Leu
    130                 135                 140

Lys Gly Gly Phe Lys Asp Gly Ser Phe Glu Lys Lys Leu His Arg Val
145                 150                 155                 160

Arg Glu Ala Asn Ile Leu Met Leu Asp Asp Ile Gly Ala Glu Glu Val
                165                 170                 175

Thr Pro Trp Val Arg Asp Glu Val Ile Gly Pro Leu Leu His Tyr Arg
            180                 185                 190

Met Val His Glu Leu Pro Thr Phe Phe Ser Ser Asn Phe Asp Tyr Ser
        195                 200                 205

Glu Leu Glu His His Leu Ala Met Thr Arg Asp Gly Glu Glu Lys Thr
    210                 215                 220

Lys Ala Ala Arg Ile Ile Glu Arg Val Lys Ser Leu Ser Thr Pro Tyr
225                 230                 235                 240

Phe Leu Ser Gly Glu Asn Phe Arg Asn Asn
                245                 250
```

<210> SEQ ID NO 19
<211> LENGTH: 12
<212> TYPE: PRT
<213> ORGANISM: Staphylococcus aureus

```
<400> SEQUENCE: 19

Gly His Val Pro Glu Asn Val Thr Asp Asn Asp Arg
1               5                  10
```